(12) United States Patent
Isaacs et al.

(10) Patent No.: US 9,593,380 B2
(45) Date of Patent: Mar. 14, 2017

(54) COMPOSITIONS AND METHODS FOR THE TREATMENT OF PROSTATE CARCINOMA

(71) Applicants: THE JOHNS HOPKINS UNIVERSITY, Baltimore, MD (US); THE REGENTS OF THE UNIVERSITY OF MICHIGAN TECHNOLOGY MANAGEMENT OFFICE, Ann Arbor, MI (US)

(72) Inventors: William B. Isaacs, Glyndon, MD (US); Kathleen A. Cooney, Ann Arbor, MI (US)

(73) Assignees: The John Hopkins University, Baltimore, MD (US); The Regents of the University of Michigan Technology Management Office, Ann Arbor, MI (US)

( * ) Notice: Subject to any disclaimer, the term of this patent is extended or adjusted under 35 U.S.C. 154(b) by 0 days.

(21) Appl. No.: 14/357,034

(22) PCT Filed: Nov. 8, 2012

(86) PCT No.: PCT/US2012/064179
§ 371 (c)(1),
(2) Date: May 8, 2014

(87) PCT Pub. No.: WO2013/070933
PCT Pub. Date: May 16, 2013

(65) Prior Publication Data
US 2014/0315746 A1 Oct. 23, 2014

Related U.S. Application Data

(60) Provisional application No. 61/583,882, filed on Jan. 6, 2012, provisional application No. 61/556,850, filed on Nov. 8, 2011.

(51) Int. Cl.
| | |
|---|---|
| *C12Q 1/68* | (2006.01) |
| *G01N 33/574* | (2006.01) |
| *C07K 14/82* | (2006.01) |
| *C07K 16/32* | (2006.01) |

(52) U.S. Cl.
CPC ............ *C12Q 1/6886* (2013.01); *C07K 14/82* (2013.01); *C07K 16/32* (2013.01); *G01N 33/57434* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

WO 2006004600 A1 1/2006

OTHER PUBLICATIONS http://www.cancer.gov/types/prostate/psa-fact-sheet#q4, Jul. 2012.*
Jung et al. "HOXB13 Homeodomain Protein Suppresses the Growth of Prostate Cancer Cells by the Negative Regulation of T-Cell Factor 4" Cancer Research 64, pp. 3046-3051 (2004).
Jung et al. "HOXB13 Induces Growth Suppression of Prostate Cancer Cells as a Repressor of Hormone-Activated Androgen Receptor Signaling", Cancer Research 64, pp. 9185-9192 (2004).
Ewing et al., "Germline Mutations in HOXB13 and Prostate-Cancer Risk", New England Journal of Medicine, pp. 141-149, (2012).
Shah et al (2010) The Hox genes and their roles in oncogenesis. Nat Rev Cancer. May 2010;10(5):361-71. doi: 10.1038/nrc2826. Epub Apr. 1, 2010.
Jung et al (2004) HOXB13 homeodomain protein suppresses the growth of prostate cancer cells by the negative regulation of T-cell factor 4. Cancer Res. May 1, 2004;64(9):3046-51.
Jung et al (2004) HOXB13 induces growth suppression of prostate cancer cells as a repressor of hormone-activated androgen receptor signaling. Cancer Res. Dec. 15, 2004;64(24):9185-92.
Ewing et al (2012) Germline mutations in HOXB13 and prostate-cancer risk. N Engl J Med. Jan. 12, 2012;366(2):141-9. doi: 10.1056/NEJMoa1110000.
Siegel et al (2011) Cancer statistics, 2011: the impact of eliminating socioeconomic and racial disparities on premature cancer deaths. CA Cancer J Clin. Jul.-Aug. 2011;61(4):212-36. doi: 10.3322/caac.20121. Epub Jun. 17, 2011.
Langeberg et al (2007) Genetic etiology of hereditary prostate cancer. Front Biosci. May 1, 2007;12:41301-10.
Kim et al (2010) Prostate cancer risk-associated variants reported from genome-wide association studies: meta-analysis and their contribution to genetic Variation. Prostate. Dec. 1, 2010;70(16):1729-38. doi: 10.1002/pros.21208.
Kote-Jarai et al (2011) Seven prostate cancer susceptibility loci identified by a multi-stage genome-wide association study. Nat Genet. Jul. 10, 2011;43(8):785-91. doi: 10.1038/ng.882.
Lange et al (2003) Genome-wide scan for prostate cancer susceptibility genes using families from the University of Michigan prostate cancer genetics project finds evidence for linkage on chromosome 17 near BRCA1. Prostate. Dec. 1, 2003;57(4):326-34.
Gillanders et al (2004) Combined genome-wide scan for prostate cancer susceptibility genes. J Natl Cancer Inst. Aug. 18, 2004;96(16):1240-7.
Xu et al (2005) A combined genomewide linkage scan of 1,233 families for prostate cancer-susceptibility genes conducted by the international consortium for prostate cancer genetics. Am J Hum Genet. Aug. 2005;77(2):219-29. Epub Jun. 29, 2005.
Lange et al (2007) Fine-mapping the putative chromosome 17q21-22 prostate cancer susceptibility gene to a 10 cM region based on linkage analysis. Hum Genet. Mar. 2007;121(1):49-55. Epub Nov. 21, 2006.

(Continued)

*Primary Examiner* — Nancy J Leith
(74) *Attorney, Agent, or Firm* — Mintz Levin Cohn Ferris Glovsky and Popeo, P.C.; Peter F. Corless; Christopher R. Cowles

(57) ABSTRACT

Compositions and methods for the diagnosis, treatment and prevention of prostate cancer, well as for treatment selection.

10 Claims, 52 Drawing Sheets

(56) References Cited

OTHER PUBLICATIONS

Lange et al (2011) Early onset prostate cancer has a significant genetic component. Prostate. Feb. 1, 2012;72(2)147-56. doi: 10.1002/pros.21414. Epub May 2, 2011.
Lange et al (2009) Genome-wide linkage scan for prostate cancer susceptibility from the University of Michigan Prostate Cancer Genetics Project: suggestive evidence for linkage at 16q23. Prostate. Mar. 1, 2009;69(4):385-91. doi: 10.1002/pros.20891.
Xu et al (2002) Germline mutations and sequence variants of the macrophage scavenger receptor 1 gene are associated with prostate cancer risk. Nat Genet. Oct. 2002;32(2):321-5. Epub Sep. 16, 2002.
Zheng et al (2007) Association between two unlinked loci at 8q24 and prostate cancer risk among European Americans. J Natl Cancer Inst. Oct. 17, 2007;99(20):1525-33. Epub Oct. 9, 2007.
Liu et al (2008) Homozygous deletions and recurrent amplifications implicate new genes involved in prostate cancer. Neoplasia. Aug. 2008;10(8):897-907.
Ng et al (2006) Predicting the effects of amino acid substitutions on protein function. Annu Rev Genomics Hum Genet. 2006;7:61-80.
Ramensky et al (2002) Human non-synonymous SNPs: server and survey. Nucleic Acids Res. Sep. 1, 2002;30(17):3894-900.
Williams et al (2005) Range of HOX/TALE superclass associations and protein domain requirements for HOXA13: MEIS interaction. Dev Biol. Jan. 15, 2005;277(2):457-71.
Haiman et al (2011) Genome-wide association study of prostate cancer in men of African ancestry identifies a susceptibility locus at 17q21. Nat Genet. Jun. 2011;43(6):570-3. doi: 10.1038/ng.839. Epub May 22, 2011.
Gudmundsson et al (2007) Two variants on chromosome 17 confer prostate cancer risk, and the one in TCF2 protects against type 2 diabetes. Nat Genet. Aug. 2007;39(8):977-83. Epub Jul. 1, 2007.
Graham et al (1994) Developmental patterning. The Hox code out on a limb. Curr Biol. Dec. 1, 1994;4(12)1135-7.
Goodman et al (2001) Human HOX gene mutations. Clin Genet. Jan. 2001;59(1):1-11.
Economides et al (2003) Hoxb13 mutations cause overgrowth of caudal spinal cord and tail vertebrae. Dev Biol. Apr. 15, 2003;256(2):317-30.
Economides et al (2003) Hoxb13 is required for normal differentiation and secretory function of the ventral prostate. Development. May 2003;130(10):2061-9.
Thorsteinsdottir et al (2001) Defining roles for HOX and MEIS1 genes in induction of acute myeloid leukemia. Mol Cell Biol. Jan. 2001;21(1):224-34.
Norris et al (2009) The homeodomain protein HOXB13 regulates the cellular response to androgens. Mol Cell. Nov. 13, 2009;36(3):405-16. doi: 10.1016/j.molcel.2009.10.020.
Kim et al (2007) Integrative analysis of genomic aberrations associated with prostate cancer progression. Cancer Res. Sep. 1, 2007;67(17):8229-39.
Fukasawa et al (2008) Genetic changes in pT2 and pT3 prostate cancer detected by comparative genomic hybridization. Prostate Cancer Prostatic Dis. 2008;11(3):303-10. Epub Oct. 9, 2007.
Edwards et al (2005) Expression analysis onto microarrays of randomly selected cDNA clones highlights HOXB13 as a marker of human prostate cancer. Br J Cancer. Jan. 31, 2005;92(2):376-81.
Thompson et al (2002) Cancer Incidence in BRCA1 mutation carriers. J Natl Cancer Inst. Sep. 18, 2002;94(18):1358-65.
Ostrander et al (2008) The role of the BRCA2 gene in susceptibility to prostate cancer revisited. Cancer Epidemiol Biomarkers Prev. Aug. 2008;17(8):1843-8. doi: 10.1158/1055-9965.EPI-08-0556.
Schehl-Sinclair et al (2000) BRCA1 and BRCA2 have a limited role in familial prostate cancer. Cancer Res. Mar. 1, 2000;60(5):1371-5.
Zuhlke et al (2004) Truncating BRCA1 mutations are uncommon in a cohort of hereditary prostate cancer families with evidence of linkage to 17q markers. Clin Cancer Res. Sep. 15, 2004;10(18 Pt 1):5975-80.
Li et al (2009) The Sequence Alignment/Map format and SAMtools. Bioinformatics. Aug. 15, 2009;25(16):2078-9. doi: 10.1093/bioinformatics/btp352. Epub Jun. 8, 2009.
Cropp et al (2011) Genome-wide linkage scan for prostate cancer susceptibility in Finland: evidence for a novel locus on 2q37.3 and confirmation of signal on 17q21-q22. Int J Cancer. Nov. 15, 2011;129(10):2400-7. doi: 10.1002/ijc.25906. Epub Apr. 20, 2011.
Gudmundsson et al (2007) Genome-wide association study identifies a second prostate cancer susceptibility variant at 8q24. Nat Genet. May 2007;39(5):631-7. Epub Apr. 1, 2007.
Yeager et al (2007) Genome-wide association study of prostate cancer identifies a second risk locus at 8q24. Nat Genet. May 2007;39(5):645-9. Epub Apr. 1, 2007.
Thomas et al (2008) Multiple loci identified in a genome-wide association study of prostate cancer. Nat Genet. Mar. 2008;40(3):310-5. doi: 10.1038/ng.91. Epub Feb. 10, 2008.
Gudmundsson et al (2008) Common sequence variants on 2p15 and Xp11.22 confer susceptibility to prostate cancer. Nat Genet. Mar. 2008;40(3):281-3. doi: 10.1038/ng.89. Epub Feb. 10, 2008.
Eeles et al (2008) Multiple newly identified loci associated with prostate cancer susceptibility. Nat Genet. Mar. 2008;40(3):316-21. doi: 10.1038/ng.90. Epub Feb. 10, 2008.
Sun et al (2008) Evidence for two independent prostate cancer risk-associated loci in the HNF1B gene at 17q12. Nat Genet. Oct. 2008;40(10):1153-5. doi: 10.1038/ng.214. Epub Aug. 31, 2008.
Yeager et al (2009) Identification of a new prostate cancer susceptibility locus on chromosome 8q24. Nat Genet. Oct. 2009;41(10):1055-7. doi: 10.1038/ng.444. Epub Sep. 20, 2009.
Gudmundsson et al (2009) Genome-wide association and replication studies identify four variants associated with prostate cancer susceptibility. Nat Genet. Oct. 2009;41(10):1122-6. doi: 10.1038/ng.448. Epub Sep. 20, 2009.
Eeles et al (2009) Identification of seven new prostate cancer susceptibility loci through a genome-wide association study. Nat Genet. Oct. 2009;41(10):1116-21. doi: 10.1038/ng.450. Epub Sep. 20, 2009.
Xu et al (2010) Inherited genetic variant predisposes to aggressive but not indolent prostate cancer. Proc Natl Acad Sci U S A. Feb. 2, 2010;107(5):2136-40. doi: 10.1073/pnas.0914061107. Epub Jan. 11, 2010.
Takata et al (2010) Genome-wide association study identifies five new susceptibility loci for prostate cancer in the Japanese population. Nat Genet. Sep. 2010;42(9):751-4. doi: 10.1038/ng.635. Epub Aug. 1, 2010.
Akamatsu et al (2012) Common variants at 11q12, 10q26 and 3p11.2 are associated with prostate cancer susceptibility in Japanese. Nat Genet. Feb. 26, 2012;44(4):426-9, S1. doi: 10.1038/ng.1104.
Schaid et al (2005) Description of the International Consortium for Prostate Cancer Genetics, and failure to replicate linkage of hereditary prostate cancer to 20q13. Prostate. May 15, 2005;63(3)276-90.
Kruglyak et al (1996) Parametric and nonparametric linkage analysis: a unified multipoint approach. Am J Hum Genet. Jun. 1996;58(6):1347-63.
Purcell et al (2007) PLINK: a tool set for whole-genome association and population-based linkage analyses. Am J Hum Genet. Sep. 2007;81(3):559-75. Epub Jul. 25, 2007.
Carpten et al (2002) Germline mutations in the ribonuclease L gene in families showing linkage with HPC1. Nat Genet. Feb. 2002;30(2):181-4. Epub Jan. 22, 2002.
Tavtigian et al (2001) A candidate prostate cancer susceptibility gene at chromosome 17p. Nat Genet. Feb. 2001;27(2):172-80.
Edwards et al (2003) Two percent of men with early-onset prostate cancer harbor germline mutations in the BRCA2 gene. Am J Hum Genet. Jan. 2003;72(1):1-12. Epub Dec. 9, 2002.
Agalliu et al (2007) Rare germline mutations in the BRCA2 gene are associated with early-onset prostate cancer. Br J Cancer. Sep. 17, 2007;97(6):826-31. Epub Aug. 14, 2007.
Iyengar et al (2007) The genetic basis of complex traits: rare variants or "common gene, common disease"? Methods Mol Biol. 2007;376:71-84.
Bodmer et al (2008) Common and rare variants in multifactorial susceptibility to common diseases. Nat Genet. Jun. 2008;40(6):695-701. doi: 10.1038/ng.f.136.

\* cited by examiner

FIG. 5

Chromosome 17q21-22: position 46719390:46827600

>17 dna:chromosome chromosome:GRCh37:17:46719390:46827600:1

CAGATGAACCGTTCGTTAGGAGCAGCGAGGTAGTCGTGAGCGCTGAGATCCAGAGACTAG
GACCCACTCCCTCTCTGAGCAGCAAATTGGGAAGAAGATGCTCACTCGGTAAGGGCGAGG
GAGCCCGGCATGGCGCCCCACCACGGGCTCGGTCTATCTGCGCGCCAAGATCCCGCTTGG
GGCGAGGCGTTGGGTCAGCGTTTAGAGCCACTCCCTGCGCTGGTGGCTGGACATAGCCTC
CCTATCCCACCTCATCTTCCCCATCCCCGACAGAGGAGGTTGTGAATCTACAGGCCCTT
GACGTTGAGGCGTCGGAGGGCGCACCTTTGTAATTGCGGCCTCCCTTCGCCCCTTAAGTG
CCGCTTCTGGGCGCCTAGGCTGGATATGAAAGCCCCGTTCCTAATCCTCTGCTCTGGTCC
CCTCCTCTGGACTGCTGGGACTCTAAGCTAGGCCCTCCCCAGGTTCCATCACTGCGGCGC
CAACCCGCGGCTGGGCTGTCCGCAAGAGGGAGTTGAAGGCGCGCGGAATCCCGAGGTGCA
GCTGACCCTCCTCTCAACGCCGACTCTGCCGCTCCCGCCCGGCCACCTCCCTGTCGGGCA
GACTTCCTGTTCTCCTGCTCACAGCAGGGAGGCAGTCGCCGAGCCGGTCAGCAGCGTGCA
CGGAGATCTTCACTCTGCGCCCAGCCCCGGGACACAGGTGCAGATCTCCAGCGGAGCACT
GCGGAGTGCGCGCCGTCGAGCACTAGGGAATCCTAGACGGAGGACTTGGTCCATTCCACG
CAGTCCCAGGCAGGTCCGCAGCGGAGGGACGCAGCGGTCTCCAACTCCTGGTCACGACTT
CGGCGACCCTCCACCCCCTGAGAGACCTGGTCCCACGGAGCTGTCCCCCAGGAGCCGCA
GCGGGAATAGCAAAGCAAAGGGGACCACTCAGCCCCCAGGAGGAGCCCTGAAGCAAAAG
GTTGCTGCGGGGAGCCACGTTCCCTCTGGTTCACCTCGAAGCCCAGGAGCTCCGGTCCCT
GGACCAAGGAGTGAACAGACCTGAGGAAGAGGTAAGAGGAGGTTTAACGAGTAAAAATTT
GGACTCTCTCCTCTTATACTGCTTTAAAGCATGAGGAATTTGGGCCCTGACTTCTCTCTC
CTTGAAGAAGTTTCTCGCGTTCTGGCCAGTCCTTGCGTGTCTGCACCCAGGGCCGGCAAC
AATTTAAGGAGGAACTTTACTGGGTGGTCGAGGCTTGAGAGTTCATAGTTACCTTTTAAA
AAAATCATTACTATTACTTAATATCTAGGTTATTTTGGACTGAGCCCCCATCTTCGCTCC
AGCCCAAATTCGGCCTTTAACAGTACTAGGGAGTGCTTCAAAAGAGGAGGGTCGTGGAGG
AAGCGACTCAGACGGCCCCAAGAGGAGAGATGGGAAGGAGTGAGGGCTTTGGCCTTAATG
ATCTCTGCAAGTTAAAGGCCATTATTCCTATAACTACAGCTGGGGAAAGGGCAGAGGAGG
TAAGGACGGAAAGTGGGCTGAGGGTGGCCACTTTGGCATCTTCTTGAGAAAGGAGACATT
TGAATTCCCGGCCCAACTAAAAGCCCTGAGATGCTTGCCCTTTGCTTTACAGACAGTGAT
GGCAAAGAAATACTGCCACCAGGGTGTTTTAAAGGTGAAGGTTGACCTGATAAGCACTG
AGATCAGACAAAGGAAAAAAAAGTAAAGCATTTGGTCTTTCAGTTTTCTGGCTAAATCT
GGCATCATTTTCCAGACACAAACTTCTCTGATTAATCCAAATAGCTCTCAACCTGAAGTT
CAAGGAATTTGAAATCCTCTGAAATTGTGGGATTTCACAGTTCTAAAAGGAAGTCAGCTG
TCACTTTCTGAGAAGCCCTGGGAGGGGAAGGAAGCAAGAGGAGGTATATGAGGAAGGGG
GTGAGAGGCCCCAGATCTAGCTCTCTAGACATTTAGTGCTGGACCCCCAAGCTCTGAAAC

FIG. 5 (continued)

```
TCAAGCTGACCCCATCTACACATTGCCAAACTGAGTAGAAAGTTGCAAGGCAGTCAAGGA
GATAAATTTTATTTACTGCTTTAAGGATGAGTTTGGGTGTCTAAGCAGATTATAAATCTG
GGTGTTTTCAGTATTTGTTTCTTTCTTTCAACTATTACTGATTTTTGGCCCAGAGTAGTT
TCTGGGGCCCTTGGGGCAGTTAGGCAAGAGAGGGACTCAGACCTCCAGTCCCTTGATCTT
GCCTTTACTTGGTGAAGAGCCCAAGATTCTCTACTGGCAGGCAAGGTCAGAACCAAGTTG
GCCCTAGGCCTTGCCCCAACCCCCCAGCCCTCAGGACTCCTTTCTCTGAGACCAGGCCTC
TGGCCAAACTGCAGACTCCCTCCACACCCGGTCACTGGAATAATGATGGCATTTTTGATT
TCTCCCATTTTTGAAAACTATAGAAGCCCCAAGGAGGAAGGAGGTACCACTGGATCTTGG
GGTGCTGGTGGGGATTCTGGAATCAAATATCCTCTAAGCCTGTGAGGACAAGGTCTACT
AGGATGACTTGGTGTCAATTACAGCTCTGAGTGCTGCCTGGATAGGTCAAATATTCCCTC
CTTTCCCTCCTCATTCCTTCCGTTCAAGCCCAGAAAATTCACAGATTTTCTGTGTGGAGA
GAGAGAAAAAAATGGGCAAAACCTGGGAGTAAAAGGGAGATGAGGGAGAAGAAAATGAG
GGAGAGAAACCAATAGACTAAAACAATGAAACTCTCTAACCCAACAGCACTTTAAGCTTG
ACTTTTAATCTGGCCAGAAAAAAAAGAAGTTGGAGGCAGGGTGGGTGGGATGTGAAGTT
CCCAGCCCAACAGATCCTCCTGTTGTCACGGGCTCTGTGCGTTCCCAGCTGGTGAGAACC
CTGTCTGTCCTGGGGGTGGGAGGGATGTCCTGGGTCTTTCAAGTTGCAGTGTGGGGAGTG
AGGCTCTTTCTAAGGGTCTCTGAGGTCTCCCACAACACCTTGCTTGGACTAGCAAAACCT
TTCTTTGCATTTCCTCTGGGGCACTGTGTATGTGTATCCCTGTGTAGGGTGGTGTTCTAA
ACCACCGCAGAAGGTGAGCAATTCTCCTCCCAGCGAGCCAAAGGCTATATGTTTGGGGTG
GAGGAGGCTTCATCCCTTCTGGACTGGAGAAATGGGGACTTGGAGCCAAGTGCGCCAGAC
TTTAGGGAAAGAGAGGAGCTCCAGCTCCAAAAGGGATTTGGAGGGAAGATCCTATCAGGA
AAGGCCCCCCAGACTTGCTTCCTCAAAGGGTTAGGGAAGTGCACTGAGAAAAGAGAACTT
TCACTTAACTCTTCTCCATTAGGCATCTTTGTGCTTCCATTTGTACTGGAAAGCACAGTC
CTGGGCAGTCAGTTGCACATTCCGCCTCTGGTATGTGGACTATGTGAAATATACCATGCA
ATGTTCTACTTTGCGAGGGGGGAGGCATATAGATGAAAATATGAATTTCCCTTCTACTGC
CTTTATTATTGAGCACAGTTGGGAGCACATAATTTCACATCTCTTTCGCATGTCTGTATA
AATCCTCAATCTTTAAACGGTGCTTGACTACTCCGAGAGGCACAGTTGCTGTCATATAAG
ATTCCTAGCCGACTCCGGCGAGTTACTAATTCCTCTCAGACTCCACAATACCCACGATGC
ACGATGCACACCCCTTTATGCTTGCTTTTCTTTACATGCCTTTTCAAAGGCGAATAATTT
TTGTATTGACCCATGAGTCAGTCCATACAGTTTGAAATCCTTTGGATGCCCTCTGCCCAC
TCCCATAAACAACAGGTCCCTCCACAAAAATGCACATGCCCCGTTTTTGTGAGTGTGGGT
TTCAAATAAGATGGCGTCTCCTGGCATTCCTTAGATTCAGATACACGCTCTCTCAGGCAG
GAGGCTGCTCACAGTCCAGAGGGGAAGAAAACCTATGAGGCCCCAAAAGCCAAAGCAAG
AGACTCCCCAAGTATTCTGCCCCCTCCACGCCAGGAGGCAGCTAGAGAGACAGCGCGCG
GGAGAGCTGATTCTGCACCTTGGGGAGCTGGGGCTTCTGTCTAGACCAAGAGTTCCAGG
CCAATTCCTAATTTCCGTTAGGAAAGTGGCCCTTCTTCCATCCCAAGCGATTCCTCACC
CCCAAGGCTGCTCAGGGCGTCTGGCCCTTGCCTCTCTCACGGCATCCGCCTGGAATCCGG
GGTTGTGAGCAGGAGGCCCAGGACGCAGGGCCTCAGGCTGGGCGGGGCACTGAGCACTCG
```

FIG. 5 (continued)

```
GCTCTGGGGAGCCAGGGTTTCCGGTAGAACGAGGGGAGGCGACCCCCTTTCCCCACACAC
ACACCTGTTGGAGAGGTAGGGTCGGGTGCCAGCGGACAGGGAGGCCAAGGCGTTTTCGGG
TGCGCCCCGAGGCCCTACCCGGGAAGCTGCCTCGGTCTGGAGATCAAGGTTAAGCCGGTG
GCCCCGGGAAGCCCACGCCTGCCACGGGCGGTTGGTCCTGAAAGCTCGGGCCACGGGCT
GCCCAGCTTGGAGAGGGGCCTTTCACGCCGCAGTCCCCAGCTGCGAGAGGAAGGGCTGCG
CCCGCCTCCTCACCTACCTCTCGGAACCACGCCGTCCCCGCGCGTCTTCGTAGACTGCA
GGAGTCCAGGGCGTCTGGGGACTGTGACGGCGCCCAAGGCGGGGATGTGGCGGCTCTGG
GTCGCCGCCTTCTGCCCCGCCTCTGTGAGGCCTCTCGAGGCAGTGTCTGTGTCTGGGGC
AGCGACGCCGACGGCGCTGGGGGCGCGAAGGGGCTCACGCTCCTGCGTTCCCTGGCGCC
GGTGAGTGGCGGGCGAGGACAGGGTCCGGGAGGGGATAGGCGAGAGCGCTTCCTGCCTC
CGCCCGGGCGGGGCTCGGCCGTCTCACCTGCCCCCACCCACGGCGCCGTCGGATCCCAGA
GCGGCTGGTGAGGAGATGGGCCTGGCGCGCCGCGGGGAGGCCAGAGGCGCGGAGGAGCAG
CGCCCAGATGGCCGGAGAGAGCAGAGAGAGAGAGAAGAGAGAGAGAAGAGAGAGAGAG
AGAAGAGAGAGAGAGGGAGAGAGGCAGAGAGGGAGAGAGGGAGGGAGAGAGGGAGGGAGG
GAGGGAGGGAGAGAGAGAGAGAGAGAGAGAGAGAGAGAGAGAATATGAGAATATGAGAAT
ATAAAAGGCAAGAGAGAAGCAGATCCAAGGGCGCGCCCAGAGAAACATCAAATGCACAAA
TAGACAAAAGAGGTAGAGGAGAAAGCTGAGTCCCAGGGGCTGAAAGAAGCCATGGGCGTC
TGAAGCGAGCGACAAGTTATCCTTGGGAGTTGGAAATGTGAGAGGGAGGGGCGAGGCCGA
AGGAGGCTGAGAAGGGGAGGGGCGCTCACACCCTGGGCGGGAGGCGACTGATCCACACT
TAGGGCTCCGAATCCGGAGAAAGAGAGCGCCGGACCCTCCTCCGCCCACCTCCCGCCCCA
GCCGCAGCCCAGCGACTTCCCGCCATCCTCGGCCACCGAGCGGCTCCTGCCTGGGGTTGT
TCGACCGGGATGGCTGCACCAGGCTGAAGGTTGTCCCTCTACCTGCCTCCTTTCTTCTGT
TCCCTGTGCCTTACATGGGTTCCTCCCTATTCTATGAACCCAGAGGGAACGACCTTGGCC
AAGGTTAGAGAAGGAGCTTGAAAGTTTCACTTTCCATCTTAGCCCTCAGGACGCCTTTGC
GTTTTGGCCCTTCGTTAGCGTGCTATCCTGGAATTGCAGGCTCTTCTCTTTATTTCTGAG
ACCCAAATAGAGGTTTAACCTCCTTAAAATCAGTGAAACTACGACAAACAGTGGCATTCC
TGGCTGTCTGGTCTCTAAGGAGTGCCCCCCCTCCCTGACCTCAGCCCTGAGACCCTGCTT
CCTCCTCAACCTGCATGGGACTGGGGACACCCCCTCACAATCCAGTCCCTTCCTGCAGGT
GGTTGTCCAGGGGGCATGTAGAGGTGTGCCTGAGCTCTGTGTCCTAAGCCTGGCTCTGCC
ACTGACTTCAGCCCCCACCCCTTCTCCTTTTAGGCCTCAGTTTTTCCTCTGTAAAATGGG
CAGAGTGATTTTACAAGTGATTTTACCAAGTGAGAACTGTTGAAATATCTTACTATAATT
GTGGATTTGTCCATTTCTCCTTTCAATTCTATCATTTTCGGTGCTTCATATATTTTTGAA
GCTCTGTTATTAGGTGTGTACATTTAAGGTTGATGTGTCTTCCTAGGTGTGTACCACATT
TAGATTTAGGATTGATGTGTCTTCTTTTTTGAGATGAAGTCTTGATCTGTCACCCAGGCT
GGAGTGCAATGGTGCAATCTCGGCTCACTGCAACCTCCGCCTCTTGAGTTCAAGCGATTC
TCCCACTTCAGCCTCCCGAGTAGCTGGGACCACAGGTGTGTGCCACCACGCCCAGCTAAT
TTGTGTAGTTTTAGTAGAGACGGGTTTTCACCATGTTGGCCAGGCTGGTCTCGGCTCCTG
```

FIG. 5 (continued)

ACGTCAGGTGATCCGCTTGCCTCAGCCTCCCAAAGTGCTGGGATTAGAGGTGTGAGCCAC
GGCTCCTAGCCATGATATGTCTTCTTATGCTTTGCTTCTGCAGCCTCCTCTCATTTGCAG
GTTCTGTTGAGCTTGAACCGCTGAGAGAAAAATGCATCCAAATGGGAATTTTATTCTATA
TCCACGTAAACATGAATATAGAAATATGACAAAACTAAATTTTGCTTCCAAAATGTTTTT
GTTTTGTTTTGTTTTTGTTTTTTTGTTTGTTTGTTTTTTCTGAGACAGAGTTTCGCTCTT
GTTGCCCAGGCTGGAGTGCAATGGCACAATCCCAGCTCACCGCAACCTCTGCCTCCCGGG
TTCTCCTGCCTCAGCCTCCCTAGTAGCTGGGATTACAGGCATGTGCCACCATGCGCAGCT
AATTTTTTGTATTTTTAATAGAGACGGGGTTTCTCCATGTTGGTCAGGCTGGTCTCGAAC
TCCCGACCTCAGGTGATCCGCCCGCCTCAGCCTCCCAAAGTGCTGAGATTACAGGCATGA
GCCACTGCACCCGGCCAACGCCCAGCTAATTTTGTATTTTTAGTAGAGATGGGGTTTCTC
CAGTTCGTCAGGCTGGTCTCGAACTCCCTACCTCAGGTCATCCGCCCGCCTCAGCCTCCC
AAAGTGCTGGGATTACAGGCGTGAGCCACCATGCCCGGCCCCAGAATTTTTTCTATTTGG
GTCTATTTTTCTACTTTTTCTTCACTTTTTGTTGATATATAGTATTATAGAACCTAATAT
TAAACCTCTGGCTCAATATATTTTTGCATAGATCCCATCTGTGTAACCACCACCTAGATC
AAGATGTTTCCGGCTTACCAGAAGGCCCCATTGTAACTCCTACCAATCAATAGCTCTCTG
GTCAATCCCTCCATACCCCCTAACAATTATTTGGCTTTCTATCACCATAGATTAGTTTTG
TCTAATCCTTCAACTTCATATAAACATAAGTATGTATTCTTTTGTCTGGCTTCATCTGCT
CAGTATTACTTGTGTGGGACTCATCCATGGTGTTGTATATGGCAGCAGTTCATTCATTTT
ATCATTGTGTCATATTAGTTGTATGAATATATTACAATGTATTTAACCTGTTTGGCTCTT
GGTGGACTTAAGGGTTATTTTCAGTTTGGAGCTATAATGAAAAAGCTGTTATGAACATTA
CATCTGTGTCTTTTGATGGATGCCTGGACTTGGAGACCCAGGAGTGGAAATGCTGGATAA
CAGAGTAGGAAAATGTTTGTTTGTTAAATAATGACAGTTTTCCAAAGTGGTTGACCAGTT
TACACTCCCACTAGTAATGTGTGAGATCCATAGAGAAGTAAGCTTTACAAAAAAAAAAA
TGACAGAGAGGACTCAGGATCCAGTTACTGCATATCCCTACCAACACCTGACACTGTCTC
TCTTCATTCTGGTGGGTTTGTGGTAATCTTGCAATGAGGTTTTTGCTTGTTTGCTTTTC
GGAGTTGTTTTTTTTTTTTTTTTTGTACATTTAAAAAATTGTGGTAAAAACATATAATA
AATTTTACCATCTTAACCTTGTTTAAGTGTACAATTCAGTATGTTAAGCACATTCACACT
GTTGTGCCACAGATCTCTAGAATATTTCCATCTTTCAAAACGGGACTCAATACCCACTGA
GTAAAAACCGCCCCCCCATTCCCCTCTTTCCCCAGCACCTGGCAATTATCATTTTACTTT
GTTTCTATAAGTTTGAATACTTTAGATACCTCATATAAGTGGAATCATACTGTATTTGTC
TTTTTCTGACTGATTTGTTTCACTTTGCATGTCTTCAAGTTTCACCCACACTGTAGCATG
TGACAGGATTTCTTTATTTTTAAAGGCTAAGTAATATTCCATTATATTTATATACTACAT
TTTGCTTATCCATTCATCCATTGATGGCCGTTTAGTTTGCTCCCACCTCTTAGCTGTTGT
GAACAGTGCTGCAATGAATATGGGTGTGCAAGTATCTCCTCAAGCTCTCTCTTGCTCTCA
GTCCTTTTGGGTATATATTAAGAAGTAGTATTGGCCAGGTGCAGTGGCTCATGCCTGTAA
TCCCAGCACTTTGTGAGGCCGAGGCAGGTGGATCACCTGAGGTTAGGAGTTCGAGACCAG
CCTGACCAACATGGTGAAACCCCATCTCTACTAAAAACACAAAATTAGCCGGGCATGATG
GCGGGTACCTGTAATCCCAGCTACTCGGAAGGCTGAGGCAGGAGAGTCACTTGAACCTGG

FIG. 5 (continued)

```
GAGGCGGTGGTTGCAGTGAGCCAAGATCGCACCATTGCACTCCAACCTGGGCAACAAGAG
CAGAACTCCATCTCAAAATAAATAAATAAATAAATAAATAAATAAATAAATAAATAAATG
AAGTAGTATTGCTGAGTCATATGGTAATCCTATTTTTAATTTTTCTGAGGAATCTGCATA
CTGTTTTCCGTAGTGGCTGCACCATTTTACAGTCCCACCAACAGAGCACAGCGTACAAAT
TACTCCACATCCTTGTCAGCACCTGTTAATTTTTGTTTTGTTTTGTTTTGTTTTTTGATA
GTGTCTATCCTAATGGGTGTGAGGTGATGGCTCACTGTAGTTTTTTGTTCTTTGGCTTTT
TTTCTTTTCTTTTTTTCGAGACAGAGTCTCGCTCTGTTGCCCAGGCTGGAGTGCAGTGGC
GCAATCTCGGCTCACTGCAACCTCCGCCTCCTGGGTTCACGCCATTCTCCTCCCTCAGCC
TCCCGAGTAGCTGGGACTACAGGCACCCACCACTACGCCTGGCTAATTTTTTGTATTTTT
AGTAGAGACGGGGTTTCACCGTGTTAGCCAGGATGGTCTCGATCTCCTGACCTCGTGATC
CGCCCACCTCGGCCTCCCAAAGCGCTGGGATTACAGGCTTGAGCCACTGGGCCTGGCCTT
TTTTTTTTTTTTTTTTTAAGATAGGGTCTCTCTCTGTCACCTAGGCCAGAGTACAGTGG
CACAATCATAGCTCACTGCAGCCTTGAACTTCTGGGCTCAAGTGATCCTCCCGCCTCAGC
CTCCCAAGTATCTGGGACTACAGGCGTGTGCCACCACTCCTGGCTTATTTAAAAAAGCAC
TGGGATTACAGGCATGAGCCTCCATGCACAGCTGTGGGAAGAGTTCTGATACAAATTCAA
TTTCTTGCCGGGCACAGTGGCTCACGCCTGTAATCCCAGCACTTTGGGAGGCCAAGGCAG
GTGGATCACCCGAGGTCTGGAGTTTGAGACCACCTTGACCAACATGGAGAAACACTGTCT
CTACTAAAAATACAAAATTAGCCGGGCGTGGTGGCACATGCTTGTAATCCCAGCTACTCG
GGAGGCTGAGGCAGGAGAATCACTTGAACCAGGGAGGCAGAGGTTGCTGTGAGCCAAGAT
CGCGCCGTTGCACTACAGCCTGGGCAACAAGAGCAAAACTCCGTCTCAAAAAAAAAAAA
AAATTCAATTTCTTTTCATACATAAGACTATTCAGATTATATATTTCTTCTTGGGAAAGC
TTTGGTAGTTTGTGTTTTTCAATAAATTTGTTAATGTATTCCATAGTGTTGAGTTTATTT
GCATATAGTTGTTCCTAATATTTCCTTAGTATCTTCTTTTTAATGTCTATATGATCTGTA
GTGATGTTCATTCATTCCTGATAATGGTAATTTGTGTTTTTTCTTTTTTTCTTGATCAGT
CTGCCTTTTAAAAAACTGGCTGTTCTTAAAACTGGCTGGTTTCATTTTCTGTATTGTTTA
CACATTTTCTATTTCAGTAATTTTCACTCATCTATATTATTTCCTTCCTTCTGCTTACTT
TGGGTTTAATTTGCTCTTTTATTTTTTTCTAACTTCTTAAGGTGCAAGCTTAAAGTGTTG
CTGCCAGACCTTTCTTCTCTTCTAATGTAAGTATTTGATGCTATAATGTCCCTGTGAGCA
CTTCCTTAACTGCATTTACACTTTGTGACATGTGGTATTGTTCAATTTCCTTTAGTTCAA
AATATTTTCTAATTTTCTTCATGCTTTCTTATTTGATCTACGGGTTAAGTTTGTGTTGTT
TCATTTCCAGATGTTTTGGCTATTGTTGTTATTGATTTTCAGTTTACTTCTGTTCTGGTC
AGGGAACATAATTTATATAATTTCAATCCTTCTCAATTTATTGAGAATTAATTTATGGCT
CAGATTATGGTCTATTTTGGTGAATGTTCCATGTACACTTGAAAAGAATGTGGACTCCGC
TATTGCTGAGTGGAATATCTGTAAAGATCGATAAGGTCAAAGTATTTGATGTTGTTCAAA
TCTTCTGTATACTTACTGATTTTCTTTTTACTTCTTCTATCAGTTACCAAGTGAAGAATG
TTGAAATATCCAACTATAATTTGTGGATTTCTCCTTTCAATGCTATCATTTTTGGTGCTT
CATGTATTTTTGAAGCTCTATTATTAGGTATGTACCACATTTAGGATTGATATATTTTCT
TAGTGAAATGACCCCTTTGTCATTATGTAATGCTCTTCTTTGTCCATGGCTATAGTCCTT
```

FIG. 5 (continued)

```
GTTCTAAAGCGTAACTTATTTTCTAATATATATATATATATATATATATATATATACATA
TATATACTAGAATATATATACAATAGATTATGTATCTATATTCTATATATGTATATATAT
ACTAGTATGTATATGTGTGTGTGTGTGTGTGTGTGTGTGTGTGTATATATATATATATAT
ATATATATATATATATATATATATGGCCAGCGTGGTGGCTCATGCCTGTAATCCCAGC
ACTTTGGGAGGCCGAGGTGGGCAGATCTTTTGAGTCCAGGAGTTTGAGACAGACTGGCCA
ACATGGCAAAACCCCACCTCTACTAAAGTATACAAATTATGCCAGACGCGGTGGCTCACA
CCTGTAATCACAGCAGTTTAGGAGGCCGAGGCGGGTGGATCACTTGAGGTCAGCAGTTTG
AGACCAGCCTGGCCAACATGGTGAAACCTCATCTCTACTAAAAATACAAAAATTAGCCTG
GTGTGGTGGTGCATGCCTGTAATCCCAGCTACTCTGGAGACTGAGGCAGGAGAATTGCAT
GAACCCAGGAGGCAGAGGTTGCAGTGAGCCGAGATGGCACCATTGCACTCCAGCAATAGA
GCGAGACTCTGTCTCAAAAAATAAAAATAAAAATAAAAAAATAACCGGGCGTGGTGGCGT
GTGCCTGTAATCCCAGCCTCTGAGGAGGCTGAGGCACAAGAATCTCTTGAACCTGGGAGG
TGAAGGTTGCAGTGAGCCATGATCACCACCACTGCACTCCAACCTGGGCAACAGAGATCC
TGTCTCAAAAAAATATATATATATATCATATTAATATAGTCACTCAAACTTTTTTTTGAT
GTGAATGGGAATTTTTATCCTTTTATTGTTGATCTATCTGTGTCTCTATATTTAAAAGCG
ATTTATTGTGGGCAGAATATGGTTGAGTCTTGTGTTTGTTTGTTTGTTTGTTTGTTTTTG
AGATGGAGTCTTGCTCTGTCACCCAGGCTGGAGTACAGTGGTGCAATCTCGGCTCACTGC
AAGCTCCGCCTCCCGGGTTCATGCGGTTCTCCAGCCTCAGCCTCCTGAGTAGCTAGGACT
ACAGGCGAGTCTTGTGTTTTTATTCAGTCTGACAATCTCTACTCTTATATTGATATTTAA
ACCTATTGACTTGGTTAAGTTGAAATCTACCATCTTGCTATCTGTTTTTTATTTATACTA
TCTGTTATTTGTTCCCCTTTTCCTCTTTTTCTGCCTTTTTTTAGATTGAATATGTTTTAA
GATTTCTTTTTGTTGTTGTTGTTTTGTTTTTGAGACGGAGTTTCATTCTTGTTCCCCAGG
CTAGAGTGCAATGGCACAATCTTGGCTCACTGAAACCTCCGCCTCCTGGGTTCAAGCGAT
TCTCCTGTCTCAGCCTCTGGAGCAGCTGGGATTACAGGCGCATGCCACCATGCCCGGCTA
ATTTTTGTATTTTTAGTAGGGATGGGGTTTCACCATGTTGGCCAGGCTGGTCTCGAACTC
CTGACCTCAGGTGATCTGCCAGCCTCGGCCTCCCAAAGTGCTGGAATTACAGGTGTGAGT
CACTGGGCCTGGTCAGGATTTCTTTCATTTCAACTAACTGTTGGCTTATTAACCCTACTT
TTTTGTTTTAATTTTTAGTGGTTACTGTTATTTTAATGTATTAGTCAGATTTTTCCAGAA
AAACAAAACCTATAGGAGATAGATAGGTAGATAGATAGATAGATAGATAGACAGACAGAG
GAGGATTTACTATAAGGAATTGGCTTGCATGATTATGGAGGCTGAGAAGTCCCAAGATCT
GCAGTTGACAAGCTGGGGACCCAGGAGCATCAGTGGCATAACTCCAGTCTGAATCTGTGT
CTAAAGGCTGGAGAAGATCAGTGTTCCAGCTCAAAAACATTCAGGCAGGGAGAGCCTTCC
ACTACTGGCAGGAGCGCCTTTTTGTTCTTGTCAGTTCTTCAATCGATTGGATGTGGTCCA
CCCATATTAGGGAGGGCAATGTGCTTTACTCAGTCTATTGATTCAAATAATGTCATGCAG
AAACACCCTTGTAGACGTACCCAGAATAATGTTTAACTGAATATCTGGCACCCCATGGCC
TAGTCAAGTTGACACATAAAATTAACCATCACATTTGAGATTTATAATTTGCATCTTTAA
CTTATCACGGTCTATCTGCAAAGAATATTATATCACTTAGCTGGGCGTAGTGCTGTGTGC
```

FIG. 5 (continued)

CTATAGTCCCAGCTACTCAGGAGGCTAAGTGGGGAGGATTGCTTGAGCCCTGAAGTTCGA
GGCTGCAGTGAGCTGCGATCACATCACTGCTCTCCAGCCTGGGCTACAGAGAAAGAGCTT
GTCTCTAAAAAAATTAAAAATAAAATAAAAAGAATATTACCTCATGTATGGTGATACAAT
AGTATACTTCTATTTCCTTCTCTTTTGTGGCTATTGCTGACATATAATTTATCTGTAGCT
ATGAGCCCTGCAGTACATTGCTATTATGTTTTGCTTAAATAGTAAATTGTCTTTTAAATA
TATTAAAATGAAATAAGGTGTTTTATATTTATATGCATATTTAACATTTGTATACTGCAG
GTATGCTGGCGACAGTTTCTTTTAGCTTTTGTCTGAAATAGTCATTTAAAGGTAAAACAT
TTTAAAACTTTATAATTTGCAATAATATTATACTTATGAAGAATTACAAAATTGCCCAAA
AAATTTCCATAAACCTATTTCCCAATTTCTTCATACGGTAACATCCACAAAACTACCATC
CAAACTAAAAGATTGACATTGATACAATACTATTAGCTCACCTGGAGACCTTATTCCAGT
TTTGTCCATTGTCCTACTATTGCCCCTTTTCTTGACCAGTATTCAATCTAGGGTTGCTTA
TTGCCTTTAATTGTCTTTTCTTCTTAGTCTCCTTTAATCTGGGATAGTTCCTCAGGCTTC
CTTTCTTGACACTTGTGCTGGTTGTTTGTGGTTGCCCTGCAGAGCAAAGATCAGCAACTC
TACCCAAATGTGGTTTGAATGTGGAGACTGATGATGCCACATATACACAAAGAGGGCATG
AGGCATTCTGGGCAGAGCACAACAGGCTCCCCAAAAGGCCCCAAAATGGCTTGAGAACAA
GGGAGGGGCAAGTTGCCTTGGGTCTTATTGAGGTTAAGGGCTGGGGATAGGGCATGGTTT
TCCCATGCACAGGCCAGTGTTTGAACTTCCCTGCTGGAGCCAAGGGAGGAAACACCTAGG
CTTTTTTGTCTACCAAATGGAGGGCAAAAGATTAAGGAGGAGTTGTGGGGCTTCAAAGCT
GTCAGTGGTCAAACATCAAATATGGAATTGGATTCTGTTACAATTCACCCCTGATGTTTA
ATGGATTACTGAAATGTATCCTGTTTTTTTAAATTAAATTTAAACCTGTTTAAGTATGCT
GTGATGGTACTCTATGAGGCCTGCAGCCTGAGGCCAGTAAGGGGGATAAAATTTCTGTTC
AATGCCTTCTTATTAAAGAGCCTAATGTTATGTATTTTGAGAAGTGAAATGAATGCCTCG
GTCACTCTCAAGAATGTATGGAACTCTGAAGGGGATAAGGAGTATCTTGGTGAGGCCTTG
TATTGTGGCTTGAGTATGTGCAGAGATATATCTGACCTTGATTTATATTTCTGGGTATCT
TCAAGCAAGACATTTCCAGAGTTCTTTACCCCAAAGAGGATGACCTTGGATAAAGAACTG
TTGTTGCCATTAGTCAGACCAGATAGCCAGGTAATTGGCAATGGCCTAAGGGTCTGAAAA
ATGTTAAGATGGGGTTGCTTATTGGGCAGGGCATCCTTTGTTGCTAAGATGACTGCTTGA
AGTTTGGCAAATTGTGTGGACCCTTGGGTCCTGTCTTTTATCAGGGATGTCTGTTAAGGG
ATGGAAAACACAAATAGAATCAGTTGTGACGGTAGCACTGCCATTTTTAAAGTATGTGAA
TTCCCTTTGCTGTTCACTCAGTTGATCCCAAAGGGATCCCCAAGAAGCCAAGGGGTCTGA
GAGAGGAATGACCTCCTTCAGCACTGTGGTGTCTGGCCAGAAACTGAGGACAGGGGAGCC
CATGGCCTCCTGCAGGCAGGATATGCTACAGGACCCAGATTTGGCTCCATACTGTAGATA
CTATTTTCATTTTAGCAAGGAAGCCTCAATAGCCATGCCAAGCTTTGGGGTGTGCCTTC
CATGGCCCAAGGCATAGCGGGCAGCTAGTGTGTCATGGTCTCAAGGCCTGTAAGAGCCTC
CTTTTTTGGAAGAGTCCAGTATGCAGTCAGCTATTGTCACTCTAATAATGTATAGCATCA
GGCTGAGGAAGGCGATTTCTTGCATCGGAAACCCACAGACTATTTATGGCCATCATAAGT
GAACCAAAGACTCTGGAAGTATGAGAGGAGGTTGCTAAAGCCTCTACAGTGAAGGAATTT
CTGGGGAGCACTAACAGTCTCTGGAAGTATGAGAGGAGGTTGCTAAAGCCTCTACAGTGA

FIG. 5 (continued)

AGGAATTTCTGGGGAGCACTAACAGTAGGGTCTGTCCTTTTGCAATTTGAACAGGTTTTA
AGCCTTTTGTTTTAGTGGACCCCATTCAGGTGAACCAATTTGTAAGGAACAGCAAAAATG
GGCTTAAGTAGGGCCGGGTGCAGTGGTTCACACCTGTAATCCCAGCACTTTGGGAGGCCA
AAGCGGGTGGATAACTTGAGGTCAGGAGTTCGAGACCAGCCTGGCCAACATGCTGAAACC
CCGTTTCTACTAAAAAATACAAAAAATTAGCTGAGCGTGGTGGTGGGTGCGTGTTATC
CCAGCTTCTTGGGAGGCTGAGGCAGGAGGATCACTTGAACCTGAGAAGCAGAGGTTGCAG
TGAGCCAAGATCATGCCACTGCAGTCCAGCCTTGGTGGCAGAGGGAGATTCTGACTCAAA
AAAAAAAACCAAAAATGTCTTAATTAAAATTTGCAAAGGAGGAACATGTTGCTTCAGAAC
CCCCAGAGTTCTAAAAGATACTGGGCTTTTAGCATTGTGGGTGCTAAGAGGGTCAATAGA
GATTTCTTGACAATGTCAGAAATGTCAAGGATAAACAGCTCTCAATTTACTAAGTAATAC
CCAGAAATTTTACTGAGGTATACTTGTGCTTGTACCTTGTACTTTGTGTGGAAGAAATGA
CCCATCCTTTTTCATGAGCTGCCTTTTGAATGTTTGTATGCGTTAAATTAGTGTATCAAA
TGAATTTCCACTGCACCCAACTACTTCAGGAGGCTGAGAGGGGAGGATCGTTTGAGCCCA
GGAGTTTGAGGCTGCAGTGTGCTATGACTGTACTTGTGAATAGCTACTGCACTCCAGCCT
GGGCAACATCATAAGATCCTGTCTTTTTATTTTTATTATTTATTTATTTATTTATTTTTT
TTTTTCGAGACAGAGTCTCACACTGTTGCCCAGGCTGGAGTGCAGTGGCGTGATCTCGGA
TCACTGCAAGCTCAGCCTCCTGGGTTCATGCCATTCTCCTGCCTCAGCCTCCCGAGTAGC
TGGGACTACAGGCACCTGCCGCCACATCCGGCTATTTTTTTTGTATTTTTAGTAGAGACG
GGGTTTCACCATGTTGGCCAGGATGGTCTCGATCTCTTGACCTCATGATCCACCCACCTC
GGCCTCCCAAAGTGCTGGGATTACAGGCGTGAGCCACCGCGCCCGGCCTCAAGACCCTGT
CTTTTTAAAAAATTAATTTCCTCTGAGAAGGATGTCATATATCTAACATCATACTTGTGT
TTCTGGAGAGAGTTGGATGCAGTTAAGGTTTTTGTTTGCAAAGATCGTGTGCAATGGCAG
GTCTGTTGGGGGTCCCATGGGTAGTTAGTATATTGTGTCCATGCAATGGTAAAGACAAGC
TGGCTGAAACGGGAACTTAAGAGAACATATTAGCCCAAATATATGATAGCAAAGTATTTG
CCAGTTGCTGATTGGAGGGAGGCAGTAATTTTAGTAGTATAGAAGCTGGCCTGTTTTTA
CTCACAACACTTCTGACACTAAATGTATGGGTTTTTTCCCCTATACCAACTGATATGGTT
TGACTGTGTTCCCACCCAAATCTCATCTTGAATTGTAACTCCCACAATTCCTACATGTCG
TGGGAGGAACCCAGTGGGAAGTAATTGAAACATGAGGGTGGGTCTTTCCTGTGCTATTCT
CATGATAGTGGATAAGTCTCACAAGATCTGATGGTTTTAAAAACGGGAGTTTCCCTGCAC
AAGCTCTCTTTCTCTTGCCTGCTGCCATCCATGTAAGATGTGATTTGTTCCTCCTTGCCT
TCTGCCATGATCGTGAGGCCTCCCCAGCCATTTGGAATTGTAAGTCCATTATACCTCTTT
TCTTCCCAGTCTCGGGTATATCTTTATCAGCAGCCTGAAAACGACCTAATACACCAACCA
ATTCTCCAACTCTCTGAAAACCAACTGGGTGTCCAGCAATTCAGTTTCATTCTGACACTA
TCTACCTGGAGTTCACATCAGTTCCCACGAGATTGCCCCATCTTTAGAGACCAGTCACAA
GTCCCAGGCCTCCTGTACTTCTGACTGGCCAGTTAAAAATCGGGTGTTCTCATGACCCCC
TCCTCAGTTTCCATAATTTACTGGAATAGCTCACAGAACTCGGGAAAATACTTTACTTAC
ATTTACTGGCTTATTATAAAGGATGCAATTCAGGAACAGCCAGATGGAAGAGATGCCCAG
GGAAGGGTATTGAGCGGGGGTGGAGGAGGGTACCCCAGAGTTTCCATGCCCTGAGTGCT

FIG. 5 (continued)

```
TCACTCTCCCGGGACCTCCACGTGTTTACAGAACCCTGTAGGGTAGAAGGGACTTATGGA
GGTTTAATTACCTAGGCATGATTGATTAAATTATTGGCCATTGGTGACTGATTCAATCTC
CAGCCCTCTCCCCGCCCCATAGGTCTGAGATGAGCCTGAAAGTTCCAAACTTTTAATGCC
TTGGTCTTTCTGATCATCAGCCCCCATCTTGAAGCTATCTAGCACTCCCAGCTAATCATT
TCATTAGCATGCAAAAGACACATATTAGCCTAAAGATTTCAAGGGTTTCAGGAGTGCCAG
GAACTCTTAAGTGGAACTGCAGCATTATGATTGTGGTAATCCACCATCAGGCATCCTTCA
TTCATTCTAGGTTTAAGACCAGGACAATTTGGAGTGGAGAAAAACTGGGGACAATCACCC
TTCTCTAAATAGGTCTTATATAATGGGTTTTGAGCTTATGGCTAGGTGCGGTGGCTCACA
TCTGTAATCCTAGCACTTTGGGAGGCTGAGGCATGTGGATTGCATGAGTCCAGGAGTTTG
AGACCAGCCTGGAAAACATGGGAAAAAACCCATCTCTACAAACAAAAATACAAAAATTAG
CCGAAACAAGTGGCGTGTGCCTGTAGTCCTAGCTACTAGGGAGGCTGAGGTGGCAGGATC
ACCTGAACCTGGGAAGGGGAAGCTGCAGTGAGCTGAGATTGCACCACTGCACTCCAGCCT
GGGCCACAGAGTGAGACCCTGTCTCGAAAAGGTCCTAGTACATTTTATTTATTTATTTTT
TATACAGAGTCACTCTCAGGATACCTAGTTTTATCTGTGTGAACAGTTTTAATAGGTTAT
GATAAAGGCTCAGGTTCTCATTTTGTTAAGCCAGTTGTAATTGCCAAAAACTTAATTTTG
TTTTTGTTTAGTACTCACTAGGCCAGAGTACATGTCCATTGTGGAATATTTTAGGGCAAC
AGGCACTATGAATATGGGGAATTTAGGCAAATCAATAGTTCTTCTTCTTCTTTTCTTTTT
TTTTTTTTTTTTTTTTTTTTTTGAGACAGAGTCTCGCTCTGTCGCCCAGGCTGGAGTG
CAGTGCCATGATCTCGGCTCACTGCAACATCTGCCTCCTGGGTTCAAGCGATTCTCCTGC
CTCAGCCTCCAGAGTAGCTGGGACTACAGGCGCGTGCCACCACACCTGGCTAATTTTTTT
GTGTGTTATCCAGGCTGGTCTCGATCTCCTGACCTCGTGATCTGCCTGCCTCGGCATCCC
AAAGAGCTTTTATTACAGGCATGAGCCACCGCGCCCAGCCTAGTTTTGTATTTTTTAGTA
GAGATGGAGTTTCACCATATTGGCCAGGCTGGTCTCGAACTCCTGACCTCAGGTAATCCA
CCTGCCTTGGCCTCCCAAAGTGTTGGGATTATAGGCATGAGCCACCACGCCTGGCCTAAA
GTTAATTTAGAACTTATGTTGTACAAGTGCAAAAGCCAACAAGACCCTCCCTTCCTTCTT
TAAATATCTTTTTATTGTATAGTTTTTAGAGTAAATTTAAGATTTGCAACTGGGTTAAAT
CATGAACCTCTGTTAAGTTGTGTGTGTGTGTGTGTGTGTGTGTGTGTGTCTGGGGGAGTTA
CTGGATGTACTTCAGGGGGAGGGAGCTTCTCTTCTCTGCTCATATTTACGTTTCTTCTTC
TGGAGAGTCCCAAATCAGTACCCTCAGGGTTAGGGGCCACTTTCATGACAGCCATTTTCT
TTTTTTTTTCTTTTTTTTTTTTTTTGAGACGGAGTCTCGCTCTGTAGCCCAGGCTGGAG
TGCAGTGGTGCGATCTCAGCTTACTGCAAGCTCCGCCTCCCGGGTTCACGCCATTCTCCT
GCCTCAGCCTCCCGAGTAGGTGGGACTACAGGGCCCGCTACGATGCCAGGCCAATTTTT
TTTACTTTTAGTAGAGACGGGGTTTCACTGTGTTAGCCAGGATTATCTAGATCTCCTGAC
CTCGTGATCTGCCTGCCTTGGACTCCCAAAGTGCTGAGATTACAAGGCGTGAGCCACTGC
ACCTGGCCTTATGGCAGCCACTTTCATGGCAATTGTTATTTTATTTGATTTAGGGACTGT
AGACTTAAGTTGGATTTTTATTTATTTTTTATTTTTTATTTTTTGGCAGTCTCGCTCTGT
CTCCCAGGTTGGAGTGCAATGGTGTGATGTTGGCTCACTGCAGCCTCAAACTCATCAGCT
```

FIG. 5 (continued)

```
CAAGTGATCCTACCACCTCATCCTCCAGAGTAGCTGGGACTATAGGCACCCAACACCACA
CCCAGCTGATTTTTGCATTTTTTGTAGAGATGGGGTTTTGCTGTGGTGCCCAGGCTAGTG
GATTTTTTTTTTTTTTTTTTGAGACAGGGTCTTACTCTGTTGCCCAGGCTGGAGTGCAGAG
GCACAATCCCAGCTCAGTCCAACCTCTGCTACTAGGTTCAAGTGATTCTCACGCCTCAGC
CTCCCCAGTAGCTGGGACTACACGCCCCCACCTCTGGCTAATTTTTGTATTTTTGGTAGA
GATGGGGTTTTGCCATGTTGGCCAGGCTGGTCTCAAACTGCTGACCTCAAGTGATCTGCC
CACCTCAGCCCCCCAAGTGTTGGGATTACAGGTACAGGCATGACTACTGCACCCAACCCC
TGGATTTTTTTAATGACAAGGTCTTACTCTGTCACCCAGGCTGGAGTGCAGTGGCACAAT
CATGGCTCACTGCAGCCTCAAACTCCAGCAATCTTCTCACCTCAGCCCCCCAAGTAGCTG
GGACTACAGGTACATGTCACCATACCTGGCTAATTTTAAAATTTTTTGTATAGATGAGGT
TTTATTTGTTTGTTTGTTTTTTTGACAGAGTCACGCTCTGTTGCCAGGCTGGAGTACAGT
GGCGCAATCTCAGCTCACTGCAACCTCCATCTCCCAGGTTCAAGCGATTCTCCTGCCTCA
GCCTCTCGAGTAGCTGGGACTACAGGCACGCACCACCACACTCAGCTAATTTTTATGTTT
TTAGTAGAGATGAGGTTTCACCATGTTGGCCAGCATGGTCTCAATCTCTTGACCTCGTGA
TCCGCCCGCCTCGGCCTCCCAAAGTGCTGGGATTACAGGCATGAGCCACCATGCCCGGCC
TAGACGAGGTCTTACTATGTTTCCCAGGCTGATCTTGAACTCCTAGACTCCAGCAATTCT
CCCACCTCAGCCTCCCAAAGCATTAAGATTACAGGCATGAACCACTGCACCCAGCCTTGA
GTTGGATTTGAATGAATCCCTTGACAGTTTGATAAGGTGCAGCACTTAATCAAACCCAGC
TTCTTTCTGGGTCTGTTTTATAGTTATCTGGTAGGGTGATGGTGGTGTCCTCTGACCCTT
TAAGAGAGATGGAGTAAGGCATTCTGGCCTAGTTTTTATAAGGGTTCATGGCATGGAGTG
CTATTGAGTGTTTTTATCTTTAATCCTGGTGACTGCGCTTCCTCACCGGAGCAACCACCA
GATGGCCCTGTATGTTGCACAGAGTATCAGCCTTTCTCCTGCACACTCTATAGAACATAG
GCTAATGCCTGGTTGGGACATACAACCAACAGTCACAAAATAATAAGTGTCATGCCCTTG
AGCCTAGGATCGGCGATGGTTTATGCCAGAATCAAGACATACAATTCAATCTAAGATGCA
CAGATAGGTCCAGACGGGGCTCACATTTTAGGGCCACTTTAAGGACATCCTCAATTTCAT
ATTTCTGTCTCAAAATGCCAATTATAGAAACTTTCAATTCAGGTCAGTTACATCTGTAAC
AGAGATTTAGTAGTCCTCAGCAAATGTGGAACAAAGCAGCACAGCTCGAAGTGTAAGCTT
GCCAATAGGCAGCAGAATCAATAGCAAGCCAAAGTGAGAGGAGAGAGACCCCTGATGGTG
GGTGGCTATCATCTAAGGTACGCTGTTCCCTGTGCCAGTTGTCTTGTGATTGCCCCACAG
AGGAAGGGATCAAATCTCTACCCCAGATTTGGTTTAGACATCAAGATTGGTGATGCCACA
TACACACATACAGAGGGTTTGAAAAGCTTATTACTCGTGTAATGAGGTTTTCTGTGCAG
AACAGGGCAGGCTCTTAAGAAGGCCTAAAAACAGCTTGAGAACAAGGAGATGCAAGTGGC
CCTGGGTTTTACTGTTAGGGAGTAAAGCTGGGGTGAGAGTTCTGATGCACAGGCCAGGGT
TTTGTGGTTTGAATTTCCCTACTGGTGCAAGGGAGGAGAGTACCCTGGCATTAAGGGAGG
AGAGTACCCTGGCATTATTATTCTTATCATTATTATTTTGGAGACAGAGTCTCACCC
TGCTGCCCAGGCTGGAGTGCAGTGGTGCAATCTCGGTTCATTGCAACCTCTGCCTCCCAA
ATTCAAGCAATTCTCGTGCCTCAGCCTCCCAAGTTGCTGGGATTACTGGCATGCGCCACC
ATGCCCAGCTAATTTTGTATTTTCAGTAGAGATAGGGTTTTGCCATGTTGGCCAAGCTGG
```

FIG. 5 (continued)

```
TCTCAAACTCCAGGCCTCAAGTGATCCGTCAACCTTGGCCTCCCAAAGTGCTGGGATTAT
AGGCGTGAGCCACCACGCCCAGCTTCTGCCTTTATTATTGGCTTGCCCAGGTTTTGGATA
AAAGGGAAAGGAGGAGTGGGGGTGGGGGCTTGAAAACTCAGCAGTTGAACATCATGGAAT
CAACTAATTTATTACACTGGTCAATTATTTTGTAAAACTCGTCTCAATTTGAGTTTCATG
TCTCTCATGACTAAACGTAAGCATACATTTTGGCATGAAAACCACAGAAGTGATGTTTAC
CTGTCTCAGTTCATGACATTATGAGGTACAGGATGCTAATAGGTGTCTCATGTTCATAGT
TTAAAGATGGAAAAATTTTAAGTTAATAGTTTTTATTTTAGTACTTTAAAGATGTTATT
CCATTATCTTCCGGTGTACATAGTTTGTGACAAGAAGTCCACTGTATTTGTCTTCTTTGC
CCTTCTAGGTAATGTGTTCATTTTTCTCTAGGTACTCTAAGATTTTCCTTATTAATTTTT
CTATTTATTTATTTATTTATTTATTTATTTATTTTTAGATGGAATCTCATTCTGTTGCCC
AGGCTGGAGTGCAGTGGTGTGATCTTGGCTCACTGCAACCTCCACCTCCTGAGTTCAAGC
AATTTTCCTGTCTCAGCCTCCCGAGTAGCTGGGATTACAGGCATGTGCCACCATGCTTGG
GTAATTTTTGTATTTTTTTTTAGACAGAGTTTCATTCTTGTCACCCAGATTGGAGTGCA
ATGGTGCAATCTCAGCTCACTGCAACCTCCACGGTTCAAGCGATTCTCCAGCCTTAGCTT
CCCGAGTAGGTGGGATTATAGGCACCTGCGCCACCACGCCCGGCTAATCTGTGTATTTTT
AGTAGAGAAGGGGTTTCACTATGTTGGCCAAGCTGGTCTCGAACTCCTGACCTCAAATGA
TCCACCCACCTCAGCCTCCCAAAGTGCTGGCATTACAGGCGTGAGCCACCTCACCCAGCC
TAATTTTTGTATTTTTAATGGAGATGGGGTTTTGCCATGTTGGCCAGGCTGGTCTCAAAC
TCCTGACCTGATGTAATCCGCCTGCCTCGGCCTCCTACAGTGCTGAAATTAGAGGCATGG
GCTACCATGCCCAGCCTATTTTATTTATTTTTACTTACTTATTTTTTTAGACAGAGTCT
CACTCTGTTGCCCAAGCTGGAGTGCAGTGCAGTGGTGCAATCTTAGCTCACTTCAACCTC
CGCCTCCCAGGTTCAAGCAATTCTCCTGCCTCAGCCTCCCCAGTAGCTGGGACTGCAGGC
GTGCACCACTACGCCTGACTACTTTTTGTATTTTTAGTAGAGACAAGGTTTTGCTATGTT
GGCCGGGCTGCTCTGCTCTTGAATTCCTGTTCTCAAGTGATCCACCTACTTCGGCCTCCC
AAAATGCTGGGATTACAGGCATGAGCCACACGCCCAGCCAACCTTTTCAATAATTTGATT
ATGATGTGTCTTGGTTTTGATATTATCTTATAAGACATTGGTGCTCTGTTATTTTTGTGG
ATTTTCTGTGCTTTATTTTCAATAGTTTTTATTGCTATATTTTCAAGTTCACCAATCTTT
TCTTATGCAGTGCTTCTGCAGTGTATAATCTGCTGTTAATTCCTCCTGTGCATCTTTCAT
TTTTAGATCATAAACTTTTCATCTCTTGAAGTTCCATTTTGGGTCCTTTAAAAATATATT
TCTTTTCTCTCTTCATCATATTTATGTTTTTCTTTATATCCTTGGGCATAATTTATGAGA
TTTATAATGGCTATTTTAAGGTCCTCACCTACTAATTTCATCATCTCTGAATATTGTGGT
CTGTTTCTATTGCTTTAGTTATCTACTGGTTATGGGTAATTTTTTCCTATTTATTTGACT
ACCTGGCAATTTTTTATTGGATGCTGAATATTGTGTATTTTGGGTTGTTGGGTGCAAGAC
ATTGTTATATTCTTTTAAAGAGTACTAGAGAAAATACAAAAATTAGCTGGGCATGGTGG
CTCATGTCTGTGGTCCCAGCTACTTGGGAAGCAGAGGTTGCAGTGAGCCGAGATCATGCC
ACTGCACTCCAACTTGGGCGACAGAGTGAGACTCTGTTTCAAAACAAAACAAAACAGAAA
AAACAAACACTCAAACAAAAAACAGAGTGCTGAACTTTGTCCTGGCATATAATTAGTTA
CTTGTGATTTGTTTTCTTCTTTTAAGTCTTGCTATTAAGTTTTGTTAGGAAAAGCCCAGG
```

FIG. 5 (continued)

```
TTGGCCTCTACTCCAGAGATATTAATAATTTAGCCCCACTAAGTCTCTATCCTTCTGAAG
ACTCTACCCAATACCTGTGTGTTATGAGGTCTCTTTACTCTGGTTGATGGAAACACAAAC
TATGCCTAGCCCTGTGTAAACTCCAACACTTGTTCGGCCTCCTGCTTTCTGGTTTTACTT
TTTCCAACCTTCTGGAATTTCACCCCACACCTGTGTAGATCAGTCCCCAAAGACTTGAGG
GAATCTCTAATGGTCTATGAGGCTTTGTCGCTTTCTCTCTGTCTCTCCCCATGCAGCTCT
TGCTTCTCCAGCACTCTCTCCCACAAATTCTAGCTGTCTTCATGTCCTTGAACTCTAAAC
CCTGTCTCCTAAACTCAGTGAGACCACGGGGCTCTGTTTGGGTACTCCATGTAGCACTCT
CTTCACTGTCTCCACGTAGTAAGCTGGGGCTCTGGTGAGGCTGAACTTATTTTTCTTTTC
TCAGAGATCTTAGTCTTGCATTGCCTGCTGTCTAATGTGTGAAAACAGTTGTTTCATATA
TTTTGTTTAATTTACTAATTTTGGGTGTGTGTGGTGGGGAAGCCATCTCTACAACAGTT
TATCCTTCATGTGCAGAAGTGGAAGTCCCACAGTGATCCCTTTAAAATACATGGCTAGGC
CAGGTGCAGTAGCTCACGCCTGTAATCCTAACACTTTGGGAGGCCAAGGCAGGTGGATTG
CTTGAGGCCAGGAGTTCCAGACCAGTCTGGGCAACATGGTGAAACCCCGTCTCTACTAAA
AATACAAAAATGAGCCAGGCATGGTGGTGTGCACCTGTAGTCCTAGCTACTCCGGAGGCT
GAGGCACAAGAATCACTTGAACCTAGGAAGTGGAGCTTGCAGTGAGCCGAGATCGCACCA
CTGCACTCTAGCCTGGGCAGCAGAGTGAGACTCTGTCTCAAAATAAATAAATAAATAAAT
AAATAAAATAAAATACATGGCTAAAATCCAACCATGTACTTAACATTTCAAATGAAGTAC
TGAAATGGCTCTATAATTCAAACTTTCAGATATATCTAGCTTTATTATTACTATATATAT
ATTTTTTGAGACAGAGTCTAGCTCTGTTGCCCAGGCTGGAGTGCAGTGGCATGATCTTGG
CTACTGCAACCTCCGCCTCCTGAGTTCAAGCAATTCTCCTGCCTTAGCCTCCCGAGTAAC
TGGGATTACAGGCGGGCACCACCATACCCGGCTAATTTTTCATATTTTTAGTAGGGACAG
GGTTTCACCATGTTGGCCAGGCTGGTTTTGAACTTCTGACCTTAAGTAATCCACCTGTCT
TGGCCTCCCAAAGTACTAGGATTACAGGCATGAGCCACCGCGCCCAGCCTAGATGTATCT
AGCTTTATATTTAAAATTCACAGGCTTCACCTACTTAAGTGTATATTTAATTGGTTTGAA
GATGATTTCGTCTCTGGAAGGTTTTCCCAAGAATCTTTTACCAAGCCAGGGAAGAAAGAG
CTTGGGACATTGGAGGAAGAGGAAGCAGGCTAGATGTGACCAGAGCAGAGGAAGAGAGGA
GAGTGGTGTAGGATGAGATTGGAGAGCCAGGTAGAACCCAGATGATGCCGGGCCTGGGAT
GTCAGAGTGAGAAGTTTGGATTTTATTCCAAGTGTAACGGGAGGTCACTGAAAGGTTTTA
AGCAAGAGAGTGACATGATCTGATTTTAAAGATCACATTGCTGTATGAATAATGGTTTCT
AGGGGGCAACGGCAGAAATAGAGACCATTTAGGAAGCTGCTGTTGTAGTCAAGGTGGACA
AATAGTGACTTGAATAAAGGTTGTGACGGCAGAAGTGTTTAGGGACTAGCGGTGTTCGAG
TATCTACTGTGTTTGTCAGCTCGAAACACATGACAGAGAAATAACAGATGAATAAGAGAA
ATAGATCCTGGCCCTGTGGGCTTCCAGACAAATGGAGTGGTTAATTCTTTTTTTTTTTT
TTTTTTTTTTTTGAGACAGAGTCTCACTCTGTCGCCCAGGCTGGAGTGCAGTGGCACGAT
CTCGGCTCACTGCAAGTTCCGCCTCCCGGGTTCACCATTCTCCTGCCTCAGCTTCCCCAG
CAGCTGGGACTATAGGCGCCCGCCACCATGCCCAGCTAATTTTTTTTGTATTTTTGGTAG
AGACGGGGTTTCACTGTGATAGCCATGATGGTCTCGATCTCCTGACCTTGTGATCTGCCT
```

FIG. 5 (continued)

```
GCCTTGGCCTCCCAAAGTGCTGGGATTACAGGTGCGAGCCACTGCGCCCGGCCTGTAGTG
GTTAATTCTTAATACTTTGGGGGTCACAGACTCCTTTGAGAATCTTACCTAAGCTACAGA
ACCTCACCACAGAAAAAAGCACATAATCACTTTTTTTATCATTTTATGAATATTTCACAT
TCATCATGATAATTTCACCTGGTCAAGTGGATATTAAACGATAAGTAAAGGCTCATATAT
GTGTGGAGAACTAGTGCATACAGAATTATGGAGAAATGATGGTGGATCAGTGGAGCAACT
GGGGAGCTGCTGGGGCACAGGAGAGTGACAGGACAGGGGCTCAGCATGCCTCCAACCCAA
TCAGCAAAGCATCCACACTTCCACAGCACTGTGCTGGGTGGGAAGCTTGTTCTTGCCCT
GGCTGAAAGACAAGATGCAAGCGATATAGTGCTTCATCAATGTTGTAGACCGAACATTTA
TCTCTCTCCAAAATGTATATGTTGAAATAGAATCTCCAATGTGATGGTATTTGGAGGTGA
GGCCTTTGAGAGGTAATTAGGTCATGAGCCTTCATGAATGGGATTAGAGCCTTCATAAAA
GAGACTCCAGAGGGCTCCCTCACCCATCTGCCATGTGAGGATACTGAGAAGATGACCATC
TACGACCCAGGAAGCAGGCTTCACCAGACACCAAATCTGCCAGCGCCTTCACCTTGTCCT
TCTCAGCCTCTAGAACTCTGAGAAGTGTTTGTGGTTTAAGCTGCCCAGTCTAGGGTGCTT
TTGCTATGGCAGCTCAAACTGCCTAAAGCAGTCAGTAACCTCAGGATAGGAGTGGGCTGC
CAGGTGGAACCCTCCCGAAAGGTTTCTGGATGGAAGATTTGAGTCACTTAAATATATATC
ATGCATCATGTGTGCGTGAAGAGAGACAGAGAGAGGCGGGTGGGGCAGGAGAATATGTAC
TGCCTCGTTATGCATGCTCATATAGTCCTGATTTGTTATGCTGTCATGTGATACATAACA
ATGTTTGGGTCAACAATGAACCACATATATGGTAGTCATCCTATAAGATTATAATACCAG
GCCAGGCACAGTGGCTCACGCCTGTAATCCCAGCACTTTGGGAGGCCTAGGCAGGCGGAT
AACCTGAGGTCAGGAGTTCAAGACCAGCCTGGTCAACGTGGAGAAACCCTGTCTCTACTA
AAAATACAAAAATTAGCTGGGCTTGGTAGCGTGCGCCTGTCATCCCAGCTACTCGGGAGG
CTGAGGCAAGAGAATCACTTGAACCCGGGAGGCGGAAGTTGCAGTGAGCCTAGACCCTGC
CATTGCACTCCAGGCTGGGCAACAAGAGCAAAACTCCATCTTAAAGATAAAAAGATTAT
AATACCGTATTTTCACTGTACCATTTCTATGTTTAGATACACAAACACCACTGTGTTACA
GTTGCCTACAGCATTCAGTATACAGTACTCATCATGCTGGATGAGTCTGTAGCCTAGGAG
CGACAGGCTACACCATATAACTTAGGTGTCTAGTGGGTTATACCATCTAGGTTTGTGTAA
GTATACTCTGATGTTATCACAATGATAAAGTCGCCTAGCAATGCATTTCTCAGAATGTTT
CCCTCTTGTTAAATGGCACATGAGTGTATTTCAGTTTCTTTCTTTCTTCTTTTTCTTTCT
TTCTTTTCCTTCTTCTTTCTCTCTCTGTTTCTTTCTTTTTCTTTTTCTTTTTTTTCATGGT
CATTCTCTTTCACCCAAGCTGGAGTGCACTGGTGCAAACACGGCTTACTGAAGCCTCAAC
TTCCTGGGCTCAAGCAGTCCTTCCACCTCTGCCCCCAAGTAGCTGGGACTACAGGCACA
CACCACCATGCCCAGCTAATTTTTTGTTGTTGTTGTTTTGTAGGGATGGGGTTTCGCCA
TGTTGCCCAGGCTGGTCTTGAGCTCTTGAGCTCAAGCAATCTGCCCACCTTGGCCTCCTC
CCAAAGTACCGGGATTGCAGACATGAGCCACCTCGCCCGGCTATTTCAATTTCTATAGTG
CTAGTAAAAATCCACTAAATTGTTTATCCAACTCATCAATAAGTTCAACCCACAGTTTGA
AAACCCTAGTCTAGATTTTTTTCTTTCTATTCCCTTCAGTATGAACATGAGAAAGGCTCA
TCATCATTCCATATTTGATATTTTGACATAAATCTGCTGGATTTAGTTAAATTACAGTTC
TCCCAAATAATCAGGAGAAATTTGACTAGAACTATCTTGGTATTGCCCATGGTTGTTGCT
```

FIG. 5 (continued)

TCTCTTTGACAGTAAACCAAAAAATTAAGCGCATGGTTATGGAGTCTGACCGCTTGAGCT
GGCTGCCCCACCTGCCTCAGTTTCTTTATCAATATCTGGGACATCATCATCTTAATAGTA
ACTGCCTCTGGGTAAGCCATGTAAGACAAATTAACACAAGGCCTGGCACATAGTAAGTGC
TCAAAAGATGTTGGCAACTATTTTTATTTATTTATTTATTTATTTATTTATTTATTTATT
TAACTATGTATTTAGTGACGGAGTCTTGCTCTGTCGCCCAGGCTGGAGTGCAGTGGCTCA
CTGCAAGCTCCGCCTCCCTGGTTCACGCCATTCTCCTGACTCAGCCTCCCGAGTAGCTGG
GACTACAGGCGCCTGCCACCACTCCCGGCTAATTTTTTGTATTTTTAGTAGAGATGGGGT
TTCACCGTGTTAGCCAGGTTGGTCTCGATCTCCTGACCTCGTGATCCGCCCGCCTCGGCC
TCCCACAGTGCTGGGATTACAGGCGTGAGCCACCGCGCCCGACCTATTTATTATTTTTA
AACTGTCAATGTTGTTGTCTTACAGCGGAGACCTGAAAGCAGCTTAGCCATGAGCAGCGC
TCAAATAAGGAAAGAAATTCTTTGCAATAAATAGGGATCTTTGAAAGGTTTTACGTTGGA
CCCGCCTTACCGTGGACAGACACTAGAGGGTGCTCCTCGCTCAGAAAGCCGAGTGTTTCC
AGGCCCGGGACCTCTGCCAGGAAGCGCTTCGACTGCCGGTTCTGAAACTCTCTCTTTGGG
TCTGGTAATTTACTGGGGAGAACTGGCTGCTGCCTTGGTTCTGAAACTAAAGGCTTTTTA
CGGAAGTAGGAGGAGACTGCAAGAGGCTATATGGAGCAGAAATGTGGCTCCTTCAAACTT
TCACCAATTGGCGTTCTGCCGGACTGTGACTTGGAGGATTCCAGCAGTGTCTCATTCACC
CATGAGCCCCAGGGTCTAGCACACATAGTGTCTGGCAGACAGTGAGCGCTTTGTAAATAT
TTATGGAATGGGACCAACCGATGGAGGCGTCTGAGACCTAAATAATTATAATTACAAATT
GGCAAGTGCTGGCACGATGACCACAGACCATTAAGGGCGCTCCCAGAAGAGTGGGGGCTG
GGGAGGATTGGCCAGAATGGCTTCCTGAAATTCAGGAGCCCTGGCACTCTCTGGGGTACA
CAGAAAAGATCTTCCACATCCGGCTTTTGGATATTTAAAAACAGCTTCATGCTCCATTTT
TTTCATGTCCTTCCTGTGGAATGATTTCTAGGCTTTTCACTAAGTTGATCGCTCCCTGCA
GACTTGTAGGAAGGCAAATAATAGGTTAGCACCTACTGGGTTCAAGCATCTCCTATGATC
TCCATTATCTGATTTAATTGTGTCTTTATCTCATTTAATCCCCACAACAACTCTCTGAGA
CTAAGGCTATTATCCACATTCTACAGATTAGAACTTGGTAAGGTTTGATAACTGGCCCAA
GATCACACCATTAGGGAGTGACAGGACCAGTATTTGAACCCAGATAGTCTAGCAGCAAAA
GATGCTTTTAAAAATTTTCACTTAAAAGAATAACAACAACAGCAACTAACAGTATGGAGG
GGGCCAGATAGTTTTCTGTGTTTTACATTTATTAACTCATTTAAGTCATTTAATTGCTAT
ACACCTAGATGTCATCCTTTCTATTAATACATTGTTAGTACTGAAAAGTGAAGAGAATGA
TACAACAAACACCCATGTACTCATCACCTGGCATGAAAAAAAGGTTAATGTTAAAGTTGA
TATTATCCAGCCACAACAATCTTGAAAAAGAACAAAGTTGGAGAACTTGGCCCAGTGCGG
TGGCTCATGCTTGTAATCCCAGCATTTTGGGAGGCCAAGGCGTGTGGATTGCTTGAGCCC
AAGAGTTCAATACCAGCCTGGGCAACATGGTAAAATACAAAAAATTTCTACAAAAAAAA
AAGTTTCTACGAAAAAATACAAAAATTAGCCTGGTGTGGTGGTGCTCGCCTGTGGTCCC
AGCTACTCAGGAGGCTGAGGTGGAGGATCACCTGAGCCCAGGGAGGTTGAGGCTGCAGT
GAGCCAAGATAGCACCACTGCACTCCAGCCTAGGCAAAAGAGCAAGACCTTGTCTCAAAA
AAAAAAAAAAAAAAAGTTGGAGAACTTACACTTTCCAAGTTCAAAAGCTACAGTAATGA
AAACAATGTGGTACTGGCATAAGGATCAACATGTACATCAATGGAATAGAATTGAGAGTC

FIG. 5 (continued)

CAGAAATAAACCTGTATGTTTACGGTCAAGGTATCAAGACAATTAAATAAGGAAATAAGT
TTTTTTCCCCACAAATAGTGCTGGGACATCTGGATAGCCACATGCAAAGAATGAATTTG
GACTCCTATCTTTTATTGTCTACAAAAATTAACTCAAAACGAATCAAAGACCTAAAGATA
AGAACTAAAACTATAAAACTCTTAGAAAAAACATAGGTGTAAACCTCTATGACCTTGGAT
TAAGCAATGGTTTCTTACATACAACACCAAAAGCACAATCAACTGAAGAAAAATAAATC
AATTAGACTTCATCAAAATTAAAAATTTGAGTGTCAAGGCCCTATCAAAGTTAAAAGATA
AATCACGGAATGGGAGAAAATTTTTGCAAATCATAGATCTGGAAAGGATCTTGTATCCAG
AAGATAGAAGAGCTGTTTTTCTGTTGTTGTTGAGACAGAGTCTTGCTCTGTCATCCAGCC
TAAAGTGCAGTGGCATCATCATAGCTCACTGCAGCTTCCACCTCGTGGGCTCAAGCAATC
CTGTCACCTCAGTCTCCCGAGTAGCTGGGACTGTAGGTGTGCACCACCATGCCTGGATAA
CTAAAAAAATTTTTTTTATAGACGAGCTCTCACTATGTTGCCCAGGATGGTCTTGAACT
CTTGGCCTCAAGCGATACTCCCACCTCTGCCATCCAAAGTGTTGGGATTAGAGTGAGCCA
CCTCATCCAGCCTATAAGAACTCTTGTAATTTAATAATAAAAAGACAAATAACCCAATTT
AAATTTGGGCAAATGACTGGAATAAGCATTTCTCCAAAGAAGATATACAAATGCCAAGAA
GCACATGAAAAGATAGTCAGCATCAGCCAGGCATGGTGGCTCATGCCTATAATCCTAGCA
CTTTGGGAGGCCAAGGCAGGTGGATCACCTGAGGTCAAGAGTTTGAGACCAGCCTGGCCA
ACATGGTGGCACCTCGCCTCCACTAAAAATACAAAAATTAGCCAGGTGTGGTGGCAGATG
TCTGTAATCCCAGCTACTCAGGAGGCTGAGGCAAGAGAACTGCTTGAACCTGGATGGTGG
AGGTTGCAATGAGCCAAGATCGCACCACTACACTCCAGCCTGGGCAACAAGAGCAAAACT
CCATATCAAAAAAAAAAAAAAAAAAAGATACTCAGTATCATTAACCATTAGGGAAATGC
AAATCAAAACTTTCAAACCCACTAGCATGGCTATAGTTTAAAAGACAATAACTAGTATTA
GCAAGGATGTAGACAAATTGGAACCCTCATAAATCACTAGTGGGAATATAAATAGGTGCA
GCCTCTGTGGAAAATGGTTTGGGAGGTCTTCAAAAAGTTCAATATAGAGTTACCGTAAGA
CCTAGAAATTCCACTGCTAGCTATATACCCAAAATAATTGAGAACATTATATATACTTGT
ACATGAGACCAGGAGCAGTGACTCACACCTATAAACCCAGTACTTGGGGAGGCCAAGGCA
GGAGGATCCCTTGAGCCCAGGAATTTGAGACCAGCCTGAGCAACATAATGAGATCCTATC
TCTACAAAATATAAAAAATCAGCTGGATGTGGTGGTGTATGCCTATAATTCCAGCTACTG
GGGAGGCTGAGGTGGGAGGATCGCTTGAGCAGAGGAGTTGGAGGCTGCAGTGAGCTATGA
TCATACCATTGCACTCCAGCCTGGGTAACACAGCAAGACTCTGTCTCAAAAAAAAAAAA
AAAAGGTGTAGCTGGATGCAGTAGCTCACGCCTGTAATCCCAGCACTTTGGGAGGCCAA
GGCGGGCAGATCACGTGAGGTCAGGAGTTTGAGACCAGCCTGGCCAACATGGTGAAACCC
TATCTCTACTAAAAATACAAAAATTAGCTGGAAGTGGTGGCGCACACCTGTAATCCCAGC
TACTCAGGAAGCCAGGATGGGAGAATCGCTTGAACCCAGGAGGTGGAGGTTGCAGTGAGC
CGAAATTGTACCACTGCACTCCAGCCTGGCCAATAAAATGAGATTCTGTCTCAAAAAAA
AAAAAAAAGATACATATACATATACATGAATGCTCATAGCAGCATTATTTATAATGACC
AAAAGGTGGAAATGTATCAGTCCATTCTCACACTGCTGTAAAGAATTGCCTAAGACTGGG
TAATTTATAAAGGAAAGGGTTTTAATTGACTCACAGTTCCGCATTGCTGGGGAGACCTCT

FIG. 5 (continued)

```
GGAAACTTACAATCATGGCAGGAAGCAAAGGAGAAACAGGCACCTTCTTCACAGGGTGGC
AGGACGGGAGTGAGTGCAAGCAGGGGAAATGCCAGATGCTTATAAAACCATCAGATCTCC
TGAGACTCACTCATTATCATGAGAACAGCATGGGGGAAACCACCCCCATGATCCAATTAC
CTCTACCTGGTCCCGCCCTTGACATGTGGGATTAATACAATTCAAGGTGAGGTTTGGGTG
GGGACACAGAGCCAAACCATATCAGGGAACAACCCAGGTGTTTATCAGTCGACGAGTGGA
TAAACAAAATGTGGTCTGTTCATGCAGTGGAATATTATTCTACCATAAAAAGGAATGAAG
TACTGATACAAGCTACAGCATGGATGAACCTTGTAAACACTATGCTAAGTGAAAGAAGCC
AGTCACAAAAGGCCATATATTATATGATTCCATTTATATTAAATGTTCAGATAGGCACAT
TCATTGAGATCTGTGGTTGTCAGGGGCTAGAAGTAGGGAGTAATGAGAAATGACTGCACA
CAGGCACAGGTTCTGGAATTGGATAGTAGTGATTGTTGAACCGCCTTGTGAATCTGCTAA
AAAACACTGAGTCATACATTTGTAAATGGTGAATTTTATAGTATATGAATTATAGCTCAA
TAAAAAAGAGAGAGAAAAAGTTGATATTTTCTTCATAGATAGCTCCATGGTTCTCAAA
CATTTTGGTCTCAAAACCCCTTTAGACTCTTAACAATTACTGAGGGCCCCAAAAAGCTCT
TGTTTATGTATTTTGTTTTTGTGTGCTTATGTTCAATATCCATTGACATTTACCATGTTA
GAAAGTAAAACAGAAATTTGTAAAAATATGCATTATTTCCTTTAAAATAGCATTAATAAA
CCATATGCTGTACATGTTATCATAAATAACAGTTGAAAAATAATTGTATTTTCCAAAACA
AAAGAATTAGTGAGAAGAGTGACATTGTTTTGCATTTTTGCTGTCAAATGTCTGGCTGAG
TAGAAGATAGCTGCATTCTCTTACCTGCTTCTACTTACATTCAATGTGTTGAGATATGTT
GTTTTGGTTGAAATATATGAAAAAAGTCTGTCTTCACACAGATACGTGGTTGAAAAAAGG
AAGACTATCTTAATAGCCTTTTCAAATAATTGTGGATATTTTCTTAGATTACATACCAA
AACTGGACAAGTATAGTTTCTTAAAGGTTAATTGCAATGTGGAACCTGAAACCATAAACT
TTTCAATTGGTCTATCATGATCATGTACTTTTTTTTTTTTTTTCAGACAGAGTCTTAC
TTTGTCGCCCAGGCTGGAGTTCAGTGGCACAATCAGGGCTTACTGCAGCCTCAACCTTCC
AGGCTCGAGTGATCCTCCCTGCTCAGCCCCTGGTGGGACTACAGGGATGCGCCACCATGC
CCAGCTAATTTTTTTTTAGTAGAGATGGGTTTTGCCTGCCTGCCTGCTTTCCTTCCTTC
CTTCCTTCCTTCCTTCCTCCCTTCCTTCCTTCCTTCCTTCCTTCTTCAGGGTCTTCCTCT
GTCACTCAAACTGGAGTGCAGTGGTATTATCTCAGCTTACTGCAACCTCCACCTCCCGGG
TTCAAGCAATTCTCATGCCTCAGCCTCCCAAGTAGCTGGGATCACAGGTATGTGTCATGA
TACCTGGCTAATTTTTGTGTTTTTCTAAAGATGGGGTTTCGCAATGTTGACCAGGCTGA
TCTTGAACTCCTGGCCTCAGGTGATCCACCCACTTCGGCCTCCCAAACTGTTGGGATTAC
AGGCGTGAGCCATCAAGCCTGACCTCAAGTTCCCTCTTTCTAATCTGGAATTGAGAATAG
CACTAGCATCCAGGCCCACCTCAAAGGGTCAGACTGAAGTTCAGATGGCCCAAGGATGCA
CTAGAAAGTTCTTTATGCAATGTAAATGAGAGTTGCCTACTCTTGTCAGGCTCAAGTACC
TTCACTCTACAGGCAACTGGCTACAGGCTTCTCACCCTGAGCGGTGGTCAGCTCAGCCAA
CTCACCCTCTCCACCCTCCTCCCTCCCTCCTTTTTCACAGGAAACTTAAGAGTCAGATCT
CTTCCACTGCAAATGGAGATTCTTGATTTGGAGAGAATAAGATAAAGGACCTGACATCAA
TCCTTACTCTTGAAAGCATGTTGTTACTTTCTAAATATTATTGAAATTAAAAAAAAAAAA
TCTTCCCCCCAAATCAGTATATTTGAATTGCTAACAAGCCTCTCTGCCTTGTTTTTATCT
```

FIG. 5 (continued)

```
CAAAGAATAAAATGCTGAGCCCTGCGTGGGATGCTAGATGCTAGAGAACTCCCCCATCTC
TCTCTCTCTCTCTCTCTCTCTCTCTCTCTCTCTCTCTCTCTCTCTCTCTCAGTTCTGAAC
AAGGAGGGAAGGGGTAAAGAGTCCTTAGTGAGCGCCTTCTGCAGGGACAACCCTTCTGGA
CCCATCTGGATGGGAGCAGCCAGGAGAGGCAAGAAGCAGCTGTATTTGGTGGCACTGCCA
CAGCGTCTCCTCAGCCCCAGCAAGTGGCCTTTGGTCTAGAGTTGGTCCATCTGGCCCGCA
CAAGGCTCGAATCCAGCCCTAGAGACGCTCCCCGCCTGCTCCAGGTGGCCGGCACCCTAG
ACGGGGCAGGAAGGGCAGGCGCCAAGCCTCAAGTCTCAAACACGGTGCGGGCTGCGCGG
CAAGGAGAAACCCAGGAGATGCTCGGGGTCGGGGCCCAGGGCAGGGAAAACCCTCAGCTC
TGGTCAAAAGCCAAGTGAGCGAAGGAGGCGATGCAACGTCACCCTGGTGGCCAAGGCAGG
CACCCAGGTCTCGAGGTTCCAGGAGAGGGACGCGCTGTGACCACCAGCCCCCTAGGCTCC
TGTCTGCTCGATGAGCGTCCACTCGCCAGTTCCAGCCGCGAGCGCCCCAGCACTCCCGG
AGCTGGGCCGGGCGCCGCCTTCCCTCGGGCGGCCGGCAGGGGTCAGTGTTTGGCCGCAGG
TGAACAGACAGCGGCCGGGGCTGAATCTGGTTCTTCTAGCTGGGTCTTGCCCCTGCCAAT
CTGTCTGGACTTGTCCCCTGGCCGTTAACTGGGTTCTAGCCTATCGAGACTCCTCATATT
CTCCCCACCCCCGACCACTACCTCCATACTGTCCTTCCTAAGTCACCAGGCCTGCACCCT
TCCAGAAGCATAGATCCCTGGATACATGGATAATTACTTCCTGGCCTTATACCAGACAGT
GATGCGAGACTGGAAAGAGGACATGGCACGGAGTCAGAAGATTTGAGTTCAAGTTCCTGC
TCTGCCAATTACCAGCTGTGTGATCTTGGGCAAGTCACTTTACCTCTCTGTGTTAAGTTT
CTCATCTTCAAAAATGAGCTAATGGCAATAGGAATGGCTATGATGCCACATGCCAAGGAC
TTATATGCCATATACTGTGTGTGTTATCATCTCGAGGGTTTAATAGGAGGAGACTATGGC
CCAGAGAGATGAACAAGCAGCAGGAAGTAGCAGAGCCAGCCTCTGAACCCAGGTCTATCC
ATTTCTACCATGTTAACCTGCTTTGCAGGGCTGTAGTGAGAATTTAAATGTGGAATTTAT
ATTATTCTCTTCTGGCAGTTTGGCCTGGATCCTGGTGGGTGAGCTTTCCCTCCTACTAAC
AGGGGAAGCAGGGAAAGGCATTTTCAATTATTAGAAACATCCTTAGTTAGTGGGGTATGA
AATGAAAATAGCCCACTAGAATACAAGCTTCAGAAGGGAAGAGGTCTCACCTGTCTTGAG
TCTGTTGCTCACATAATTCCTGATATATAGTAGATGCACAAGCAATATGAAGAAATGTAA
ACATGTGTACACCTCCTACCTTCATTATAAGATGGATTCTAACACAGAGTCATTTTTCAT
ACCAACCGTGCAATTACCAGGCAAGTGATGCTAATTACTAGTTCTCATGACCACTATTGA
GTTTAATTCAAGAGTTTTATTGGATCCCCTGAAGCTCCTACAACCCTCTAAATCATGGGG
ATTCAATAACAGTCTTTTTATCAGTATGTTCACAAGATAAATTGAGTAAACCAGCTTAAT
GACTCATCTTCATGACTTATGACGTTAAGAATAAGATGGGGGGAAATGACAAATGTGATA
AAAACTGATGGCTCTGAGAAAATGTCATGGGCATGTGGTTCTGAATGCTCTCCCATGTGG
CTCTAGGGGCCTCAGCAACCTTCAGTCCCGTGTCCACCCTCACTCCGCTTCAATAATCAA
TTTGTTCTTATCCAAAGCATTTTTGAGGACCTTGTTACTCTTCTTCTCTGTGTTAATCAG
GCACACAGGCCTAAAATATCAAATCCTAGGCAGATGCATGAACCCACAGGACAGCAACAT
CGGGAGGGCAGAGTAGAGGCAGGCTTCAGTTCAAAGCAGGCATAGGCTTGGAGAGGGAAA
CTGGGAAATGAAAACAAGTTGTCTATATAGACTCTCTCCCTAGAAGTCCATTTAAAGAAA
ATAGAAGCTCAGTAAAATCAAAATCCATGGGCAGTGGTGCCATGCAAAGAGCAAAGACCT
```

FIG. 5 (continued)

```
GAATCTGAGTCTTGGATCAGTGAGCGTCTTAGCTTTGCCTCCAAGCTCCAGTTTCCTCCA
CTCTAACTGGGGACGTATTCTCTCCTCTCTCCTGGTTTCCTCCAGTTTCTCTGAACATTC
TTTTCATTTTGGTTGTGAGTTCTTCTGCTGCTCTCTCCTGCACCCTTGGTAGGTTCTATG
CTGACTTTTATTTTTCTCCTCTTATATGCTCTTGTTGGAAAGTCTCATCCTTTTGTGAAT
CCAACTGCTGCCCACGTGGGGTGATTCCCAGGTTTATGTCACCAGTCCTGCCTTCTCTAC
TACTCTTTAAATTTGAAAACAAGGGCCGGGTGCAGTGGCTTATGCCTGTGATCTTGGCAC
TTTGGGAGGCCAAGGCAGGAGGATCACTTGAGGCCAGGAGTTTGAGACCAGCCTGGGCAA
TATGACAAAACCTCATCCCTACAAAAAATACAAAATTAGCTGGGCATGGTGGCAAGCACC
TGTAGTCCCAGCTACTTGGGAGGCTGAGGCAGGAGAATCACTTGAACCCAGGAGGCAGAG
GTTGCAGTGAGCTGAGATCGCATCACTGCACTCCAGCCTGAATGACAGAGTGAGACAGTC
TCAAAAAACAAACAAACAAAACCCAACTTTGGGTCACGCATCCATCCTTGACCAATTAGC
TGTAGCTAGGGAAGTGGAGTCCTACGGACACAGCAAACCACCACGAGAATCATGGAGATG
AATAGGGGCAGGATAATTTACCAGAGGAAGCCTAGAGTGGAGTGCTGGACAGACCACCAT
GTGGAGTTGCCATCTGAGGACATTGCTACTTGGATACCCCACAGGTATTTCACCATCTT
CCCCTGAACTCATAATCTTCCCCTGAAAACCTGAATCTCCTCTTCTCCTAACCCCATGA
AGGGGCTGTCATCTACCAAGTCACCCCACCTAGAGATGTGAGAATCATTCTGGAATCTCC
CTCTCTATCACGAACCCCAATACTTCTAGCTAATCACCATGTCTCTAATTCTACTTTC
TAAATATTTCTCTTGTCCATGCTACTTCTGTTTTCTGAGCTCAGGCCCTCCTCATAGATC
TGGAACATTGCAATTGCAATAACTTCTTTCTTTCTTTCTTTTTCTTTTCTTTCTTTTTTT
TTTTTGACAGAGTCTTGCTATGTTGCCCAGGCTGGAGTGCCCAGCTAATTTTTGTATTTT
TATTAGAGACAGGGTTTCGCCATATTGGCCAGGCTGGTCTCGAACTCCTGACCTCAAGCA
ATCTGCCCGCCTCGGCCTCCCAAAGTGCTGGAATTACAGGCGTGAGCCACTGCTCCTGGC
CTGCAATAGTTTCTTAGCTGGTCTCTCTGCTTCTAGTCATGCTCCCCTAATCTACTGTCC
TCACTGCTGGCAGCCATCTGCCTTTGTTTTCCTAAATGAAATAGATTATTTTCTGATTAT
ATTAAAAATACATGTTCAGCCAGGTATGGTGGCTCATGCTTATAATGCCAGCACTTTGGG
AGGCTGAGGCAGGAAGACTGCTTGAGGCCAGCCTGAGCAACATAGTGAGATCTCATCTCT
ACAAGAAATTTAAAAATTAGCCAGGCATGGTGTCACACACCTGTTGTCCAAGCTACTGGG
AAGACTGAGGTGGGAGGATAGGTTGAGTCATGGGAGGTCAAGGCTGCTGTGAGCTGAGAT
CCTGCCACAGCACTCCAGCCTGTGTGACAGGGTGAGACCTGTCTCAAAAGAAGCAACAAC
AAAAGACATGATCATTTTAAAAATTAATAAGGAAAAAATAAAAGAATGTAAACTTTGC
CTAAAATTTTACCACCGTGAGAGAACCATGTTATTTTGGTGATCATTCTTCTTTGCATTT
TTTATTCCTATTTTTAAAAATTACATATCATACACGCAGTGAGTGGGTTTTTTCCACTCT
CCAGCTTCATTGCAGGACATGCCTTGCCTTGCACCTTAAGGCTGTAAATACGGAGTTGCC
TATAATCTCTTTGAGTACACCATGTTGTTTCTCACCTCTCTGCCTGTGGTTATACACCCT
GTATTAATTTCCTAGGGTTGAAGTAACAAAGTGCAGGACTTAAAAATAGCAGAAATTTAT
CCTCTTACAGTTCTGGAAGCTAGAAGTCTGAAATCAAGGGGTTGGCAGGACCATGACCCT
TCCAGAACTTCCAGGGGGAGGATCCTTCCTTGCCTCTTTCAGTTCCTGGTAGGCCCAGGC
```

FIG. 5 (continued)

ATTCCTTGACTTGTATAGCAAAACTCCAAACTCATGTGATCATCTTCATGTGGCCATCGT
CTCTGAGTCTGTGTGTCTCTCTGTCTTCACATGGCATTATCCCTGTGTGTCTGTCTCTGT
GTCTAAATTTTCTTCATCTTAAAAGGACGCCCAGCCAGGCATGATGACTCACATCTGTAA
TCCCAGCACTTTGGGAGGCTGAGGCAAGAGGATTGAGGCCAAGAGTTCAAGACCAGCCGG
GGAAGCATAGTAAGTCCCTGTTCTCCACAAAAATACAAAAATTAGTCCCAACTACTTGGG
AGACAGGCAGAAGGATCACTTGAGCCCTGGAGATAGAGGCTGCAGTGAGCTATGATTGTA
CCACTGCACTCCAGCCTGGGTGGCAGAGCAAGACTCTGTCTCAAAATAAAAGAAAAAAC
AAAAAAGGACACCAGTTGTATTGGATTCTAGCCCACGCTACTCCAGTATGCTAAGGTTCC
CTGCAGCCTCAACATCCTGGGCTCAAGCAATATTCTCACCTCAACTTCCCAAGTAGCTGA
GACCACAGATGCATGTCACCATGCCCTGCTAATTTTGTTTATTTTTTGTGGAGACGGGGT
CGCACAATGTTGCTGAAGCTGGTCTCGAACTCCTGGACTCAAGCGATCTTCCTGTCTCAG
CCTCCCAAAGTGCTGGGATTACAGGCATAAGCCATCACATTTTCAACGACCCTATTTCTA
AATAAGGTCACATTCTGAGGTACTGGGATTTAGGACTTCAACATGTCTTTTGCTGGAGGG
GGACAAAATGTAACCCATAATATACCCTTTTCCATTTTCTCACCTGACCAGCCTCTCTTG
AACCTTCACAGTCCAGCCGAGCTGCCATCTCTTCAAGGAAGTTTTCCCTGAAGCCCTCAG
GTAGACCCGTTTTTCCATGGCGGCCACATCAGCATGCAGCACATTTAATTGGAAGTCTCC
ACATATGAGTTGGTTTTCCTTACTTAAAATATGCTTATCATCCCTTGGAGGTAAGGACTG
TATCTTTTCCATCTTTAATATGCCCAGCACTTGTCTCTTATATTAATTAGTTCAAGACTA
AGTGGGCTGGAGGCTCAAAACTACAGTGGCTTGCCAGGCATGGTGGCTCACACCTGTAAT
CCCAGCACTTTGGGAGGCCAAGGCAGAAGGGTCACTTGAGCCCAGGAGTTCAAAATCAGC
CTAGGCAATAGACTGAGACCATATCTTTACAAAAAAATTACAGTGACTTAAGGAAGAAT
AGAAGTTCATTTCCCTCCCTCATAGCAGTCCTGAGTTGAATAGTGCAGTTTGGTAAGGAT
CTTGCCCCACATGGCCATCTGAAGACTCTAGTTCCTTCCAGATTGTTGCTTTGCAAATGT
AAGGACTCTGTCCTCATCTGCTTGACAGAAGCTGGATAGCAGGCACATCGGTCTTCCAGG
TTGGAGAAAGAGGGAAGAGACTGTGGGAAAATACGTGCCTGGTGCCTAAAAGTTCAGACC
CAAAGCAGCCCTCATGACTTCTGCTCATATTCTCTTGCTGAGAGCTTAGCCACATGGCTA
CACTTAGTTGAAAGAAAGGCTAGAAATGTGTCATCAATTGAACAGCAATGACTATATTAC
AACTCTATTATAGTTCCATAACTCCTTATCTCCAAGTTCTGAAATCTCAAAAGCTGTGAA
AATTGGAAAGGTGTGTGTGTGTGTGTGTGTGTGTGTGTGTGTGTGTGTTGTTGTTGTT
GTTGTTGTTGTTGAGACAGGGTCTTTCTCTGTCACCCAGGCTGGAGTGCAGTGGCATGAT
CACGGCTCACTGCAGCCTCAACCTCCCAAGCTCAAGGGATTCTCCCACCTCGGACTCCCA
AGCAGCTAGGGCTACAGGTGTGTGCCATTGTGCCCAGCTAATTTTCTTACTTTTATAGAG
ACTGGGGTCTTGCTATATGGTCCAGGCTGGACTTGAACTCCCAGGCTCAAGCGATTGTCC
TGCTTTGGCCTCCCAAAATGTTAGAATTACAGGCATGAGGCCGGCCAAAAGTTTTTTCTT
AAGTTTGGCACAGACTCAAGTGGTGGCAAAATCTGACTTGAAATGACATGAGGAATTTAT
AGAGACATCTATAGACTATTTATAGTCTTTATTTCATTCACTTAGAATGAATATTAATGT
ATTTTGTTGCAAAAGTGCCAACATATTTGCTCAAGCTCTCCCCAGACCCCACTGGGGGAA
TGAATAATATGCAGTGTGTGCAGCATATCTCTCTGAAAACTGAACACTTCTAAATTTCAG

FIG. 5 (continued)

GGCTCATCTTAGACCCACGCAAGAGGACCCCACATTTTGGAGGGCCTTACTTTGCCCTTC
TTCTAGATAGCCCTTGCTGATTAGGTAGGCCTGTGAGGCAAAATGAAGGGCCTCTCACCA
CCTGAGCACCGCCCCCCCAACTCTAGATCATGTCCCAGGTACCTGGGCCACTGGAGTTTG
CTGCCCAAGTGGTCCAAAGTCTGTGCAGATCTCTTTAATTGGTCTACCCTCTGGATGGGT
GGGGGGTGGGGGTTACCGCTGTCATATGCACTCTTAAGGCCAAGACATAACCAAAGAGCA
GCTGTTTGCAGCAGGTATGGATAGAGGCTGGTTGTGCAAACTAAATGTCCACACATGTG
CCCGTGAGACCACTCAAGGTAAGGATAGAATTGAGTGTGCAAAGAGAAAGGGGATAGATA
TAGTTATCCAAAATTGTAAATTTGACCCTGGCTATATCTATCAACATAGGACAGAACACA
GCTCTTATTTATTTATTTGTTTGTTTGTTTAGTTTCAAAGAGATGGGGGTCTCACTATGG
TGCCCAGGCTGTTCTTGAACTCCTGGGCTCAAGTGATCATCCCGTCTCAGCCCCTCAAAG
TGCTCAGATTATAGGCATGAGCCACCATGCGCAACTCAGAAGACAGTTCTTATTTAGTAG
CTTGTTAACTTGATTTACATATCGTAAATATATTAGGCATGGATATGTGGGCCTCCAGGC
CTGCATGTTCGAGTGAGTCTGTACGTCAGCCCCAGATATTTTATTTTATTTTATTTTATT
TTATTTTTGAGATGGAGTCTCTCTCTGTCGCCCAGGCAGGAGTGCAATGGCGCGATCTCG
GCTCACTGCAACCTCTGCCTCCTGGGTTCAAGCAATTCTCCTGCCTCAGCCTCCTGGGTA
GCTGGAATTACAGGTGCTCGTCAACACGCCCGGCTAATTTTTGTATTTTTAGTAGAGATG
GGGTTTCACCATGTTGGTCAGGCTGGTCTCGAACTCCTGACCTCAGGTGATCCACCTGCC
TTGGCCTCCCAAAGTGCTGGGATTATAGGCATGAGCCACCGCACCTGGCTGAGCCCCAGA
GATTTTAGAGAGGGATTGTGTACTCGTGCTATGGGAGAACAGGAGAATGGACTCTACAGC
TTGGTTCCTGGCACTTAGTAGGTACTTGATAAAGGACTGTTGAACTGAAATAGGAACAAC
AACTAGCTCACAGGATTCCTGGGACGATCACAGATAGCATATGTGAAAGCCTGACTTGAA
TTATGAAGGGGTCCCCGAATGTGGAGGAGGAGGAAGAGGATGGACGGAGTGGAGAAGTTC
AGGGAGACCCGAGAGTAGATGCAGAGTAGATGATTGAACAACAGAATATGCCAAATGGTA
TTTGACAAATGATTGAGGAATGTTAGCAGTTGCATTAGTTATGAATCTTGTTGAAACACC
AGAAACCAACTCAAGATAGCTTAAACAAGTTGGGGGCAGAGGGGAGGATGAAGAGAGGTG
GGTTAAAGGGTACAAACATACAGTTAGATAGAAGGCATAAATTCAATGTTTGATAGCAGA
GTAAGGTGACTACCGTTAATAAAAATGTATTGTATTGGGAGGATGGACACCCTAAAAACC
CTGACTTCTTTGTTATGTATTATATACATGTAATAAAATTTCACATGTACCCCATGGATC
GTATGAAAAACAAGATAGCTTAGCCAGGCGTCGTGGCTCACGCCTGTAATCCCAGCACTG
TGGGAGGCTGAGGCGGGCAGATGGCTTGAACCCAGGAGTTCAAGAACAGCCTGGGCAACA
TGGAGAAGCCCCGTCTCTACAAATACAAAAAATTAGCTGGGCCTGACAGCGTGCACATG
TAGTTTCAGCTTGGTAGGCTGAGGTGGGAGGATCACTTGAGCACAGGAAGTCGAGACTGC
AGTGAGCTATGATTGCACCACTGCACTCCAGCCTGGGTGACAGAGTGAGACCCTGTCTCA
AAAATATATATATATACAGTCCCAACCTGTAGTCCCACCTCCTGGCGGAGGCTGAGCCCA
GGAGTTCAAGGCTGCAGTGAGCCATATGTGTGTGTGTGTGTGTGTGTGTGTGTGTGTGTG
TGTGTACGTAATAATACATATATGTGTGTATTCACACATACATATGTACATATACACA
TTTATATATATACATTTATATTTAGATATATTATATAAATATTATAGATATATATACACA
CACGGCTCACTGTAGCCTTGAAATTCATATCTATATGAATTTATATATATATACACATTT

FIG. 5 (continued)

ATATATACACATTTATATATTTATATGTTATATATAAATACACATTTTTATATATATACAC
ATTTATATATATATACACTCACATGGCTCACTGCAGCCTTGAAATTCATATATATATGAA
TTTATATATATACGCATTTATACATATGCACATTTATATATTATATATACACATTTATAT
ATATACATATTTATATATATATATATATATACACACACACACACACACACACACACACAC
ACACACACACACACAGCTCACTGCAGCCTTGAACTCCTGGGCTCAGCCTCCCCCAGGA
GCTGGGACTACAGGCTGGGACTGTATATATATATATTTTTGAGACAGGGTCTCACACATA
CATATATACACATATGTATATATACACACACACACATATATACATACATATATATAGCTA
GAACAAAAAAGGGGAATTGATGAAAGAAAATAGAACGCATTCAATCCAGATCTCCTCTC
ATGGAACAAGTTGTCATCGACTTCTCATCTCTGCTTCTTTTTTCTTCAGGTCTGATGCAT
TTTTCTGTCTCTGCAGACCAGCTCCTCCCCCCTCCAAATCTCAATGGAAGAATGCGACAT
TCTGGATTCAGCTACCCAAAGAGGGGTTTTTTCCCCCTCTTTGTCTCTATTATACATTTT
ATAGGAAGGAATTCTGTCCCAGTTAATTCAAACTGGGACCAGAGGAACAGGGTCCCGCTG
CTCAAAATGGCTGTCACCCGTGGGTAAGGGGAGCAGTCAGAGAGTCATTGTGACTGGGGT
GGCAGTCCCACTCCAATCTGCCTTGTGGCTTCCTAGCCTGCAACATACATCCTCCCAGAC
ATACAAAATGTGCCTCTGCCTGAGTCTTCCTGGCAGGGAGTTTGGTACCCCCAACATTG
GGAGGGGAGCTTACAACACAGGACTATCTCTTCCCATAGATAATCTCCTCACAAAGCTCC
ACTCAGGACCACTTATATTCTTGAGGTAAGGGAGGAGGTTCAAATGTCATGTAACAGTTT
TTTGTTTGTTTGTTTGTTTTGAGGGAGGGTCTCGCTTTGTCACCCAACCTAGAGTGCAGT
GGCGCGATCATGACTCACTGCAGCCTCAAATTCCTGAGTTCAGCCTCCCCAGTAGCTAGG
ACTACAGGTGCTTGCCACCACGCCCAGCTGATTTTTTTTTTTGGGAGAGACAAAGTCTCT
CGATGTTGACTAGGCTGGTTTTGAACTCCTGGACTCAAGCAATCCTCCTGCCTTGGCCTC
CCAAAGTGTTGGGATTACAGGCATAAGCCACTGTACCTGGCCCATATAACAGATTCTTAA
GGTTATTTCTTTTGAAAGTTTGCATATAGTGACTTCACACATCACATTGTTTTACAACTA
AGGTATATTAATGCTTAATGGAAATTTCCATTTTATTATTTATTTATTTTTATTGTATTT
ATTTATTTATTTTTGAGACAGAGTCTCGCTCTGTTGCCCAGGCTGGAGTGTAGTGGCGTG
ATCTTGACTCACTGAAACCTCCACCTCCCAGGTTCAAGCGATTCTCCTGCCTCAGCCTCC
CAAGTAGCTGAGATTACCGGTGCCTGCCATCATGCCTGGCTAATTTTTATATTTTTAGTA
GAGACAGGGTTTCACCATGTTGGACAGGCTGGTCTCGAACTCCTGACCTCAGATGATCCA
TCTGCCTCGGCCTCTCAAAGTGCTGAGATTACAGGCGTAAGCCCTCACACTCAGCCTATT
TATTTATTTTTTGAGACAAAGTCTTGCTCTGTCGCCCAGGCTGGAGTGCAATGGCATGAT
CTTGGCTCACTGCAAGCAATTTTCATGCCTCAGCCACCCGAGTAGCTGAGACTACAGGCA
TGCACCACCACACTTGGCTAATTTTTGTATTTTTTAGTAGAGACCAGGGTTTCACCATGT
TGGCCAGGCTGGCCTCAAACTCCTGACCTTAGGTGATCCACCGCCTCGGCCTCCCAATGT
GCTGGGATTACAGGCATGAACCACCATACTTGGCTGGAAATTTCCATTTTAATATCTTGT
TTACAGATAGCTTGAATAATGCTGGGTAGTGGGATGGTACACAGAATAGAATATATTCTT
CTATATGTGCATATATTTGATTGCATATATAATACATATTATTATATATTAGGCAGGGTT
CTGAGTTGCAACTCTAAGCAGGTTAAAGGAATTAAGGATAGACTTTGTTTTCTGACATAA

FIG. 5 (continued)

CTGAAACGTTCAGGGAGCTTCAGGTGCTATTGAATTCAAGGGGTTCGACAACCCCATTAGC
TTGCCCTTAGTGGTTCTGTGTCCTTTCCTCTCTCCTTCTCACCCTCTTTCCCTCCCTTCA
TTTCTCAGCTCTGCTTTCCTTTGGCTTCACATAACTCCAGGCTCATGTCATCCTTTTTGT
CCCAATCTGAGATAAAAAGACCATCTTTCCTTTCAGGCAATAGAATATGATTGGCTAGGC
CTAGGTCACTTGTCAACCTCTATACCCTTACGTTTTTGGAGTGGGGTAGGAGTAGGAGAA
ATAAAGAATTCTACTTTATGTGTTTGTGTATGTATCATTTCTATGAGAAAAAGTTTAGCA
GGAAGCTTTAATGTTAAATAAATAATGGCATATTGACACCAAAAAATATATACATAGCAG
TTAAAAGAGCAAGGTTTCTACATACTGCATAGAAAGGTATCCTCAGCATGTTATTAAAGA
CAATTTGCAGAACAGAAGGTATAATATCATATGATGTTTTAAGAAAATATTTTTTTGTTT
GTTTGTTTGAATCAGGGTCTCACTCTGTCACCCAGGCTGAAGTGCAGTGGCTTGATCTCA
GCTCACTAAGCCTCAAACCACTGAGCTCAAGCAATCCTCCCACCTCAGCCTCCCAAGTAG
CTGGGACCACAGCTCTGCACTACCATGCCTAGCTAATTTTTGTATTTCTTGTAGAGATGG
GGTTTTGCCATGTTGCCTAGGCTGGTCTCAAACTCCTGGCCTCAAGCGATTCACCCACCT
CGGCCTCCCAAAGTGCTGGGGTTGCAGGTGTGAACCACCATGCCCAACCTAAGAAAAGAT
TTTAAGCATGGTTGCAAATTCAGAGAAAATGTCTGTACAGGTATACAATAAATTATTAAT
AATGATAGCCGCTGAGAAGTAAAAGGAGGCCTAGAGGAACAGGAGTTCCAGGTTACTTTA
GTCTCCTGCACTATTTGGGCTTCTTTTTTATTTCTTAAACATTTTACTATGAAAAAACTT
CAACATACAGAAAAGTTGAAAGTTTTACAGGAAACATCCGATATCCACCTCCTACATTGT
TCCTTTGACAATTTGTAATACTTGCTTTGTCACATGTTTATTCATCCCACCACTCAGCAT
GCGTGTCATTAACTGCTTCCCTGGTTTGTCTTTTAATTAAACTTTTCATTTTGAGATAAT
TGTAGGTTCACATGCAATTGTAAAAGAAACCCCATGTACAGAGATCCAGTGTGCCCTAT
AGCCATTCTCCCAATGGTAACATGTTGCAAAACTCCAAGAAGACTGAGTTCTATATTGAT
GTGATTGAAGTCCCTCCACAGGGTTCCTCTGGGGCCCTTCACAACTGTGTATCCCTTCAG
AGTGATGTTAACATTTTCTGGAATGTCAACAGTCTGATTGCTGAGAATGGTCTTCATTCT
CGCAGTAGACGTGGCTAATAGCACAATATCACAACCAGGATACTGACACTGATAGGTCAA
GATATAGAACAGTTTCATCACCATAAGGATCTCTCATGTTTCCATTTTATAGCTGCCCGC
ATTTCCTCCATTTCCTTACTGCTCCTGCTCCCTGCTCTTTTGTTTGTTTGTCTTTCTTGC
TTTTCTTTTCTTTCTTTCTTTTTTTTTTTTTGAGACAGGATATCATTCTGTCACCCAGG
CTGGTGATCACGTGGTGCGATCATGGCTAAAGGCAGCCTTGACCTCCTGGGCTCAGGCGA
TCCTCCTGCCTCAGCCTCCTGTATAGCTGGGATCACAGGCTCATGCCGCCATGCCCACCT
AATTTTTTGAAATTATTATTATTATTATTTCCAAATCAGTAGGTCTTTTATTGTATCATT
TAAATATCACAAATAGGTCTTAGGAATCATCCAGCATCTTGTTTGTGTAGGTGGACAACT
CTCAAATCTTATTCATCAGCCTGCTGAACAGTTCCCTTTTCAGAGACGTAGATACCGTTC
AAAAATTTCCTGATATCCTTGTTTTTAACTGTTGTGGCTTGCTGAATCAAAGCCGCTGAA
TTTGAAACAAGCTCAATGTCATTTCCTTCAAGGATGAATTCATCTTTCTGGGCTTGAGAT
ACTGAACAAGCAACACCTGGTCTCATCTGAACCCCGTGGATGTATTTTCACCCAATAAA
TTTTGGATTTCAACAACAGACCCATTCTCCTAGATAACAGTGTTGACGGGGAAGTGAGCA
TACACAGACCTCATCTTGTAACTGAGGCCCAGTGTAACACCCTTGATCGTGTTCTGTACA

FIG. 5 (continued)

```
TGACTACAAATATTCTGAACGGCAGCCAGTTCCTCTCTGTTACCCCACCGTTTGTCAACC
TGGAGCCTCTGTTTTTTCTTTCCAAGAAGACTGAGTTCTATATGGATGTGACTGAAGTCC
CTCCACAGGGTTCCTCTGGGGCCCTTCACAATAACTGTGCATCCCTTCAGAGTAATGTCA
ACATTTTCTGGAATGTCGACAGTCTGATTGCTGAGAATGGTCTTCATTCTCGCAGTAGAC
GTGGCTAAAAATTATTTTAGAGTTGGGTCTCCCTATGTTGCCCAGGCTAACCTCAAACT
CCTGGGCTCAAGCAGTCCTCACACCTTGGCTTCCCCAAGTGCTGGGATTACAGGTGTGAG
CCACTGTGCCTGGCCTCCTGCTCCCCGCTTAACCCCTGGCAACTACTAATCTGTTCTCCA
TTTCTATAATTTTTTTTTCAAGAGTGTTATATATATAATGGAATCAAGCAGTATGTAACC
TTTTGGGATTGACTTTCTTCACTCGGCATAATTCTCAGGAGATTCATCCAGTTTGTTGCA
TGGTTCAACAGTTCATTCTTTTTTATTGCTATATAGTATTCCATGGTACAGATGTACTAC
AGTTTGTTTAACCATTCAGCCATTGATGGACATTTGAGTTGTTTCCAGTTTTTGGCCATT
ACGAATAGATTTACTATAAACACTCATGTATTCTTTTTTATGAACATAAATTTTTATTTC
TCTGGAATAAATTCCCAAGAGCCCATATGGTAGTTCCATGTTTAGTTTTTTTAAGAAACT
GCTGACTGGGCATGGTGGCTGACACCTATTATCCCAGCACTTTGGGATGCCAAAGTGGGC
AGATCACTTGAGCCCAGGAGTTCAAGACCAGCCTAGGCAACATAGCAAAATCCCATCTCA
TACAAAAAATTAGCTGCACATGGTGGTGCCTGCCTGTTGTTCCTTGCTACTTGGGAGGCT
GGGGTGGGAGGATCACTTGAGCCTGGGAGGCAGAGGTTGCAGTGAGCGGTGATTGCGCTA
CTGCACTCCAGCCTGGGCGACAAAGACCCTGTCTCAAAACACATACAAAATTTTCCAAAC
CATTTCTAAAGTGGCTGTATCATTTTACATTTCCACCATCAATGTGTGAGTGACTTAGTT
TCTCCACATCCTCACCAACATTTGGTATTGTCACTTTTAAAAATGTTAGCATTCTGATAG
GTGTGTAGCCATATCTCATTATGGTTTTATTTTGCATTTCCCTATTGACAATGACACTGA
ATCTCTTTCATGTGCTTATTTGCCATCTGTATTTCCACTTTTGTGAAATGTTCTCTTCAT
GTCTTTTGCCCATTTTCTAATTAGATTGTTTGTGTTTTTATTGTTGCATTTTTAGAGTTC
TTTAATATTCTATTTACTAGTCTTTTGTTGGATAAATGGTTTGCAAATATTTTCTCCTCT
CTAGCTCATCTTTTTGTCTTTTTACAGATTATTTCACAAAAGTTTTAAGTTTTGATAATG
TCTAATTTATCGATTTTCCTTTTATGGATTGTACTTTGGTGTCAACTTTAAGAGCTGTTT
GCTTAGTCCTAGACCTTGAAGATTTTCTTCTATTTTTTTTCTGAAAGGTTTTCTTTTTTT
TTTTTTTTCTTTTTTTGAGACAGGGTCTCGCTCTGTCACGCAGGCTGAAGTACAGTGGCA
CAATCACAGCTCTTGCAGCCTTGATCTCCCAGGCTCAAGCAATTCTCCTGCCTCAGCCTC
TGAAGTAGCTGGGATTACAAACATGTGCCACCACAACTGGCCAATTTTTGTATTTGGGTT
TTTTCTTTTTTTTTTTTGTAGAGATGGAGTTTCCCAAAGTGCTGGGACTATAGGCATGA
GCCACCACACCCAGCCTACATGTTTATCTTGTATCCTGTGACATTCCTGAATTCACTTAT
TTCTAGGGGGTTTGTTTGTTTGTTTTGTAGACTCTTTGAGATTTTCTATATATATAATC
ACGTCATCTGCAAATAGGAAGAGTTTTGCCTCTTCATTGCCAATCTTTTATTTCCTTCTC
TTATTGCACAGACTAGAGCTACCAGCACTATGTTGAATAAAATTGGTGCTTTATTCCCAC
TATTAGGGGCAAAGCATTCAGTCTTTTACCATTAAGTATAATGTTAGTGGGTTTTTCATA
GTTGCTGCTTATCAAGTTAAGGACATTCCCCTCTATTCCTATTTTTTCTTACAGGTGTTT
TTGTTTGTTTGTTTGGTTTTTGTTTTTTGAGACGAAATTTCGCTCTTGTGGCCCAGGCTG
```

FIG. 5 (continued)

```
GAGTACAATGGCACGATCTTCACTCACTATAACCTCTGCCTCATGGGTTCAAGAGATTCT
CCTGCCTCAGCCTCCTGAGTAGCTGGGATTACAGGCATGCGCCACCACACCCGGCTAATT
TTGCATTTTTAGTAGAGATGGTGTTTCTCCATGTTGGTCAGGCTGGTCTCGAACTCCTGA
CCTCTGGTGATCTGCCGGCCTCAGCCTCCCAAAGTGCTGGGATTACATCACACCAAGTCA
GGTTTTTTTTTTTTTTTAATTATTAAATGGGTGTTGAATTCCGTCAAATGTCTTTTCTTC
ATCATTGCTATGACTATATGGATTTTCCTCTTTATACTGTTAACATGGTGGATTACATTG
ATCAATTTTTGGATATTGAATCAGCCTTGCATCCCTGAAATGCAACTGTATAATTCTTTT
TATATATTGCTGGAGTCCATTTGCTACTATTTTGTTAAGGATTTTTGCTTGTATATTCAT
GCAGGATATTGGTCTATAGTTTTCTTTTTGTTCTACTGTCCTCATCTGGTTTTGATAATA
TTAACCTTATAAAATTAATTGGAAAACATTTTCTCTCTTCTGTTCTCTGGAAGAGATTGT
GAAGAATTAAATTCTTCTTTAAGTGGTAGAATTCTCCAGTGAAACCATCTGGATCAGGAA
ATATTGAGAGGGAGGGAGGATGGTTTTATTACAAATTCAATTTTCTTAATAGTTATAGGG
CTATTCAAATTAAACTAATACCCTAAAATTAAACTAATTTAAACTAATACCCTAAAAAAA
AAACCTCTACACATATAAACTCATACTGGATGAGTTAGGTAGTTTGTGTTTTGAGGGGAA
TTGGTTTATTTTATTTAAGTTGCCAAATTTATGCATGTAGAGATTTTTTGGAGGATATTA
ATTTCTTGGGGCTGCTGCAACAAATTAACACAACTTAATAACTTGAACAACAGAAATTTA
TTCTCTCACAGTTATGGAGGCCAGAAGTTCAAAATCAGCATCAATGGTCAAATCAAGGCA
TTGGCAGGACCACACACTTTTCAGAAGCTCTATAGAAGAATTCATTTTTTGCCTCTTCAA
GTTTCTGGTGGCAACCAACATTCCTTGGCTTGTGGCCACATTGCTTCAATCTCTGCCTCC
ATGGTTGCATTCCCTTCTCTTTTGTCCACAACTCCCTCTGTTACTCTCTTATAAAGACAT
TTGTCATTGCACTTAAGGTCTACTAGGATAATCTCATCTCAAAATCCTTAATCGCATCTA
CAAACGCTCTTTTTCCATATAAGGTAATATTTACAGGTTCCAGGGATTAGGACCTAATTA
ACGCTTTGGAGGTCTACTGAGGCTGACTAATGGCCTCCAAACATAATTCTCTATTTCTTT
CATTTTTTTTTTTTTTTTTTGAGTCTCGCTCTGTCGCCCAGGCTGGAGTGCAGCGGCGC
CATCTTGGCTCACTGCAAGCTCCGCCTCCCGGGTTCACGCCATTCTCCTGCCTCAGCCTC
CCGAGTAGCCAGGACTACAGACGCCCGCCACCACGCCTGGCTAATTTTTTGTATTTTTAG
TAGAGACGGGGTTTCACCGTGTTAGCCAGGATGGTCTTGATCTCCTGACCTCGTGATCCG
CCAGCCTCTGCCTCCCAAAGTGCTGGGATTACAGGCATGAGCCACCGTGCCCGGTCATAA
TTCTCTATTTCATTTTATTTCCCTATTATTAAGTCCCACGGTGTTTCCCTATTATCCTTT
TGATGCCTACAGGGTCCATGTGATATCTTTTCTTTCATTGCTAATGTATTTCTCCTCTTT
TAAAATTTGTCAGTCTTGCTAGAGATTTATTGATCTTTTCAAATAATTAGCTCCTTGTTT
CGTTGGTTTTCTCCTTTTCTTTTCAGTTTTCTGTTTCTTTTTTATTTTCAATTTCATGG
ATTTCTGCCTTTTTTTTTTTTTTTTTTGGAGACAGGGTCTTTCTCTGCCGCCCAGGCT
GGAGTGCAGTGGCATGATCATAGCTCACTGCAGCTTCCAGCTCCTCAGCTCAACTGAGCC
TCCCACCTTAGCCTCCCAAGTAGCTGGAACCACAGTTGTGTACCACCATGATAGGTAAAT
TTTTAATTTTTAACGTTTTTCAGAAATAGGGTCTCATTATGTTGCCCAGGCTGCTCTCAA
ACTCCTGAGCTCAAGCAATTCTGCCACCTTGGTCTCCCAGAGTGTTGGGATTACAGGTGT
```

FIG. 5 (continued)

```
GAGCCACCATGCTCAGCCCTGCTCTTATCTTATTATTTCCTTCCTTCTGTTGGCTTTGGA
TTTATATTTTTCCCAAGTTCTTGAGGTATGAGCTTAGATCATTGATTTGATAAAGACTTT
TCTACTTTTCATTTATTTTCTTTTTTCCTTTCTTTCTTTTTGACACAGGATCTCGCTCTG
TCACCCAGGCTGGAGTGCAGTGGCACAATCTCAGCTCACTGTAGCCTTGATCTCCCCAGC
TCAAGTGATCCTCCCACCTCAGCCTCCTGAGTAACTGAGACCACAGGGACACGCCACCAT
ACCTGGCTAATTTTTGTATTTGGGTTTGTTTGTTTGTTGTTGTTTTTTGTGTGTGTT
TTTGTACAGCTGGAGTTTCGCCATGTTGCCCAGGCTGCTCTCGAACTCCTGGGATCAAGC
GATCTGTCCACCTTGGCCCCCAAAATACTAGGATTACAGGCATGAGTTACCATACCTGG
GCCTCTACTGTCCTAATATGTGCATTTAATGCTATACATTTTCTTCATCTGTGTCCCACA
GATTTTGTTACATTATATTTTCATTTCACTCGCTTCAGTGTATTTTACAATTTCCCTTGG
CCAGGTGCAGTGACTCACACCTGTAATATCAGCACTTTGGGAGGCAGAGGCGGGTGAATC
ACATGAGTGCAGGAGTTGGAGACCAACCTGGGCAACACAGGGAGACCCCATCTCTACAAA
AAAATCCAAAAATTAGCCAAGCGTGGTAGTGTGATCTTGTAGTCCTAGCTACTCGGGAGG
TTGAGGCTGCAGTGAGCTGTGATAGCGCCACTGCATTCCAGCCTAGGCAACAGAGCGAGA
GCCCATCTCTAAAAATGAATAAATATATAAATGTATATTTTTATATGTATTATATAATAG
TATAATATATTATAATAGTATAATATTATACTATTATATAATAGTAGTAGTATATATTAT
GTATTATACTATTTATATAATATATAATACATGCAATACATATACATATATGTGTATTTTT
ATACATGTATTATATATACACATACAATATATAGATGTATATATAATATTGTATATATAA
AATATTTTATATATACACATATATAATTTCTCTTGAGACTTCCCTTTTTCGTCCATGGAG
TACTTAGAAGTGTGTTGTTTAGTTTCCAAGCATTTGGAAATTTTTCTGTTATCTTTTTGT
TATTGATTTCTAGTTTGATTCCATTGTGGTCAGAGAACACACTTGGTATTAATTCAGTTG
TTTTACATCTGTTTGTTTTATGGCCCAGGATATGGTCTATTTTGAAATGTGTTACCTGAG
TAGTCGAAAAGAATGAACATTTTGCTGTTGTTGGGTGAAGTGTTCTATAAATATTCATTA
GATCTTGTTGGTTGATGATTTTGTTGAACTCTTCTATATCCTTGTTGATTTTCTGTCTAG
CTGTCGTATCAATTGTTAAGAAGGAGGATTGAAGTCTTCAGCCCCAGTTGCCGATTTTT
CTATCTCTCCTTTCAGTTCTATCAGTTTTGGCTTCATATGGACTGCAGTTCTGTTGTTTG
GTGCATACACATTTAGGATGATTTGTTTTCTCACTAGATTGGCTCTTGTATCATTGTACA
ATGTCTCTGTCTCTAGAAAAGTTTCTTTGCTCTGAAGCCCACTTTATCTGACATATATAC
ATGCACAATATATATATGTATAGCTACTCTCCTGCTTTCTTTTGTTTAATGTTTACATAA
CCTATCTTTCCTATCTTTTTTCATCTTTTTACTTCCAACCTACCTTTATTGCTATACTTA
CAATGACTTTATGCACCACATCTAGTTAGGTCATGTTTTTTAATCCACTCTATCAATTGC
TTTTAAATAGATATCAATCTTTTGCATTTAGACCATTTACATTCAATATAACTATTGATA
TGTTAGGGAATAAGCCTGCTGTTTTATTTTTTGTTTTATGTTTTTCTCTCCTTTTTTTTT
TCCTGAGATGGAGTCTTTGTCTATTTCCAGGCTGGAACGCAGTGGCATGATCTCGGCTC
ACTGCAACCTCCGCCTCCCGGGTTCAAGTGATTCTTGTGCCTCAGCCTCCTGAGTAGCCT
GGATCACAGGCACCTGCCACCACACCTGGCTAGTTTTGTATTTTAGTAGAGACGTGGT
TTCAATGTTGACCAGGCTGGTCTTGAACTTCTGAGCTCAAGTGATCTGCCTGCCTCGGCC
TCCCAAAGTTCTGGGATTATAGGCGGGAGCCACCGTGCCAGGCCCACTTTTCATTTTTCT
```

FIG. 5 (continued)

ATTTTCTTTTCCCTGCCTTCCTGTGGGCTACTTGAACATTTTCATTAGAATCATCTTTTT
ATTTATCTGTAGTATTTGGGGATATTTCTTTACATGTAACTTTTTTTTTTTAGAGGCAG
TCTCACTCTGTCGCCCAAGCTGGAGTGCAATGGCATGATCTCAGTTCACTGCAGCTTCTG
CCTCCTGGGTTCAAGTGACTCTAATGCCTCAGCCACTCAAGTAGCTGGGATTATAGGCAT
GCACCACCACGACAGGCTAATTTTTGTATTTTTAGTAGAGATGTTAGCCAGGCTGGGCTC
AAACTACAGGCCTCACATGATCCACCCGCCTCGGCTTCTCAAAGTACTGGGATTACAGAC
ATGAGCCACCAAACCTGGCCTACACGTAACTTTTTTAGTGACTTATCTAGGTATTACATT
GTATGTACATGGCTTAATACAGTGTACTGGTTTTACCAGTTAAAGTGAAATATAGAAACC
TTACCTCCCAAGCTGGGCGTGGTGACTCACGCCTGTGATTCTAGCACTTTGGGAGGCCCA
GGTGGGAGGATCCTTTGGACGTAGGAGTTCAAGACTAGCCTGGGCAACATAGCGAGAACA
AGTCTCTAAAAAATTTAAAAATTAGCAGGTTGTGATGGTGTGCCTGTAGTCCCAGCTACT
TGGGAGGCTGTGGTGGGAGGATCACTTAAGTCTAGAAAGTCGAGACTGCAGTGAGCCATT
ATCATGCCATTACACTCCAGCCTGGGCAACAGACTGAGACCCTGCCTCAAAAAGAAAAAA
AAAGAAATATTACTTCTCTTTACATCCCTTTGCCAGCCTCCATTTATAATATGATTGCCT
TAAATATTTCCTCTGCATATTTTTAGAACCACAACAGACTGTATTGTAATTTTTGCTTCA
ACTATCAAAAATAATTTAGAAAACTCAAGAAGGGGCCAGGTGCAGTGTCTCATGCCTGTA
GTCCCAGCACTTTGGGAGGCCAGGGTGGGTGGATCACGAGGTCAGGAGATCGAGACCATC
CTGGCCAACATGGTGAAACCCCGTCTCTACTAAAATACAAAAACAGCTGGGCATGGTGGC
GCACGCCTGTGGTCCCAGCTACCTGGGAGGCTGAGGCAGGAGAATAACTTGAACCCGGGA
GGCAGAGTTGCAGTGAGCCAAGATCACACCACTGCACTCCAGCCTGGCTAGAGAGTGAGA
CTCTGTCTCAAAAAAAAAAAAAGAAGAAAAGAAAAGAAAAAGAAAGAAAAGAAAGAAAG
AAAACTCAAGAAGAAAAGGAGGCCAGATGAGGTGGCTCATGCCTGTAATCCCTGCACTTT
GGGAGGCCAAGGCAGGCAGACCACTTGAGATCAGGAGTTGAAGACTAGCCTGGCCAACAT
GGCAAAATCCCGTCTCTACTAAAAATACAAAAAAATTAGCCAGGCACGGTGGTGGGCGCC
TATAGTCCCAGCTACTCAGGAGACTGGGGCACGAGGATCGTTTGAACTTGGGAGGTAGAG
GTTGCAGTGAGCCAAGATCCTGCCACTGCAGTCCAGCCTGGGTGATAGAACAAGACTCAG
TCTAAAAAAAGAAAAGAAAAGAAGAAAAGGAGGCTGGGCATGGTGGCTCACACCTGTA
ATCCCAGCACTTTGGGAGGCCGAGGCGGGCAGATCACGAGGTCAGGAGATCGAGACCATC
CTGCCTAACATGGTGAAACCCCATCTCTACTAAAAATACAAAAATTAGCCAGGTGTGGTG
GTGGGCACCTGTAATCCCAGCTACTCAGGAGACTGAGGCATGAGAATAGCTTGAACCTGG
GAGATGGAGGTTGCAGTGATCCAAGATTGTGCCACTGCCCTCTAGTCTGGGTGGCAGAGT
GAGACCCTGTATTGAGGAGGAGGAGGAGGAAGAAGAGAAGGAGGAGGAAGGGGAGGAGG
AGGAGGAGGCGGAAGGGGAAAGGAAGGGATGGGAAGAAGAAGAAGAAAAGTGTTTTTGA
ACAATGAGAATACGTGGATGGGGAGGGCAATCACACACCAGGGTCTGTTGTGGGGTGGG
GGGCTGGGGGAGGGATAGCATTAGGAGAAATACTTAATGTAGATGACGGGTTGATGGGTG
CAGCAAATCACCATGGCATGTATATACCTATGTAACAAACCTGCACATTCTGCACATGTA
CCCCAAAACTTAAAGTATAATAAAAAAAAGAAGAAGAAAAGTGTTTTATATTTAACCAT
GTCTTTGCTCACTGTGTTCTTTCTCCCTTCCTGATGTTTGTTTTCTTTCTTTTTAGAGAA

FIG. 5 (continued)

ATTTATTGTGCTTTACCCTTTATTCCTGAAATATAATTTCACAGGCAATAGAATTCTGGG
TTGACTATTTTTTTTTTCTTTCAGCACTTGAAAATATTGGCTATTTCCTTCTGACCCCCA
TGGTTTCTTTTAAAAAATTTGCTGTTGTTTGAATTATTTTTCTCTACAGGTAAGGTTCAT
TTCCGTCTTGCTGCTTTCAAGAGTTTTCTTTGCCTTTACTTTTTTTAAAAAAATGTTTTA
AATTTTATAGAAACAGGGTCTCACTGTTATCCAGACTGGTCTTGAACTCCTGGACTCAAA
TGATCCTCTTGCCTCAGCCTTCCAAATTACTGGGATTACAGACATGAGCCATCATGCCCG
GCCTGCCTTTAATATTTAGAAATTTGGCTTTAATATATCTTGGTATTTCTTGAGTTTATC
CTGTTTTGATGTGTTATCTTGTTCACTCAGCTTATTGAATCTGTAGGCTAATGGGGCTCT
TTTTTGCCAAATTTGGGGAGTTTTAAGCCATTACTTTTTTCTATTTTTTTTTTTCTTTT
TGAGATGGTGCCTTGCTCTGCCACCCAGACTGGAGTGCGATGGCGCGATCTCGGCTCACT
GCAACCCCTGCCTCCTGGATTCAAGCGATTCTCCAGCCTCAGCTTCCTGAACAACTGGGA
CTACAGGCACCTGCCACCACACCTGGCTAATTTTTGCATTTTTATTAGAGACGGGGTTTC
ACCATGTTGGCTAGGCTGGTCTCAAACTCCTGACCTCAAATGATCCACCCACCTCAGCCT
CCCAAAGTGCTGGGATTATAGGCGTGAGCCACTGCGCTCCGCCAGCCATTACTTTTTGAG
TACTTTTTTTAGCTGTGCCCTCTTTCTCATTTCTTCCAGGATTCTGATGACATGAATTTT
AGATCTTTTCATCTAGTTCCACAGGTCCCTGTGGCTTTTTTCATTTTCTTCAAACTGTTT
TCTCTCTGTTTCTCAGATTGGGTGATTTTTAATTATTCTATTTTCAGGTTCACTTGTTCT
TTCCTCTGTCCCCTCCATTCTACTGTTTAGTCCATTTACTGAGGTTTTTTTACTTCGGTT
ATTATGTTTTTCAGGTTTAAACATTCCATTTAGCTCTTCTTTATATTTTCTGTTTCTTTA
CTAATACTTTCTATTTTTTTTGCTTTGTTTCAAATGTGTTCTTAATTATTTGTTGAAGCA
TCTCTCTGATGGCTGCTTTAAAATCTTTGTCAGATAATGTTAACATCTGGTATCTTTGTA
TTGTTGATTGTCTTTTTAAAATCAGTTTGAGATTTTTCTGATTCTTGGTAACATGAGTGA
TTTTCAGTTGATACCTAGATATCTCATATTATTTTATAGGCTCTGGATCTTATTTAAGTC
TTCAGTCTTAGCTGGTTTTCTCTGAAACTGCTCCTACAGAGGAAGGGTGGGGGACTGTTA
CTTCTTTATTGCCAAGTGGTGGTAGAAGTCCAGCTTCTCCACTTGGCCTCCATTGACACT
TCAAGGAGTGGGTGTTTCTCATTACTGCTGGTCAGGGGTGGGCGTTCTGCCTCCCCACAT
GGTTTCTGCTGATATCATGGTGGGGATAGGCTTGTTACTACTACGTAATGGTGAAAGTCC
TGCCTCTTTACTAGGTCTCTACTCTAGTGGAAAGGGAGAAGGACATCTCGTTGCTTCTAG
GTGAAGAGTAGGTTTCCGATGTAGTCTCCACTGACACAGGTTGACACTGAGGAGGTGGGG
GTGGGACCCAGGGACATGGGTACAGGCCTGCAAGGATAAAAGTCCCTGATCTCTACATGG
CCTCCTCTGACACCACCCAGTAGAGGTGCCGGGGGCCTTGTTACAGCTTCGCCTTCAAA
AGCGTGAAAGTCTCAGCTTCTCCCTCAACCTTTGCTGGTGTGAGTGGGACCAGTTTTTTT
CTGTAGCGTTTGATTGGCGCGGAACTGTTATTGTCTTCAAAGTTTTCTGTCTTGCTGGGC
TGTCCCTTTCCTAGTCCTTTGTCTAGTGAGAGCAGGCTTTTTTTCAGGCTCCTCTTTCTC
CTTCTTATTCTTCTCCTCCCGTCTGAACCCATTGGCATTTCTAGGTTGCTGCTCCAAGCC
TTGGATATATGACACCGTAATAAAATCGAGAGAATGCACCACCATGTTTTCCTCAGCCCA
GGTCCATAGCCTGTCTGCCATCTTTGTATCTTTCCTAGTCTTCTAATGTCTGTTTTATAG

FIG. 5 (continued)

ACAATGTCCAGAGTTCTTAGCTGTATTTAGGAGGAGGAATAGGGAGAAGTACAGCTCCTC
TGTATTCCTGGAGTGGAATTCTCTGCCTCTCTGATTTTAAACAAGCCAAACTCACAAGAG
GGCAAGCAGAAAGCAATTTCATTCTTTCTCACGACTATCCCTTTCAATCGGGCCTGTGGC
TTCATTCTTCTAGATGAAATTTCAGGCAGATTCATAGCCTTTTCAATCCCTTTCAGTTAT
AAATATGTGCATGTGTGTTTGTTCGTATTAACATCAATCCTCTGAACTCTTGTCCAATCT
AATCTTTTGCCCTCCCAAACTTGGACTTATCTCAGGGCCTATCTATATCTATGGTAGAAA
GAGGGGCTCTTGGGGGTCTTGGTTAGCTTCTTTGCTATTTCCCTCCTTACTCTTTTCTT
CTCCCCTGTCTCCCTTTTTCTTTTTTATTTATTTTTAGAGCTAGAGTCTCGCTACATTGC
CCAGGCTAGACTCAACTCCTGGGCTCAAGCGATCCTCTTGCCTCAGCTTCATGAGTAGCT
GGGACTACTGCAGGCAGCTCCCCTTTATTTTCTGTATTGCATCTGGCTCCGCTAGTGTTG
AAGTGAGAGAGATCAAGGAGAAATACAGGGCAAGAAAGATCCTGTGTCTGTTATAGTTT
TAATCAGGTGTTGGAGCTCTCCAGATGTAGCCAAAGGCCAACTCTTTTCTATGGGCCCA
TTTGTGGATTTTTCAGTTCCTCCCATTTCTGGTTATTATTTGGAATCAGAATACCAATAA
TTGAAAAGAAATAGCATTTCAAGCAAGGGAATATCTGTTCTGGCTTGGAAAAAATCTATT
TCATACACATTTTCATTTTTAGAAAGAATATTGTTGTTTAGAAGGAGTATTTAAAAGTTT
ATATTTAGAATGCTGTCGAAAGTTCCAAATTATTTGTTAAATATTTAGAAGATTTTATAG
AAAAGGAGCATTTCAAATAAAACTCAAGTATTAAAGAAGAATATCAATTAGGCAATAATA
CCAATTAAGCATAAAAAAGAGAATACCAGTTAGGCAACCCACTCTCCTGTTGGGCTGTG
AACTGGCCATGCCCCTTTTTGCCTACATTTTTTGCTCATGCCATTCACTGGCTGAAATGC
CTTCCCCTTCCTCTAGCCAAATCCTGCTTTTCCTTTGAGGCCCAAGTAGCACCTCCTCAT
GAAAGCCTCCCATGACTACCCCAACTCACTTCTCTTTTTCCTCTCGCATTTAGGTATTGA
CTGCTGCCTCATGAAGGCTGGTCCTGTCTCTATAGTGAATATTGTGCACCTCAGGGTAGA
ATGGAGAGCAGAAGACTTCAAATCAGGCAGTCTGGGTTCAGACCCCAATTCTAGTGCTAA
ATAGCTACGTGACTTTAGGCCGATTGTGTGTGACTTCCCTGAGCCCCAGTCTCTTTGCCT
GCAAAATGAGAAAAATTATAACAATGTCATCGGTTGTTCTGAGGATTCTGAGAGGAATTA
GTAGGAGAGAGAACTAAGAAGCTGCGGGCCTCTACAGAGCCATTCAACTGGCATTTCGGA
AGATGTTGCCCATCAGAGTCAGACCTTCTTAGCATCTTCCGGCTGGGCCCAAACTTCCCA
AGACCATTTGGACAAGGTCATCTCTATCCCACCATGGCCTCCTCCCAGAGGAGGAGAAGA
ATCATGCTGTTACAGCAGAACCGAAGATTTGGGCAAGGGAGCTAATGATTATGTTCTGCG
TCAGGTCAGAGATGGGCTGGGAAAGCCACTCCAAAGCCAAGACAAGCAGTTTCCTGGAAA
AAGAAGGCTGCGCGGAGCCCAGAGTGGCCTGGATCCTGCCTCATTTCCTGGACCAGCTCC
TTAGGTGGTTACTGGATTGCCAATAAAGCAGAGCTTATTAAAGTCAACGAGCTCAGGCTT
CATCGCCGCCATGGTATCCAAGCACCAGTCTGTCTGGGATTTCATTTGCCAGATGGACAA
AGGAGAGGTTGTTCCAATACATATCCTGAGTGGTGGGGGTGGGGAGAGAAGGGGAAGAAT
GCTCTCTAGAGAATTCTCTTTGTCCTCTGAAGTAAATAGAGATCATGTCTTCCCCAGCCA
CACTCAGTGATCTGAATCTCTTGGACTGTGGATTTTTCCTTTACCTGCTGTGAAGCCTTG
AAAAGTATGAATTAGCTTGATAATGATCCTCTAAAGATGTTCAAGAGTTAAAGACGTGTT
TAAGTTCTTCAGGCAATCCAATATGACTACGGGTTTCCAAAAATTTGAAGGAAACTGAAA

FIG. 5 (continued)

ATCATAGTTCCCAAACCAGATATTTTCCGGTGTCCAGATGTTCACTGGCATGCAAACCAA
ATGTCTGGATTATGAGCTCCTTTTTTCATTTCTTTTTATCAGCTTACATCCAGATGTTGG
ATCCAACTGGTCAGAGGCCTGGGGCAGAGACAGAAATCAAATCTAGGGTGTTCATCTAGA
GTCTCCTGCTCCTCCATTCCTGCTTCCTCCTCACGCTGCCCCCACATCCTCCCCAACTCA
CCTTCATGCTACATCTCGGCAAATACAGCTCATATCCAGGCACGGTGCAGCCCTTGACAG
CTGGGTCCGCAAAGGCAGATCGGGTATATCTTTAAAGAAAAGTTATCTTAACCATTGAGA
AGCCTTCCTTCCTCAGAGGAGAGCACCTCCCCAGCAGACCTCCGAGGAGACCAAGGGCAG
GACAGGAAGGGTGAAAGGAAGTTTCAGGACTGCAGGAAATAAGAGCTTGGAGGTCAAGGG
AGAGATCAGATAAAACATGAATCTGATCAGCATCCTAGTGGTCTAGAGTGGAGACAATCT
GCGGAGTCAACCTCAGTAAGGACACACATAGAGAAGAACCAAAGCCTCTAAAGACGAAGC
TGAGAAGTGTACGGTCGTAGAAGACTCGTGTCTGTTATTCTTAAAAGCTCAAGGAGGTAT
AAACTGCATAAGATTTAAATGGAGGAACACACGATCTTACTTGCTTTCAGAGGATTTTGG
GGTCCCCATTCTCCCATTAGCAGCCAGGCAACTCTCTCTGTCCTCTCCAAAGGGAGGAGT
GGAAAGGCTTCAAAATCCCTAGGAAATAAATGTCCCCTCCACCCAAAGTCCAGTGTGTAG
CCTGAGGACAGGACTTTCACTGAGAGAAATATATAAAAGAAGGGGATAGAAGCCAGGCAC
CCAGGTGGTGGGTAACAGAAGGGAACTTTCTAGCTGGTTTTATTTAGGGAGGGCATCCTG
GGCAAAAGTCAGAATGCAACTTTTTTTTTAAACCCCTTTTAACAAGATGCTGTTGAATTC
CTCTTTTGCAGATGTTCTGCCAATTGAATGGAAACTGTCCATAGTGGGGAGCAGAGAGCC
TCATCTTTTCTGGAACTGAACATCCATCCTTAAGGCCAGATTTCTCCCATCACCAACTTT
AACTCCTGCCCTAGCCCTCTCTCTTCCTTTTCAAAACCCTCTCCACCCAGGAAGGGAGAT
TCTGGAGCCAAGACTGTACCAGCCACACCTCCCCAGAGTTGTTAAGGAAGGAACTCGAAG
CCAGGGGTGGTCTTCTGGCAAGCACCCCCACTACCAGTAGCAGGACAGATGTGTTTCTAA
TGGACTACACTATCCCCGGAGGTCACATGATTCAGGCTGCCAAGGGTACCTGCCCTTGGG
AAATCAACTCCCGAAGATAAATTGGGATTGGGTCCTGAGAAGATCCATGGAAGCCCAGAG
GACCCTGCCTCTCTCTGTTGCTTCATGCTGTAGAGGCAGTACTGGGGAGGGCCTGCCCCA
CATCCGGCAGGGCAGCTGGAACCATGTGTTTGATGACACTCTGCTCCCTCAATGTGGAGC
CTCATCCTCATCTCACAGTCTAGCAGGCCTCTGGTGGGTTAGGCTTGTCTCACCCAGTGT
GTGAGTTTTTTTGGAAGTGACCTGATTTTGGAGTTTCCCTCCAAGCCTTTCTCAGGTACA
TGCTTTCTCTTTTATTCTGTCTTCTTTTTTTGATCTTCTTAAATCTGATTTTCTCCTTTT
TCCCTCTCTTGTCTCCATCTTTTTTCCAGTCTCTCGCTTCTCTTTATTTCTCCCCATATT
TCACTCTGTTCTCTCACCCCAACCTTTCCCTTCTGTTTCTCTCCCTCCCTCTCTTCCCAC
CCCCTGCCTGGCCTTCCATATATCAAGCAGAGTTTTATCACCTTATGCAGGGGCAGCCCT
GCCACCTGCCATAAAGTTGATAGGCTAATGACATTTTGTGGATATTGCCATGTCACAAGT
CCAGGACAGCATCAAAAATAGCCCTGATGTCTAAACCACTTCAGCTATCTTTTTTATTTT
TAAAATAAATACATTCACATGCTTTTAAGAAACTATAAAAATATATAAAGTAAAAGATC
TTTCTCTCACACTGTCTCCACCTCTCCTGGTCTCACCGTTGTGCTTAGGGGAAACCATTG
TGATTAGTTTCTCCTGTGTCCTTCCAGAGTGTCTTTATGCAAATGAAAATTATTGTGATA
ATATATTCCTATTTTCCCCCTTACTACACAAAAGATAGACTACCATAATCCCATTCTGCA

FIG. 5 (continued)

```
CTTTTTTTTCACTTGATAATAAAAACATGATTTTATTAATGGGTGTTTATGGAGTGATTA
CCATGTGCTATGTGCCTGCTGGGCACTGCAGAACATACACTGGTGAACAAGACACAATCA
CAATCCCCGTATTCAAGGATCTGAAGACCGTCTAGTGACAAAGCCCAACAGGCTCATCTA
CATTCAGCCATGCGATAGAGGGCTGAATGTCTTTAAATAAGTAAAGTCGGCCAGGCATGG
TGGCTCCTCCCTGTAATCCCAGCACTTTGGGAGGCCGAAGCAGGAGGATCACTTGTGTCC
AGGAGATCGAGACCAGCCTGGGCGACACAGTGAGACCCTGTCTCTACAAAAAATAAAAAA
TTAGCTGGGCATGGTGTGGTGGTGTGTGCCTGTAGTTCCAGCTACATGGGAGGCTGAGGT
AGGAGGTTTGCTTGAGCCCAGGATGTTGAGGCTGCAGTGAGTCATGGTTTGTGCCACTGC
ATTCCAGTCTGGGGTGACAGAGCAAGACCCTGTCTCAAAAAAATAATAAACAAAATAAGT
AAAATCAAGGAACAATGAGTGCACAGAAGAGGGAGATTAAATCCAACCTTGAGGACTCAT
GGTGGGGATGGTGTCTGAGCTGAACTACGCAGAATGGATGGGATTCTGCACACACAGAGC
TGGGGAAGTGGAGGGTTTCATGTGGTCAGAGATGTCAAGGTGAGAAAGTTCTGGCACATA
CAAGGAAGTGAACGGCAGAAGCCCAGGGGGTTGGGAAAGGATACAGCTGGAGGGGCAGTG
TGTGCAGTAGGAAACTTAGAGAACTGGGGTCAACCACCTGGATTTAAGTCCTGGTTCTAC
CTCCTACTAGCTAGTCAGTTCTTCATCTGTGAAACGGGGTAAAAATTATCTCCCGCATTA
TTAGAAGGATTAAATGAGGCAACATCATGAAGACCTCACAATGAAGGACTGCACAGGGTG
AGGTGTTAAGCCTGAAAAGACAGGTTGGAATTTGATCTTATATGGCCCTGGGGGCCATGA
TGCAGAGCTCAGGCCTTATACTGAAGGCTTTGGAGAAGGGAACAGTGAAGTGTTTGGGAT
AAAGAAATAACATATAGGACCAAGGAGAGAAGGTGCGGGTGGTAGGACAGGCATTTCATG
AAATGCTATAAATCTTTTCTCTTGGTTACCAATGAAAGACAACTACACATCAGATAAACT
TTTACTTTATTATAAAAATGATTTATAGTTTCACTTAGGAATGCAACTTCAGTGGGTAGT
AACTCTGTAACTATATGGTGGCATCCTTGGAATATATTGATTTATTCACTCCTCATTTAT
TTATTCATTTGATCAACATTTGTCCAGCACCTATGAACAGTTAGGCGCTTGTGCCATACC
TTCTATCCTGAAGTCAGTTTACCAGACAACATACCATGAAGGCTGACTGAAGAGGGTCTG
CTGAGTTCCACAACTCTCAGTCTTGCCCCAGTGCCTCTTTGGAACATCATGGCACAGAAA
GGAAGTTCACATATTTCTCTGACTTCTAGCTCCCTGCAGTTAGAAGAAGTCAACCACGGC
AGGGCTGAGGACAACAGAAGAGTCAGGTCCAGAGGATAAAGTCATGATGTCAACAGTGTG
GATCAAGACTGGCCAAGGCTGGGTGCAATAGTACACACCTGTAGTCCCAGCTACTCAAGA
GGCTGAGGCAGGAGGATCGCTTGAGTGCAGGAGTTCAAGTCTAGCCTGGGCAACATAGTG
AGACCCTCCCCATTTCTTAAAAAAAAAAAAAGAAAAGAAAAGAAAAAGATTAGCCAAG
CCAAGAGAAGTCCAGGGCAGAACATTTTATTTCAGGTAATTGGGAATTGATGATGTATCA
TTACTGGGCTCTGTTCTCCCTTTAGGGGGTTCAAGCCAAGTGGAGGAAATGCTTCATTCC
CACTTGCCTTTCTGACCAGATTCTCCTGCAGTGCTGCAGTTTTCTGCTTTTAGGGAGCTG
AGGATATAGATTGAGGTATGGTAGAAACTACAGAGTGAGCCTCATCTGCCTCATTTTTTT
GTTTGTTGTGGGTTTTTTGTTTTGTTTTGTTTTTTGTTTTATTGAGAAGTTTTGCTGTT
GTTGCCCAGGCTGGAGTGCGGTGGCGTGATCTCAGCTCACTACAACCTCTGCCTCCCGGG
TTCAAGGAATTCTCCTGCCTCAGCCTCCTGAGTAGCTAGGATTATAGGCATACACCACCA
CCCCCGGCTAATTTTGTATTTTTAGTAGAGACAGGGTTCCTCCATGTTGGTCAGGCTGGT
```

FIG. 5 (continued)

```
CTCGAACTCCAGACCTCAGGTGATCCACCCGCCTTGGCCTCCCAAAGTGCTGGGATTACA
GGCGTGAGCCACCGCGCCCGGCCCATCTGCCTCTTCAATGAGCTGAGGTGGCAGAGACGG
CACCCTCAGCCCAGCCACTGGAAAAACCCTTGCCAAGTTGGAGGAAGACCTCTCAGCCCA
GAGTCACACTTATACCTAACAGCTGTGCCAAATATGATTCTGGGCCATGGAAACATTCAG
AGTAAAAATAGTATATGGGGCATATTGAGATGCTTCCACGGAAACCTTCTGGGGGACAAA
TAAAATGTTTTTATTGAGAAGGTCTCGCATCTATCATCTAAATCATTTCTGAAATGAAA
CAACAGTCTCTGGTTACTCACACCTGGGTTGAAGGAGCCACTCCTCTGGGGAATCCCTTG
TAGCTTTACACGTGAATGGGGAATCCTTTGTTTTAGAGCCACAGCTTACTCTTCAGAGAA
AGGGCGTTAGGAAGGGAGACAGCTGATTCTTAGGTCCAAAGCCCAGAAAGTAGTTCCGCC
TCTAAGGCCGAGTGAGCCCCACCTTGGGCCAAGCTGGGAATGAAGCAGCACTGGTTTTAT
TTTTTTGTTTTTATTTTTTACCTTTTTTTTTTTTTTTTTGAGATAGCATCTCACTCTGTC
TCCCAGACTGGAGTGCAGTGGTGCGATTTAGGCACACTGCAACTTCCGCCTCCCAGGTTC
AAGTGATTCTCCTGCCTCAGCTTTCTGAGTAACTGGGATTACAGGTGTGTGCCACCAAGC
CCAGCTAATTTTTGTATTTTCAGTACAGACAGGGTTCCACCATGTTGACCACACTGATGG
CCAACTCCTGACCTCAAGTGATCCACCTGCCTCTGCCTCCCAAAGTGCCGGGATTACAGG
CATGAGGCACTGTGCCCAGCCCAACACTGGTTTTGTCACCTGTACACATACTCCACAAGG
GCCCCTGACAACCAAGTTTTCAGCTCTCCCAAGCCTCAGACCACATGGCACCAAACAGCT
AGATGAAAAATTCAATTAGACTCACAGGCACTATTTTCCTACAGGTTACTGAGGTATTAA
AACAACTGGAAATTTAGATGAGTTTGTGTTGCTTATCCAAATATTTTATTAAAATATTTT
ATAAAAAGGGGAGAAGAGGCAGAAGAAAATAATCAGGTAGACTGCCAGGGTAAGGAGGGA
CAGGAAGAGGAACACAGCATGTGCTCCCAAATTCCCAGAGGGACAAAACTTTTTAGGGC
AGTTTTATTTAACTGCTATAAATTGTCAAAAACATGAAATCATCCACATACATTGTGAA
ACATCTGACATTCCATGACAACCATGTCAAATGCATGCAGATCATTAAGATAGAAACCAA
AACTCATAAAATCATAGATATGTTGCTCTGATGCAGCTGTAAATTATCCTTCAACTTCAC
TCCGTAGGGGGATCTCTAACCAGTTTCCTCAATTCCCATGCTTCCATGCCAAGCATTTTC
AATGGGATATCTACCAACATGCTAAAAATGTACTTCGTTCAATTGTGTGGCCAATTCTTG
ACCTGACCGTTCATATCATTTGCTTAGATCTCCCCTTTACTGTGCCTAAGCACACCCAGC
CCTGTATGACACAGAAAGTTCACTGACAGTTTGAATAATTCAGCCAGGAATGTCCCCTGG
AAGACCACATGGGTAGAGAAGCTCTAAGGAGGCAGAAAAACTGGCTCATCCCTGAGAGAG
CTCCAGGAACAGTCTCCCCCACGCCTCCTCTCCCACCCATCCAAATTTCTCAGAGCTGCT
CTCAAAGCTGCACAGAAAGATTTGGAGACAAAAGGCAATAAGGGGCCGGGTGCAGTGG
CTCATGCCTGTAATCCTAGCACTTTAGAAGGCTGAGGTTGGTGGATCACTTGAACCCAGG
AGTTCGAGACCAGCCTGGGCAACATAGGGAAACTCTACAAAAAATACAAAAAATTAGCCA
AGCGTGATGGTATGCACTTGTAATCCCAGCTACTCCAAAGGTGGAGGGAGAGGATCGCTT
GAGCCTGGGAGTTCAAGGTTGCAGTTGAGTGATGATTGTGCCACTGTATGCCAGCCTGGG
TGACCAAGCAATACCCCATCTCAAATAAAATAAAGTTAAATTAAAATAAAATAAAACCCT
GCCGGGCGCAGTGGCTCACGCCTGTAATCCCAGCACTTTGGGAGGCCAACGCGGGTGGAT
```

FIG. 5 (continued)

```
CACCTGAGGTCAGGGGTTCGAGACAAGCCTGGCCAACATGGTGAAACCCTGTCTCTACTA
AAAATACAAAAGTTAGCCAGGTGTGGTGGTGGGCACCTGTAATCCCAGCTACTCAGGAGG
CTGAGGCAAGAGAATCGCTTGAACCCCGGAGGCGGAAGTTGTGGAGAGCTGAGATCACAC
CACTTCACTTCAGCCTGGGCGACAGAGCGAGACTCTGTCTCAAAAAAAAAGAAGAAAAAA
AAAAAGCCAGTGAGGGGAGGCTCCTCTCACCTCCAATAATAAGAAGGAACTGGCTCAAAG
ATATCCATTTACCCTTTCTGTAAAATGGACATTCTTTCCCTTTCCCTGTACCTCACCATA
CATGAGATGAAAGATGTGAAGTACACAGGTACTTGGAAAATGAAAAAGTTTCATACCAAT
GTAAGAGGGCTTTTTCCCTAGACCACAGCAGGACTTGAATCCAACCCATTGGCTCGAAGT
CCAGCGCTCATTCTATTCTGCCACAGCTACTGAGCAATGAGGCAAGTTCTACCTTGGGCC
AGGGCAGGGCCAGCCCACGGCAGCAGGTAAGAGCCTGTGAGTTGTATTAACCTGCTAGAA
TAGGGGAGTGTGACCTGTGAAATAAAGATCCTAATGCTCCCTGCTCCCAGAGTGCAGAAA
TAGCACTGAGTTTCCTTCCTCTTGAATTTTAAAATGCCTCGTAATACTCTCCCCATGTCC
TAGATTATGATATGGAGCTAGAAATTAGCATTCTATTCCAACACACTGTGGGCCTTCGC
TTTGGGGTTTGAAATGATGGTTTTTAATAAGCTGGCTCCAGGTACCTGTCACCAGTAATA
GAAGTTCTGCCCGGGAAGATAGATCGCTTCTTGTTAAAAGACCATGGGGCAATAAATTTC
CTGAGGCATAACTCAGCTTCCAAATCAGGACTCAGGAGAATCGCTTCTACCTTCTGACAC
TAACCCTTTGGCCTCTGGTCCCTGCTGACCCTGACCATTAACCTCAGTCACAGCTCTTCT
TTGCCCAGGTCATTGTGCTTGCATTTAGGGGAGTTTGGTGAGATCCACAAGGGCATAACT
TGCAGGTGTGACTGTGCCCCAGGACTGGGGTCAGTGGAGGGAGATCATAGAGAGGACCAG
AGCCATGAGTCTTGATGGTCTGCCGTGAGCAAACGCATATCTCTGCTGTCCCAAGGATCC
AGGCCATCAAGACTGCAAAATAAGCTCATCATAGAAATTTAAGCAGTTCTGTCAGACACT
GGCATCTTTGCTGAGGCATCAGGGGAGTCTTTAAGTGCACAGTGGCTCACACCTGTAATC
CCAGCACTTTGGGAGGCCAAGGCAGGCAGATCGCCTGAAGTCAGAGTTCGAGACCAGCCT
GGCCAACATGGTGAAACCCCATCTCTACTAAAAATACAAAAATTAGCTGGGCATGGTGGC
ACATGCCTATAATCCCAGCTACTTGGGAAGCTGAGGCAGTGGGATCACTGGATCCCAGGA
AGTTGAGGCTACAATGAGCCAAGATCACACCACTGCACTGCAGCCTGGGTGACACAGTGA
GACCCTGTCTCAAAAAAAAAAAAAAAAAAAAAAAAAGACCCAAATCAAGAATAAGACCAG
CCAGGCACGGTGGCTCACACCTGTAATCCCAGCACTTTGGGAGGCCGAGGCAGGTTGATT
ACCTCAGGAGGTCAGGAGTTCCAGAGTAGTCTGGCCAACTTGGGGAAACCCTATCTCTAC
AAAAATACAAAAATTAGCCAGGCATGATGGCAGGTGCCTTTAGTCCCAGCTAGTCAGGAG
GCCGAGGCGGGAGAATTGCTTGAACCCACAAGGCGGAGGTTGCAGTGAGCTGAGATCGTG
CCGTTGCACTCCAGCCTGGGAGACAGAGCAAGACTCCTTCTCAAAAAAAAAAAAAAAGA
ACTACAAGACCGCTCTTTTTGACAGCAGCTTCCCCAACCAGAACCAGCCCAGGAACTGCT
TGCAGGACTACCTGGACTTCCACCTCTGTGAGAAGGCAGTGATTGCTAAAGGGACAATG
TCTTTGTATGTGAATGGTACCAGCCTGTGTACAAGTCCCTCATTCCCATATCCTGGATCT
CAGCCTGGGACGACCACTGGGCAGAAGCCACATTTCCCTGGGAAGATTTGAACTGGCTGC
ACCCCACCTTTCCTCTGTCCTCCGTCCTTCTCCCAGGGTGGTAAAAGGGGACCTGGGTAC
ATGGCGATCCCCACCCTGGAACCCTCAATCATGACTTGACTAATAATAAAACTTATTGGA
```

FIG. 5 (continued)

AAGTGAAAGAAAGAAAGAAAAGAAAGAAAGAGGCCAGGTGTGGTGGCTCACACCTGTAAT
CCCAGCACTTTGGGAGGCCAAGGTGGGAGGATCACTTGAGGCCAGGAGTTCAAGACCAGC
CTGGCCAACATGGGGAAACCCTGTCTCTACTAAAAATAGCAAAAATTAGCTGGGTGTGGT
GACACATCACCACTACTCGGGAGGCTGAGGCAAGAGAATCGCTTGAAACTGCGGAGGTTG
CAGTGGGCCGAGATTGCACCACTGCACTCTCCGGCCTGGGTGACACAATAAGACTCCGTC
TAAAAAAAAAGAGAGAGAGAGAAATCCAAGCAAATGTAATCAATCATGTTATTCAATCT
GACCACTTGCTTGTGGGGATTGGAGACTGATATATGGATAATGAACTTTTAAAAATACCA
CAGAGGTAGTAAATTAAACATATATAGTGCCTACCCTATAACCCAGAAATTCTACAAGAA
ATGTGATTCAATTTGTTCACCAAAAGACTTGTTCAAGAATATTGATAGTAGCTTTATTTG
TAATAGACAAAAATATAGACAACTCAAATGTCCATCAACAAATGAATGGATAAACTAGTT
GCGGTGTATCCATACAGTGGAATAGCAGAACGCAATTAAAAATAATAAACTGTCAATACA
CACAACAACATGGAGATTAATCTCACAGACATTTTGTTGAATGGAAGAAACCCAGACCCC
AAAGAGTACACACTGTGTAATTCTACTTATAAAAAGTTCAAGAACAGTCAAAACAAGTCA
ATGTCAATAGATGCGGGGATTTGAGACTGATCAGAACGGCAGTTACGGCCAGGCACAGTG
GCTCATTCCTGTAATCCCAGCACTTTGGGAGGCCGAGGCAGGTGGATCACCTAGGGTCAG
GAGTTCGAGACCAGCCTGACCAACATGGTGAAACCCTGTCTCTACTAAAAATAGAAAAAT
TAGCTGGGCATGGTTACATTACAGGTGGAAGCCTGTAATCCCAGCTACTCAGGAGGCTGA
GTCAGGAGAATTGTTTGAACCCAGGAGGCAGTGGTTGCAGTGAGCCACACTCCAGCCTGG
GCGACAGAGCGAGACTCCGTATCAAAAACAAAAACAAAAAGAATGGCAGTTACCTCTGG
AATATTATACTGGAAAGGGTCTGGAGGGAACACACAGGGATAGAGGAAATGAAATGTTTT
CTATCTTATTCTGAATGGTGTTTATCTAGGTAAATAGGTAACTTCAAGCTATACACAAGA
TTAATACACTTTATTGTATATATGTTATACTTGGAAAAAGGAAAGCTGTTTTGTAAAACA
TCCATAGTGGTTTTTTTGACACGAAAATGTGTCTCATGTCTTTCTTTATAAAATATTAAA
AATCCAACTTTATCCTGATTTTAAGTGAAAAGGAATAAAATGACAGTAAAAAAATAAGAA
GTCACCACTAAATATGAATGTGTGAAGCCGTTGTAGCAGTTCCCTGTCTGAAGCACAAAC
AGGAAGTAACTCTGGTGCCCAATAGCATAAAGGGTTTTTTTCCCCCTCTCCTCAGCATCC
CAAGGATTAACCATATGCTCTGGCCAGCACGCAGCCCCAATGACCTCACGTGACAATGCC
AATAAAACCAGACTCAGACACCAGACTCCACTCCAGTCCCTCCAGGTCCTTATTGTCACC
TACGAGAGCAGTTGTCCTTGCAATCCCCAAGTTCTGCCTGTTGTATTTTAACTGAAAGT
AGGTTACAAAGTAAATAAAAAATCAATCTATTTCTGAAAAAAAATTATTATTATATTTTA
AAATCCCATTTCTATTTCACATGACACTGTTAGATGAGTCAGCTGTGTATCTGTTCATTT
TAACTCTTTTAAAATATTTTCTACCCTGTTTTTATCCCTCTTCTATTCATTAGAGAAGGT
CAATGCCACAGGAGTGCAACAATAATAGGAAAAAATCCTCTCTATCTAACAAGGGCTAG
CATTGGGGTTGGGAAGAAGGGCCAAGCACTTCGCCCCCACCCACCCATCATCACTAACTG
TCAAATATTTACTTCTGGTAAATATTTTAGTCTCTGAACCAAAGATAATAACCTAGGAAG
GGGTGAATCAATCCAGTTTGGGTTGGTCCCACCCCTTCTTTGCTTCCTCCACCTATTTCC
TGCATTGCTCTTTTTCTTTGTAAACAGGCACAGGCTTTCAGGGGGTGGGAGAGCAGTGTT
AAAATTTTAAAAGTAAAACACACAAATCTTGAATGTTTAGTTTAATGAATTTTTACACAT

FIG. 5 (continued)

```
GTATACAGGCACATAACCACCACCTTGATCAAAACACGGAACATTTTGAGCACCTTAAAA
GGCCCCCTTTTATTTCCTTCTAACAATGGGGACTTTTTTTTTTTTTAAGACACAGTGTC
TGCTGGGCCTCATGGCTCATGCCTGTAATCCTAGCACTTTGGGAGGCCGAGGCAGGGGGA
TCACTTGAGCCCAGGAGTTCGAGACCAGCCTGGGAAATATGGCAAAACCCCATCTCTACC
AAAAATACAAAAAATTAGCTGGGCTTGGTGGTGCACACCTGTAGTCTCAGCTACCTGGGA
GGCTGAGGTGGGAGGGGAGGATCACTTGAGCCTGGGAGGTTGAGGCTGCAGAGAACAGT
GATCACACCACTGCACTCCAGCCTGGGCAACAGAGCAAGACCCTGTCTCAAAAGAGAGAG
AGAGAGAGAAGCTCATTGCAGCCTCGAACTCCCGGGCTTAAGCAATCCTGCCACTTCA
GCCTCCTGAGTAGCTAGGACTACAGGTATGCACCACATCTGGCTATTTCAGAAGGGGGAA
TTTTTAACCTAGAATTTTTGAAGCATTCTATTTCAGGGGATACTACTCTCATGTCTCTAA
CAAACATACTCAGTGGCATAACAATTTCACTCTTAGGAATTATTTTTAAAAGTAAACATG
GAAACAAAAAATCGAAATGATTTTTAGATAAATAAATGCAATCATTAAAATCAAGCTTTT
GAAGAATATTTAATAACACTGGGAAATGTTCATAATCTAACATTAAATAAAAGGCAAGAC
AAAAAAATTCTTGCAGAATCTCAGTTTTGAAATTGTACATATGTGCAAGGAAAAATAACT
GAAGAAAATATAACAAAGAGTAGCTTGGTAAACTTTGGGTGGTAGTATATGGGGTGAAT
TTTATTTCCTTCTTTATAATTATTTTATATTTTGAAATTCTTAATAATAAGAATGTGTT
ACTTTTCTAATCAAGAAAAAATTTCTTCTTTTCATTTGTTTGTTTTCTAGAGACAGGGT
CTTGCTCTGTTGACCAAGCTGGAGTACTTTTCTAATCAGGAAAGAAATTCTTCATTTTA
TTTATTTATTTTCTAGAGACAGGGTCTTGCTCTGTTGACCAAGCTGGAGTAGACTAGGCT
GGAGTGCAATGGCAGGATCAAGGCTCACTGCAGCCTGAAACTCCCTGGCGATCTTCCTAC
CTCTGCCTCCGGAGTAGCTGGGACTACAGGCAAGTGCCACCATGCCTGGCTAATTAAAAA
AAAAAAATTGTAGAGACGGAATCTGGCTATATTGCCCACGGTGGTTTTGAACTCCTGGCC
ACAAGCAATCCTCCCATCTTGTCCTCCCAAAGTGTTGAGATTATAGGTCAGCTGCGGTGT
CCAGCTGAAACTCCTCTTTTTAAATATGGGTACAGCCTAAAAGACTAACTTTAGGGAAAT
CGTTTTCTAAATTATGACAACTTCTTTCATTGCATATTATGCAATCTAAAAATAGCACTT
AGAAGACTGCAATAACTTGAGGAATTGCTTAGGACACAGAAAATGTACAGTATGTTTTCA
AACCAAATTAGGTTGTGTATAACTAGGTTGAGGGGAAGGGGAACAAAAAGTAACTATTAA
CAGTGGTTAAAAATTATAAAACATACACGTTGAAACAATTTTTTTAATTTAAAAGGGGCT
GTTTATAAAAAGTTTTAAAAGTAGCTCTGTGTTTTAAGACCCGTGTTCTACTTGCTGCG
ATCGGGATAGTTTTTTTTTCCACTTTGAGGCTCTTTTTTTTTTTTTTAAGGGGCAGGAA
CATCATTTTGCATCAGGCCCTGTAAAAAAAAAAGGGGGGGGGGTGGGTAGGAACCAGG
ATGTTGGGGAAATTATTTCAATGTGTTGAGTCTGAAGCTTTTTGGAAAGCAATGTAGAT
GTGATCTCGTTTGCTCTGAATCGAATTCCACAGAAACCGCTGTGCCGAATACTGCAAATC
CTTAACTTTCATAAACGCCGGCACCGAACTCAACGCAAAACTACCCAAGTGCCAAAGACC
ATTTCTGGGAAGCTCATTCCATGAGACCTTCGCATTTTTCCAAATCAAAGGCTTCCCTTC
GGATCTAATTATTTCTCCTCTACAGGGCTGCGGGAGGGGGAGGGGATGTGAGACTAGGGC
AACAGATTAAGATTGAAAGTCCTTTCTCGCAGCTTCATTTTCGCCCCCACACTGTCCCAA
```

FIG. 5 (continued)

```
ATGCTTAGAACCCTCCTCGTCAGAATGGGAACGGTGCCCCGCTTGTCCTAAAAGACACA
GACCAGGTCCGTGAACTTGACCCAGGCGCCCACGCCTCTTTTCCCCGAAGGTCAGACAAA
GGCAGAAGGGTTGGCTGGATTCTTTCCCGGGCCGCGAAGGCCTGGGGATCGCAAGTTGAG
GAGGAGAAGACCGCAAACCCCTTTGGTTCAAGCAAGCTCTGCGGCAGGTAAAAGGCAAAT
TGGTGGGGACGGGTAGGACAGGGAGAGCATTATCTGGCTAACTCCCGCAGGCCTCTTCCG
ATTTGTCGGCGGGGACCTGACTCCCTGCGGTGTCTCTGGCCCCAAATACGGAGGCCAGGA
GCTTTTCGTTGTCTCGCCCGATTTGGTATCTTATTAGCCGGTGTCGCTGAGCCGCGGGGG
ACTCCCGGCTGGAAAGGAAGCCCTGCGCTCGAAGCGCCCACGCCAGACGGAGTGGCCCC
TGCGCCTCCCCGCGCGCCGGCGCGCCCTGTTCACCTTCGACTGGATGTTACCGAGCCAGG
GAGAGACCCGGAGATCGAGTGTTTGATCTTCCCTTGCTCCAGGATCCTGAATTCTTTAAA
CACACTCGCACGCGCTCGCACACAAACACACACACACACACACACACACACACACACGCA
CACGCAGCACTACTACCGTCTGAGCAGGCCGCTCCTCGCAGCCTCCGCAGTCGGCGGGTC
GCCTGGAAAGACGCGCCGGTTTCCCGGGTCGGATGGCTCTCCAGGCCGCTATTTCCTCCG
CCACCGAGTAGGGAGACGCCCCATTTGCGAAGTTTAAGTTTCCAGGTCCTGGGAAGGCAG
CTGGGAAACCCGCGGGGCTCGGCAGCCGCCCTGGTAGCAGCCAGGGATCGGATAGCGCGG
CGGGCGACAGCCCCCCGGATAACCCCGCCGAGGGAGGGGCGCTTGTAAAACCGAGCGGCG
ACGGCCTCGTTACGACCGACTCGAACATTCTCTAATAAATCATCGGCCTTAGCTAGTATT
CGTTTGTGTACGCATCTGTTTATCCTGATTATTAAAATAAATTAAGGATTAGACTGCCTA
GAATAAGGTAAACGAACATGAAATGCCAAGGAGGAAAACAGAAAAAGTTACACCATGTCG
ATCCCGACCAAAACATTGGCCTGACTTGCCGGATGGCCTCAAGAATCCGGCTTTTAGCTG
CAGGCCCGGCGGGTGTTCCCCGGAAGGCAAGGATTGGAAGCTCTTTGATAAAGCCGCGCG
AGGCCCGGTTTCTCGCGTTTCGGGTCGCTCCACAGCCCCCTCCGCCCTTCCCCTCCACCC
CTCCGCGTCTCGGCCTGGCTCCGGAGGGGTGAAGGAATGTTTATAGCCTGACTCAAGTTC
AATGACAAAAACCTGCCTGGAATGGGAGGTGCGGCGAGCTTCAGCCATCAACATGACAAA
GGCTGGACGCAGGTCTCGGGCGGGGGCGACGGGCTGGGCCCACCTAGAGATGGGGAGCTG
AGGGCCCACAGGATGGGTACGGACCCCGCAGACCAAGAGCTGCCTCTCTGCCCTCAGCCT
GGGGTCTGCGGAGTTTGGCGAGTAGTGCGGGTGTGCCCGCCTGGATGAGGGTAAGGCG
ATCAGCCTCTGAGTGGGCAAGGGGACGTCTGATTACTGCCCAGGCTTCGCCTGGGGGTCC
AGGACCCTGTGAGATGCCCCTGCTCTCTGCCTGGCCAGCTCTAGCTCACCCGGAGTAAGG
ATCCGCACCGTCCTTCTATCCACCGCGACCTGCATTTTCTGGCCTCCTCCGAGTTTTGTT
CACATCTTCCCTCCCGGATTTGATATTCCAAGCATCTTCTCCAGGGAAGACTCCCAGAAG
CCTTGCTTGTCTGTGTGTGTGTATCTTTCTCTTTCCCTGTTCCCCGTCCTGTTCCCCA
TTTGTTCTGATTGTAGTCATTTGGTCATGGAATAAAATCCTCTGGCCTCAGGTCACATAT
GGGGAAGCTGCAGACCCAAGATTTACCAGCATAGGAGTCAGGCCTGGTGGGAAGGGAGAG
CATATTTCCAACTCTTTCCTCCTGTCTTCCACCCCTAGTGGAAGATTTTGCATACTCAAT
TAATGAGTAGTTGGTTGACAAAAATGTCCACACGTGTTTAATCCCCTGTTTGCATATATG
CAGATCTGTCCAGTGCCTGAGGAGGGGCTGGGTCTAGGGTGTTTGGGTGCACCTGTGTGA
TCTCAGCTGGGTGACTCCGGATGGAAGCAGGTGCTTGTTAGTGTCTGAAGGGCCTTGCAG
```

FIG. 5 (continued)

```
GGAGAGGTATGTTGACAATAGAGGAGTCCCTGGGCTTTCTATTTTTTCAGTTGGTGGTAG
AGGTTAAGCGCTCCTGTTTTGGGACCCAGATCAAGTAACTTACCCTCTTAGTTTCAATTT
CTTTAGGTTATAAAGTGCTCACTCAATTGTGGGTTTTGTCATTATGGGAGGGGGAACTGG
CAGGGAAGGAGCCAGCTGTGGGGAGAAGAGAGTTAGGTGAGTCCTGAGTGTTTTTGTGGA
TTACTGTGCCCACCCCAAGACCAATGACTTGGCAATATCAGTGGTTGGCTGAAGATGTGA
GCATGTGGTCCCCAGCCTGCTTCTGTACTGGACCCAGAGCCCCTGTGCGCACACATGCCT
GCTGTGGCATTGATCCCACACTTGGCAAGGCAGAGCTTCTGAGAGGGTGCAGGAAAGGGA
ATAAGGAAGCCAGGGGCCCAGAGAAAAAGGTGCAATTATTATTATTATTATTTGTCA
CAGAGTCTCACTCTGTCACATAGGCTGGAGTGCAATGGCATAATCTCAGCTCACTGCAAC
CTCCACCTCCCAGGTTCGAGCAATTCTTGTGCTTCAGCCTCTTGAGTAGCTGGAATTACA
GGTGTGAGCCACCATGCCCAGCTAATTGTTGTATTTTTAGTAGAGACAGTTTTCACTATG
TTGGCCAGGCTGATCTCAAACTCTTGGCCTCAAGTTATCTGCCCACTTCAGCCTCCCAAA
GTGCTGGGATTACAGCCATGAGCCACTATGCCTGGCCCGTTTTTATTTTTTTAAGGCCCA
GAGCTTTTGCCTTAAGGATGAGTTAGTTTAAAAAAGAAAAATTGTTATAATCACAGTTAA
CTTTCACCCAGTTTCCTTTTTTAAAAAAATTTTATTGTATAAATAGAGACAGCGTCTTGC
TACATTGCCCAGGCTGGTCTGGAACTCCTGTGCTCAAGGAATCTTCCTGCCTCGGCCTCC
CGAAATTCCAGAATTACAGGCTGAGCCATCACTCCTGGTCTCGCCCAGTAGATGTTTCAA
AGTAGATGTTTTCTAAAATATTTTACAATATTTACAAATTTTAAATAATAATAACGTTAT
CAATATTAATTTTGCTTATGCCAGGACTCCATCCCATTGGAGACAAACATTAAGTCTTAT
GGCAGACCTTACAGCGGGTGCTAGTTCCCACTCCCAAGCCTCTCCCCCGCCTAGGTCCTG
CAGGTCCCGCGTGCTGCGAAACATTTTCTTTGTCCCTTTCTGCCCAGGGCGGCTGCCGGT
CTCTCCAGGAACCGCGAGTAGGTGCTCCCGCCAGGTGGTATCGGTGAAAGCCTGCTGCTC
ACCCTTCCCTTGTTTCCCAAAACTTCTGAAGGCTCCCAAATTCCTGGGAGACCCTCTCCC
AGGGCCTCCTGATGCAGCTACCATACTGAGCGATCCGTCGATAACGCCCTTGGCCCACCG
ATCAGTTTACCTTATTAGAGAGAAAAGCACTCTTGGAGGTAGTAAGATGGGCCGGTCCTT
GATCTGAGAAATGGGCGCACAACATCGCTGTTCTCTCTGCAAAGGTGGGGACCAGAATCC
AGCTTGCCTGACCTTGCAAGCAAGCATCGGCCTAAAGGTTTCAGCCTCCCAGTGGCGCTC
TGTTTGCACGCCTTAGGCTAGGAGAGGAAGGACGGGAGCACAGCACTGGGTGCCCCTCTC
CCTGTAGAGTCTGGGGCGGGGCTCAGTAAGAAGGCCTGCGGTTGGTGGCTCCCCACCTCA
TAGCTGCAAGTAGGGGCGAAAGCTGGAGTGTCTCCTCCCAGCAGCCTCCTCGCCTCCCCG
CAAACCTCCGAATCTCCCTGGACCTCCTGGTTGCTGTGGCCCTTCCTCCCCTGATTGGCT
TCCTCCCTCTTTCCCAAGGCCAGAGAAGTCCTCTCTTCCCCTCACCTTCCTCCCTCTTCC
CATAAAACTTTTAGGAAAATGGGGGCGGGGGCGGTGGAGACCACCAGCCTGGAACTTCAA
GTTCAATGGCAAAGTCCCTGACCCTCCCCCAGGCTGGGCGCCAGCATTATTCTAGGGGC
GATTAAACTCTTTTGCTGCCCCTGTGCACCTCCCAGTTCGGGGCAGTTTAGGGGAGGA
GAGAAGGTAATGGTGGAATTCTTTCCCTCACTCTCCCCCGACCACTTCGTCCCCTCCCCC
TCATCCCCTCTACACAGAACTAACTGGTAGGGAGAGAGGAAGAAAGGCTGGCATCGGTTC
CTCATTGGATGTTTTAAATCTGTCTCAGGCCCAGGCCAGTGCCTGGGGGGAGGGGCGGGG
```

FIG. 5 (continued)

```
TGTCCTGCTTTTGGGCTAGAGGCCCGGGGCCGCTCCCGAGCTTTCTCCCCTCTTCCCTGG
AGAGCGACTGTTCGGGAGGGTGAGAATGGTATAAATTTCAAAAACAACGAAACCTTCTTT
TGCCCCCTCCGCAGCAGTCGCCTCCGGGCTTTATTGCAAGTTTACGGTAACGAGTTCATC
TATTTAATTCGCGGTTGCAGCTCGGGGATTTCTATTAGACAGGACGGGTTGGGGCCGGGG
GGCACAGGGTCTCCCCTGAAGGAAACCCAATTAGAGTGCAGCACTTAGCACCTTCAATAT
AACTTTAATGAAGGGGGGGAGGGGAGCTGCAGGGAAGAGAAGTTTGCTCTAGGTTGGGGA
AGGAAAGCTGGAGCTGCTCCCGAGAACTGGGGGGCCTGGATGAGGCTTTTTCCTGCTTCG
AGGGCTTTCCAGCTTCCGGCCCGGGAACTACTATTTGGAGTAGGGATCGCCTGCAGGGAA
GGCGGGGCGGATTCTCGGCTGGCGGCGGCCTCGCAGGGTTCCCGGAAGCGCTAGCCAGCC
GGAGTAAAACCCGAAAGATGGAGCCTCAGGTTCGCGCTCTGCGTTGCGGGTGCTGGAACC
GAGATTCAAAAGAGCTTCCGGAGGTAGTTTCTACGCATTGCGCCACTACTCCCTTATTC
GGCTTCTGGAGGCCTAATAAAATCCACTTGCTTTGGAGTTAGAAATTATTTCGGGCCTGG
AGCCCGCGTAGACGCGACCCTGTGATCCCATTTCGTAGCTTGCTGAGAGATTCGCTGCGG
GAGTTTGGCTCTGAGGGAGGGGAACGGTCTGGAGGGCAGCTCAGGGTACAATTGCGCCTT
GTTAGTGAAAAGGCGCCCTGCTTATTTTCCGGAGTATATGTGTGTGCCTCTGCGTTTATT
CGTCTGTGAGCTCATTGTCTGGATTCACCTATTGTGACATTGTGTTCACACGTTTGTCCG
AATGGTAAGCAAAACATTTCCTCCTGTAGCTTAACATAGCCCTTATGTAAAAATAAATAT
CTGCAGGCGAATATAGGTTTGTAGATTTTGTTGTGATTTAAACACAAATAAGTGAGAGAT
TTCAATGTGGTCGTCCAGGGATAGGTGGGAGACTAAAATTGGGAAGGGATTCCCAATGAA
AGCGTTTAATACAAAACGAAATTAAATATTTTTTGCACAGGTTCCATACAAGTAAATCCG
AAAAAAAGTGTGTGTGGGGGGGTCCACACCACTAATTATTATGGCGAGGAAGATAAAGAA
GACATGGACAGAAGGCGGATGGCTCTGCGGCCTGGCTCCCGCAGACCGACCGCCTTCTTC
TTCCATTCGAGATGGCTCGTACCGAACCTCCTTGCCTTCTTCCTGGGTCTCTCGGGGCT
GGACCAATACATCTGCCGATGCCCTGGCCGAATGGCAGGCGACATCGGGTCCTGGACCCC
CACACGCAGCTCAGTACCCACGAGGCCCCAGGCCGCTGGAAGCCTGTAGCTCCGCGGACG
ATGAAAGCCTGCCCGCAGGTTCTCCTGGAGTGGTGAGCCTCTGTCGGAAGGGGGCGCCCA
CGTCTTTTTAATGGTCCTAACACACCAGTGGAATAAATCTCTAAGATTCCACATCTTTTG
TTTGCTCTGAATTTATTGCGAGTGAAAAACAGAGAAAATCCTCAAGTTTAAGTTTCTGAT
AGCAGAGTGTGGGAGTTAGAGCATGGGGAGTCCAGAGGTTCCAGACCCCCAAAGGTCTCT
ACCAGGGCCATCTCCGTTAGTGGCGGTGGCAGCCCTCTTGTGGCCTTTTTCCTCTCTCC
AAGGGGTCACCCCGCACCATGCCGCTCCCCCTCATCTATCTTGCCCCCTCCCCACAGGCC
CATCTGCGCTGAACTCTCGCCAGTTCCGAAGTCGGCGAGGGAGGGGGTTTACTTGCCCGA
TCGTTGGTGGGTTTGAGCTTATAGAGGCAGAGGAGTAAGAACCTGCGATATTGAAAGCTA
CCCACATGGGGCTTCCTTGAAGGAGGACGTGGAAGGCAGAAAGTGACCTGCTCTGAGCGG
CGCATGTAACCGAGGACCTTAAGCTGGACCACGGGCTTGGACGATTTTTTAAATCAGGA
AATCGACCTCATCTTCCTCCTCCTCGTCCTCTTCCCCTGAACCCCCAGTCCGCATGCACT
CACACTCTTTGGCCTTTTCCCTCAGTCCCGGGCTCCTCTTTGGTAAATAGATTTGTAGGT
```

FIG. 5 (continued)

```
GTCTAAGTCACGTCCCACCCTCACTCCTTCCCAGGAGAGGAGACAGGGCTAGGATCCCAC
CCGACCGCGGGCCATAAACACTTGGCTGCGGCGGCCGCCGCGGGGTTTCTAGGAGAGCTG
GCTCCGGGAGGGAAATGTCCTCGAGGTAGTGGCGGCCGCGGCCCACCACCAACTGCTCGC
CACCGACCCCACTACTCGCCACCGACCCGCTGCTCGGAGCTTCGGTTCTGCGGGTTGTCC
AGACTTCAGGCCTGTGCGCTCAATCGTGGAGAATGCGCCGGCAGGCCCCCACCCCCAGC
CTAAGGTGCAGGAAGGACCAGCACGAACCCGCTGGCTTTGCTGCGCGGCCAGGAGATGAG
TCCCACCGGGCACTGAGCCCAGGTACAGGACATCAGAGAATGAACACAGAGGCAGAGGCC
CTCATGTCCCTCTCAGAGTCCCGGCTCTGCAAAGAGCCCGTCTGTCTCCAGCTTCCAGAA
TTCCGCACTGTGAATCTGTCTACGTGGACTGGGAAAACAGGGTTGGCACCACTCTGCCAC
TCCGTTTGTGCCTGGGAAGGGCTAAGTATGCAAGGCTACAAACATCTACTTCACTGGGAT
CCCAAATGCTCAACAAACCATGACCTGCTTTGGTCAGAACCACCAGAAATATTAAGGGAA
GACTCAGAGAGTTTGGGGGAGGAAATTAATGGTGAATTACCCAGGCACTTTCTCAAATCT
CTTTTTCTCTGGAAGGAAGGACTGACTAGGGGCAGCCTGCTGGCTTCATTTTCACACGAC
AGAAAAATCATCGTATTAAGGATGGGTGCTTCCAAGACCAGTGGGTACACCCTATGGGGT
GGACAAGGAGGGAGGAAGAGACAGCCTCTACAATTGTCCACCTACCCAGCTGTCAGCTGA
GAAAAATGCTAAACGGACATCACAGCCACACAACGAATCTGCCCGTTCCCTCTCCTCAG
TCTTCCTGCTGTTACCAGGGTGAGAGGTGTAATGGAAGGGGGTCTGAGAGAAAGCTTCCC
TGCAAAGGGATCGCCTTCCAAATTTATTCATAATTAGCTCAATTCATGAAAGCGGTTTCT
AAAGTGCTCTACAGAGCTCTAGATAGAAAATATGAGGCTAACGATCATGGCAGCTAGTAC
TGGTTATCGTGATTATTGCCACTGTCAGGATGAATGATTATGACTGGGCCAGGTTCTTTG
GGAACCCTGGTGGAGTGGGCTGTCACATGGGGTTCCGTCTCCCTGCACATACTGGGTACC
CAGGCCGCTCCTGAGGAACAGTCCAGCAGCCAGTGGCCTGGGAAGGGTGTTGTCTCTAGG
GGCCTCTCAGCAGAGTCCTTGGCCCCAGCCTGGGCTTGGCAGGTTCCTGGTCTCCCCAGG
ACACCCCACTTTCGCTCCTCCCACCCAGGCAAGGAGATCTCTTAAGGGGTAGCGCTGTT
CTTCACCTTGGCGAGAACCTTCTTCTCTTTGACCCGGCGGTTCTGAAACCAGATGGTAAT
CTGGCGCTCCGAGAGGCTGGTGGCTGCCGAGATCTTGCGCCTCTTGTCCTTGGTGATGAA
CTTGTTAGCCGCATACTCCCGCTCCAGCTCCCGCAACTGCCCCTTGCTGTACGGAATGCG
TTTCTTGCGGCCGCGACGAAAGGCGCAGGCGTCAGGAGGGTGCTGCCCGCTGGAGTCTGC
GCGGCGTGAAAGGGAGGGAGGAAAAGGCATGGTCAGATACCCACCCATGCAGACCCAGGC
CTTGCAAGCCCCAAGCTAAGTCATCTCACAGGTGCACACAGGTCACCCTACAGGCGCACG
TGCAATCCTGTTCCTCCAAAGCATACCAGGACAGCACCCTGGCTTCCGGCTTGTTCTCTC
ACCACCGCTCAGCCTTGGCTCCTGAAGGCCACCCTCACCCATCACTGCTCTCACACCCGC
GAATCTGCAAACATACCCACACACCACACACAGTCAGGCCTTTGCCCACCATCACATACG
TCCAGTCTTCATGCATTTCCAGACTCTTGGCCACTCTTTTAGATTCTACAGGCAAATTCT
GGAAACACGTTTCTGCCCCACTCCCAATACATGCGCATACACACACACACACACATT
AACCCATCCCAGTGCACACACATATGTCACGGCTGCAGGAAACCTAAATTTTTCTTTGGA
AATTGGAAAACTCATCTAATAGAAAGTGAGAGGTTGTATTCTCTACAGTACATCCAATAC
CTTTTTACCCATCTCCCACACCCACTCCCCACGCACCGAATTGAGAGTTATTTAGCTTTT
```

FIG. 5 (continued)

```
GTGTAGAATTAGTTTGGAATTGTGCTGGGTAGGGACACCCTGATCCCCACTCAACAGCAA
AGAGATCTAAACCTCTCAGACATGTTGAAAGGCTGGTCCCAGGGCCTCCTGGAGAAGTGA
GGTGGCCTTCAGGCTTCAGATAGCACCCAGCTCAGGCCCCTCACACTGACCTCCATCCAG
GCCCTCCAGCTACTCAGACCTCCTTCAGAGTCCTAATAACCAAGGGAGGAGCACCAAGCT
CATCCTCACCAGCTCCAAGTCTCCCTCCTCCTCCTCCCAGGGAAATGCCATTGGGACCCA
CAACCCCAGGCTCAGAGACAAGGGGACCCAGGGTAATAGAGGTACCTGCAAATGCTGCCT
TCCAAAAGGGACCTGGTGGGTTCTGTTCTCCCTGGCAACACATCTGGCTGTTCCAGCCAC
CAGCGAGAGCCCAAGACTGGTAACTGTCCACAGGCAACAGGGAGTCATGTCGCGGTTCTC
CAGGAGCACCCAGAGTCTGCACCACAGACACGTCCAGGTAACTGGCCATAGGCTGGTAGG
TTCCCGGATATCCCGGATAGAAGGCAAACTCAGTGGGGCGGCTGGGGTACTCTTCCCCGG
CCGTGGGAGTCTCCGCGGGGTACGCGGCCAGGGTGGCTGCCTGGGCACAGGGTTTCAGCG
AGCTCCGGGACACTCGGCAGGAGTAGTACCCGCCTCCAAAGTAACCATAAGGCACGGGAG
CTGGGGACGTCCCCTGGGGCACCCCAGGGCATGGGTGGCATTGCTTTGGCGGCTCCGCCG
AGCCTGGCAGATCCAAGGGGGCATAGTTGACAGCAGGCATCAGCGTAGGCGCCGCTGGGT
GGCTGGTCAGAGGGGAGTGGGCGACCAGATTCCGCCCCCTCCCGCTCCCAGCAAGCCTT
CGATATCCTTGGCTCCATCCAAGGTGGCATAATTGCCGGGCTCCATGGAGCCGAGGGTCG
GCTCATGAGGTGCGGGGCGGGGAATCTAGGGGGCACCCAGCTCGCTCTCCCCACCCAGG
CCGGGGGAATCCAAAGCGTTTTAAATCGCTCCCAGCTCGCAAGTCGCCTGCATTCGCTCA
GCACGGCCGTCTTGACGCAAGAGACGCAGGGGCCCGGGCACGCGCGCTGATTGGCTGCGG
CCTGGGGGAGAGAAGCTAATAAAATCCTAAAGGCAGAAACTGCGAAAATACTTTACCCCA
GCTTATTCTCTCTCTCTCTCTCTCTCTTTCTCTCTCTCTCTCTCTCTCTCTCTCTCTCTG
TCTCTGTCTCTCTCTCTCGCTCTCTCGCTCTTTCTCTCCTCTCTCTCTTCTCCCTCTCTC
TCTTCTTTTCCCTCTCCACTCCTCTCTCTCATTCCACTTAAAAACAACAAGAGAGAAA
AGGAAGGAGGTGTCCTTTCGCTGCTTTCCAGTTTGCAGAGTCTCATTTACACGTCCGGGG
GGAGGGGAGGCGTGGTGGGCGGAGGAAGAGGGGACGAGGAGCCGGGCCCCACCTCCTTCT
CCTCCTCTCCCTCCCTAGCTTTCTGTCTCCTGCGCTTTGACAGGTTTAACGAGAGAATAA
AAAGCTCTCTCTATAAAGTGTCCATCTCCTGGGGGGAAGGGGAGTCGGGGGTGGGCTG
GGAGGCCGCTCCCGGCCTCAGAGGAGAACCCGGGAATGCGCCTGTGTAAGAGGAGGCTGG
GAAATGGGGGTTAATAGGTATTTCTGGCAGCCCCTGGCTTTGGGTCCTGGGTACTAGCAC
CCCAGTTCATTCCCGGTACCCTTCCTGTCCCAGATGTCCTGGAATGAGCTGCTCCGGGCC
CCAGGGAGGTGCCCTGGACGCCCCTTACCCAGGGACTCGCTACTGCCCAGAATGCTCTGG
AGGCCCTGATTCGGGTGAGGCTGAGGGAAGAGGCGGGAGACACGAACGTAGACGTAGAAG
ACATGCGATCTGGATGGAACCCAGGACACTCCACTTCCGGACCTGAAGGGGAAATGGAGC
CTCTAGAGTGGCCTGTGGAAGGGTCTGGATTTCCCTTTAAGTAAAGACATACGGAGGGAC
GGAGACCCACAGGACTTGAGGGAGGGACGGGGAGAGGGAGAGATGAGACTCAGGGACAGC
AACACAAAGAGGGAAAGAGAGAAGCTGACAGAGCGGATGGGACAAAATCTTGTAAAATCC
TGAAGTGTCAGTCAGAAAAGAGAAAGAAGAGAGGCACTTTCCCCCTTTTTTGGGATCTAA
AGAAGTCTGAGGAAGCCAAGCCTGGCTGACTGCCAGAAACCAGCTGCGGGAGTTCTGGAC
```

FIG. 5 (continued)

```
CCCAAGAATACAGACGCCTGTGTGGAGATGCCAGTCTCCCTGCCCTGCAGTCCTCTCCCT
ATGGTCTGCAAGGGGCCCAGGAAACTGTCCCTGATACTGGCATACTCCCACACAAGCTGA
GTACCCAGAAAGCCCAAGACCCCTATCTGCCTCCTGCAAGCTTTAAACTTCCTTACAAGG
AAAAGGGAATGGAAGGGGAAACCCCAGCCACTGGCAGAATTGCTTGAGGCCCCTCTGTTG
GGGCCTAATGTGCAGTGCAATTCAGAAGAATCAAACGGTTTGTTTCACAAATCTGTCTTT
AGAGGTTTTCCGCTTCCTTTACTACCCCTCCCAAATCAAATCCTTCTGTCTGCTTTTTCT
AGAACTCCCAGTTTTTCTGGAGAAGACAGGAATGTTTCCATTCTACACGAGGGTCTTGAC
AATTATATGGAATGGCTTACCCTAAACTCTGGGCAGACTCAATCATAGCCTCTCACCAAC
CTGACCTTGAACTTGAGCCACTTTGTGGGAAAGGGCCCACAGGCAGTAGTGTACATCACT
CCTAATGAGCATTGCTATAATTGAAGACACCAAGCACGAAATCTTCACTAGATCGCATTT
GAAAACAATATGGAAGAAAAGGGAGGAGATGTCTCTTCAGTGCTTTCCAGTTTCTCACCA
GAGTTTCTTGCTTGTCTAATTATGAACTGCAGAAATATCCAGACTTTTACCTAAAGACTA
AGAATTTTTCACCAATTTTTACTTGGTAGATGATAGATATGTAGGGCATGTCCACAGTTT
TAGTTTCCACTAGGCAAACACCCACACATGCACATTTATTCATCCTTGTACAGTAGAGGC
ATTAATAGATCCCTAAATTTAAAAAATAATAATAGTCATAGTCATGCCCTATGACCCAGC
AATTCCATTCCTGGGCATAAACCCAACAGAAATGAACCTTTATATCCATCAAAAGTCATG
TACTAGTAGGTCCACAGCAGCTTTATCTGTAGTTGCTCAAAGCCACCCATGGCAGCGCAC
GCCTGTAATCCTAGCTACTAATCCTAGTGGAGGTGGGAAGATCGCTTGAGCCCCGGTGTT
CAAGACTAGCCTGGGGCCAGGCACAGTGGCTCAGGTCTGTAATCCCAGCACTTTGGGAGG
CCAAGGCAGGTGGATCACTTGAGGTCAGGAGTTCGAGACCAGACTGGCTAACATGGTGAA
ACTCTCTCTATACTAAAACTACAAAAAAAAAAAAAAAAAAAGCCAATTGTGGTGGTGGAC
ACCTATAACCCCAGCTACTCAGGAGGCTGAGGCAGGAGAATCGCTTGAATTTGGAAGGCA
GAGTTTGCAGTGAGCCGAGATCGTGCCACTGCACTCCAGCCTGGGTGACAGAGCAAGACT
CCATCTCAAAAAAAAAAAAAAAAAAAAAAAAAAAAAAAAAAAACCAGCCTGGGCAACAGGG
GTAATAGGGATAATAGGGATACCCCATCTCATAATGAAATCAAAATATAGTAGCTCAAAA
CTAGAAACAACCCAAAAGTCTATCAGCAGTAGCATGAATAAAGAAAGCACAGTATAATTA
TACAATGAAGTACTACACAGCCATTTGAAAAGAATAAACCACTACTACACACAACATTG
ATGAATCACAGATATGTGGATGAAAGAAGCCAGACACAAAGAGTAACTTTTGTATGATT
CAGTTTCTACATTTCTATGCAGTTCAATGACAAGCAAAATTATGGTATAGTGATAGAGGT
CAGAATAGAGATTGGCATGGGGAGAGGTCTCCTGACTGGAAAAGGACATAAAGAAGCCTT
CTGGGGTGCTGGAAATAGTCTCCATCTCAATCTGTCTGCTAGTTACAAGACTTTGTTCAC
TGTGAAAATTCATCAAGCTATACACTTGGTATTTCTGCACTTTATTGCATATCAGCTATA
TCTCAAATGTTAAGGAAAATAATTAAAAACAAAAATTTTTTTAATTCATTGCAACACTTC
CTGAAACTGTGCTTTTGGATGTATAGCATTCTTATCCATGTTCATTGAAATAAGTAGCCA
AGTGCATGTAACTGCAGTGTTGTGGAATGCAGAGATGGTTAACTTAAACTTGGCGGGAGT
GAAGGTCACCAGCTGTGCTGGAGACCCTCCTGTAAATGGATACATTTCAATACAAATAAA
TTCTATAGTGCTTGTTTTATTTGCTTTACAATTTATTTAGCATCTGCTAGATCCCAGGGA
```

FIG. 5 (continued)

ACAGTTCTGGATCTCATTTTTCTTTCATTTCATTTCATTTATTTTGAGACAGAGTCTCAC
TCTGTCACCCAGGCTGGAGTGCAATTGTACAATCTCAGCTCACTGCAACCTCCGCCTCCC
AGGTTCAAGTGATTCTCATGCCTCAGCCTCCTGAGTAGCTGGGATTACAGGTGTGTGCCA
CTATGGCCCAGCTAATTTTCTATATTTTTAGTAGAGACAGGGTTTTGCTGTGTTGGTCAG
ACTGGTTTCGAACTCCTGGCCTCAAGTGATCCCCCTGTCTTGGCCTCCCAATGCGCTGGG
ATTACAGGCATGAGCCACCACACCCAGCTTTGGATCTCATATTTATTAACACTTGGGTAT
GTGCCCCTATTTCCTGTACATAGGTATGTGTGTGCATCTGCCCATGACCTATCATAGATC
TCAACCGGCATCAGGTAAAGTAAGATTAAGTCTCCTTATCTGTAAAATATGGATAATAAT
TCTTTCCTCACATACTGTGATGATATAATGAGATTTTGCACATAAAAGCATTTCACAATC
TGAATAAATATGAGCTCTATTTGTATTCCTCCATGTGTTTCTGTTTCTAATGAATTACAA
GCAACCTGCTTTTACCTGAAAAGGACAGTTGCCCTAAAGAGTGTCAGTCACTTCTCACTT
GCCCCCTCAGCCCTGCGTAAGCTACATAGTTCTCGCATCGGGAAACTGAGGCTCAGAGCC
TCCAAGTCCTCCCTGGGGCTCTACATGGGTTCAGCGGGGAAGTCCCTGCACAACCCAGGC
GTCCTGATCTTCCAGACTGACTGGGCTGAGCCTGGCCTTCCCTAACCCCACAGATGCCT
TTGTGTCCTGCTGGGAGCCTCCTGGCAGACCCTCCGGGAGCCCGGAGCCTCCCCCAGCTT
TCTTTACTGACCCAGCCAAAAGCGCTGAAAGCCTCAGCGTGCTCCTTTACATACCCGCCA
GACACCTCCAGGAAGGTAAAGGCCAAGTTGAAAGTTAAGAGTCTGTTTACCTCCAGGAGC
CCATTCAGCTCGGCCCCACAGACAGCCTGTGACCTTTACAGCCCGGCCTTTGAGCGCGGC
CGCCGCGCCCCGGGGGTTCCGGCAACGGGACTTGGCACCTCGGTGTCAGCTCCCGCCC
CCACCCAGGCTAGGGACCCGCCAACGAGGGGTGGGGGCGGGAGGCGCCCACCCGTCGCAC
TAGTGGGCATTTGCTAAACTACGTTTTATTTTTTGTAAAGTGAGCGCCCGCTGCCTTCG
TTCTCCCAACTGGAGCAAACTCTGTGGCGGCGACGATGGCGGCCGTCAGGTCGGTGGTGA
TGAATAGAGAGGATTTCTCTGCAGCGCGACGCTCCCCTCTCCCGAAAGGTTGGCTCCACG
GTCCCGCCGGCCGCGCAGGTCTGGCTGAACTGCTTGGGGTCGCCCGGCTCCTCTCGATTT
TATGAAAATGGCCTAATTGAGGTGTGCTCTTTTCTTTCCTTCCTCTTTTCATCTTTTCCT
TCCGTCTGCATTTTCTCTCCTCTGTCTTAGGCTTGGTATCTTCTTTTCTTTTTATATTTG
TGTTTTTCTCACCGCCTTTGCTTCCTTCCATTTCAGTTATCTTGCTTTTTGTGTGTTCTT
TCTTGATTTCTTTCTTTCCTTTTCTTGTTATTGCTCACTCTCTGGCTCCGCCACCCACCC
CTTGCTCTATCTTCATTTTCCCTTTAGTACTTTTCTCCCTATCTTTCATCTCACTTACAC
TATTTTTCTCTTTGTTTGCTTTTTCTTCCTCATTTTTCCTTCTTCAGTTTTCTCATTTTT
CCTTCCTCCTTCCTTTTTTTCCTCTCTCTTCTCTATTTCTTTTTTCTTTCTCTCATCTC
CGTTTTACTTCCCTTCCTCCGCCCGCCACACACGTTTTTCCTTTGCAGCGCTCTCGCCCA
GTTTTTCCATTGTTCTTCTCTGAAGTCTGGAAAGGGCCTGCGGGCTATAGCTCTCAGCG
GCCGGAGCCTGCGCTTGGCAGGGGACGGCCTGGAGGACGGCCTAGTGTGGCTGGTGGGTT
CGCGGAGCCCTGCCCTGGAGCTCTGCCTGAGGCTAGAACAGCACCCGCTGGAGATGAAGG
GTGACTCCGGCCTTTCGCCCTGAAACGAAGTCAAGCGGGGCCTCTCCTGGCCTTAGAGGA
AAATCTTTTGGACAACTTGACAGAGGGATCCCAGAGCTAAGAGCTCAGAGGATGGAGGCA
TGGCTGGTCAGGAGGAGGCCCCTCTCACCTCCTCCTTCCTTCTCCAACCCAGTCAGCCCT

FIG. 5 (continued)

```
GCGACATCCTCAGGAATTAGAACCCTCTCGGGATAAGCCTAAGTGCCTCTGAGGCCAGGG
CTGAGGGAGCCAGCTATCAAAACCATGGGACAAATGGATCTGAGGAGGAATCGAAGGATG
GACAGCTGAAGGGAGAGGCTTGCTCCAACAACAGGGCGGCCACGGCAGCTGCTGCGCGCC
CTGACGCCGCCTAGAAACCGGAGGAGGGCCTAGCCAAGCCCAGAGAACTGTGAGTGGGGT
CCAAAGAGGAGGGAGGGAGGAGAAAGGGAGGAAGGGGGTCAAATATGAGGGTCACTGAAC
ACAGACCAAGAGTCTCCCTTCCTCTGGTCCGGCAGCTCTAGGGGAACAAGCCAGCTGTTC
TTGCCTATCACGCATCACACGTGCTGAGTAGGGAGACTGGCTGGCCCCAGAGTCCCCAGC
CCCCTTCTCCAAACCTGGGCTTTAATGGGGAGTTACCCAATTCGGAGAAACAGCCCAGAT
CAGACCCCAACCATTAGGAAGTCTGGTCCTAGGTGGCTGCACTGCAGAGCAATGCAGAGT
CTCATGTAAGGTTCTGTTCTAGCTCAGTGTGCTGGACCAAGTCAGTTGCCCTCTCTGTGC
CTCAGTTTTCCTATCTGCACTGTGTAAGGAGGGAAGGACTGGACCAGCGGACCTTTGAAT
CCCTGCCAGTGTTCACCTTGCACAGAAGAGTGACGACGGGCAGCAGGAGGGAAGGGAGCT
TTACCGGAAGGAGAGGGAAGAAAACTGTAGAAGGAACAAGAAAGAGTCCAGGAAGCTGCC
ACGGATTTTTCATGCGTGTCTAGTGCAGGCACGGTTATTAGTGCTTTGAGGGAGCCCAGC
CTCTGTGGAGGCAACTGTCATGTTCTGACTCAGTTGGAGCAGCCAGCCCCACAGTGTAAA
TTCTGCAGTGGCTCATTAAAGGGGACCAAACTGTGTGGGAGTTCACCTCCTCCCTACTTT
CCCTATAAATCCCTCCAGCCACCCAGCACAGAGACACTTGAAAGTAAAGGAATAGGAATG
GGATCCTCAAATGGGGACCCACAATTAGAGTCTTTAGGGGTTTCAACGACTTCCAGGGTC
ATGGGAGACTGGGCTTTCTTTGTTCCAACCCCTGGGATACTGGATAGGACTCAGGAATTA
GGAATGTATCAAAAAACCTATCTGCAAATTGAAGAAAGCAATTTGAGTCACTTCAAGCTC
TCCCACCATCTCCACTTTGTTTTTCCTTTCAGGGAATGTGGGTGTTGATGATATAACTAT
TAGGAAAATGCTGGCTACTCTCAGGACTGCTAGTGTAGACCCTGCCAGAGATAAAGATCG
AGTCTTCATTTCTTAAATCAAGAGGAATGTCAGCACCAAGGCCCTGGCCCCTCAAGTCCT
AAACCCACCTATTTGGCCTGAAGTGGAGCTGTAGCATTAACGCCTAGGGGAAAGTACAGT
TTGAAAGATTTGATTTCTTACTTTGATTCCCCATTTACCTTAATGAAAGTCCTGGGATC
CTTCCAAAAACCCAGAACGTGACCATCTTGTGGCCTACCTCCCTCCTCACTGTCCCCTCA
ACCCCAATCCCTACAGCAAAAGCCTTTCCCCTGTCTTCCCACTAAGATCTCTGTTCCAAG
AAACAAAGTTGGGAGAGGAAGAAGGCAGGCATTTCGCACACACACAGACACACAAGGTGG
AGGAAAAAAATGGTCCATAATTCATCCCTACCAAGTCCTATCCAATTCATGGTGCTCATG
GGTTCCCACTCCTGAGTGCCACAAAAGACTACCCTCTTGGGGCTCAATGAAGGCTTGAAA
ATAACACTGCTCCAAGAGTATCTGCCTTTCTGAATCTCAGCCCCAGCTTGAGATGAGCAT
TGGGCAGTTCCAAGTTACTGCCCTGAGGACTCTAACCTGGGGAAAGTCCATGTTAGCCAG
GCCCTCAAGGTTCTGGGCCAGCCATTTACCCCAAATCCTGACACCTTCTGAGACTGGAGA
AGTCTGGCTGATGGTCTGCAGCCTGTCTGCATTGACCCTACTAGTCCAGAAGTGATATCG
GGCCATACACATAGGACTCCTCATCAAAGTGGGATTTGGGATTGGAACAGAGCTCTGGGC
TTTTAGTCTGCCTTGGCTCTGAATCACTTGAACTTAAACTGATCATTCTTTCCCTTTACT
CCTTCAGAGGTTTTCTAAGAGTTCTGAGAGGGAAAGTAAAATGCTCTTCACTTTAAATTG
TAAAATCATGCACTTAGGAAGGCCGAGGTGGGAGGATCACTTGAACTCAGGATTTCGAGA
```

FIG. 5 (continued)

```
CCAGCCTGGGCAACATGGCGAAACCCCATCTCTACAAAAAATAGCCCAGTGTGGTGGCAC
ACGCCTGTAGTCCCAGCTACTTGGGAGGCTGAGGCGAGAGGATCACTTGAACCTGGGAGG
TTGAAGCTACAGTGAGCCGAGACTGTGCCACTGCTCTCCAGCCTTGGTGACAGAGTGAGA
CCCTGTCTCAAAAAAAAAAGAAAAAGAAAAAGAAAAGAAAAAAGAAAGAAAAAGAAAAA
AAAAAAGAAAAGGGAAAATTACTCGGAGGTTTTTTTTTTTCTATTTGGTCCCTGTAACG
TCTATGGTTTTGTTCATAATTGGAAGGGACTCTAGCCACTGCTGAAGAGACAATGAAGAT
CTTTGCTCTCCCCTCATGTTGCTCATAGGTAGGGCTTGGATTTGAGAGGAGATTCCAATT
CTGGAGGCTACTGTGTTGAAACTGACACCAGGGGAAGCTTAGAAGCTTAGAAAAGCTTCC
TCCTGGCCGGGCGCAGTGGCTCAAGCATGTAATCCCAGCACTTTGGGAGGCCGAGGCGGG
TGGATCACCTGAGGTCAGGAGTTCAAGACCAGTCTGGCCAACTTGGTGAAACTCCATCTC
TACTAAAAATACAAAGAATTAGCTAGGCGTGGTGGTGGGTGCCTGTAATCTCAGCAACT
TGGGAGGCTGAGGCACGAGAATCGCTTGAATCCAGGAGGTGGAGGTTGCAGTGATCCAAG
ATGGTGCCACTGCACTCCAGCCTGGGCAACTGAGAGGGACTCCTTCGAAAGAGAGAAAGA
GAGAAAGAAAGAAAGAAAGAAAGAGGAAGGAAGGGAAAGAAAGAGAGACAGAAAGAGAGA
GAGGAAGAGAGAGAAAGGGAGAGAGAGAAAGAGAGAAAGAAAGAAAAAGAAAGAAAAGAA
AAGAAGGAAGGAAGGAAAGAAGGAAGGAAGGAGAATCCTTCTATGAAATCCTTAATTAGG
GCTCTCTGCTTAGGGGATATGTAGAGCTCCCCACCTTTCCCTTCTCTTAAAGAGCAGAGA
GCTCCAAATTCCCTGGCTCCCCAAACTAGTCAGTTGGTGTTTGGGGTTAGGAGAATCCTT
GGAGATCATGCAGTGCTAGCAAGCTTTGTACTTGGGTAGCTGGGTGGCAGATGCCTTGGC
AAGTTTGCTGTCTTGCCCAATTCAGAGAGAAATGACCTCAGGCAACCCATGGCCAGTTCT
GTGGTACCAGGCAGCTCTGAGCTACTGAAGTGGGAGCAGGAGAAGAAATAAAGAATACAA
AAGGCAGACAGCTATGGCAGCTGGATGCAGTTTTAGAGTTTCTGGTGATGCCCTGACTGT
TCTCCATGCCTGCCCCAGGAGAATCCAAAAAGTCAGGCAGTCCGGGACTTGTGTATGTGG
AAGCTCACACATTCAGGATGTTGTTCTGGTTCCAGCTCAATGTCCACTAAGTCCTAAGGA
CTCAAAGCTTGGTCACAAGGGTAGCCCCTCCCAGGCTGAAAAACTGCTGGTCTAGCTCTG
TGAGGCAAGGCCAGGGCTCCCCGTTTCTTAATTTCGAGGTGAACCTGGAAACTTTCCCTA
GAAATGGTGCTTAGCCCCAGAGACAGGTTGGGGAGCTGGGAAGAACCATGGGAAGCAAA
CCCTGGTCTCTCCATGCCCTCCACCCTCTCAATAACCTGTCCGGCCCAGACCCAGCCCAG
ATCTCCAGCTGCCTTGGGTGGGGGATGCAGATAGAGATTGTGGGGCAGGGGTGCTCTCT
GCCCTGGAATTGGAATCCCCCACACCAGTCTACCGGTAGATTCTGCTTCCTTTGCCCCTT
TATCCTCCACCCCCATCTGCATGGTTTTTCTAGCCTCGGGAATCACCTGCCCTGGGAGTG
CAGGCCAAGCTTTGGACGAGGGAAAGCACAGACTGACGCCGACCAGCCCATCCTCCCCGG
CCTTGCACTGCCCGAGATCCGTGCAGGTCAAGCGGGCAAGGTGGGACGCTCTCAGGTGGG
AGAATTCATAGGAATTAAGGGGAACCCACTAACTCTTCATCAAGACTAGAGGCCAGCCTA
AAGAATTTTCCCCCTTTTTGTCCCAGAGACATTCTTTCCTTCCTTCTGCGTGTGTAAACA
CACCTGGTCGGGCAGATTTTTCAGTAATCCCAATACTGAGTCACCTCACCGGCCGGGGTT
TACTCCCCAGCTCCTGGATGGTAAAGCGCCCTGCGGCCCGCGGGTCAGGTCTTTAACGGT
```

FIG. 5 (continued)

CCAGCCAGCGCAGCAAGAGAGCTGGGGAGTCTTCTTGCAGTCCCTTCCTCCTACTCACGC
AAAGATCTCCTCTATGCTGGTAGGTGCACCTGCCCTCCACCGATCCTCACCCTGAGCGCA
GGTCGTACCTCAAGGCGAAAACCCGCTTAGTGCGTTGGCGGGTGGAGAGCTGCCGCCTTC
TTGATCCGGGACTGAGAAGCTGCACTCCCTGACGCCACTGTGGCCAGCACCTCGGCCGC
GCAGACCCCTACATCTCTAATCCCATAGCCCTCCAGGGGTCCTTGGGGCAGTCCCTTTGG
AAAGTCTTCGAAGTGCAGGGTACTTTAAGTACCCTGTAGACGCCTTTTATTTAATCCGCA
CAACAAAAGAACGGGGCAGGAGTGGGGGGAAATTGTTACTTCCGTTTTGTAGATAAGAGA
ACTGAGCCGGGACGGTGGCTCACGCCTGCAGTCCCAGCACTTTGGGAGGCCAAGGCCGGC
GGATCGCTTGAGCCCAGGAGTTCCAGATCAGCCTGGCTTGAACCCTGAATTTCTGTTGAA
TCCGAAGTTGGATGGTGCAGTGAGCCGTGATTGCGCTGCTGCACTCCAGCCAGGGAGACA
GAGGGAGAACCAGTCTCAAAAAAGTAAAAGAAAACAAGAAAGCTGAGGTTTAGGAGATAA
TTTGTCCAACTTCTAGAGGCAAATCGAGGCTTTATGGCACCAAATCCTGATTCTGATATT
TTCACTTCTCTTCCCTCTCCAAACACAAATCGTTGACACATTTTTATTTTATTTTATTTT
ATTTTATTTTATTTTATTTTATTTTATTTTGACACAGGGTCTCATTCCCTCACCTAGCCT
GGAGTGCATTGGCGCGATCTCGACTCACTGCAGCCTCGACCTCCCGAGCTCAAGCAATCC
TCCCACTTCAGTCCCCTCAGTAGCTGGGACCACAGGCACTTACCACCACGCCCAGCTAAT
TTTAAAATTTTTTATAGAGACGAGGTCTCGCCATGTTACCCAGGCTGGTCTCAAACTGCT
GAGCTCAAGCGACCCTTCCACCTCAGCCTCCCAAAGTGCTGGGACGACAGGCATGAGCCA
CTGCAACCGACCATGACAAATTTTAAAATGGAAATAAATTTCATTATATCTCATTAGTAT
CTCAAACTAATACTAAAAACAGACTTAAGATATTTGGGAAATTATTAAAGGGAAAAGGGA
AAAATTAAGGAATTTGGAAAAATCAAAACATGAACTCTAAAATAAAGAAACCCGGCTGGG
AGTGGTGGCTCAAGCCTATAATCTCAGCATTTTGGGAGGCCGAGGCAGGTGGATCCTTGA
GGTCAGGAGTTCAAGTCCAGCCTGGCCAACATGGTGAAACCCCATCTCTACAAAAATAAA
TAAATAAATAAATAAATTAGCCGGGCGTGGTGGCATATGCCTGTTGTCCCAGCCACTCGG
GAGGCTAAGGCAGGAGAATTGCTTGAACCCGGGTGGCAGAGGTTGCAGTGAGCCAAGATC
GTGCCACTGCACTCCAGCTTGGGTGACAGAGTGAGACTCCGTCTCAAAAAATGAAATAAA
ATGAAGAAAACCCTTTAATACACTGTCATCTTTTTTATCAGTGCCCCCCATGACTTCTAA
AACTACAAAAGTGGGAACCAATTTCTGTCCTCTTCCTCCCACCCCATTCCTCCCACCCTG
TTTTACTTTGGAGGCTGAGTCCACATGAGTAACAAAGGAGCTATACCTGGCAAATGTTCA
CCTAGAGTTGAATTGTGGGAGGCTCAAACTCCTCTAATGGCTCTGTTACCCACACTGACA
GCAGAAAACTGTCATGTTTGGGTCAACAAGCATGGTTGGGTCAACCTGGTGCCAAAACAC
CTTCCAAGCCTGTCCCTTCTATGGGGAAAAAATGGGTATTTGGTGGGCACTGAGGATT
CTGAATTTGATTTTATGGGTGGCTCTCAAAGCCTCACCCTTTAAAATTGAGGGTGAACAT
TGGTGTACATGTGTGGTTTTTAGGACATGAGCCTACTGCTTTATTCTTTTCTTTTTCTT
GAGACGGAGTCTCGCTCTGTTGCCCAGGCTGGAGTGTGGTGGCGTGATCTCGGCTCACTG
CAACCTTCGCCTCCCGAGTTCAAGCGATTCTCCTGCCTCAGCCTCCTGAGTAGTTGGGAT
TATAGGCACACATCACCATGCCTGGCTAATTCTTGTATTTTTAGTAGAGACAGGGTTTCA
CCATGTTGGTCAGGCTGGTCTTGAACCCCTGACCTCGTGATCCACCCGCCACAGCCTCCC

FIG. 5 (continued)

```
AAAGTGCTGGGATTACAGGTGTGAGCCACCGTGCCCAGCCTATTGATTTGTTTTCTAATG
GCAAATTTTACAGATACAGAAAAGTAAACAAAAAAGTGTAATTCAACCCCTCATACCTAT
CACTCAGCTTCAACAATAATCAACTCATAGCCCATCTTATTGCATTTCTTTCTGGAGGTT
TTTTGTTTCGTTTTGTTTTGTTTTGTTTTGTTTTTTGAGACAGAGTCTCACTCTGCCTC
CCAAGTAGCTGGGACTACAGGCGCCCACCACCACACCTGGCTAATTTTTTGTATTTTTAG
TAGAGACAGGGTTTCACCTTGTTAGCCAGGATGGTCTCCATCTCCTGACCTCGTGATCCA
CCCACCTTGGCCTCCCAAAGTTATGATGAGCACCGGGCTCAGCCTTCTTTCTGGAGTATT
TTAAAGCAAATCCCAGACTTCTTTTCTTTTTTTTTCTTTTTTTTTGTTCCAAAATTCTTC
AGTTTGAATCTTTAACAGGTTTAAAAAAATTTTTTTTTGTTTTTAGAGATGGATCTTGCT
CTGTCACCCAGGCAGGAGTGCAGTGTCACTGAAGCCTTGAACTCCTGGGCTCAAGGGATC
CCACGCCTAGGACTACAGGACTACAGGCATGTGCTACCATGCCTGGGTACATTTTTTTTT
TTTTGGTCGAGACGGGGGTTCCCAGATGGGTCTCAAACTCCCTTGTTCAAGTGATCTGCC
TCTTTGGCTTCCCAAAGTGGTGGGATTATAGGCATGAGCCACTGCGCCCAGCCTAGTTTT
ATTTTATTTTTTGTAGAGACAAGGTCTCGCTTGTTGCCCAGGCTGGTCTCTAAACTCCTG
GCCTCAAGGGATCCTCCAACCTTGGCCTTTTGAAGTGTTGGGATTATGGGCGTAAGCCAC
TCTTCTTTTGCTTTTTTTATATATAACCTTTATGTGATTGTCACACAGGACAAAATTGAG
AATAATTCCTTAATACTATCCATGTTTGAATTTCCTAAGTTTTCTCAAAAATGTCTTTTT
ACAGTTAGTTTAAGTCAGGATCTAAACAAAGTTCATACATTACATTTGCTTGATGTCTCT
CAACTGTCTTATAACCTATAACAATTGCTCCCAATCCATTTTTCATGCCATTACTTTATT
TAAAAACCTGGGCCAACCCAGTTCTCAAAAGGTATTGGACATCCTCAGAAAAGATGACTG
CTCTATGTTGAACCAAACAACTGATTCTTACAGGTTTCTTCCTCACTTGTCCTCTGGCTG
TGGCAGCCAGATATGGACAGGAGAGCTACATCCTTCCCTCCACTCCCTGCCAAAGAAAGG
AGAGCTGGGATAAGCAGTGCCCTCCCCTGCCCACCCACTATGTCACTTTCTGACTCCCTT
TGGTCCCCTCATTGCTCTTGGAGTGAGAGACCTCATTCCTTCTCTCACTGGAGGCAGCCA
AGAATGGGATCCTCTGGTGGGTCTTTGGATTATGTAAGTTTCAAACACTGGATACACAGC
TCCAGATCTAAAGGCAAGATTGCTGCTCTAGAGGCAGGACTGTTCATTTCCTGCCTTGGG
GATGCACCCAGAGGCCTGAATGCTTCCCAAGGAAACCAAAGAAAGAACATGGTCTGTTTC
AGAGGTGGAGTGGCCAGTCTAGCTCTGCCATCTCTCACTCCTTCCTGCCTTTAGGGTACC
ACTGAGGTGGAAAGCCTGAACTGCTGTCTCTGCTCTGGCTTGTGCTCAAGCTGTGTGTCC
TTGGACTGGCCATCTCCTCTCTGCAGCCCTCGGTCTTCTCATTTGTAAAATGGAAGTGAT
CCTCTCTGCCCATACTTCCTTACAGGGCTGCTTGGAGACAATCAATCAAGATGAGGGAAA
TTGAGATTCTACAAAGAGTGTGATGCCTACATAACAAAGTATTGTTTTTCTCACAGTTGG
TGGTATTTGAGGAGAAGGTGAAGATTTTGGTTGGAAGAGGGACCAGCAGACAAACTTGTT
CTCTTGTGTATAAAAAGCCATAACACGCCCACATCCCTCAAGCTAGGAAGAAACCTGGG
CTGGATGGTGACCCACTGGAGAAGCTGTGACATCCTAGCATGGGGAAGAGTACCAGGATG
CCCACTCCTCTTCCCCAGGAACCACCAAGGAGCCTGGAGCCTGGCTTTATCTCAGCCCTG
AGTCCCCCTCTCCCGGTGCGCACACCCCTAACTTTTTTTTTTAGATGGAATCTTGCTCT
GTCGCCCAGGCTGGAGTGCAACGGCAGCTCACTGTAACCTCCACCTCCCAGGTTCAAGCG
```

FIG. 5 (continued)

ATTCTCCTGCCTCAGCCTCCCGAGTAGCTGGGATTACAGGCGCGTGACTCCATGCCTGGC
TAATTTTTGTATTTTTAGTAGAGGTAGGGTTTCACCATGTTGACCAGGGTGGTCTGGAAC
TCCTGATCTCAGGTGATCTGCCTGCCTCCACCTCCCAAAGTGCTGGAATTACAGGTGTGA
GCTACCGCGCCCGGCCAATCTGGGGCTCCTAGCTTTGGTGCACCAACTACTCAAATCCCC
AACTTCTCTCCAAGAGGAATTTCAAGAAACACTGACCAATCTGGTTACAGAAGCTGAAGG
GGCCCCAACCAGGCTGCAATAAACCTGCTTTACCCTTCTAAGCTGAAGTCTCTCTTGCCC
AAAACTTTGTTCTCTGGGACCTGGTGAGAGGGTGACTCCGTGAGTGCAGAATGCAGTGCA
GACGTTATTGAAGAGGCCTCACATTTTTCATTTCCAGACTACACCTAGCTCGTAAGAAGC
CAGGGAATATAATAAATTCTCCCCTGCAGGACCTGGTTTTAATTAATTATTGGGTTATTC
AAGGTGACTCATGTGTGAAATGCAATGTGCACTCGTAAACTGAATCTCACATAATCCATT
CTAAGTAACTGGCTGCGAGCTATCCTCTCCAGAGACTTACACAAAACTTATATTTATCCT
TTGAGGGTCTTGGGGCAAAATGTAAGGGTGACTTCAGTTTAAAGAGAGCTCACTTGGCTG
GCTAGGGGTACTAAGAAACTGGGTCTTGTTTTCTCAACTGCTGATTTGATGAGGTTTATT
TCTTAGAACATCTGGTGTTTTATATGTATAGTATATATATAAGATATATGTATACGTGT
ATACACACATATACATTTATATATTTTAGTCATTTGTTTTGCAGTATCTGCAAAGGATAT
GTGAAGCCAGCTCATTGCAGAATAGAAATTGATGCTGAGTTTTTCTACAGCTAACCTGGC
AGCTGAAGCTCCTCCTACTGCCAGGACCTCTGAAATTTGGTCTTTATCACCCACGATCCA
TGTTCATCTCACATCTCAAGGTCTCTCCTGTACAGCGTGGAATTGCTCTTGTCTGGGATT
TATATTCCCTTCTGTGTAACTTAAAAACTCCAGGCCCCATATCTTCAAAACAGGCTTCTG
TTCAGAATGGGTGTGAGTCTCCCGCAAAGAGCCATTAACACTGCAGAGCCTCTTGGTCTG
CAGCATTAGGGAGTCTACATTTTTGAAACCATTTTGGGATGGTAGGGTTGGGGGCTGAGT
CTGTTCATGTAAACAGGATCTGGAAATGGTGAGGGAGTGCATCTGGCTACTCTACATAGC
TCCACCTGTTTGCCAGGTGCCTTCTCCAGACCCAGGCAATGCAGAGGAGGGGGTTGGGTG
GGGGAGGGGAAGGGATCCAAGGGAGACTGTGAGCCCCCTACCCAGAGTTCAGCCAGAGAA
GGAAAGGGAGACTCTGGCATTGCACCTGGGTTCCTGCCCCAGAAAAGAGGGTAAGATCTG
ATTTTTTTTGGCGAAGGAAGGAAGGAGAAACTGAAGGAAGAACGGGATGGTTTATTTTCT
CTCAGTTTTTGTCTGACCCCTGGGTTGGAAGTGGAAGGCTCTGCTAGGGCCCTGCACTA
AGCCAGTTCTGAGCGGAGGAAGCCTCCAGCTTTTTTTCTTCCTGGTTTTCTTTTCCCTTT
TGCCTCCTTTAATTCCCTTTCTTGACCTGGAAGCCAGACATTTTTTTTTCTAGGTAAAAG
AGAGGCTAGATTCCAAATACCCCCTCAGCTCCCTGCAGACCCTGGAACTCTGTCCTGACT
GGTCCCTGAAGTTCCTCTGGGCCTTCCAAACAGTGGATAAAGTCTGTGTCTCAGCTAGAG
TCTCAGCCTGGAATTTCTTTTTCATGCATGGGCAGGCCTAGGGACTCTAAACTTTTGAAA
AAAAATAAAATTTTCTTCCTTTCTCTGACCTACTTGAACTTTCAGTTCCAGGAGGAAGGA
AATAAATGTGATGTAGTTTCAAAGTATGTGGAATTTAATAAATGCAGGCCGTGGAGGGT
CACTTTCCCCATGAAGACAACTTTATCTGCCCCACTAGGCATCTGAAACAGTGCCATCCG
AAACAGTGCCATGCGAAACAGTGCCCACAAGCACCCACCTGCAAAAAGACACAGTGACGG
AGCAACAGCAGCTGCGTCCTTACACGCAGATGAGCTGATCCAGGCTTTGAAGGAGCCAGT

FIG. 5 (continued)

```
TAACCAGAGATGGGTTAATTCCTTTGCCAGACCAGAGGTATTGAATCCAGAGAACCCTCA
CTCCAGAGAAATGGAAGAAGTCTGTGACAGACAGGCAGAGGGACAGAGGGACAGATGGGA
GCTCACATAGGGAAAAGAAAAAGGATGAAAATTGTAGTTAAAGAAATCAGGGACTTTCAG
GGCACGCAGAGCAGAGCTGATGGGAAGTCCCAGAGAGCTGGATAGGAGGGTAGTGGAGGC
TGGGATTATCCAGAACTTGTTTTAACACAGGTATACCTGGCTCGGCTCAGCACCTGCTAG
GTTGGCTTTCTAGGATGACAAAATAACCAGCCAGCCCTGCCAATTCTGGGAGAAATCAGC
CAGAGCCATTGTTTGGCTTGTCTTCGACCAAACAATAGTTGATTGGCTGGAATTTTCACT
TTCCCTGAGTTGTTAGCTCCTGTAAGGAGCTGGTCAAGTCCCCTTGCCCTTAGCTAAGAG
TAGACCCCAGCCCCTTCTCTCCCGGCCAAGAGCTGATCGACCTGTCAGTGCAGGAAAATC
TCTCAATTACTCACCTCTACCGATTGAATATTGAGAGGGAAGTGTTTTGGTTTGTTGCTT
GTAAACAAAACAATCTAGAGTGATCCAGAAGTTTTATCAGCTCTAATCTCATCTCTTTCA
TCAAGTTATAGGCCCAGAATCAGGACTAGAGACCCACCCACATTTTTAAAGCCCCAGACA
GCCTACACGTTTGTGTGTGTGTGTGTGTGTGTGTGTGTGTGTGTGGTGTGCGTGTGTT
TGGTAGCCTGTATAGGGAAGTTTTTATTTTTATTTTCATTTTCATCATTAGTCTTATTCT
TGGTTATCTCTACTTGTTTGATGTGACAGAGCCACAGCTATATTCACAACAAAGAAGGCT
GAAGCATTTGGGCAAATACTCAGATTCTAATCTCCGCCCCAACCCCCCACCCCTCCATTT
AGCCACATCAGTCAGAGGGCCCCCCGCCAGGGGAAAGAGAGTGGAATGGGGGATTGAGAA
ACAAGATTCCAAGGGCCGTGCTTGGCTGACAGTGGTCTTTCCTTCTTTTAGTAGTTTCTT
TGGAGGGACTGATGAGGGACAGCAGAATCCCCAGGAAGGGAGTGGAGGAGGTGAAATGCT
GCCATCAGTGAAATGGAGAAAGAAGGAAAGCGGAGGGTTTGCTGGTTCCGGGGGGGAGTA
AATCAGTCGCTTTATAATTCCACGATGTTTGCATCATTTTGGCTTCTGAGAGGCTGCGTT
TTGAGGAGACACCAGAAGCCTGGGAAGTTCGCTTACTGGTTCTCAAGTCAGAGTCCCCCT
TCCCGGGGCTCCTTCTGGGGACTCCGGGGGAGAGGGATCTCTCTGTCCATCCTGCAACTC
CTCTCCTGGCATAGATGCCCCGCACCCCCACCTTGGGCCATCCTTATCTGCCTGTTCCCC
ATCACGATTGATCCTCCAGGGTCGCCAAGGCTCCTGCTGACTACAAAAACATCCCCAAGA
TTCCCTTCTTGACCCGGTTCAGGCATATCTCTTTATACTTCCATGTCTCCGTTTCTCTAT
ATTTTTACTGTGGAGGACTCAGAAGAGAGCTGAGGCTATTGTCCGGGGAGGAAAGGAATT
CGGGCAAATTTGTGGGTAGGGGCCCAGACCCAAGACCCGTGTTTCTCCTGCGTGGGTTGG
AGTCTGTCTCAGGTCGCTCCAGGGACATCAAGAGCCCGCGCCGCCGAGAGCCCGCGCCGC
CGTCCAGCGGGAAGCAGCGGACCCACAGGGGCCTCCAGCCGCCTCCCCGCTCCCGCCCCG
TGTTTCTCCTGGGCCTCCAGCTCCGTGGAGAGAGCTGAGAGTTCTCGGCCCGCGGGCTTC
CTCACCAAATCCCCAAAAACCGACGCAGGCACAGAGGGCTGACTGTGTTTTGAGTAATGC
ACGCGAGGCAGTCCAATCCGGCGAGATGGCCCGAAGCGGGGCCCAGCGGTCGGGGGTGTG
GGTCTGGAGAGAGAGGGTCTCCCCACTTCCTTCCTCCGGCTGCTCGGTCACCCATCGACT
ACCCGGGCGGAAGCGGGGCGCAGAGGGGCGCAGAGGGAGGCATTGCCCTCCAGGAGTATC
TATTCCCATCGGGGTATGGTGAATGCCATCTAGGCCCATGCTCCATTCCCAGGGCCCCCT
CGGTTCCTCCAAAGGCGTCCACCCAGAAGCAGCCCCAGTGTCGCGCATTGACTCCCGCCG
GCCAAGTCGCCGCCGAAACAGGATCTCCTAAAGCGGGCTCCACCGGGTCCCAGGGCGAAA
```

FIG. 5 (continued)

AGGTCCGAAGATCTACGCTGTCGGAAAGACCTGGAGAACTCGGGAAGCCCAGCAACAACA
AACAGGTTTCAACTTGGAAACAAACCATTAAAGTTTGGCTTAGTTTTTGGTGTGAATGGT
GCAAATAATTTCTCCTCTTCACTCTTCAGTCGATCTCAGCTGTATAGAGCTGCTCTGCAA
GCTAAAAAGAAATTAGTATCTATTCCCCCGCCAACAATTTTTTTTAACCCGGGCTACC
AGCTTAAGCAACTGGTATCATTCTTGTTGAATTAAGCTCTGAAAGCTCGCCTCAGAAAAA
AAGTTTTTATTTTAAAAAACGAATTATTAAGTCGGCAGTCTGATTTTTATTGGTTTTAAT
TATCTGAGAAAACTCTGCCTTTTAGTTGTGATAACGAGTATGTAGAACAGACCTTAATAA
GCAGAAATGTAATTAATTTAAAATCCATAGTAGTTTTATTACCTACATATTTAAAAACAA
ACACTACTAAAATAATTTCCCGATTTTAATCTATCTTTAAAAAATAGGGGCCGGTGTAGT
GGCTTACAACTGTAATCCCAGCACTTTGGGAGGCTGAGACGGGAGCATCTCTTGAGCCCA
GGAGTTAGAGACCTGCCTGGGCATTAGAGTGAGAACCCCAGTTTCTATTTTTTTTAATAA
AATAAAGAAAAAGAAAAAATAGGTAATGTATGCTAAAGGAAAGAGTCAAAAGTTACATTG
GGGACATACATTAAAAAGTAAAATAGGTCTTCCTCTCACCTCTTATCCCAGCTTCCCTTC
CAAAAAGCAACTACGATTCCCATAGTATCCTTAGAGAAATGTATATAAATAAAAATTTTT
AAGACAAATGACAACATTCCACATACCGAGCTTTATATTTCGCCTTTTATTTTAAAAACT
TAGTGCAACTTAATGACGATTTTATATCTTTACTACTGCCTCTTCCTTTATAATGGTTCC
ATTTCGTTTTCTGAATATATCTTAATTTATGTAATTAGATGACAATTGAGAAATATTTAG
ATTGTTTCCAATTTTATTTTCTTCTTTTTTCTGGTGGTGCACACAATATACACTATTCTG
TGTATATGCAAGTATATCTGTATGATATATTGTTAGAAATGGATGATCTCAAAGGACTTG
TGCACTTTAAAATTTTGAAGTGGTTGAACATATTTGCAGAATTACAAGCAATTTGTATGT
TCTTTTCCAGAAAACTTTGTTCATGTTTTCCCATTTTCTGTTGTTTTTCATTGTTCTCGT
AATTTGTTTTTATCGTATTTTGTGTTTCGTTGTTCTCATAATTTGTTTTCATGGTATTTT
GCTAAAATGTAAGATTGTGTTTCGGTTTGGTTTTGTCAATAAAAGTTATGCTCGTGACTA
ATGTAAAGTCTCTCCGTCTATACTTATTGGAATTTTCCAGACAATTTTTCCTAGAGATGG
AGGACAAAATGGAGGGGATGCCGAATGTCGACTATTGTCAGCTTAGATTTTTTTCTCTTA
CGGAATTCCGACCTTATTGAAAAAAATGAGGAGAGGTTTGTTTTGTTTCTTAATCATTTC
TTCGCCATCTCTGACTCTCTTTAAGGTTAGAAGACACGGAAAAGTTCCACATTGGGCCGG
GATGGCAAAGGCTGGATCACTGCAGAACAAAGACCTCAGTCCTCGCATCCCCACCCCGAC
CCCCGGCAGCCTCTTTCGCTCTAAGCCTCAGCCTAGGGCAAACTCCCCTCCGCAGGTCAT
CAGCCTCCCATGCCTGAGCCTCACGGAAAACCACTAGAAGGAAAGTAAGCTAGGGTCTAA
GCTGTAGCCCCTCCAGGCACCTGGCTTGTTGACATTACCCCTTCCTCCCAAGCAGAGGGG
TGTCGGTCAGGCAGAGGGTGTCGATTGCCTTGGCCTCCAGTTCCCAGTGAACTAAGAGA
AAGCAGCTGGTCCCCATTCCCAGCTCCTGGGACCTAGTGATCGCCATGAGCTTATGTATG
TTCCTTGGAGGACAGGCGGCTGCTTAGGAGTGGGACAGTAAGGACTAGGCTGGGTCTGGA
GGGCTGGCGGGGCAGGAGTTGGGGGCCAGGTAGGAAAGCCAGGGGTCGAAGGGATCGATT
CTAGGGGCCGCAGAGGCTACTCTCGTGCTCTGGAGAAGCACCGCATCTTTCTCCGGACCC
CCGCGCTCAGCCAATCGCCCCAAAGTCTCCAGGTGGGGCTCCGCATTACCAGTCTTGGT
CGCAAAAGCAGCCCTTTCAATCGCACCGAAT

SEQUENCE LISTING

<160> NUMBER OF SEQ ID NOS: 5

<210> SEQ ID NO 1
<211> LENGTH: 108211
<212> TYPE: DNA
<213> ORGANISM: Homo sapiens

<400> SEQUENCE: 1

| | | | | | | |
|---|---|---|---|---|---|---|
| cagatgaacc | gttcgttagg | agcagcgagg | tagtcgtgag | cgctgagatc | cagagactag | 60 |
| gacccactcc | ctctctgagc | agcaaattgg | gaagaagatg | ctcactcggt | aagggcgagg | 120 |
| gagcccggca | tggcgcccca | ccacgggctc | ggtctatctg | cgcgccaaga | tcccgcttgg | 180 |
| ggcgaggcgt | tgggtcagcg | tttagagcca | ctccctgcgc | tggtggctgg | acatagcctc | 240 |
| cctatcccac | ctcatcttcc | cccatccccg | acagaggagg | ttgtgaatct | acaggccctt | 300 |
| gacgttgagg | cgtcggaggg | cgcacctttg | taattgcggc | ctcccttcgc | cccttaagtg | 360 |
| ccgcttctgg | gcgcctaggc | tggatatgaa | agccccgttc | ctaatcctct | gctctggtcc | 420 |
| cctcctctgg | actgctggga | ctctaagcta | ggccctcccc | aggttccatc | actgcggcgc | 480 |
| caacccgcgg | ctgggctgtc | cgcaagaggg | agttgaaggc | gcgcggaatc | ccgaggtgca | 540 |
| gctgaccctc | ctctcaacgc | cgactctgcc | gctcccgccc | ggccacctcc | ctgtcgggca | 600 |
| gacttcctgt | tctcctgctc | acagcaggga | ggcagtcgcc | gagccggtca | gcagcgtgca | 660 |
| cggagatctt | cactctgcgc | ccagccccgg | gacacaggtg | cagatctcca | gcggagcact | 720 |
| gcggagtgcg | cgccgtcgag | cactagggaa | tcctagacgg | aggacttggt | ccattccacg | 780 |
| cagtcccagg | caggtccgca | gcggagggac | gcagcggtct | ccaactcctg | gtcacgactt | 840 |
| cggcgaccct | ccaccccctg | agagacctgg | tcccacggag | ctgtcccccc | aggagccgca | 900 |
| gcgggaatag | caaagcaaag | gggaccactc | agccccagg | aggagccctg | aagcaaaaag | 960 |
| gttgctgcgg | ggagccacgt | tccctctggt | tcacctcgaa | gcccaggagc | tccggtccct | 1020 |
| ggaccaagga | gtgaacagac | ctgaggaaga | ggtaagagga | ggtttaacga | gtaaaaattt | 1080 |
| ggactctctc | ctcttatact | gctttaaagc | atgaggaatt | tgggccctga | cttctctctc | 1140 |
| cttgaagaag | tttctcgcgt | tctggccagt | ccttgcgtgt | ctgcacccag | ggccggcaac | 1200 |
| aatttaagga | ggaactttac | tgggtggtcg | aggcttgaga | gttcatagtt | accttttaaa | 1260 |
| aaaatcatta | ctattactta | atatctaggt | tattttggac | tgagccccca | tcttcgctcc | 1320 |
| agcccaaatt | cggcctttaa | cagtactagg | gagtgcttca | aaagaggagg | gtcgtggagg | 1380 |
| aagcgactca | gacggcccca | agaggagaga | tgggaaggag | tgagggcttt | ggccttaatg | 1440 |
| atctctgcaa | gttaaaggcc | attattccta | taactacagc | tggggaaagg | gcagaggagg | 1500 |
| taaggacgga | aagtgggctg | agggtggcca | ctttggcatc | ttcttgagaa | aggagacatt | 1560 |
| tgaattcccg | gcccaactaa | aagccctgag | atgcttgccc | tttgctttac | agacagtgat | 1620 |
| ggcaaagaaa | tactgccacc | agggtgtttt | taaaggtgaa | ggttgacctg | ataagcactg | 1680 |
| agatcagaca | aaggaaaaaa | aaagtaaagc | atttggtctt | tcagttttct | ggctaaatct | 1740 |
| ggcatcattt | tccagacaca | aacttctctg | attaatccaa | atagctctca | acctgaagtt | 1800 |
| caaggaattt | gaaatcctct | gaaattgtgg | gatttcacag | ttctaaaagg | aagtcagctg | 1860 |
| tcactttctg | agaagccctg | ggaggggaag | gaagcaagag | gaggtatatg | aggaaagggg | 1920 |
| gtgagaggcc | ccagatctag | ctctctagac | atttagtgct | ggaccccaa | gctctgaaac | 1980 |
| tcaagctgac | cccatctaca | cattgccaaa | ctgagtagaa | agttgcaagg | cagtcaagga | 2040 |
| gataaatttt | atttactgct | ttaaggatga | gtttgggtgt | ctaagcagat | tataaatctg | 2100 |

```
ggtgttttca gtatttgttt cttttctttca actattactg attttttggcc cagagtagtt    2160
tctgggccc ttggggcagt taggcaagag agggactcag acctccagtc ccttgatctc        2220
gcctttactt ggtgaagagc ccaagattct ctactggcag gcaaggtcag aaccaagttg       2280
gccctaggcc ttgccccaac ccccagccc tcaggactcc tttctctgag accaggcctc        2340
tggccaaact gcagactccc tccacacccg gtcactggaa taatgatggc atttttgatt      2400
tctcccattt ttgaaaacta tagaagcccc aaggaggaag gaggtaccac tggatcttgg       2460
ggtgctggtg ggggattctg gaatcaaata tcctctaagc ctgtgaggac aaggtctact       2520
aggatgactt ggtgtcaatt acagctctga gtgctgcctg gataggtcaa atattccctc      2580
cttccctcc tcattccttc cgttcaagcc cagaaaattc acagattttc tgtgtggaga        2640
gagagaaaaa aaatgggcaa aacctgggag taaaagggag atgagggaga agaaaatgag      2700
ggagagaaac caatagacta aaacaatgaa actctctaac ccaacagcac tttaagcttg       2760
acttttaatc tggccagaaa aaaaaagaag ttggaggcag ggtgggtggg atgtgaagtt      2820
cccagcccaa cagatcctcc tgttgtcacg ggctctgtgc gttcccagct ggtgagaacc       2880
ctgtctgtcc tggggtggg agggatgtcc tgggtctttc aagttgcagt gtggggagtg       2940
aggctctttc taagggtctc tgaggtctcc cacaacacct tgcttggact agcaaaacct      3000
ttctttgcat ttcctctggg gcactgtgta tgtgtatccc tgtgtagggt ggtgttctaa      3060
accaccgcag aaggtgagca attctcctcc cagcgagcca aaggctatat gtttgggtg       3120
gaggaggctt catcccttct ggactggaga aatgggact tggagccaag tgcgccagac       3180
tttagggaaa gagaggagct ccagctccaa aagggatttg gagggaagat cctatcagga      3240
aaggcccccc agacttgctt cctcaaaggg ttagggaagt gcactgagaa aagagaactt      3300
tcacttaact cttctccatt aggcatcttt gtgcttccat ttgtactgga aagcacagtc      3360
ctgggcagtc agttgcacat tccgcctctg gtatgtggac tatgtgaaat ataccatgca      3420
atgttctact ttgcgagggg ggaggcatat agatgaaaat atgaatttcc cttctactgc      3480
ctttattatt gagcacagtt gggagcacat aatttcacat ctctttcgca tgtctgtata      3540
aatcctcaat ctttaaacgg tgcttgacta ctccgagagg cacagttgct gtcatataag      3600
attcctagcc gactccggcg agttactaat tcctctcaga ctccacaata cccacgatgc      3660
acgatgcaca cccctttatg cttgcttttc tttacatgcc ttttcaaagg cgaataattt      3720
ttgtattgac ccatgagtca gtccatacag tttgaaatcc tttggatgcc ctctgcccac      3780
tcccataaac aacaggtccc tccacaaaaa tgcacatgcc ccgttttgt gagtgtgggt       3840
ttcaaataag atggcgtctc ctggcattcc ttagattcag atacacgctc tctcaggcag      3900
gaggctgctc acagtccaga ggggaagaaa acctatgagg cccccaaaag ccaaagcaag      3960
agactccccc aagtattctg cccccctccac gccaggaggc agctagagag acagcgcgcg     4020
ggagagctga ttctgcacct tggggagctg ggggcttctg tctagaccaa gagttccagg      4080
ccaattccta atttccgtta ggaaaagtgg cccttcttcc atcccaagcg attcctcacc      4140
cccaaggctg ctcagggcgt ctggccctg cctctctcac ggcatccgcc tggaatccgg       4200
ggttgtgagc aggaggccca ggacgcaggg cctcaggctg ggcggggcac tgagcactcg      4260
gctctgggga gccagggttt ccggtagaac gaggggaggc gaccccctt ccccacacac       4320
acacctgttg gagaggtagg gtcgggtgcc agcggacagg gaggcaagg cgttttcggg       4380
tgcgccccga ggccctaccc gggaagctgc ctcggtctgg agatcaaggt taagccggtg      4440
```

```
gccccgggaa gcccacgcct gccacgggcg gttggtcctg aaagctcggg ccacggggct    4500
gcccagcttg gagaggggcc tttcacgccg cagtccccag ctgcgagagg aagggctgcg    4560
cccgcctcct cacctacctc tcggaaccac gccgtccccc gcgcgtcttc gtagactgca    4620
ggagtccagg gcgtctgggg actgtgacgg cgcccaaggc gggggatgtg gcggctctgg    4680
gtcgccgcct tctgcccccg cctctgtgag gcctctcgag gcagtgtctg tgtctggggc    4740
agcgacgccg acgcgctggg gggcgcgaag gggctcacgc tcctgcgttc ccctggcgcc    4800
ggtgagtggc gggcgaggac agggtccggg aggggatag gcgagagcgc ttcctgcctc     4860
cgcccgggcg gggctcggcc gtctcacctg cccccaccca cggcgccgtc ggatcccaga    4920
gcggctggtg aggagatggg cctggcgcgc gcgggggagg ccagaggcgc ggaggagcag    4980
cgcccagatg gccggagaga gcagagagag agagaagaga gagagaagag agagagagag    5040
agaagagaga gagagggaga gaggcagaga gggagagagg gagggagaga gggagggagg    5100
gagggaggga gagagagaga gagagagaga gagagagaga gaatatgaga atatgagaat    5160
ataaaaggca agagagaagc agatccaagg gcgcgcccag agaaacatca aatgcacaaa    5220
tagacaaaag aggtagagga gaaagctgag tcccaggggc tgaaagaagc catgggcgtc    5280
tgaagcgagc gacaagttat ccttgggagt tggaaatgtg agaggagggg gcgaggccga    5340
aggaggctga aaggggagg gggcgctcac accctgggcg ggaggcgact gatccacact    5400
tagggctccg aatccggaga aagagagcgc cggaccctcc tccgcccacc tcccgcccca    5460
gccgcagccc agcgacttcc cgccatcctc ggccaccgag cggctcctgc ctggggttgt    5520
tcgacccgga tggctgcacc aggctgaagg ttgtccctct acctgcctcc tttcttctgt    5580
tccctgtgcc ttacatgggt tcctccctat tctatgaacc cagagggaac gaccttggcc    5640
aaggttagag aaggagcttg aaagtttcac tttccatctt agccctcagg acgcctttgc    5700
gttttggccc ttcgttagcg tgctatcctg gaattgcagg ctcttctctt tatttctgag    5760
acccaaatag aggtttaacc tccttaaaat cagtgaaact acgacaaaca gtggcattcc    5820
tggctgtctg gtctctaagg agtgcccccc ctccctgacc tcagccctga gaccctgctt    5880
cctcctcaac ctgcatggga ctggggacac cccctcacaa tccagtccct tcctgcaggt    5940
ggttgtccag ggggcatgta gaggtgtgcc tgagctctgt gtcctaagcc tggctctgcc    6000
actgacttca gcccccaccc cttctccttt taggcctcag ttttcctct gtaaatggg     6060 cagagtgatt ttacaagtga ttttaccaag tgagaactgt tgaaatatct tactataatt    6120
gtggatttgt ccattctcc tttcaattct atcattttcg gtgcttcata tattttgaa     6180 gctctgttat taggtgtgta catttaaggt tgatgtgtct tcctaggtgt gtaccacatt    6240
tagatttagg attgatgtgt cttctttttt gagatgaagt cttgatctgt cacccaggct    6300
ggagtgcaat ggtgcaatct cggctcactg caacctccgc ctcttgagtt caagcgattc    6360
tcccacttca gcctcccgag tagctgggac cacaggtgtg tgccaccacg cccagctaat    6420
ttgtgtagtt ttagtagaga cgggttttca ccatgttggc caggctggtc tcggctcctg    6480
acgtcaggtg atccgcttgc ctcagcctcc caaagtgctg ggattagagg tgtgagccac    6540
ggctcctagc catgatatgt cttccttatgc tttgcttctg cagcctcctc tcatttgcag    6600
gttctgttga gcttgaaccg ctgagagaaa aatgcatcca aatgggaatt ttattctata    6660
tccacgtaaa catgaatata gaaatatgac aaaactaaat tttgcttcca aaatgttttt    6720
gttttgtttt gtttttgttt tttgtttgt ttgttttttc tgagacagag tttcgctctt      6780
gttgcccagg ctggagtgca atggcacaat cccagctcac cgcaacctct gcctcccggg    6840
```

```
ttctcctgcc tcagcctccc tagtagctgg gattacaggc atgtgccacc atgcgcagct    6900
aatttttgt attttaata gagacggggt ttctccatgt tggtcaggct ggtctcgaac    6960
tcccgacctc aggtgatccg cccgcctcag cctcccaaag tgctgagatt acaggcatga    7020
gccactgcac ccggccaacg cccagctaat tttgtatttt tagtagagat ggggtttctc    7080
cagttcgtca ggctggtctc gaactcccta cctcaggtca tccgcccgcc tcagcctccc    7140
aaagtgctgg gattacaggc gtgagccacc atgcccggcc ccagaatttt ttctatttgg    7200
gtctattttt ctacttttc ttcactttt gttgatatat agtattatag aacctaatat    7260
taaacctctg gctcaatata tttttgcata gatcccatct gtgtaaccac cacctagatc    7320
aagatgtttc cggcttacca gaaggcccca ttgtaactcc taccaatcaa tagctctctg    7380
gtcaatccct ccatacccc taacaattat ttggctttct atcaccatag attagttttg    7440
tctaatcctt caacttcata taaacataag tatgtattct tttgtctggc ttcatctgct    7500
cagtattact tgtgtgggac tcatccatgg tgttgtatat ggcagcagtt cattcatttt    7560
atcattgtgt catattagtt gtatgaatat attacaatgt atttaacctg tttggctctt    7620
ggtggactta agggttattt tcagtttgga gctataatga aaaagctgtt atgaacatta    7680
catctgtgtc ttttgatgga tgcctggact tggagaccca ggagtggaaa tgctggataa    7740
cagagtagga aaatgtttgt tgttaaata atgacagttt tccaaagtgg ttgaccagtt    7800
tacactccca ctagtaatgt gtgagatcca tagagaagta agctttacaa aaaaaaaaa    7860
tgacagagag gactcaggat ccagttactg catatcccta ccaacacctg acactgtctc    7920
tcttcattct ggtgggttg tggtaatctt gcaatgaggt ttttgcttg tttgctttc    7980
ggagttgttt ttttttttt ttttgtaca tttaaaaaat tgtggtaaaa acatataata    8040
aattttacca tcttaacctt gtttaagtgt acaattcagt atgttaagca cattcacact    8100
gttgtgccac agatctctag aatatttcca tctttcaaaa cgggactcaa tacccactga    8160
gtaaaaaccg cccccccatt ccctctttc cccagcacct ggcaattatc attttacttt    8220
gtttctataa gtttgaatac tttagatacc tcatataagt ggaatcatac tgtatttgtc    8280
ttttctgac tgatttgttt cactttgcat gtcttcaagt ttcacccaca ctgtagcatg    8340
tgacaggatt tctttatttt taaaggctaa gtaatattcc attatattta tatactacat    8400
tttgcttatc cattcatcca ttgatggccg tttagtttgc tcccacctct tagctgttgt    8460
gaacagtgct gcaatgaata tgggtgtgca agtatctcct caagctctct cttgctctca    8520
gtccttttgg gtatatatta agaagtagta ttggccaggt gcagtggctc atgcctgtaa    8580
tcccagcact ttgtgaggcc gaggcaggtg gatcacctga ggttaggagt tcgagaccag    8640
cctgaccaac atggtgaaac cccatctcta ctaaaaacac aaaattagcc gggcatgatg    8700
gcgggtacct gtaatcccag ctactcggaa ggctgaggca ggagagtcac ttgaacctgg    8760
gaggcggtgg ttgcagtgag ccaagatcgc accattgcac tccaacctgg caacaagag    8820
cagaactcca tctcaaaata aataaataaa taaataaata aataaataaa taaataaatg    8880
aagtagtatt gctgagtcat atggtaatcc tatttaat ttttctgagg aatctgcata    8940
ctgttttccg tagtggctgc accattttac agtcccacca acagagcaca gcgtacaaat    9000
tactccacat ccttgtcagc acctgttaat ttttgtttg tttgttttg tttttgata    9060
gtgtctatcc taatgggtgt gaggtgatgg ctcactgtag ttttttgttc tttggctttt    9120
tttcttttct ttttttcgag acagagtctc gctctgttgc ccaggctgga gtgcagtggc    9180
```

```
gcaatctcgg ctcactgcaa cctccgcctc ctgggttcac gccattctcc tccctcagcc    9240
tcccgagtag ctgggactac aggcacccac cactacgcct ggctaatttt ttgtattttt    9300
agtagagacg gggtttcacc gtgttagcca ggatggtctc gatctcctga cctcgtgatc    9360
cgcccacctc ggcctcccaa agcgctggga ttacaggctt gagccactgg gcctggcctt    9420
tttttttttt ttttttttaa gatagggtct ctctctgtca cctaggccag agtacagtgg    9480
cacaatcata gctcactgca gccttgaact tctgggctca agtgatcctc ccgcctcagc    9540
ctcccaagta tctgggacta caggcgtgtg ccaccactcc tggcttattt aaaaaagcac    9600
tgggattaca ggcatgagcc tccatgcaca gctgtgggaa gagttctgat acaaattcaa    9660
tttcttgccg ggcacagtgg ctcacgcctg taatcccagc actttgggag gccaaggcag    9720
gtggatcacc cgaggtctgg agtttgagac caccttgacc aacatggaga acactgtctc   9780
ctactaaaaa tacaaaatta gccgggcgtg gtggcacatg cttgtaatcc cagctactcg    9840
ggaggctgag gcaggagaat cacttgaacc agggaggcag aggttgctgt gagccaagat    9900
cgcgccgttg cactacagcc tgggcaacaa gagcaaaact ccgtctcaaa aaaaaaaaa     9960 aaattcaatt tcttttcata cataagacta ttcagattat atatttcttc ttgggaaagc   10020
tttggtagtt tgtgttttc aataaatttg ttaatgtatt ccatagtgtt gagtttattt   10080
gcatatagtt gttcctaata tttccttagt atcttctttt taatgtctat atgatctgta   10140
gtgatgttca ttcattcctg ataatggtaa tttgtgtttt ttcttttttt cttgatcagt    10200 ctgccttta aaaaactggc tgttcttaaa actggctggt ttcattttct gtattgttta    10260
cacattttct atttcagtaa ttttcactca tctatattat ttccttcctt ctgcttactt    10320
tgggtttaat ttgctctttt atttttttct aacttcttaa ggtgcaagct taaagtgttg    10380
ctgccagacc tttcttctct tctaatgtaa gtatttgatg ctataatgtc cctgtgagca    10440
cttccttaac tgcatttaca ctttgtgaca tgtggtattg ttcaatttcc tttagttcaa    10500 aatatttct aatttttcttc atgctttctt atttgatcta cgggttaagt ttgtgttgtt    10560
tcatttccag atgttttggc tattgttgtt attgatttc agtttacttc tgttctggtc    10620
agggaacata atttatataa tttcaatcct tctcaattta ttgagaatta atttatggct    10680
cagattatgg tctattttgg tgaatgttcc atgtacactt gaaaagaatg tggactccgc    10740
tattgctgag tggaatatct gtaaagatcg ataaggtcaa agtatttgat gttgttcaaa    10800
tcttctgtat acttactgat tttctttta cttcttctat cagttaccaa gtgaagaatg    10860
ttgaaatatc caactataat ttgtggattt ctcctttcaa tgctatcatt tttggtgctt    10920
catgtatttt tgaagctcta ttattaggta tgtaccacat ttaggattga tatatttct    10980 tagtgaaatg accctttgt cattatgtaa tgctcttctt tgtccatggc tatagtcctt     11040
gttctaaagc gtaacttatt ttctaatata tatatatata tatatatata tatatacata    11100
tatatactag aatatatata caatagatta tgtatctata ttctatatat gtatatatat    11160
actagtatgt atatgtgtgt gtgtgtgtgt gtgtgtgtgt gtgtatatat atatatatat    11220
atatatatat atatatatat atatatggcc agcgtggtgg ctcatgcctg taatcccagc    11280
actttgggag gccgaggtgg gcagatcttt gagtccagg agtttgagac agactggcca    11340
acatggcaaa accccacctc tactaaagta tacaaattat gccagacgcg gtggctcaca    11400
cctgtaatca gcagttta gggaggccgag gcgggtggat cacttgaggt cagcagtttg    11460
agaccagcct ggccaacatg gtgaaacctc atctctacta aaaatacaaa aattagcctg    11520
gtgtggtggt gcatgcctgt aatcccagct actctggaga ctgaggcagg agaattgcat    11580
```

```
gaacccagga ggcagaggtt gcagtgagcc gagatggcac cattgcactc cagcaataga   11640
gcgagactct gtctcaaaaa ataaaaataa aataaaaaaa ataaccgggc gtggtggcgt   11700
gtgcctgtaa tcccagcctc tgaggaggct gaggcacaag aatctcttga acctgggagg   11760
tgaaggttgc agtgagccat gatcaccacc actgcactcc aacctgggca acagagatcc   11820
tgtctcaaaa aaatatatat atatatcata ttaatatagt cactcaaact ttttttgat   11880
gtgaatggga attttatcc ttttattgtt gatctatctg tgtctctata tttaaaagcg   11940
atttattgtg ggcagaatat ggttgagtct tgtgtttgtt tgtttgtttg tttgttttg   12000
agatggagtc ttgctctgtc acccaggctg gagtacagtg gtgcaatctc ggctcactgc   12060
aagctccgcc tcccgggttc atgcggttct ccagcctcag cctcctgagt agctaggact   12120
acaggcgagt cttgtgtttt tattcagtct gacaatctct actcttatat tgatatttaa   12180
acctattgac ttggttaagt tgaaatctac catcttgcta tctgtttttt atttatacta   12240
tctgttattt gttcccttt tcctctttt ctgcctttt ttagattgaa tatgttttaa   12300
gatttcttt tgttgttgtt gttttgtttt tgagacggag tttcattctt gttccccagg   12360
ctagagtgca atggcacaat cttggctcac tgaaacctcc gcctcctggg ttcaagcgat   12420
tctcctgtct cagcctctgg agcagctggg attacaggcg catgccacca tgcccggcta   12480
attttgtat tttagtagg gatggggttt caccatgttg gccaggctgg tctcgaactc   12540
ctgacctcag gtgatctgcc agcctcggcc tcccaaagtg ctggaattac aggtgtgagt   12600
cactgggcct ggtcaggatt tctttcattt caactaactg ttggcttatt aaccctactt   12660
ttttgtttta attttagtg gttactgtta tttaatgta ttagtcagat ttttccagaa   12720
aaacaaaacc tataggagat agataggtag atagatagat agatagatag acagacagag   12780
gaggatttac tataaggaat tggcttgcat gattatgag gctgagaagt cccaagatct   12840
gcagttgaca agctggggac ccaggagcat cagtggcata actccagtct gaatctgtgt   12900
ctaaaggctg gagaagatca gtgttccagc tcaaaaacat tcaggcaggg agagccttcc   12960
actactggca ggagcgcctt tttgttcttg tcagttcttc aatcgattgg atgtggtcca   13020
cccatattag ggagggcaat gtgctttact cagtctattg attcaaataa tgtcatgcag   13080
aaacacccctt gtagacgtac ccagaataat gtttaactga atatctggca ccccatggcc   13140
tagtcaagtt gacacataaa attaaccatc acatttgaga tttataattt gcatctttaa   13200
cttatcacgg tctatctgca aagaatatta tatcacttag ctgggcgtag tgctgtgtgc   13260
ctatagtccc agctactcag gaggctaagt ggggaggatt gcttgagccc tgaagttcga   13320
ggctgcagtg agctgcgatc acatcactgc tctccagcct gggctacaga gaaagagctt   13380
gtctctaaaa aaattaaaaa taaaataaaa agaatattac ctcatgtatg gtgatacaat   13440
agtatacttc tatttccttc tcttttgtgg ctattgctga catataattt atctgtagct   13500
atgagccctg cagtacattg ctattatgtt ttgcttaaat agtaaattgt cttttaaata   13560
tattaaaatg aaataaggtg ttttatattt atatgcatat ttaacatttg tatactgcag   13620
gtatgctggc gacagtttct tttagctttt gtctgaaata gtcatttaaa ggtaaaacat   13680
tttaaaactt tataatttgc aataatatta tacttatgaa gaattacaaa attgcccaaa   13740
aaatttccat aaacctattt cccaatttct tcatacggta acatccacaa aactaccatc   13800
caaactaaaa gattgacatt gatacaatac tattagctca cctggagacc ttattccagt   13860
tttgtccatt gtcctactat tgccccttt cttgaccagt attcaatcta gggttgctta   13920
```

```
ttgcctttaa ttgtcttttc ttcttagtct cctttaatct gggatagttc ctcaggcttc   13980 cttcttgac acttgtgctg gttgtttgtg gttgccctgc agagcaaaga tcagcaactc    14040
tacccaaatg tggtttgaat gtggagactg atgatgccac atatacacaa agagggcatg   14100
aggcattctg ggcagagcac aacaggctcc ccaaaaggcc ccaaaatggc ttgagaacaa   14160
gggaggggca agttgccttg ggtcttattg aggttaaggg ctggggatag ggcatggttt   14220
tcccatgcac aggccagtgt ttgaacttcc ctgctggagc caaggaagga aacacctagg   14280 ctttttgtc taccaaatgg agggcaaaag attaaggagg agttgtgggg cttcaaagct     14340
gtcagtggtc aaacatcaaa tatggaattg gattctgtta caattcaccc ctgatgttta   14400
atggattact gaaatgtatc ctgtttttt aaattaaatt taaacctgtt taagtatgct     14460
gtgatggtac tctatgaggc ctgcagcctg aggccagtaa gggggataaa atttctgttc   14520
aatgccttct tattaaagag cctaatgtta tgtattttga gaagtgaaat gaatgcctcg   14580
gtcactctca agaatgtatg gaactctgaa ggggataagg agtatcttgg tgaggccttg   14640
tattgtggct tgagtatgtg cagagatata tctgaccttg atttatattt ctgggtatct   14700
tcaagcaaga catttccaga gttctttacc ccaaagagga tgaccttgga taaagaactg   14760
ttgttgccat tagtcagacc agatagccag gtaattggca atggcctaag ggtctgaaaa   14820
atgttaagat ggggttgctt attgggcagg gcatcctttg ttgctaagat gactgcttga   14880
agtttggcaa attgtgtgga cccttgggtc ctgtctttta tcagggatgt ctgttaaggg   14940
atggaaaaca caaatagaat cagttgtgac ggtagcactg ccattttaa agtatgtgaa    15000 ttcccttttgc tgttcactca gttgatccca aagggatccc caagaagcca aggggtctga  15060
gagaggaatg acctccttca gcactgtggt gtctggccag aaactgagga caggggagcc   15120
catggcctcc tgcaggcagg atatgctaca ggacccagat ttggctccat actgtagata   15180 ctatttcat tttagcaagg aagcctcaat agccatgcca agctttgggg gtgtgccttc     15240
catggcccaa ggcatagcgg gcagctagtg tgtcatggtc tcaaggcctg taagagcctc   15300
cttttttgga agagtccagt atgcagtcag ctattgtcac tctaataatg tatagcatca   15360
ggctgaggaa ggcgatttct tgcatcggaa acccacagac tatttatggc catcataagt   15420
gaaccaaaga ctctggaagt atgagaggag gttgctaaag cctctacagt gaaggaattt   15480
ctggggagca ctaacagtct ctggaagtat gagaggaggt tgctaaagcc tctacagtga   15540
aggaatttct ggggagcact aacagtaggg tctgtccttt tgcaatttga acaggtttta   15600 agcctttttgt tttagtggac cccattcagg tgaaccaatt tgtaaggaac agcaaaaatg   15660
ggcttaagta gggccgggtg cagtggttca cacctgtaat cccagcactt tgggaggcca   15720
aagcgggtgg ataacttgag gtcaggagtt cgagaccagc ctggccaaca tgctgaaacc   15780
ccgtttctac taaaaaaata caaaaaaatt agctgagcgt ggtggtgggt gcgtgttatc   15840
ccagcttctt gggaggctga ggcaggagga tcacttgaac ctgagaagca gaggttgcag   15900
tgagccaaga tcatgccact gcagtccagc cttggtggca gagggagatt ctgactcaaa   15960
aaaaaaaacc aaaaatgtct taattaaaat ttgcaaagga ggaacatgtt gcttcagaac   16020
ccccagagtt ctaaaagata ctgggctttt agcattgtgg gtgctaagag ggtcaataga   16080
gatttcttga caatgtcaga aatgtcaagg ataaacagct ctcaatttac taagtaatac   16140
ccagaaattt tactgaggta tacttgtgct tgtaccttgt actttgtgtg aagaaatga    16200 cccatccttt ttcatgagct gccttttgaa tgtttgtatg cgttaaatta gtgtatcaaa   16260
tgaatttcca ctgcacccaa ctacttcagg aggctgagag gggaggatcg tttgagccca   16320
```

```
ggagtttgag gctgcagtgt gctatgactg tacttgtgaa tagctactgc actccagcct    16380
gggcaacatc ataagatcct gtcttttat ttttattatt tatttattta tttattttt     16440
tttttcgaga cagagtctca cactgttgcc caggctggag tgcagtggcg tgatctcgga    16500
tcactgcaag ctcagcctcc tgggttcatg ccattctcct gcctcagcct cccgagtagc    16560
tgggactaca ggcacctgcc gccacatccg ctattttt tgtatttt agtagagacg        16620
gggtttcacc atgttggcca ggatggtctc gatctcttga cctcatgatc cacccacctc    16680
ggcctcccaa agtgctggga ttacaggcgt gagccaccgc gcccggcctc aagaccctgt    16740
cttttaaaa aattaatttc ctctgagaag gatgtcatat atctaacatc atacttgtgt     16800
ttctggagag agttggatgc agttaaggtt tttgtttgca agatcgtgt gcaatggcag      16860
gtctgttggg ggtcccatgg gtagttagta tattgtgtcc atgcaatggt aaagacaagc    16920
tggctgaaac gggaacttaa gagaacatat tagcccaaat atatgatagc aaagtatttg    16980
ccagttgctg attggaggga ggcagtaatt ttagtagtat agaagctggc ctgttttta    17040
ctcacaacac ttctgacact aaatgtatgg gtttttcc ctataccaac tgatatggtt      17100
tgactgtgtt cccacccaaa tctcatcttg aattgtaact cccacaattc ctacatgtcg    17160
tgggaggaac ccagtgggaa gtaattgaaa catgagggtg ggtcttcct gtgctattct     17220
catgatagtg gataagtctc acaagatctg atggtttaa aaacgggagt ttccctgcac     17280
aagctctctt tctcttgcct gctgccatcc atgtaagatg tgatttgttc ctccttgcct    17340
tctgccatga tcgtgaggcc tccccagcca tttggaattg taagtccatt atacctctt     17400
tcttcccagt ctcgggtata tctttatcag cagcctgaaa acgacctaat acaccaacca    17460
attctccaac tctctgaaaa ccaactgggt gtccagcaat tcagtttcat tctgacacta    17520
tctacctgga gttcacatca gttcccacga gattgcccca tctttagaga ccagtcacaa    17580
gtcccaggcc tcctgtactt ctgactggca agttaaaaat cgggtgttct catgaccccc    17640
tcctcagttt ccataattta ctggaatagc tcacagaact cgggaaaata ctttacttac    17700
atttactggc ttattataaa ggatgcaatt caggaacagc cagatggaag agatgcccag    17760
ggaagggtat tgagcggggg tggaggaggg taccccaga gtttccatgc cctgagtgct     17820
tcactctccc gggacctcca cgtgtttaca gaaccctgta gggtagaagg gacttatgga    17880
ggtttaatta cctaggcatg attgattaaa ttattggcca ttggtgactg attcaatctc    17940
cagccctctc cccgcccat aggtctgaga tgagcctgaa agttccaaac ttttaatgcc     18000
ttggtcttc tgatcatcag ccccatctt gaagctatct agcactccca gctaatcatt      18060
tcattagcat gcaaaagaca catattagcc taaagatttc aagggtttca ggagtgccag    18120
gaactcttaa gtgaactgc agcattatga ttgtggtaat ccaccatcag gcatccttca     18180
ttcattctag gtttaagacc aggacaattt ggagtggaga aaaactgggg acaatcaccc    18240
ttctctaaat aggtcttata taatgggttt tgagcttatg gctaggtgcg gtggctcaca    18300
tctgtaatcc tagcactttg ggaggctgag gcatgtggat tgcatgagtc caggagtttg    18360
agaccagcct ggaaaacatg ggaaaaaacc catctctaca aacaaaaata caaaaattag    18420
ccgaaacaag tggcgtgtgc ctgtagtcct agctactagg gaggctgagg tgcaggatc     18480
acctgaacct gggaagggga agctgcagtg agctgagatt gcaccactgc actccagcct    18540
gggccacaga gtgagaccct gtctcgaaaa ggtcctagta catttattt atttattt      18600
tatacagagt cactctcagg atacctagtt ttatctgtgt gaacagtttt aataggttat    18660
```

-continued

```
gataaaggct caggttctca ttttgttaag ccagttgtaa ttgccaaaaa cttaattttg    18720
tttttgttta gtactcacta ggccagagta catgtccatt gtggaatatt ttagggcaac    18780
aggcactatg aatatgggga atttaggcaa atcaatagtt cttcttcttc ttttcttttt    18840
tttttttttt tttttttttt ttttgagaca gagtctcgct ctgtcgccca ggctggagtg    18900
cagtgccatg atctcggctc actgcaacat ctgcctcctg ggttcaagcg attctcctgc    18960
ctcagcctcc agagtagctg ggactacagg cgcgtgccac cacacctggc taattttttt    19020
gtgtgttatc caggctggtc tcgatctcct gacctcgtga tctgcctgcc tcggcatccc    19080
aaagagcttt tattacaggc atgagccacc gcgcccagcc tagttttgta tttttttagta   19140 gagatggagt ttcaccatat tggccaggct ggtctcgaac tcctgacctc aggtaatcca    19200
cctgccttgg cctcccaaag tgttgggatt ataggcatga gccaccacgc ctggcctaaa    19260
gttaatttag aacttatgtt gtacaagtgc aaaagccaac aagaccctcc cttccttctt    19320
taaatatctt tttattgtat agttttaga gtaaatttaa gatttgcaac tgggttaaat     19380
catgaacctc tgttaagttg tgtgtgtgtg tgtgtgtgtg tgtgtgtctg ggggagtta     19440 ctggatgtac ttcagggga gggagcttct cttctctgct catatttacg tttcttcttc    19500
tggagagtcc caaatcagta ccctcagggt taggggccac tttcatgaca gccatttttct   19560 ttttttttc tttttttttt tttttgaga cggagtctcg ctctgtagcc caggctggag     19620
tgcagtggtg cgatctcagc ttactgcaag ctccgcctcc cgggttcacg ccattctcct    19680
gcctcagcct cccgagtagg tgggactaca ggggcccgct acgatgccag gccaattttt    19740 tttacttta gtagacggg gtttcactg tgttagccag gattatctag atctcctgac      19800
ctcgtgatct gcctgccttg gactcccaaa gtgctgagat tacaaggcgt gagccactgc    19860
acctggcctt atggcagcca ctttcatggc aattgttatt ttatttgatt tagggactgt    19920
agacttaagt tggattttta tttatttttt atttttatt ttttggcagt ctcgctctgt    19980
ctcccaggtt ggagtgcaat ggtgtgatgt tggctcactg cagcctcaaa ctcatcagct    20040
caagtgatcc taccacctca tcctccagag tagctgggac tataggcacc caacaccaca    20100
cccagctgat ttttgcattt tttgtagaga tgggttttg ctgtggtgcc caggctagtg    20160
gatttttttt ttttttttg acagggtc ttactctgtt gcccaggctg gagtgcagag       20220
gcacaatccc agctcagtcc aacctctgct actaggttca agtgattctc acgcctcagc    20280
ctccccagta gctgggacta cacgccccca cctctggcta attttgtat ttttggtaga     20340 gatggggttt gccatgttg gccaggctgg tctcaaactg ctgacctcaa gtgatctgcc    20400
cacctcagcc ccccaagtgt tgggattaca ggtacaggca tgactactgc acccaacccc    20460 tggattttt taatgacaag gtcttactct gtcacccagg ctggagtgca gtggcacaat    20520
catggctcac tgcagcctca aactccagca atcttctcac ctcagccccc caagtagctg    20580
ggactacagg tacatgtcac catacctggc taattttaaa atttttttgta tagatgaggt   20640 tttatttgtt tgtttgtttt tttgacagag tcacgctctg ttgccaggct ggagtacagt    20700
ggcgcaatct cagctcactg caacctccat ctcccaggtt caagcgattc tcctgcctca    20760
gcctctcgag tagctgggac tacaggcacg caccaccaca ctcagctaat ttttatgttt    20820
ttagtagaga tgaggtttca ccatgttggc cagcatggtc tcaatctctt gacctcgtga    20880
tccgcccgcc tcggcctccc aaagtgctgg gattacaggc atgagccacc atgcccggcc    20940
tagacgaggt cttactatgt ttcccaggct gatcttgaac tcctagactc cagcaattct    21000
cccacctcag cctcccaaag cattaagatt acaggcatga accactgcac ccagccttga   21060
```

```
gttggatttg aatgaatccc ttgacagttt gataaggtgc agcacttaat caaacccagc   21120
ttctttctgg gtctgtttta tagttatctg gtagggtgat ggtggtgtcc tctgaccctt   21180
taagagagat ggagtaaggc attctggcct agttttata agggttcatg gcatggagtg    21240
ctattgagtg tttttatctt taatcctggt gactgcgctt cctcaccgga gcaaccacca   21300
gatggccctg tatgttgcac agagtatcag cctttctcct gcacactcta tagaacatag   21360
gctaatgcct ggttgggaca tacaaccaac agtcacaaaa taataagtgt catgcccttg   21420
agcctaggat cggcgatggt ttatgccaga atcaagacat acaattcaat ctaagatgca   21480
cagataggtc cagacggggc tcacatttta gggccacttt aaggacatcc tcaatttcat   21540
atttctgtct caaatgcca attatagaaa ctttcaattc aggtcagtta catctgtaac    21600
agagatttag tagtcctcag caaatgtgga acaaagcagc acagctcgaa gtgtaagctt   21660
gccaataggc agcagaatca atagcaagcc aaagtgagag gagagagacc cctgatggtg   21720
ggtggctatc atctaaggta cgctgttccc tgtgccagtt gtcttgtgat tgccccacag   21780
aggaagggat caaatctcta ccccagattt ggtttagaca tcaagattgg tgatgccaca   21840
tacacacata cagagggttt gaaaaagctt attactcgtg taatgaggtt ttctgtgcag   21900
aacagggcag gctcttaaga aggcctaaaa acagcttgag aacaaggaga tgcaagtggc   21960
cctgggtttt actgttaggg agtaaagctg gggtgagagt tctgatgcac aggccagggt   22020
tttgtggttt gaatttccct actggtgcaa gggaggagag taccctggca ttaagggagg   22080 agagtacccct ggcattatta ttcttatcat tattattatt ttggagacag agtctcaccc   22140
tgctgcccag gctggagtgc agtggtgcaa tctcggttca ttgcaacctc tgcctcccaa   22200
attcaagcaa ttctcgtgcc tcagcctccc aagttgctgg gattactggc atgcgccacc   22260
atgcccagct aattttgtat tttcagtaga gatagggttt gccatgttg gccaagctgg    22320 tctcaaactc caggcctcaa gtgatccgtc aaccttggcc tcccaaagtg ctgggattat   22380
aggcgtgagc caccacgccc agcttctgcc tttattattg gcttgcccag gttttggata   22440
aaagggaaag gaggagtggg ggtgggggct tgaaaactca gcagttgaac atcatggaat   22500
caactaattt attacactgg tcaattattt tgtaaaactc gtctcaattt gagtttcatg   22560
tctctcatga ctaaacgtaa gcatacattt tggcatgaaa accacagaag tgatgtttac   22620
ctgtctcagt tcatgacatt atgaggtaca ggatgctaat aggtgtctca tgttcatagt   22680
ttaaagatgg aaaaaatttt aagttaatag ttttattttt agtactttaa agatgttatt   22740
ccattatctt ccgtgtaca tagtttgtga caagaagtcc actgtatttg tcttctttgc    22800
ccttctaggt aatgtgttca ttttctcta ggtactctaa gattttcctt attaattttt     22860
ctatttattt atttatttat ttatttattt attttttagat ggaatctcat tctgttgccc   22920
aggctggagt gcagtggtgt gatcttggct cactgcaacc tccacctcct gagttcaagc   22980
aattttcctg tctcagcctc ccgagtagct gggattacag gcatgtgcca ccatgcttgg   23040 gtaattttg tatttttttt ttagacagag tttcattctt gtcacccaga ttggagtgca    23100
atggtgcaat ctcagctcac tgcaacctcc acggttcaag cgattctcca gccttagctt   23160
cccgagtagg tgggattata ggcacctgcg ccaccacgcc cggctaatct gtgtattttt   23220
agtagagaag gggtttcact atgttggcca agctggtctc gaactcctga cctcaaatga   23280
tccacccacc tcagcctccc aaagtgctgg cattacaggc gtgagccacc tcacccagcc   23340 taattttgt atttttaatg gagatggggt tttgccatgt tggccaggct ggtctcaaac    23400
```

-continued

```
tcctgacctg atgtaatccg cctgcctcgg cctcctacag tgctgaaatt agaggcatgg   23460
gctaccatgc ccagcctatt ttatttattt ttacttactt attttttta gacagagtct    23520 cactctgttg cccaagctgg agtgcagtgc agtggtgcaa tcttagctca cttcaacctc   23580
cgcctcccag gttcaagcaa ttctcctgcc tcagcctccc cagtagctgg gactgcaggc   23640
gtgcaccact acgcctgact acttttttgta tttttagtag agacaaggtt ttgctatgtt  23700
ggccgggctg ctctgctctt gaattcctgt tctcaagtga tccacctact tcggcctccc   23760
aaaatgctgg gattacaggc atgagccaca cgcccagcca acctttcaa taatttgatt    23820 atgatgtgtc ttggttttga tattatctta taagacattg gtgctctgtt attttttgtgg 23880 attttctgtg ctttatttttc aatagttttt attgctatat tttcaagttc accaatcttt  23940
tcttatgcag tgcttctgca gtgtataatc tgctgttaat tcctcctgtg catctttcat   24000
ttttagatca taaacttttc atctcttgaa gttccatttt gggtccttta aaaatatatt   24060
tcttttctct cttcatcata tttatgtttt tcttatatc cttgggcata atttatgaga    24120
tttataatgg ctatttaag gtcctcacct actaatttca tcatctctga atattgtggt    24180
ctgtttctat tgctttagtt atctactggt tatgggtaat ttttttcctat ttatttgact  24240 acctggcaat ttttattgg atgctgaata ttgtgtattt tgggttgttg ggtgcaagac    24300
attgttatat tcttttaaag agtactagag aaaaatacaa aaattagctg gcatggtgg    24360 ctcatgtctg tggtccagc tacttgggaa gcagaggttg cagtgagccg agatcatgcc    24420
actgcactcc aacttgggcg acagagtgag actctgtttc aaaacaaaac aaaacagaaa   24480
aaacaaacac tcaaacaaaa aaacagagtg ctgaactttg tcctggcata taattagtta   24540 cttgtgatt gttttcttct tttaagtctt gctattaagt tttgttagga aagcccagg     24600 ttggcctcta ctccagagat attaataatt tagccccact aagtctctat ccttctgaag   24660
actctaccca atacctgtgt gttatgaggt ctctttactc tggttgatgg aaacacaaac   24720
tatgcctagc cctgtgtaaa ctccaacact tgttcggcct cctgctttct ggttttactt   24780
tttccaacct tctggaattt cacccccacac ctgtgtagat cagtccccaa agacttgagg  24840
gaatctctaa tggtctatga ggcttttgtcg ctttctctct gtctctcccc atgcagctct  24900
tgcttctcca gcactctctc ccacaaattc tagctgtctt catgtccttg aactctaaac   24960
cctgtctcct aaactcagtg agaccacggg gctctgtttg ggtactccat gtagcactct   25020
cttcactgtc tccacgtagt aagctggggc tctggtgagg ctgaacttat ttttctttc    25080 tcagagatct tagtcttgca ttgcctgctg tctaatgtgt gaaaacagtt gtttcatata   25140
ttttgtttaa tttactaatt ttgggtgtgt gtggtggggg aagccatctc tacaacagtt   25200
tatccttcat gtgcagaagt ggaagtccca cagtgatccc tttaaaatac atggctaggc   25260
caggtgcagt agctcacgcc tgtaatccta acactttggg aggccaaggc aggtggattg   25320
cttgaggcca ggagttccag accagtctgg caacatggt gaaacccgt ctctactaaa     25380 aatacaaaaa tgagccaggc atggtggtgt gcacctgtag tcctagctac tccggaggct   25440
gaggcacaag aatcacttga acctaggaag tggagcttgc agtgagccga gatcgcacca   25500
ctgcactcta gcctgggcag cagagtgaga ctctgtctca aaataaataa ataaataaat   25560
aaataaaata aaatacatgg ctaaaatcca accatgtact taacatttca aatgaagtac   25620
tgaaatggct ctataattca aacttttcaga tatatctagc tttattatta ctatatatat  25680
attttttgag acagagtcta gctctgttgc ccaggctgga gtgcagtggc atgatcttgg   25740
ctactgcaac ctccgcctcc tgagttcaag caattctcct gccttagcct cccgagtaac   25800
```

```
tgggattaca ggcgggcacc accatacccg gctaattttt catatttta gtagggacag    25860
ggtttcacca tgttggccag gctggttttg aacttctgac cttaagtaat ccacctgtct    25920
tggcctccca aagtactagg attacaggca tgagccaccg cgcccagcct agatgtatct    25980
agctttatat ttaaaattca caggcttcac ctacttaagt gtatatttaa ttggtttgaa    26040
gatgatttcg tctctggaag gttttcccaa gaatcttta ccaagccagg gaagaaagag    26100
cttgggacat tggaggaaga ggaagcaggc tagatgtgac cagagcagag gaagagagga    26160
gagtggtgta ggatgagatt ggagagccag gtagaaccca gatgatgccg ggcctgggat    26220
gtcagagtga gaagtttgga tttattcca agtgtaacgg gaggtcactg aaaggtttta    26280
agcaagagag tgacatgatc tgattttaaa gatcacattg ctgtatgaat aatggtttct    26340
aggggcaac ggcagaaata gagaccattt aggaagctgc tgttgtagtc aaggtggaca    26400
aatagtgact tgaataaagg ttgtgacggc agaagtgttt agggactagc ggtgttcgag    26460
tatctactgt gtttgtcagc tcgaaacaca tgacagagaa ataacagatg aataagagaa    26520
atagatcctg gccctgtggg gcttccagac aaatggagtg gttaattctt ttttttttt    26580
ttttttttt ttgagacaga gtctcactct gtcgcccagg ctggagtgca gtggcacgat    26640
ctcggctcac tgcaagttcc gcctcccggg ttcaccattc tcctgcctca gcttccccag    26700
cagctgggac tataggcgcc cgccaccatg cccagctaat tttttttgta ttttggtag    26760
agacggggtt tcactgtgat agccatgatg gtctcgatct cctgaccttg tgatctgcct    26820
gccttggcct cccaaagtgc tgggattaca ggtgcgagcc actgcgcccg gcctgtagtg    26880
gttaattctt aatactttgg gggtcacaga ctcctttgag aatcttacct aagctacaga    26940
acctcaccac agaaaaaagc acataatcac tttttttatc atttatgaa tatttcacat    27000
tcatcatgat aatttcacct ggtcaagtgg atattaaacg ataagtaaag gctcatatat    27060
gtgtggagaa ctagtgcata cagaattatg gagaaatgat ggtggatcag tggagcaact    27120
ggggagctgc tggggcacag gagagtgaca ggacaggggc tcagcatgcc tccaacccaa    27180
tcagcaaagc atccacactt ccacagcact gtgctgggtg ggaaagcttg ttcttgccct    27240
ggctgaaaga caagatgcaa gcgatatagt gcttcatcaa tgttgtagac cgaacattta    27300
tctctctcca aaatgtatat gttgaaatag aatctccaat gtgatggtat ttggaggtga    27360
ggcctttgag aggtaattag gtcatgagcc ttcatgaatg ggattagagc cttcataaaa    27420
gagactccag agggctccct cacccatctg ccatgtgagg atactgagaa gatgaccatc    27480
tacgacccag gaagcaggct tcaccagaca ccaaatctgc cagcgccttc accttgtcct    27540
tctcagcctc tagaactctg agaagtgttt gtggtttaag ctgcccagtc tagggtgctt    27600
ttgctatggc agctcaaact gcctaaagca gtcagtaacc tcaggatagg agtgggctgc    27660
caggtggaac cctcccgaaa ggtttctgga tggaagattt gagtcactta aatatatatc    27720
atgcatcatg tgtgcgtgaa gagagacaga gagaggcggg tggggcagga gaatatgtac    27780
tgcctcgtta tgcatgctca tatagtcctg atttgttatg ctgtcatgtg atacataaca    27840
atgtttgggt caacaatgaa ccacatatat ggtagtcatc ctataagatt ataataccag    27900
gccaggcaca gtggctcacg cctgtaatcc cagcactttg ggaggcctag gcaggcggat    27960
aacctgaggt caggagttca agaccagcct ggtcaacgtg gagaaaccct gtctctacta    28020
aaaatacaaa aattagctgg gcttggtagc gtgcgcctgt catcccagct actcgggagg    28080
ctgaggcaag agaatcactt gaacccggga ggcggaagtt gcagtgagcc tagaccctgc    28140
```

```
cattgcactc caggctgggc aacaagagca aaactccatc ttaaagataa aaagattat   28200 aataccgtat tttcactgta ccatttctat gtttagatac acaaacacca ctgtgttaca   28260
gttgcctaca gcattcagta tacagtactc atcatgctgg atgagtctgt agcctaggag   28320
cgacaggcta caccatataa cttaggtgtc tagtgggtta taccatctag gtttgtgtaa   28380
gtatactctg atgttatcac aatgataaag tcgcctagca atgcatttct cagaatgttt   28440
ccctcttgtt aaatggcaca tgagtgtatt tcagtttctt tctttcttct ttttctttct   28500
ttctttcctt cttctttctc tctctgtttc tttctttttc tttttctttt ttttcatggt   28560
cattctcttt cacccaagct ggagtgcact ggtgcaaaca cggcttactg aagcctcaac   28620
ttcctgggct caagcagtcc ttccacctct gcccccaag tagctgggac tacaggcaca   28680
caccaccatg cccagctaat tttttgttgt tgttgttttt gtagggatgg ggtttcgcca   28740 tgttcccag gctggtcttg agctcttgag ctcaagcaat ctgcccacct tggcctcctc   28800
ccaaagtacc gggattgcag acatgagcca cctcgcccgg ctatttcaat ttctatagtg   28860
ctagtaaaaa tccactaaat tgtttatcca actcatcaat aagttcaacc cacagtttga   28920
aaaccctagt ctagattttt ttcttttctat tcccttcagt atgaacatga gaaaggctca   28980
tcatcattcc atatttgata ttttgacata aatctgctgg atttagttaa attacagttc   29040
tcccaaataa tcaggagaaa tttgactaga actatcttgg tattgcccat ggttgttgct   29100
tctctttgac agtaaaccaa aaaattaagc gcatggttat ggagtctgac cgcttgagct   29160
ggctgcccca cctgcctcag tttctttatc aatatctggg acatcatcat cttaatagta   29220
actgcctctg ggtaagccat gtaagacaaa ttaacacaag gcctggcaca tagtaagtgc   29280
tcaaaagatg ttggcaacta ttttatttta tttatttatt tatttattta tttatttatt   29340
taactatgta tttagtgacg gagtcttgct ctgtcgccca ggctggagtg cagtggctca   29400
ctgcaagctc cgcctccctg gttcacgcca ttctcctgac tcagcctccc gagtagctgg   29460
gactacaggc gcctgccacc actcccggct aattttttgt attttttagta gagatggggg   29520 ttcaccgtgt tagccaggtt ggtctcgatc tcctgacctc gtgatccgcc cgcctcggcc   29580
tcccacagtg ctgggattac aggcgtgagc caccgcgccc gacctattta ttattttta   29640 aactgtcaat gttgttgtct tacagcggag acctgaaagc agcttagcca tgagcagcgc   29700
tcaaataagg aaagaaattc tttgcaataa atagggatct ttgaaaggtt ttacgttgga   29760
cccgccttac cgtggacaga cactagaggg tgctcctcgc tcagaaagcc gagtgtttcc   29820
aggcccggga cctctgccag gaagcgcttc gactgccggt tctgaaactc tctcttttggg   29880 tctggtaatt tactggggag aactggctgc tgccttggtt ctgaaactaa aggctttta   29940 cggaagtagg aggagactgc aagaggctat atggagcaga aatgtggctc cttcaaactt   30000
tcaccaattg gcgttctgcc ggactgtgac ttggaggatt ccagcagtgt ctcattcacc   30060
catgagcccc agggtctagc acacatagtg tctggcagac agtgagcgct tgtaaaatat   30120
ttatggaatg ggaccaaccg atggaggcgt ctgagaccta aataattata attacaaatt   30180
ggcaagtgct ggcacgatga ccacagacca ttaagggcgc tcccagaaga gtgggggctg   30240
gggaggattg gccagaatgg cttcctgaaa ttcaggagcc ctggcactct ctggggtaca   30300
cagaaaagat cttccacatc cggcttttgg atatttaaaa acagcttcat gctccatttt   30360
tttcatgtcc ttcctgtgga atgatttcta ggcttttcac taagttgatc gctccctgca   30420
gacttgtagg aaggcaaata ataggttagc acctactggg ttcaagcatc tcctatgatc   30480
tccattatct gatttaattg tgtctttatc tcatttaatc cccacaacaa ctctctgaga   30540
```

```
ctaaggctat tatccacatt ctacagatta gaacttggta aggtttgata actggcccaa    30600
gatcacacca ttagggagtg acaggaccag tatttgaacc cagatagtct agcagcaaaa    30660 gatgcttttα aaaattttca cttaaaagaa taacaacaac agcaactaac agtatggagg    30720
gggccagata gttttctgtg ttttacattt attaactcat ttaagtcatt taattgctat    30780
acacctagat gtcatccttt ctattaatac attgttagta ctgaaaagtg aagagaatga    30840
tacaacaaac acccatgtac tcatcacctg gcatgaaaaa aaggttaatg ttaaagttga    30900
tattatccag ccacaacaat cttgaaaaag aacaaagttg gagaacttgg cccagtgcgg    30960
tggctcatgc ttgtaatccc agcatttTgg gaggccaagg cgtgtggatt gcttgagccc    31020
aagagttcaa taccagcctg gcaacatgg taaaaataca aaaaatttct acaaaaaaaa    31080
aagtttctac gaaaaaaata caaaaattag cctggtgtgg tggtgctcgc ctgtggtccc    31140
agctactcag gaggctgagg tgggaggatc acctgagccc agggaggttg aggctgcagt    31200
gagccaagat agcaccactg cactccagcc taggcaaaag agcaagacct tgtctcaaaa    31260
aaaaaaaaaa aaaaagttg gagaacttac actttccaag ttcaaaagct acagtaatga    31320
aaacaatgtg gtactggcat aaggatcaac atgtacatca atggaataga attgagagtc    31380
cagaaataaa cctgtatgtt tacggtcaag gtatcaagac aattaaataa ggaaataagt    31440
ttttttcccc acaaatagtg ctgggacatc tggatagcca catgcaaaag aatgaatttg    31500
gactcctatc ttttattgtc tacaaaaatt aactcaaaac gaatcaaaga cctaaagata    31560
agaactaaaa ctataaaact cttagaaaaa acataggtgt aaacctctat gaccttggat    31620
taagcaatgg tttcttacat acaacaccaa agcacaatc aactgaagaa aaaataaatc    31680
aattagactt catcaaaatt aaaaatttga gtgtcaaggc cctatcaaag ttaaagata    31740 aatcacggaa tgggagaaaa tttttgcaaa tcatagatct ggaaaggatc ttgtatccag    31800
aagatagaag agctgttttt ctgttgttgt tgagacagag tcttgctctg tcatccagcc    31860
taaagtgcag tggcatcatc atagctcact gcagcttcca cctcgtgggc tcaagcaatc    31920
ctgtcacctc agtctcccga gtagctggga ctgtaggtgt gcaccaccat gcctggataa    31980 ctaaaaaaa tttttttat agacgagctc tcactatgtt gcccaggatg gtcttgaact    32040
cttggcctca agcgatactc ccacctctgc catccaaagt gttgggatta gagtgagcca    32100
cctcatccag cctataagaa ctcttgtaat ttaataataa aaagacaaat aacccaattt    32160
aaatttgggc aaatgactgg aataagcatt tctccaaaga agatatacaa atgccaagaa    32220
gcacatgaaa agatagtcag catcagccag gcatggtggc tcatgcctat aatcctagca    32280
ctttgggagg ccaaggcagg tggatcacct gaggtcaaga gtttgagacc agcctggcca    32340
acatggtggc acctcgcctc cactaaaaat acaaaaatta gccaggtgtg gtggcagatg    32400
tctgtaatcc cagctactca ggaggctgag gcaagagaac tgcttgaacc tggatggtgg    32460
aggttgcaat gagccaagat cgcaccacta cactccagcc tggcaacaa gagcaaaact    32520 ccatatcaaa aaaaaaaaa aaaaaagat actcagtatc attaaccatt agggaaatgc    32580
aaatcaaaac tttcaaaccc actagcatgg ctatagttta aaagacaata actagtatta    32640
gcaaggatgt agacaaattg gaaccctcat aaatcactag tgggaatata aataggtgca    32700
gcctctgtgg aaaatggttt gggaggtctt caaaaagttc aatatagagt taccgtaaga    32760
cctagaaatt ccactgctag ctatatccc aaaataattg agaacattat atatacttgt    32820
acatgagacc aggagcagtg actcacacct ataaacccag tacttgggga ggccaaggca    32880
```

-continued

```
ggaggatccc ttgagcccag gaatttgaga ccagcctgag caacataatg agatcctatc    32940
tctacaaaat ataaaaaatc agctggatgt ggtggtgtat gcctataatt ccagctactg    33000
gggaggctga ggtgggagga tcgcttgagc agaggagttg gaggctgcag tgagctatga    33060
tcataccatt gcactccagc ctgggtaaca cagcaagact ctgtctcaaa aaaaaaaaa     33120 aaaaaggtgt agctggatgc agtagctcac gcctgtaatc ccagcacttt gggaggccaa    33180
ggcgggcaga tcacgtgagg tcaggagttt gagaccagcc tggccaacat ggtgaaaccc    33240
tatctctact aaaaatacaa aaattagctg gaagtggtgg cgcacacctg taatcccagc    33300
tactcaggaa gccaggatgg gagaatcgct tgaacccagg aggtggaggt tgcagtgagc    33360
cgaaattgta ccactgcact ccagcctggc caataaaatg agattctgtc tcaaaaaaaa    33420
aaaaaaaaag atacatatac atatacatga atgctcatag cagcattatt tataatgacc    33480
aaaaggtgga aatgtatcag tccattctca cactgctgta aagaattgcc taagactggg    33540
taatttataa aggaaagggt tttaattgac tcacagttcc gcattgctgg ggagacctct    33600
ggaaacttac aatcatggca ggaagcaaag gagaaacagg caccttcttc acagggtggc    33660
aggacgggag tgagtgcaag caggggaaat gccagatgct tataaaacca tcagatctcc    33720
tgagactcac tcattatcat gagaacagca tgggggaaac caccccatg atccaattac     33780 ctctacctgg tcccgccctt gacatgtggg attaatacaa ttcaaggtga ggtttgggtg    33840
gggacacaga gccaaaccat atcagggaac aacccaggtg tttatcagtc gacgagtgga    33900
taaacaaaat gtggtctgtt catgcagtgg aatattattc taccataaaa aggaatgaag    33960
tactgataca agctacagca tggatgaacc ttgtaaacac tatgctaagt gaagaagcc     34020 agtcacaaaa ggccatatat tatatgattc catttatatt aaatgttcag ataggcacat    34080
tcattgagat ctgtggttgt caggggctag aagtagggag taatgagaaa tgactgcaca    34140
caggcacagg ttctggaatt ggatagtagt gattgttgaa ccgccttgtg aatctgctaa    34200
aaaacactga gtcatacatt tgtaaatggt gaattttata gtatatgaat tatagctcaa    34260
taaaaaaaga gagagaaaaa agttgatatt tcttcatag atagctccat ggttctcaaa     34320
cattttggtc tcaaaacccc tttagactct taacaattac tgagggcccc aaaaagctct    34380
tgtttatgta ttttgttttt gtgtgcttat gttcaatatc cattgacatt taccatgtta    34440
gaaagtaaaa cagaaatttg taaaaatatg cattatttcc tttaaaatag cattaataaa    34500
ccatatgctg tacatgttat cataaataac agttgaaaaa taattgtatt ttccaaaaca    34560
aaagaattag tgagaagagt gacattgttt tgcattttg ctgtcaaatg tctggctgag     34620
tagaagatag ctgcattctc ttacctgctt ctacttacat tcaatgtgtt gagatatgtt    34680
gttttggttg aaatatatga aaaaagtctg tcttcacaca gatacgtggt tgaaaaaagg    34740
aagactatct taatagcctt tcaaataat tgtggatatt tttcttagat tacataccaa     34800
aactggacaa gtatagtttc ttaaaggtta attgcaatgt ggaacctgaa accataaact    34860
tttcaattgg tctatcatga tcatgtactt tttttttttt ttttcagac agagtcttac     34920 tttgtcgccc aggctggagt tcagtggcac aatcagggct tactgcagcc tcaaccttcc    34980
aggctcgagt gatcctccct gctcagcccc tggtgggact acagggatgc gccaccatgc    35040
ccagctaatt ttttttagt agagatgggt ttttgcctgc ctgcctgctt ccttccttc     35100 cttccttcct tccttcctcc cttccttcct tccttcttc cttcttcagg gtcttcctct     35160
gtcactcaaa ctggagtgca gtggtattat ctcagcttac tgcaacctcc acctcccggg    35220
ttcaagcaat tctcatgcct cagcctccca gtagctggg atcacaggta tgtgtcatga     35280
```

-continued

```
tacctggcta attttttgtgt tttttctaaa gatggggttt cgcaatgttg accaggctga    35340
tcttgaactc ctggcctcag gtgatccacc cacttcggcc tcccaaactg ttgggattac    35400
aggcgtgagc catcaagcct gacctcaagt tccctctttc taatctggaa ttgagaatag    35460
cactagcatc caggcccacc tcaaagggtc agactgaagt tcagatggcc caaggatgca    35520
ctagaaagtt ctttatgcaa tgtaaatgag agttgcctac tcttgtcagg ctcaagtacc    35580
ttcactctac aggcaactgg ctacaggctt ctcaccctga gcggtggtca gctcagccaa    35640
ctcaccctct ccaccctcct ccctccctcc ttttttcacag gaaacttaag agtcagatct    35700
cttccactgc aaatggagat tcttgatttg gagagaataa gataaaggac ctgacatcaa    35760
tccttactct tgaaagcatg ttgttacttt ctaaatatta ttgaaattaa aaaaaaaaaa    35820 tcttccccc aaatcagtat atttgaattg ctaacaagcc tctctgcctt gtttttatct    35880
caaagaataa aatgctgagc cctgcgtggg atgctagatg ctagagaact cccccatctc    35940
tctctctctc tctctctctc tctctctctc tctctctctc agttctgaac    36000
aaggagggaa ggggtaaaga gtccttagtg agcgccttct gcagggacaa cccttctgga    36060
cccatctgga tgggagcagc caggagaggc aagaagcagc tgtatttggt ggcactgcca    36120
cagcgtctcc tcagccccag caagtggcct ttggtctaga gttggtccat ctggcccgca    36180
caaggctcga atccagccct agagacgctc cccgcctgct ccaggtggcc ggcaccctag    36240
acggggcagg aagggcaggc gccaagcctc aagtctcaaa cacggtgcgg ggctgcgcgg    36300
caaggagaaa cccaggagat gctcgggtc gggcccagg gcagggaaaa ccctcagctc    36360
tggtcaaaag ccaagtgagc gaaggaggcg atgcaacgtc accctggtgg ccaaggcagg    36420
cacccaggtc tcgaggttcc aggagaggga cgcgctgtga ccaccagccc ctaggctcc    36480 tgtctgctcg atgagcgtcc actcgccagt tccagccgcg agcgccccca gcactcccgg    36540
agctgggccg ggcgccgcct tccctcgggc ggccggcagg ggtcagtgtt tggccgcagg    36600
tgaacagaca gcggccgggg ctgaatctgg ttcttctagc tgggtcttgc ccctgccaat    36660
ctgtctggac ttgtccctg gccgttaact gggttctagc ctatcgagac tcctcatatt    36720
ctcccccacc ccgaccacta cctccatact gtccttccta agtcaccagg cctgcaccct    36780
tccagaagca tagatccctg gatacatgga taattacttc ctggccttat accagacagt    36840
gatgcgagac tggaaagagg acatggcacg gagtcagaag atttgagttc aagttcctgc    36900
tctgccaatt accagctgtg tgatcttggg caagtcactt tacctctctg tgttaagttt    36960
ctcatcttca aaaatgagct aatggcaata ggaatggcta tgatgccaca tgccaaggac    37020
ttatatgcca tatactgtgt gtgttatcat ctcgagggtt taataggagg agactatggc    37080
ccagagagat gaacaagcag caggaagtag cagagccagc ctctgaaccc aggtctatcc    37140
atttctacca tgttaacctg ctttgcaggg ctgtagtgag aatttaaatg tggaatttat    37200
attattctct tctggcagtt tggcctggat cctggtgggt gagctttccc tcctactaac    37260
aggggaagca gggaaaggca ttttcaatta ttagaaacat ccttagttag tggggtatga    37320
aatgaaaata gcccactaga atacaagctt cagaagggaa gaggtctcac ctgtcttgag    37380
tctgttgctc acataattcc tgatatatag tagatgcaca agcaatatga agaaatgtaa    37440
acatgtgtac acctcctacc ttcattataa gatggattct aacacagagt cattttttcat    37500 accaaccgtg caattaccag gcaagtgatg ctaattacta gttctcatga ccactattga    37560
gtttaattca agagttttat tggatcccct gaagctccta caaccctcta aatcatgggg    37620
```

```
attcaataac agtctttta tcagtatgtt cacaagataa attgagtaaa ccagcttaat    37680
gactcatctt catgacttat gacgttaaga ataagatggg gggaaatgac aaatgtgata    37740
aaaactgatg gctctgagaa aatgtcatgg gcatgtggtt ctgaatgctc tcccatgtgg    37800
ctctaggggc ctcagcaacc ttcagtcccg tgtccaccct cactccgctt caataatcaa    37860
tttgttctta tccaaagcat ttttgaggac cttgttactc ttcttctctg tgttaatcag    37920
gcacacaggc ctaaaatatc aaatcctagg cagatgcatg aacccacagg acagcaacat    37980
cgggagggca gagtagaggc aggcttcagt tcaaagcagg cataggcttg gagagggaaa    38040
ctgggaaatg aaaacaagtt gtctatatag actctctccc tagaagtcca tttaaagaaa    38100
atagaagctc agtaaaatca aaatccatgg gcagtggtgc catgcaaaga gcaaagacct    38160
gaatctgagt cttggatcag tgagcgtctt agctttgcct ccaagctcca gtttcctcca    38220
ctctaactgg ggacgtattc tctcctctct cctggtttcc tccagtttct ctgaacattc    38280
ttttcatttt ggttgtgagt tcttctgctg ctctctcctg caccctt ggt aggttctatg    38340 ctgactttta ttttctcct cttatatgct cttgttggaa agtctcatcc ttttgtgaat    38400
ccaactgctg cccacgtggg gtgattccca ggtttatgtc accagtcctg ccttctctac    38460
tactctttaa atttgaaaac aagggccggg tgcagtggct tatgcctgtg atcttggcac    38520
tttgggaggc caaggcagga ggatcacttg aggccaggag tttgagacca gcctgggcaa    38580
tatgacaaaa cctcatccct acaaaaaata caaaattagc tgggcatggt ggcaagcacc    38640
tgtagtccca gctacttggg aggctgaggc aggagaatca cttgaaccca ggaggcagag    38700
gttgcagtga gctgagatcg catcactgca ctccagcctg aatgacagag tgagacagtc    38760
tcaaaaaaca aacaaacaaa acccaacttt gggtcacgca tccatccttg accaattagc    38820
tgtagctagg gaagtggagt cctacggaca cagcaaacca ccacgagaat catggagatg    38880 aatagggggca ggataattta ccagaggaag cctagagtgg agtgctggac agaccaccat    38940
gtggagttgc catctgagga cattgctact tggatacccc cacaggtatt tcaccatctt    39000
cccctgaact cataatcttc ccctgaaaac ctgaatctcc tcttctccta acccccatga    39060
aggggctgtc atctaccaag tcaccccacc tagagatgtg agaatcattc tggaatctcc    39120
ctctctatca cgaaccccaa tacttctagc taatcaccat gtctctctaa ttctactttc    39180
taaatatttc tcttgtccat gctacttctg ttttctgagc tcaggccctc ctcatagatc    39240
tggaacattg caattgcaat aacttctttc tttctttctt tttcttttct ttcttttttt    39300
tttttgacag agtcttgcta tgttgcccag gctggagtgc ccagctaatt tttgtatttt    39360
tattagagac agggtttcgc catattggcc aggctggtct cgaactcctg acctcaagca    39420
atctgcccgc ctcggcctcc caaagtgctg gaattacagg cgtgagccac tgctcctggc    39480
ctgcaatagt ttcttagctg gtctctctgc ttctagtcat gctcccctaa tctactgtcc    39540
tcactgctgg cagccatctg cctttgtttt cctaaatgaa atagattatt ttctgattat    39600
attaaaaata catgttcagc caggtatggt ggctcatgct tataatgcca gcactttggg    39660
aggctgaggc aggaagactg cttgaggcca gcctgagcaa catagtgaga tctcatctct    39720
acaagaaatt taaaaattag ccaggcatgg tgtcacacac ctgttgtcca agctactggg    39780
aagactgagg tgggaggata ggttgagtca tgggaggtca aggctgctgt gagctgagat    39840
cctgccacag cactccagcc tgtgtgacag ggtgagacct gtctcaaaag aagcaacaac    39900
aaaagacatg atcattttaa aaattaataa ggaaaaaaat aaaagaatg taaactttgc    39960 ctaaaatttt accaccgtga gagaaccatg ttatttggt gatcattctt ctttgcattt    40020
```

```
tttattccta ttttttaaaaa ttacatatca tacacgcagt gagtgggttt tttccactct  40080
ccagcttcat tgcaggacat gccttgcctt gcacctttaag gctgtaaata cggagttgcc  40140
tataatctct ttgagtacac catgttgttt ctcacctctc tgcctgtggt tatacaccct  40200
gtattaattt cctaggggttg aagtaacaaa gtgcaggact taaaaatagc agaaatttat  40260
cctcttacag ttctggaagc tagaagtctg aaatcaaggg gttggcagga ccatgaccct  40320
tccagaactt ccaggggggag gatccttcct tgcctctttc agttcctggt aggcccaggc  40380
attccttgac ttgtatagca aaactccaaa ctcatgtgat catcttcatg tggccatcgt  40440
ctctgagtct gtgtgtctct ctgtcttcac atggcattat ccctgtgtgt ctgtctctgt  40500
gtctaaattt tcttcatctt aaaaggacgc ccagccaggc atgatgactc acatctgtaa  40560
tcccagcact tgggaggct gaggcaagag gattgaggcc aagagttcaa gaccagccgg  40620
ggaagcatag taagtccctg ttctccacaa aaatacaaaa attagtccca actacttggg  40680
agacaggcag aaggatcact tgagccctgg agatagaggc tgcagtgagc tatgattgta  40740
ccactgcact ccagcctggg tggcagagca agactctgtc tcaaaataaa agaaaaaaac  40800
aaaaaaggac accagttgta ttggattcta gcccacgcta ctccagtatg ctaaggttcc  40860
ctgcagcctc aacatcctgg gctcaagcaa tattctcacc tcaacttccc aagtagctga  40920
gaccacagat gcatgtcacc atgccctgct aatttttgttt atttttttgtg gagacggggt  40980
cgcacaatgt tgctgaagct ggtctcgaac tcctggactc aagcgatctt cctgtctcag  41040
cctcccaaag tgctgggatt acaggcataa gccatcacat ttcaacgac cctatttcta  41100
aataaggtca cattctgagg tactgggatt taggacttca acatgtcttt tgctggaggg  41160
ggacaaaatg taacccataa tatacccttt tccatttttct cacctgacca gcctctcttg  41220
aaccttcaca gtccagccga gctgccatct cttcaaggaa gttttccctg aagccctcag  41280
gtagacccgt ttttccatgg cggccacatc agcatgcagc acatttaatt ggaagtctcc  41340
acatatgagt tggttttcct tacttaaaat atgcttatca tcccttggag gtaaggactg  41400
tatcttttcc atctttaata tgcccagcac ttgtctctta tattaattag ttcaagacta  41460
agtgggctgg aggctcaaaa ctacagtggc ttgccaggca tggtggctca cacctgtaat  41520
cccagcactt tgggaggcca aggcagaagg gtcacttgag cccaggagtt caaaatcagc  41580
ctaggcaata gactgagacc atatctttac aaaaaaaatt acagtgactt aaggaagaat  41640
agaagttcat ttccctccct catagcagtc ctgagttgaa tagtgcagtt tggtaaggat  41700
cttgccccac atggccatct gaagactcta gttccttcca gattgttgct ttgcaaatgt  41760
aaggactctg tcctcatctg cttgacagaa gctggatagc aggcacatcg gtcttccagg  41820
ttggagaaag agggaagaga ctgtgggaaa atacgtgcct ggtgcctaaa agttcagacc  41880
caaagcagcc ctcatgactt ctgctcatat tctcttgctg agagcttagc cacatggcta  41940
cacttagttg aaagaaaggc tagaaatgtg tcatcaattg aacagcaatg actatattac  42000
aactctatta tagttccata actccttatc tccaagttct gaaatctcaa aagctgtgaa  42060
aattggaaag gtgtgtgtgt gtgtgtgtgt gtgtgtgtgt gtgtgtgtgt tgttgttgtt  42120
gttgttgttg ttgagacagg gtcttttctct gtcacccagg ctgagtgca gtggcatgat  42180
cacggctcac tgcagcctca acctcccaag ctcaagggat tctcccacct cggactccca  42240
agcagctagg gctacaggtg tgtgccattg tgcccagcta atttttcttac ttttatagag  42300
actggggtct tgctatatgg tccaggctgg acttgaactc ccaggctcaa gcgattgtcc  42360
```

-continued

```
tgctttggcc tcccaaaatg ttagaattac aggcatgagg ccggccaaaa gttttttctt  42420
aagtttggca cagactcaag tggtggcaaa atctgacttg aaatgacatg aggaatttat  42480
agagacatct atagactatt tatagtcttt atttcattca cttagaatga atattaatgt  42540
attttgttgc aaaagtgcca acatatttgc tcaagctctc cccagacccc actgggggaa  42600
tgaataatat gcagtgtgtg cagcatatct ctctgaaaac tgaacacttc taaatttcag  42660
ggctcatctt agacccacgc aagaggaccc cacattttgg agggccttac tttgcccttc  42720
ttctagatag ccccttgctga ttaggtaggc ctgtgaggca aaatgaaggg cctctcacca  42780
cctgagcacc gcccccccaa ctctagatca tgtcccaggt acctgggcca ctggagtttg  42840
ctgcccaagt ggtccaaagt ctgtgcagat ctctttaatt ggtctaccct ctggatgggt  42900
gggggtggg ggttaccgct gtcatatgca ctcttaaggc caagacataa ccaaagagca  42960
gctgtttgca gcaggtatgg atagaggctg gttgtgcaaa ctaaaatgtc cacacatgtg  43020
cccgtgagac cactcaaggt aaggatagaa ttgagtgtgc aaagagaaag gggatagata  43080
tagttatcca aaattgtaaa tttgaccctg gctatatcta tcaacatagg acagaacaca  43140
gctcttattt atttatttgt ttgtttgttt agtttcaaag agatgggggt ctcactatgg  43200
tgcccaggct gttcttgaac tcctgggctc aagtgatcat cccgtctcag cccctcaaag  43260
tgctcagatt ataggcatga gccaccatgc gcaactcaga agacagttct tatttagtag  43320
cttgttaact tgatttacat atcgtaaata tattaggcat ggatatgtgg gcctccaggc  43380
ctgcatgttc gagtgagtct gtacgtcagc cccagatatt ttattttatt ttattttatt  43440
ttatttttga gatggagtct ctctctgtcg cccaggcagg agtgcaatgg cgcgatctcg  43500
gctcactgca acctctgcct cctgggttca agcaattctc ctgcctcagc ctcctgggta  43560
gctggaatta caggtgctcg tcaacacgcc cggctaattt ttgtattttt agtagagatg  43620
gggtttcacc atgttggtca ggctggtctc gaactcctga cctcaggtga tccacctgcc  43680
ttggcctccc aaagtgctgg gattataggc atgagccacc gcacctggct gagccccaga  43740
gattttagag agggattgtg tactcgtgct atgggagaac aggagaatgg actctacagc  43800
ttggttcctg gcacttagta ggtacttgat aaaggactgt tgaactgaaa taggaacaac  43860
aactagctca caggattcct gggacgatca cagatagcat atgtgaaagc ctgacttgaa  43920
ttatgaaggg gtccccgaat gtggaggagg aggaagagga tggacggagt ggagaagttc  43980
agggagaccc gagagtagat gcagagtaga tgattgaaca acagaatatg ccaaatggta  44040
tttgacaaat gattgaggaa tgttagcagt tgcattagtt atgaatcttg ttgaaacacc  44100
agaaaccaac tcaagatagc ttaaacaagt tgggggcaga ggggaggatg aagagaggtg  44160
ggttaaaggg tacaaacata cagttagata gaaggcataa attcaatgtt tgatagcaga  44220
gtaaggtgac taccgttaat aaaaatgtat tgtattggga ggatggacac cctaaaaacc  44280
ctgacttctt tgttatgtat tatatacatg taataaaatt tcacatgtac cccatggatc  44340
gtatgaaaaa caagatagct tagccaggcg tcgtggctca cgcctgtaat cccagcactg  44400
tgggaggctg aggcgggcag atggcttgaa cccaggagtt caagaacagc ctgggcaaca  44460
tggagaagcc ccgtctctac aaatacaaaa aaattagctg ggcctgacag cgtgcacatg  44520
tagtttcagc ttggtaggct gaggtgggag gatcacttga gcacaggaag tcgagactgc  44580
agtgagctat gattgcacca ctgcactcca gcctgggtga cagagtgaga ccctgtctca  44640
aaaatatata tatatacagt cccaacctgt agtcccacct cctggcggag gctgagccca  44700
ggagttcaag gctgcagtga gccatatgtg tgtgtgtgtg tgtgtgtgtg tgtgtgtgtg  44760
```

```
tgtgtacgta ataatacata tatgtgtgtg tattcacaca tacatatgta catatacaca    44820
tttatatata tacatttata tttagatata ttatataaat attatagata tatatacaca    44880
cacggctcac tgtagccttg aaattcatat ctatatgaat ttatatatat atacacattt    44940
atatatacac atttatatat tatatgttat atataaatac acattttat atatatacac     45000 atttatatat atatacactc acatggctca ctgcagcctt gaaattcata tatatatgaa    45060
tttatatata tacgcattta tacatatgca catttatata ttatatatac acatttatat    45120
atatacatat ttatatatat atatatatat acacacacac acacacacac acacacacac    45180
acacacacac acacacagct cactgcagcc ttgaactcct gggctcagcc tcccccagga    45240
gctgggacta caggctggga ctgtatatat atatattttt gagacagggt ctcacacata    45300
catatataca catatgtata tatacacaca cacacatata tacatacata tatatagcta    45360
gaacaaaaaa ggggaattga tgaaagaaa atagaacgca ttcaatccag atctcctctc     45420
atggaacaag ttgtcatcga cttctcatct ctgcttcttt tttcttcagg tctgatgcat    45480
ttttctgtct ctgcagacca gctcctcccc cctccaaatc tcaatggaag aatgcgacat    45540
tctggattca gctacccaaa gaggggtttt ttccccctct ttgtctctat tatacatttt    45600
ataggaagga attctgtccc agttaattca aactgggacc agaggaacag ggtcccgctg    45660
ctcaaaatgg ctgtcacccg tgggtaaggg gagcagtcag agagtcattg tgactggggt    45720
ggcagtccca ctccaatctg ccttgtggct tcctagcctg caacatacat cctcccagac    45780
atacaaaatg tgcctctgcc tgagtcttcc tggcagggag tttggtaccc cccaacattg    45840 ggagggagc ttacaacaca ggactatctc ttcccataga taatctcctc acaaagctcc     45900
actcaggacc acttatattc ttgaggtaag ggaggaggtt caaatgtcat gtaacagttt    45960
tttgtttgtt tgtttgtttt gagggagggt ctcgctttgt cacccaacct agagtgcagt    46020
ggcgcgatca tgactcactg cagcctcaaa ttcctgagtt cagcctcccc agtagctagg    46080
actacaggtg cttgccacca cgcccagctg attttttttt ttgggagaga caaagtctct    46140
cgatgttgac taggctggtt ttgaactcct ggactcaagc aatcctcctg ccttggcctc    46200
ccaaagtgtt gggattacag gcataagcca ctgtacctgg cccatataac agattcttaa    46260
ggttatttct tttgaaagtt tgcatatagt gacttcacac atcacattgt tttacaacta    46320
aggtatatta atgcttaatg gaaatttcca ttttattatt tatttatttt tattgtattt    46380
atttatttat ttttgagaca gagtctcgct ctgttgccca ggctggagtg tagtggcgtg    46440
atcttgactc actgaaacct ccacctccca ggttcaagcg attctcctgc ctcagcctcc    46500
caagtagctg agattaccgg tgcctgccat catgcctggc taattttat attttagta    46560 gagacagggt ttcaccatgt tggacaggct ggtctcgaac tcctgacctc agatgatcca    46620
tctgcctcgg cctctcaaag tgctgagatt acaggcgtaa gccctcacac tcagcctatt    46680
tatttatttt ttgagacaaa gtcttgctct gtcgcccagg ctggagtgca atggcatgat    46740
cttggctcac tgcaagcaat tttcatgcct cagccacccg agtagctgag actacaggca    46800
tgcaccacca cacttggcta atttttgtat tttttagtag agaccagggt ttcaccatgt    46860
tggccaggct ggcctcaaac tcctgacctt aggtgatcca ccgcctcggc ctcccaatgt    46920
gctgggatta caggcatgaa ccaccatact tggctggaaa tttccatttt aatatcttgt    46980
ttacagatag cttgaataat gctgggtagt gggatggtac acagaataga atatattctt    47040
ctatatgtgc atatatttga ttgcatatat aatacatatt attatatatt aggcagggtt    47100
```

```
ctgagttgca actctaagca ggttaaagga attaaggata gactttgttt tctgacataa   47160
ctgaaacgtt cagggagctt caggtgctat tgaattcaag ggttcgacaa ccccattagc   47220
ttgcccttag tggttctgtg tcctttcctc tctccttctc accctctttc cctcccttca   47280
tttctcagct ctgctttcct ttggcttcac ataactccag gctcatgtca tccttttgt    47340
cccaatctga gataaaaaga ccatctttcc tttcaggcaa tagaatatga ttggctaggc   47400
ctaggtcact tgtcaacctc tataccctta cgttttggga gtggggtagg agtaggagaa   47460
ataaagaatt ctactttatg tgtttgtgta tgtatcattt ctatgagaaa aagtttagca   47520
ggaagcttta atgttaaata aataatggca tattgacacc aaaaaatata tacatagcag   47580
ttaaaagagc aaggtttcta catactgcat agaaaggtat cctcagcatg ttattaaaga   47640
caatttgcag aacagaaggt ataatatcat atgatgtttt aagaaaatat ttttttgttt   47700
gtttgtttga atcagggtct cactctgtca cccaggctga agtgcagtgg cttgatctca   47760
gctcactaag cctcaaacca ctgagctcaa gcaatcctcc cacctcagcc tcccaagtag   47820
ctgggaccac agctctgcac taccatgcct agctaatttt tgtatttctt gtagagatgg   47880
ggttttgcca tgttgcctag gctggtctca aactcctggc ctcaagcgat tcacccacct   47940
cggcctccca aagtgctggg gttgcaggtg tgaaccacca tgcccaacct aagaaaagat   48000
tttaagcatg gttgcaaatt cagagaaaat gtctgtacag gtatacaata aattattaat   48060
aatgatagcc gctgagaagt aaaaggaggc ctagaggaac aggagttcca ggttacttta   48120
gtctcctgca ctatttgggc ttcttttttta tttcttaaac attttactat gaaaaaactt   48180
caacatacag aaaagttgaa agttttacag gaaacatccg atatccacct cctacattgt   48240
tcctttgaca atttgtaata cttgctttgt cacatgttta ttcatcccac cactcagcat   48300
gcgtgtcatt aactgcttcc ctggtttgtc ttttaattaa acttttcatt ttgagataat   48360
tgtaggttca catgcaattg taaaagaaa cccatgtac agagatccag tgtgccctat    48420
agccattctc ccaatggtaa catgttgcaa aactccaaga agactgagtt ctatattgat   48480
gtgattgaag tccctccaca gggttcctct ggggcccttc acaactgtgt atcccttcag   48540
agtgatgtta acatttttctg gaatgtcaac agtctgattg ctgagaatgg tcttcattct   48600
cgcagtagac gtggctaata gcacaatatc acaaccagga tactgacact gataggtcaa   48660
gatatagaac agtttcatca ccataaggat ctctcatgtt tccatttat agctgcccgc    48720
atttcctcca tttccttact gctcctgctc cctgctcttt tgtttgtttg tcttttcttgc   48780
ttttctttttc tttctttctt ttttttttttt ttgagacagg atatcattct gtcacccagg   48840
ctggtgatca cgtggtgcga tcatggctaa aggcagcctt gacctcctgg gctcaggcga   48900
tcctcctgcc tcagcctcct gtatagctgg gatcacaggc tcatgccgcc atgcccacct   48960
aatttttttga aattattatt attattattt ccaaatcagt aggtctttta ttgtatcatt   49020
taaatatcac aaataggtct taggaatcat ccagcatctt gtttgtgtag gtggacaact   49080
ctcaaatctt attcatcagc ctgctgaaca gttcccttt cagagacgta gataccgttc     49140
aaaaatttcc tgatatcctt gttttttaact gttgtggctt gctgaatcaa agccgctgaa   49200
tttgaaacaa gctcaatgtc atttccttca aggatgaatt catctttctg ggcttgagat   49260
actgaacaag caacacctgg tctcatctga accccgtgga tgtattttc acccaataaa    49320
ttttggattt caacaacaga cccattctcc tagataacag tgttgacggg gaagtgagca   49380
tacacagacc tcatccttgta actgaggccc agtgtaacac ccttgatcgt gttctgtaca   49440
tgactacaaa tattctgaac ggcagccagt tcctctctgt taccccaccg tttgtcaacc   49500
```

```
tggagcctct gttttttctt tccaagaaga ctgagttcta tatggatgtg actgaagtcc   49560
ctccacaggg ttcctctggg gcccttcaca ataactgtgc atcccttcag agtaatgtca   49620
acattttctg gaatgtcgac agtctgattg ctgagaatgg tcttcattct cgcagtagac   49680
gtggctaaaa attatttta gagttgggtc tccctatgtt gcccaggcta acctcaaact    49740
cctgggctca agcagtcctc acaccttggc ttccccaagt gctgggatta caggtgtgag   49800
ccactgtgcc tggcctcctg ctccccgctt aaccccctggc aactactaat ctgttctcca  49860
tttctataat ttttttttca agagtgttat atatataatg gaatcaagca gtatgtaacc   49920
ttttgggatt gactttcttc actcggcata attctcagga gattcatcca gtttgttgca   49980
tggttcaaca gttcattctt ttttattgct atatagtatt ccatggtaca gatgtactac   50040
agtttgttta accattcagc cattgatgga catttgagtt gtttccagtt tttggccatt   50100
acgaatagat ttactataaa cactcatgta ttcttttta tgaacataaa ttttatttc    50160 tctggaataa attcccaaga gcccatatgg tagttccatg tttagttttt ttaagaaact   50220
gctgactggg catggtggct gacacctatt atcccagcac tttgggatgc caaagtgggc   50280
agatcacttg agcccaggag ttcaagacca gcctaggcaa catagcaaaa tcccatctca   50340
tacaaaaaat tagctgcaca tggtggtgcc tgcctgttgt tccttgctac ttgggaggct   50400
ggggtgggag gatcacttga gcctgggagg cagaggttgc agtgagcggt gattgcgcta   50460
ctgcactcca gcctgggcga caaagaccct gtctcaaaac acatacaaaa ttttccaaac   50520
catttctaaa gtggctgtat cattttacat ttccaccatc aatgtgtgag tgacttagtt   50580
tctccacatc ctcaccaaca tttggtattg tcacttttaa aaatgttagc attctgatag   50640
gtgtgtagcc atatctcatt atggttttat tttgcatttc cctattgaca atgcactga   50700 atctctttca tgtgcttatt tgccatctgt atttccactt ttgtgaaatg ttctcttcat   50760
gtcttttgcc cattttctaa ttagattgtt tgtgttttta ttgttgcatt tttagagttc   50820
tttaatattc tatttactag tcttttgttg gataaatggt ttgcaaatat tttctcctct   50880
ctagctcatc ttttttgtctt tttacagatt atttcacaaa agtttttaagt tttgataatg   50940 tctaatttat cgattttcct tttatggatt gtactttggt gtcaacttta agagctgttt   51000
gcttagtcct agaccttgaa gattttcttc tatttttttt tctgaaaggt tttcttttt    51060 tttttttct tttttgaga cagggtctcg ctctgtcacg caggctgaag tacagtggca    51120
caatcacagc tcttgcagcc ttgatctccc aggctcaagc aattctcctg cctcagcctc   51180
tgaagtagct gggattacaa acatgtgcca ccacaactgg ccaattttg tatttgggtt    51240 ttttcttttt ttttttttgt agagatggag tttcccaaag tgctgggact ataggcatga   51300
gccaccacac ccagcctaca tgtttatctt gtatcctgtg acattcctga attcacttat   51360 ttctagggg tttgtttgtt tgttttgta gactctttga gattttctat atatataatc    51420
acgtcatctg caaataggaa gagttttgcc tcttcattgc caatctttta tttccttctc   51480
ttattgcaca gactagagct accagcacta tgttgaataa aattggtgct ttattcccac   51540 tattagggc aaagcattca gtcttttacc attaagtata atgttagtgg gttttttcata   51600 gttgctgctt atcaagttaa ggacattccc ctctattcct attttttctt acaggtgttt   51660
ttgtttgttt gtttggtttt tgttttttga gacgaaattt cgctcttgtg gcccaggctg   51720
gagtacaatg gcacgatctt cactcactat aacctctgcc tcatgggttc aagagattct   51780
cctgcctcag cctcctgagt agctgggatt acaggcatgc gccaccacac ccggctaatt   51840
```

```
ttgcattttt agtagagatg gtgtttctcc atgttggtca ggctggtctc gaactcctga   51900
cctctggtga tctgccggcc tcagcctccc aaagtgctgg gattacatca caccaagtca   51960
ggttttttt  ttttttaat  tattaaatgg gtgttgaatt ccgtcaaatg tcttttcttc   52020
atcattgcta tgactatatg gattttcctc tttatactgt taacatggtg gattacattg   52080
atcaatttt  ggatattgaa tcagccttgc atccctgaaa tgcaactgta taattctttt   52140
tatatattgc tggagtccat ttgctactat tttgttaagg attttgctt  gtatattcat   52200
gcaggatatt ggtctatagt tttcttttg  ttctactgtc ctcatctggt tttgataata   52260
ttaaccttat aaaattaatt ggaaaacatt ttctctcttc tgttctctgg aagagattgt   52320
gaagaattaa attcttcttt aagtggtaga attctccagt gaaaccatct ggatcaggaa   52380
atattgagag ggagggagga tggttttatt acaaattcaa ttttcttaat agttataggg   52440
ctattcaaat taaactaata ccctaaaatt aaactaattt aaactaatac cctaaaaaaa   52500
aaacctctac acatataaac tcatactgga tgagttaggt agtttgtgtt ttgaggggaa   52560
ttggtttatt ttatttaagt tgccaaattt atgcatgtag agatttttg  gaggatatta   52620
atttcttggg gctgctgcaa caaattaaca caacttaata acttgaacaa cagaaattta   52680
ttctctcaca gttatggagg ccagaagttc aaaatcagca tcaatggtca aatcaaggca   52740
ttggcaggac cacacacttt tcagaagctc tatagaagaa ttcatttttt gcctcttcaa   52800
gtttctggtg gcaaccaaca ttccttggct tgtggccaca ttgcttcaat ctctgcctcc   52860
atggttgcat tcccttctct tttgtccaca actccctctg ttactctctt ataaagacat   52920
ttgtcattgc acttaaggtc tactaggata atctcatctc aaaatcctta atcgcatcta   52980
caaacgctct ttttccatat aaggtaatat ttacaggttc cagggattag gacctaatta   53040
acgctttgga ggtctactga ggctgactaa tggcctccaa acataattct ctatttcttt   53100
cattttttt  tttttttttt tgagtctcgc tctgtcgccc aggctggagt gcagcggcgc   53160
catcttggct cactgcaagc tccgcctccc gggttcacgc cattctcctg cctcagcctc   53220
ccgagtagcc aggactacag acgcccgcca ccacgcctgg ctaattttt  gtattttag    53280
tagagacggg gtttcaccgt gttagccagg atggtcttga tctcctgacc tcgtgatccg   53340
ccagcctctg cctcccaaag tgctgggatt acaggcatga gccaccgtgc ccggtcataa   53400
ttctctattt cattttatt  ccctattatt aagtcccacg gtgtttccct attatccttt   53460
tgatgcctac agggtccatg tgatatcttt tctttcattg ctaatgtatt tctcctcttt   53520
taaaatttgt cagtcttgct agagatttat tgatctttc  aaataattag ctccttgttt   53580
cgttggtttt ctccttttct tttcagtttt ctgtttcttt tttattttc  aatttcatgg   53640
atttctgcct tttttttttt tttttttg   gagacagggt cttttctctgc cgcccaggct   53700
ggagtgcagt ggcatgatca tagctcactg cagcttccag ctcctcagct caactgagcc   53760
tcccaccttt a gcctcccaag tagctggaac cacagttgtg taccaccatg ataggtaaat   53820
ttttaattt  taacgtttt  cagaaatagg gtctcattat gttgcccagg ctgctctcaa   53880
actcctgagc tcaagcaatt ctgccacctt ggtctcccag agtgttggga ttacaggtgt   53940
gagccaccat gctcagccct gctcttatct tattatttcc ttccttctgt tggctttgga   54000
tttatatttt tcccaagttc ttgaggtatg agcttagatc attgatttga taaagacttt   54060
tctacttttc atttattttc ttttttcctt tctttcttt  tgacacagga tctcgctctg   54120
tcacccaggc tggagtgcag tggcacaatc tcagctcact gtagccttga tctccccagc   54180
tcaagtgatc ctcccacctc agcctcctga gtaactgaga ccacagggac acgccaccat   54240
```

```
acctggctaa ttttttgtatt tgggtttgtt tgtttgttgt tgttttttttg tgtgtgtgtt    54300 tttgtacagc tggagtttcg ccatgttgcc caggctgctc tcgaactcct gggatcaagc    54360
gatctgtcca ccttggcccc ccaaaatact aggattacag gcatgagtta ccatacctgg    54420
gcctctactg tcctaatatg tgcatttaat gctatacatt ttcttcatct gtgtcccaca    54480
gattttgtta cattatattt tcatttcact cgcttcagtg tattttacaa tttcccttgg    54540
ccaggtgcag tgactcacac ctgtaatatc agcactttgg gaggcagagg cgggtgaatc    54600
acatgagtgc aggagttgga gaccaacctg gcaacacag ggagacccca tctctacaaa    54660
aaaatccaaa aattagccaa gcgtggtagt gtgatcttgt agtcctagct actcgggagg    54720
ttgaggctgc agtgagctgt gatagcgcca ctgcattcca gcctaggcaa cagagcgaga    54780
gcccatctct aaaaatgaat aaatatataa atgtatattt ttatatgtat tatataatag    54840
tataatatat tataatagta taatattata ctattatata atagtagtag tatatattat    54900
gtattatact attatataat ataaataca tgcaatacat atacatatat gtgtatttt    54960 atacatgtat tatatataca catacaatat atagatgtat atataatatt gtatatataa    55020
aatattttat atatacacat atataatttc tcttgagact tcccttttttc gtccatggag    55080 tacttagaag tgtgttgttt agtttccaag catttggaaa ttttttctgtt atcttttttgt    55140 tattgatttc tagtttgatt ccattgtggt cagagaacac acttggtatt aattcagttg    55200
ttttacatct gttttgttta tggcccagga tatggtctat tttgaaatgt gttacctgag    55260
tagtcgaaaa gaatgaacat tttgctgttg ttgggtgaag tgttctataa atattcatta    55320
gatcttgttg gttgatgatt ttgttgaact cttctatatc cttgttgatt ttctgtctag    55380
ctgtcgtatc aattgttaag aaaggaggat tgaagtcttc agccccagtt gccgattttt    55440
ctatctctcc tttcagttct atcagttttg gcttcatatg gactgcagtt ctgttgtttg    55500
gtgcatacac atttaggatg atttgttttc tcactagatt ggctcttgta tcattgtaca    55560
atgtctctgt ctctagaaaa gtttctttgc tctgaagccc actttatctg acatatatac    55620
atgcacaata tatatatgta tagctactct cctgctttct tttgtttaat gtttacataa    55680
cctatctttc ctatcttttt tcatcttttt acttccaacc tacctttatt gctatactta    55740
caatgacttt atgcaccaca tctagttagg tcatgttttt taatccactc tatcaattgc    55800
ttttaaatag atatcaatct tttgcattta gaccatttac attcaatata actattgata    55860
tgttagggaa taagcctgct gttttatttt ttgttttatg tttttctctc cttttttttt    55920
tcctgagatg gagtctttgt ctatttccca ggctggaacg cagtggcatg atctcggctc    55980
actgcaacct ccgcctcccg ggttcaagtg attcttgtgc ctcagcctcc tgagtagcct    56040
ggatcacagg cacctgccac cacacctggc tagttttttgt attttttagta gagacgtggt    56100 ttcaatgttg accaggctgg tcttgaactt ctgagctcaa gtgatctgcc tgcctcggcc    56160
tcccaaagtt ctgggattat aggcgggagc caccgtgcca ggcccacttt tcattttttct    56220 atttttcttttt ccctgccttc ctgtgggcta cttgaacatt ttcattagaa tcatcttttt    56280
atttatctgt agtatttggg gatatttctt tacatgtaac ttttttttttt ttagaggcag    56340 tctcactctg tcgcccaagc tggagtgcaa tggcatgatc tcagttcact gcagcttctg    56400
cctcctgggt tcaagtgact ctaatgcctc agccactcaa gtagctggga ttataggcat    56460
gcaccaccac gacaggctaa tttttgtatt tttagtagag atgttagcca ggctgggctc    56520
aaactacagg cctcacatga tccacccgcc tcggcttctc aaagtactgg gattacagac    56580
```

```
atgagccacc aaacctggcc tacacgtaac ttttttagtg acttatctag gtattacatt    56640
gtatgtacat ggcttaatac agtgtactgg ttttaccagt taaagtgaaa tatagaaacc    56700
ttacctccca agctgggcgt ggtgactcac gcctgtgatt ctagcacttt gggaggccca    56760
ggtgggagga tcctttggac gtaggagttc aagactagcc tgggcaacat agcgagaaca    56820
agtctctaaa aaatttaaaa attagcaggt tgtgatggtg tgcctgtagt cccagctact    56880
tgggaggctg tggtgggagg atcacttaag tctagaaagt cgagactgca gtgagccatt    56940
atcatgccat tacactccag cctgggcaac agactgagac cctgcctcaa aagaaaaaa    57000 aaagaaatat tacttctctt tacatccctt tgccagcctc catttataat atgattgcct    57060
taaatatttc ctctgcatat ttttagaacc acaacagact gtattgtaat ttttgcttca    57120
actatcaaaa ataatttaga aaactcaaga aggggccagg tgcagtgtct catgcctgta    57180
gtcccagcac tttgggaggc cagggtgggt ggatcacgag gtcaggagat cgagaccatc    57240
ctggccaaca tggtgaaacc ccgtctctac taaaatacaa aaacagctgg catggtggc     57300 gcacgcctgt ggtcccagct acctggggag ctgaggcagg agaataactt gaacccggga    57360
ggcagagttg cagtgagcca agatcacacc actgcactcc agcctggcta gagagtgaga    57420
ctctgtctca aaaaaaaaa aagaagaaa agaaagaaa aagaaagaaa agaaagaaag    57480
aaaactcaag aagaaaagga ggccagatga ggtggctcat gcctgtaatc cctgcacttt    57540
gggaggccaa gcaggcaga ccacttgaga tcaggagttg aagactagcc tggccaacat    57600
ggcaaaatcc cgtctctact aaaaatacaa aaaattagc caggcacggt ggtgggcgcc    57660
tatagtccca gctactcagg agactgggggc acgaggatcg tttgaacttg ggaggtagag    57720
gttgcagtga gccaagatcc tgccactgca gtccagcctg ggtgatagaa caagactcag    57780
tctaaaaaaa agaaaagaaa aagaagaaaa ggaggctggg catggtggct cacacctgta    57840
atcccagcac tttgggaggc cgaggcgggc agatcacgag gtcaggagat cgagaccatc    57900
ctgcctaaca tggtgaaacc ccatctctac taaaaataca aaaattagcc aggtgtggtg    57960
gtgggcacct gtaatcccag ctactcagga gactgaggca tgagaatagc ttgaacctgg    58020
gagatggagg ttgcagtgat ccaagattgt gccactgccc tctagtctgg gtggcagagt    58080
gagaccctgt attgaggagg aggaggagga agaagagaag gaggaggaag ggggaggagg    58140
aggaggaggc ggaagggggaa aggaagggat ggggaagaag aagaagaaaa gtgttttga    58200 acaatgagaa tacgtggatg gggaggggca atcacacacc agggtctgtt gtggggtggg    58260
gggctggggg agggatagca ttaggagaaa tacttaatgt agatgacggg ttgatgggtg    58320
cagcaaatca ccatggcatg tatataccta tgtaacaaac ctgcacattc tgcacatgta    58380
ccccaaaact taaagtataa taaaaaaaaa gaagaagaaa agtgttttat atttaaccat    58440
gtctttgctc actgtgttct ttctcccttc ctgatgtttg ttttctttct ttttagagaa    58500
atttattgtg ctttacccctt tattcctgaa atataatttc acaggcaata gaattctggg    58560
ttgactattt tttttttctt tcagcacttg aaaatattgg ctatttcctt ctgaccccca    58620
tggtttcttt taaaaaattt gctgttgttt gaattatttt tctctacagg taaggttcat    58680
ttccgtcttg ctgctttcaa gagttttctt tgcctttact tttttaaaa aaatgtttta    58740 aattttatag aaacagggtc tcactgttat ccagactggt cttgaactcc tggactcaaa    58800
tgatcctctt gcctcagcct tccaaattac tgggattaca gacatgagcc atcatgcccg    58860
gcctgccttt aatatttaga aatttggctt taatatatct tggtatttct tgagtttatc    58920
ctgttttgat gtgttatctt gttcactcag cttattgaat ctgtaggcta atggggctct    58980
```

```
tttttgccaa atttggggag ttttaagcca ttactttttt ctatttttt tttttctttt    59040
tgagatggtg ccttgctctg ccacccagac tggagtgcga tggcgcgatc tcggctcact    59100
gcaaccctg  cctcctggat tcaagcgatt ctccagcctc agcttcctga caactggga    59160
ctacaggcac ctgccaccac acctggctaa ttttgcatt  tttattagag acggggtttc    59220
accatgttgg ctaggctggt ctcaaactcc tgacctcaaa tgatccaccc acctcagcct    59280
cccaaagtgc tgggattata ggcgtgagcc actgcgctcc gccagccatt acttttgag    59340
tactttttt  agctgtgccc tctttctcat ttcttccagg attctgatga catgaatttt    59400
agatctttc  atctagttcc acaggtccct gtggcttttt tcatttctt  caaactgttt    59460
tctctctgtt tctcagattg ggtgattttt aattattcta ttttcaggtt cacttgttct    59520
ttcctctgtc ccctccattc tactgtttag tccatttact gaggttttt  tacttcggtt    59580
attatgtttt tcaggtttaa acattccatt tagctcttct ttatattttc tgtttcttta    59640
ctaatacttt ctattttttt tgctttgttt caaatgtgtt cttaattatt tgttgaagca    59700
tctctctgat ggctgcttta aaatctttgt cagataatgt taacatctgg tatctttgta    59760
ttgttgattg tcttttttaaa atcagtttga gattttttctg attcttggta acatgagtga    59820
ttttcagttg atacctagat atctcatatt attttatagg ctctggatct tatttaagtc    59880
ttcagtctta gctggttttc tctgaaactg ctcctacaga ggaagggtgg gggactgtta    59940
cttctttatt gccaagtggt ggtagaagtc cagcttctcc acttggcctc cattgacact    60000
tcaaggagtg ggtgtttctc attactgctg gtcaggggtg ggcgttctgc ctccccacat    60060
ggtttctgct gatatcatgg tggggatagg cttgttacta ctacgtaatg gtgaaagtcc    60120
tgcctctttta ctaggtctct actctagtgg aaagggagaa ggacatctcg ttgcttctag    60180
gtgaagagta ggtttccgat gtagtctcca ctgacacagg ttgacactga ggaggtgggg    60240
gtgggaccca gggacatggg tacaggcctg caaggataaa agtccctgat ctctacatgg    60300
cctcctctga caccacccag tagaggtgcc ggggggcctt gttacagctt cgccttcaaa    60360
agcgtgaaag tctcagcttc tccctcaacc tttgctggtg tgagtgggac cagtttttt     60420
ctgtagcgtt tgattggcgc ggaactgtta ttgtcttcaa agttttctgt cttgctgggc    60480
tgtccctttc ctagtccttt gtctagtgag agcaggcttt ttttcaggct cctctttctc    60540
cttcttattc ttctcctccc gtctgaaccc attggcattt ctaggttgct gctccaagcc    60600
ttggatatat gacaccgtaa taaaatcgag agaatgcacc accatgtttt cctcagccca    60660
ggtccatagc ctgtctgcca tctttgtatc tttcctagtc ttctaatgtc tgttttatag    60720
acaatgtcca gagttcttag ctgtatttag gaggaggaat agggagaagt acagctcctc    60780
tgtattcctg gagtggaatt ctctgcctct ctgattttaa acaagccaaa ctcacaagag    60840
ggcaagcaga aagcaatttc attctttctc acgactatcc ctttcaatcg ggcctgtggc    60900
ttcattcttc tagatgaaat ttcaggcaga ttcatagcct tttcaatccc tttcagttat    60960
aaatatgtgc atgtgtgttt gttcgtatta acatcaatcc tctgaactct tgtccaatct    61020
aatcttttgc cctcccaaac ttggacttat ctcagggcct atctatatct atggtagaaa    61080
gaggggctct tggggggtctt ggttagcttc tttgctattt cccctcctta ctcttttctt   61140
ctccctgtc  tccttttttc ttttttattt atttttagag ctagagtctc gctacattgc    61200
ccaggctaga ctcaactcct gggctcaagc gatcctcttg cctcagcttc atgagtagct    61260
gggactactg caggcagctc ccctttattt tctgtattgc atctggctcc gctagtgttg    61320
```

| | |
|---|---|
| aagtgagaga gatcaaggag aaatacaggg caagaaaaga tcctgtgtct gttatagttt | 61380 |
| taatcaggtg ttggagctct ccagatgtag ccaaaggcca actcttttct atggggccca | 61440 |
| tttgtggatt tttcagttcc tcccatttct ggttattatt tggaatcaga ataccaataa | 61500 |
| ttgaaaagaa atagcatttc aagcaaggga atatctgttc tggcttggaa aaaatctatt | 61560 |
| tcatacacat tttcattttt agaaagaata ttgttgttta gaaggagtat ttaaaagttt | 61620 |
| atatttagaa tgctgtcgaa agttccaaat tatttgttaa atatttagaa gattttatag | 61680 |
| aaaaggagca tttcaaataa aactcaagta ttaaagaaga atatcaatta ggcaataata | 61740 |
| ccaattaagc ataaaaaaag agaataccag ttaggcaacc cactctcctg ttgggctgtg | 61800 |
| aactggccat gcccctttt gcctacattt tttgctcatg ccattcactg gctgaaatgc | 61860 |
| cttcccttc ctctagccaa atcctgcttt tcctttgagg cccaagtagc acctcctcat | 61920 |
| gaaagcctcc catgactacc ccaactcact tctctttttc ctctcgcatt taggtattga | 61980 |
| ctgctgcctc atgaaggctg gtcctgtctc tatagtgaat attgtgcacc tcagggtaga | 62040 |
| atggagagca gaagacttca aatcaggcag tctgggttca daccccaatt ctagtgctaa | 62100 |
| atagctacgt gactttaggc cgattgtgtg tgacttccct gagccccagt ctctttgcct | 62160 |
| gcaaaatgag aaaaattata acaatgtcat cggttgttct gaggattctg agaggaatta | 62220 |
| gtaggagaga gaactaagaa gctgcgggcc tctacagagc cattcaactg gcatttcgga | 62280 |
| agatgttgcc catcagagtc agaccttctt agcatcttcc ggctgggccc aaacttccca | 62340 |
| agaccatttg gacaaggtca tctctatccc accatggcct cctcccagag gaggagaaga | 62400 |
| atcatgctgt tacagcagaa ccgaagattt gggcaaggga gctaatgatt atgttctgcg | 62460 |
| tcaggtcaga gatgggctgg gaaagccact ccaaagccaa gacaagcagt tcctggaaa | 62520 |
| aagaaggctg cgcggagccc agagtggcct ggatcctgcc tcatttcctg gaccagctcc | 62580 |
| ttaggtggtt actggattgc caataaagca gagcttatta aagtcaacga gctcaggctt | 62640 |
| catcgccgcc atggtatcca agcaccagtc tgtctgggat ttcatttgcc agatggacaa | 62700 |
| aggagaggtt gttccaatac atatcctgag tggtgggggt ggggagagaa ggggaagaat | 62760 |
| gctctctaga gaattctctt tgtcctctga agtaaataga gatcatgtct tccccagcca | 62820 |
| cactcagtga tctgaatctc ttggactgtg gattttcct ttacctgctg tgaagccttg | 62880 |
| aaaagtatga attagcttga taatgatcct ctaaagatgt tcaagagtta agacgtgtt | 62940 |
| taagttcttc aggcaatcca atatgactac gggtttccaa aaatttgaag gaaactgaaa | 63000 |
| atcatagttc ccaaaccaga tattttccgg tgtccagatg ttcactggca tgcaaaccaa | 63060 |
| atgtctggat tatgagctcc ttttttcatt tcttttatc agcttacatc cagatgttgg | 63120 |
| atccaactgg tcagaggcct ggggcagaga cagaaatcaa atctagggtg ttcatctaga | 63180 |
| gtctcctgct cctccattcc tgcttcctcc tcacgctgcc cccacatcct ccccaactca | 63240 |
| ccttcatgct acatctcggc aaatacagct catatccagg cacggtgcag cccttgacag | 63300 |
| ctgggtccgc aaaggcagat cgggtatatc tttaaagaaa agttatctta accattgaga | 63360 |
| agccttcctt cctcagagga gagcacctcc ccagcagacc tccgaggaga ccaagggcag | 63420 |
| gacaggaagg gtgaaaggaa gtttcaggac tgcaggaaat aagagcttgg aggtcaaggg | 63480 |
| agagatcaga taaaacatga atctgatcag catcctagtg gtctagagtg gagacaatct | 63540 |
| gcggagtcaa cctcagtaag gacacacata gagaagaacc aaagcctcta agacgaagc | 63600 |
| tgagaagtgt acggtcgtag aagactcgtg tctgttattc ttaaaagctc aaggaggtat | 63660 |
| aaactgcata agatttaaat ggaggaacac acgatcttac ttgctttcag aggattttgg | 63720 |

```
ggtccccatt ctcccattag cagccaggca actctctctg tcctctccaa agggaggagt    63780
ggaaaggctt caaaatccct aggaaataaa tgtcccctcc acccaaagtc cagtgtgtag    63840
cctgaggaca ggactttcac tgagagaaat atataaaaga aggggataga agccaggcac    63900
ccaggtggtg ggtaacagaa gggaactttc tagctggttt tatttaggga gggcatcctg    63960
ggcaaaagtc agaatgcaac ttttttttta aacccctttt aacaagatgc tgttgaattc    64020
ctcttttgca gatgttctgc caattgaatg gaaactgtcc atagtgggga gcagagagcc    64080
tcatcttttc tggaactgaa catccatcct taaggccaga tttctcccat caccaacttt    64140
aactcctgcc ctagccctct ctcttccttt tcaaaaccct ctccacccag aagggagat    64200 tctggagcca agactgtacc agccacacct ccccagagtt gttaaggaag gaactcgaag    64260
ccaggggtgg tcttctggca agcacccca ctaccagtag caggacagat gtgtttctaa    64320
tggactacac tatccccgga ggtcacatga ttcaggctgc caagggtacc tgcccttggg    64380
aaatcaactc ccgaagataa attgggattg ggtcctgaga agatccatgg aagcccagag    64440
gaccctgcct ctctctgttg cttcatgctg tagaggcagt actggggagg gcctgcccca    64500
catccggcag ggcagctgga accatgtgtt tgatgacact ctgctccctc aatgtggagc    64560
ctcatcctca tctcacagtc tagcaggcct ctggtgggtt aggcttgtct cacccagtgt    64620
gtgagttttt ttggaagtga cctgattttg gagtttccct ccaagccttt ctcaggtaca    64680
tgctttctct tttattctgt cttctttttt tgatcttctt aaatctgatt ttctcctttt    64740
tccctctctt gtctccatct tttttccagt ctctcgcttc tctttatttc tccccatatt    64800
tcactctgtt ctctcacccc aacctttccc ttctgtttct ctccctccct ctcttcccac    64860
cccctgcctg gccttccata tatcaagcag agttttatca ccttatgcag gggcagccct    64920
gccacctgcc ataaagttga taggctaatg acattttgtg gatattgcca tgtcacaagt    64980
ccaggacagc atcaaaaata gccctgatgt ctaaaccact tcagctatct tttttatttt    65040
taaaataaat acattcacat gctttttaaga aactataaaa atatataaag taaaaagatc    65100
tttctctcac actgtctcca cctctcctgg tctcaccgtt gtgcttaggg gaaaccattg    65160
tgattagttt ctcctgtgtc cttccagagt gtctttatgc aaatgaaaat tattgtgata    65220
atatattcct attttccccc ttactacaca aaagatagac taccataatc ccattctgca    65280 ctttttttc acttgataat aaaaacatga ttttattaat gggtgtttat ggagtgatta    65340
ccatgtgcta tgtgcctgct gggcactgca gaacatacac tggtgaacaa gacacaatca    65400
caatccccgt attcaaggat ctgaagaccg tctagtgaca aagcccaaca ggctcatcta    65460
cattcagcca tgcgatagag ggctgaatgt ctttaaataa gtaaagtcgg ccaggcatgg    65520
tggctcctcc ctgtaatccc agcactttgg gaggccgaag caggaggatc acttgtgtcc    65580
aggagatcga gaccagcctg ggcgacacag tgagaccctg tctctacaaa aaataaaaaa    65640
ttagctgggc atggtgtggt ggtgtgtgcc tgtagttcca gctacatggg aggctgaggt    65700
aggaggtttg cttgagccca ggatgttgag gctgcagtga gtcatggttt tgtgccactgc    65760 attccagtct ggggtgacag agcaagaccc tgtctcaaaa aaataataaa caaaataagt    65820
aaaatcaagg aacaatgagt gcacagaaga gggagattaa atccaacctt gaggactcat    65880
ggtggggatg tgtgtctgagc tgaactacgc agaatggatg ggattctgca cacacagagc    65940
tggggaagtg gagggtttca tgtggtcaga gatgtcaagg tgagaaagtt ctggcacata    66000
caaggaagtg aacggcagaa gcccaggggg ttgggaaagg atacagctgg aggggcagtg    66060
```

```
tgtgcagtag gaaacttaga gaactggggt caaccacctg gatttaagtc ctggttctac    66120
ctcctactag ctagtcagtt cttcatctgt gaaacgggt aaaaattatc tcccgcatta    66180
ttagaaggat taaatgaggc aacatcatga agacctcaca atgaaggact gcacagggtg    66240
aggtgttaag cctgaaaaga caggttggaa tttgatctta tatggccctg ggggccatga    66300
tgcagagctc aggccttata ctgaaggctt tggagaaggg aacagtgaag tgtttgggat    66360
aaagaaataa catataggac caaggagaga aggtgcgggt ggtaggacag gcatttcatg    66420
aaatgctata aatcttttct cttggttacc aatgaaagac aactacacat cagataaact    66480
tttactttat tataaaaatg atttatagtt tcacttagga atgcaacttc agtgggtagt    66540
aactctgtaa ctatatggtg gcatccttgg aatatattga tttattcact cctcattat    66600 ttattcattt gatcaacatt tgtccagcac ctatgaacag ttaggcgctt gtgccatacc    66660
ttctatcctg aagtcagttt accagacaac ataccatgaa ggctgactga agagggtctg    66720
ctgagttcca caactctcag tcttgcccca gtgcctcttt ggaacatcat ggcacagaaa    66780
ggaagttcac atatttctct gacttctagc tccctgcagt tagaagaagt caaccacggc    66840
agggctgagg acaacagaag agtcaggtcc agaggataaa gtcatgatgt caacagtgtg    66900
gatcaagact ggccaaggct gggtgcaata gtacacacct gtagtcccag ctactcaaga    66960
ggctgaggca ggaggatcgc ttgagtgcag gagttcaagt ctagcctggg caacatagtg    67020
agaccctccc catttcttaa aaaaaaaaa aagaaaagaa aagaaaaaag attagccaag    67080
ccaagagaag tccagggcag aacattttat ttcaggtaat tgggaattga tgatgtatca    67140
ttactgggct ctgttctccc tttaggggt tcaagccaag tggaggaaat gcttcattcc    67200
cacttgcctt tctgaccaga ttctcctgca gtgctgcagt tttctgcttt tagggagctg    67260
aggatataga ttgaggtatg gtagaaacta cagagtgagc ctcatctgcc tcattttttt    67320
gttttgttgt gggttttttg ttttgtttg ttttttgttt tattgagaag ttttgctgtt    67380
gttgcccagg ctggagtgcg gtggcgtgat ctcagctcac tacaacctct gcctcccggg    67440
ttcaaggaat tctcctgcct cagcctcctg agtagctagg attataggca tacaccacca    67500
cccccggcta attttgtatt tttagtagag acagggttcc tccatgttgg tcaggctggt    67560
ctcgaactcc agacctcagg tgatccaccc gccttggcct cccaaagtgc tgggattaca    67620
ggcgtgagcc accgcgcccg gcccatctgc tcttcaatg agctgaggtg gcagagacgg    67680
caccctcagc ccagccactg gaaaaccct tgccaagttg gaggaagacc tctcagccca    67740
gagtcacact tataccctaac agctgtgcca aatatgattc tgggccatgg aaacattcag    67800 agtaaaata gtatatgggg catattgaga tgcttccacg gaaaccttct ggggggacaaa    67860 taaaatgttt ttattgagaa aggtctcgca tctatcatct aaatcatttc tgaaatgaaa    67920
caacagtctc tggttactca cacctgggtt gaaggagcca ctcctctggg gaatcccttg    67980
tagctttaca cgtgaatggg gaatcctttg ttttagagcc acagcttact cttcagagaa    68040
agggcgttag gaagggagac agctgattct taggtccaaa gcccagaaag tagttccgcc    68100
tctaaggccg agtgagccccc accttgggcc aagctgggaa tgaagcagca ctggttttat    68160
ttttttgttt ttattttta cctttttttt ttttttttg agatagcatc tcactctgtc    68220
tcccagactg gagtgcagtg gtgcgattta ggcacactgc aacttccgcc tcccaggttc    68280
aagtgattct cctgcctcag cttctgagt aactgggatt acaggtgtgt gccaccaagc    68340
ccagctaatt tttgtatttt cagtacagac agggttccac catgttgacc acactgatgg    68400
ccaactcctg acctcaagtg atccacctgc ctctgcctcc caaagtgccg ggattacagg    68460
```

```
catgaggcac tgtgcccagc ccaacactgg ttttgtcacc tgtacacata ctccacaagg   68520 gccccctgaca accaagtttt cagctctccc aagcctcaga ccacatggca ccaaacagct   68580
agatgaaaaa ttcaattaga ctcacaggca ctattttcct acaggttact gaggtattaa   68640
aacaactgga aatttagatg agtttgtgtt gcttatccaa atattttatt aaaatatttt   68700
ataaaaaggg gagaagaggc agaagaaaat aatcaggtag actgccaggg taaggaggga   68760
caggaagagg aacacagcat gtgctcccca aattcccaga gggacaaaac tttttagggc   68820
agttttattt aactgctata aattgtcaaa aaacatgaaa tcatccacat acattgtgaa   68880
acatctgaca ttccatgaca accatgtcaa atgcatgcag atcattaaga tagaaaccaa   68940
aactcataaa atcatagata tgttgctctg atgcagctgt aaattatcct tcaacttcac   69000
tccgtagggg gatctctaac cagtttcctc aattcccatg cttccatgcc aagcattttc   69060
aatgggatat ctaccaacat gctaaaaatg tacttcgttc aattgtgtgg ccaattcttg   69120
acctgaccgt tcatatcatt tgcttagatc tccccttac tgtgcctaag cacacccagc   69180
cctgtatgac acagaaagtt cactgacagt ttgaataatt cagccaggaa tgtcccctgg   69240
aagaccacat gggtagagaa gctctaagga ggcagaaaaa ctggctcatc cctgagagag   69300
ctccaggaac agtctccccc acgcctcctc tcccacccat ccaaatttct cagagctgct   69360
ctcaaagctg cacagaaaag atttggagac aaaaggcaat aagggggccg ggtgcagtgg   69420
ctcatgcctg taatcctagc actttagaag gctgaggttg gtggatcact tgaacccagg   69480
agttcgagac cagcctgggc aacataggga aactctacaa aaaatacaaa aaattagcca   69540
agcgtgatgg tatgcacttg taatcccagc tactccaaag gtggagggag aggatcgctt   69600
gagcctggga gttcaaggtt gcagttgagt gatgattgtg ccactgtatg ccagcctggg   69660
tgaccaagca atacccatc tcaaataaaa taaagttaaa ttaaaataaa ataaaaccct   69720
gccgggcgca gtggctcacg cctgtaatcc tagcactttg ggaggccaac gcgggtggat   69780
cacctgaggt caggggttcg agacaagcct ggccaacatg gtgaaaccct gtctctacta   69840
aaaatacaaa agttagccag gtgtggtggt gggcacctgt aatcccagct actcaggagg   69900
ctgaggcaag agaatcgctt gaaccccgga ggcggaagtt gtggagagct gagatcacac   69960
cacttcactt cagcctgggc gacagagcga gactctgtct caaaaaaaaa gaagaaaaaa   70020
aaaaagccag tgaggggagg ctcctctcac ctccaataat aagaaggaac tggctcaaag   70080
atatccattt acccttctg taaaatggac attctttccc tttccctgta cctcaccata   70140
catgagatga aagatgtgaa gtacacaggt acttggaaaa tgaaaaagtt tcataccaat   70200
gtaagagggc ttttccccta gaccacagca ggacttgaat ccaacccatt ggctcgaagt   70260
ccagcgctca ttctattctg ccacagctac tgagcaatga ggcaagttct accttgggcc   70320
agggcagggc cagcccacgg cagcaggtaa gagcctgtga gttgtattaa cctgctagaa   70380 tagggggagtg tgacctgtga aataaagatc ctaatgctcc ctgctcccag agtgcagaaa   70440
tagcactgag tttccttcct cttgaatttt aaaatgcctc gtaatactct ccccatgtcc   70500
tagattatga tatggagcta gaaattagca ttctattcca acacactgtg gggccttcgc   70560
tttggggttt gaaatgatgg ttttaataa gctggctcca ggtacctgtc accagtaata   70620
gaagttctgc ccgggaagat agatcgcttc ttgttaaaag accatggggc aataaatttc   70680
ctgaggcata actcagcttc caaatcagga ctcaggagaa tcgcttctac cttctgacac   70740 taacccttg gcctctggtc cctgctgacc ctgaccatta acctcagtca cagctcttct   70800
```

```
ttgcccaggt cattgtgctt gcatttaggg gagtttggtg agatccacaa gggcataact    70860
tgcaggtgtg actgtgcccc aggactgggg tcagtggagg gagatcatag agaggaccag    70920
agccatgagt cttgatggtc tgccgtgagc aaacgcatat ctctgctgtc ccaaggatcc    70980
aggccatcaa gactgcaaaa taagctcatc atagaaattt aagcagttct gtcagacact    71040
ggcatctttg ctgaggcatc aggggagtct ttaagtgcac agtggctcac acctgtaatc    71100
ccagcacttt ggaggccaa ggcaggcaga tcgcctgaag tcagagttcg agaccagcct    71160
ggccaacatg gtgaaacccc atctctacta aaaatacaaa aattagctgg gcatggtggc    71220
acatgcctat aatcccagct acttgggaag ctgaggcagt gggatcactg gatcccagga    71280
agttgaggct acaatgagcc aagatcacac cactgcactg cagcctgggt gacacagtga    71340
gaccctgtct caaaaaaaaa aaaaaaaaaa aaaaagacc caaatcaaga ataagaccag    71400
ccaggcacgg tggctcacac ctgtaatccc agcactttgg gaggccgagg caggttgatt    71460
acctcaggag gtcaggagtt ccagagtagt ctggccaact ggggaaaacc ctatctctac    71520
aaaaatacaa aaattagcca ggcatgatgg caggtgcctt tagtcccagc tagtcaggag    71580
gccgaggcgg gagaattgct tgaacccaca aggcggaggt tgcagtgagc tgagatcgtg    71640
ccgttgcact ccagcctggg agacagagca agactccttc tcaaaaaaaa aaaaaaaaga    71700
actacaagac cgctctttt  gacagcagct tccccaacca gaaccagccc aggaactgct    71760
tgcaggacta cctggacttc cacctctgtg agaaggcagt gattgctaaa ggggacaatg    71820
tctttgtatg tgaatggtac cagcctgtgt acaagtccct cattcccata tcctggatct    71880
cagcctggga cgaccactgg gcagaagcca catttccctg ggaagatttg aactggctgc    71940
accccacctt cctctgtgtcc tccgtccttc tcccagggtg gtaaaagggg acctgggtac    72000
atggcgatcc ccaccctgga accctcaatc atgacttgac taataataaa acttattgga    72060
aagtgaaaga aagaaagaaa agaaagaaag aggccaggtg tggtggctca cacctgtaat    72120
cccagcactt tgggaggcca aggtgggagg atcacttgag gccaggagtt caagaccagc    72180
ctggccaaca tggggaaacc ctgtctctac taaaaatagc aaaaattagc tgggtgtggt    72240
gacacatcac cactactcgg gaggctgagg caagagaatc gcttgaaact gcggaggttg    72300
cagtgggccg agattgcacc actgcactct ccggcctggg tgacacaata agactccgtc    72360
taaaaaaaaa agagagagag agaaatccaa gcaaatgtaa tcaatcatgt tattcaatct    72420
gaccacttgc ttgtggggat tggagactga tatatggata atgaactttt aaaaatacca    72480
cagaggtagt aaattaaaca tatatagtgc ctaccctata acccagaaat tctacaagaa    72540
atgtgattca atttgttcac caaaagactt gttcaagaat attgatagta gctttatttg    72600
taatagacaa aaatatagac aactcaaatg tccatcaaca aatgaatgga taaactagtt    72660
gcggtgtatc catacagtgg aatagcagaa cgcaattaaa aataataaac tgtcaataca    72720
cacaacaaca tggagattaa tctcacagac attttgttga atggaagaaa cccgaccccc    72780
aaagagtaca cactgtgtaa ttctacttat aaaaagttca agaacagtca aaacaagtca    72840
atgtcaatag atgcggggat ttgagactga tcagaacggc agttacggcc aggcacagtg    72900
gctcattcct gtaatcccag cactttggga ggccgaggca ggtggatcac ctagggtcag    72960
gagttcgaga ccagcctgac caacatggtg aaaccctgtc tctactaaaa atagaaaaat    73020
tagctgggca tggttacatt acaggtggaa gcctgtaatc ccagctactc aggaggctga    73080
gtcaggagaa ttgtttgaac ccaggaggca gtggttgcag tgagccacac tccagcctgg    73140
gcgacagagc gagactccgt atcaaaaaca aaaacaaaaa agaatggcag ttacctctgg    73200
```

| | |
|---|---|
| aatattatac tggaaagggt ctggagggaa cacacaggga tagaggaaat gaaatgtttt | 73260 |
| ctatcttatt ctgaatggtg tttatctagg taaataggta acttcaagct atacacaaga | 73320 |
| ttaatacact ttattgtata tatgttatac ttggaaaaag gaaagctgtt ttgtaaaaca | 73380 |
| tccatagtgg ttttttttgac acgaaaatgt gtctcatgtc tttctttata aaatattaaa | 73440 |
| aatccaactt tatcctgatt ttaagtgaaa aggaataaaa tgacagtaaa aaaataagaa | 73500 |
| gtcaccacta aatatgaatg tgtgaagccg ttgtagcagt tccctgtctg aagcacaaac | 73560 |
| aggaagtaac tctggtgccc aatagcataa agggttttt tccccctctc ctcagcatcc | 73620 |
| caaggattaa ccatatgctc tggccagcac gcagccccaa tgacctcacg tgacaatgcc | 73680 |
| aataaaacca gactcagaca ccagactcca ctccagtccc tccaggtcct tattgtcacc | 73740 |
| tacgagagca gttgtccttg caatccccaa gttctgcctg ttgtattttt aactgaaagt | 73800 |
| aggttacaaa gtaaataaaa aatcaatcta tttctgaaaa aaaattatta ttatatttta | 73860 |
| aaatcccatt tctatttcac atgacactgt tagatgagtc agctgtgtat ctgttcattt | 73920 |
| taactctttt aaaatatttt ctaccctgtt tttatccctc ttctattcat tagagaaggt | 73980 |
| caatgccaca ggagtgcaac aataatagga aaaaaatcct ctctatctaa caagggctag | 74040 |
| cattggggtt gggaagaagg gccaagcact tcgcccccac ccacccatca tcactaactg | 74100 |
| tcaaatattt acttctggta aatattttag tctctgaacc aaagataata acctaggaag | 74160 |
| gggtgaatca atccagtttg ggttggtccc acccttctt tgcttcctcc acctatttcc | 74220 |
| tgcattgctc ttttctttg taaacaggca caggctttca gggggtggga gagcagtgtt | 74280 |
| aaaattttaa aagtaaaaca cacaaatctt gaatgtttag tttaatgaat ttttacacat | 74340 |
| gtatacaggc acataaccac caccttgatc aaaacacgga acattttgag cacccttaaaa | 74400 |
| ggcccccttt tatttccttc taacaatggg gactttttt ttttttaag acacagtgtc | 74460 |
| tgctgggcct catggctcat gcctgtaatc ctagcacttt gggaggccga ggcaggggga | 74520 |
| tcacttgagc ccaggagttc gagaccagcc tgggaaatat ggcaaaccc catctctacc | 74580 |
| aaaaatacaa aaaattagct gggcttggtg gtgcacacct gtagtctcag ctacctggga | 74640 |
| ggctgaggtg ggaggggggag gatcacttga gcctgggagg ttgaggctgc agagaacagt | 74700 |
| gatcacacca ctgcactcca gcctgggcaa cagagcaaga ccctgtctca aagagagag | 74760 |
| agagagagag aagctcattg cagcctcgaa ctcccgggct taagcaatcc tgccacttca | 74820 |
| gcctcctgag tagctaggac tacaggtatg caccacatct ggctatttca gaaggggaa | 74880 |
| tttttaacct agaattttg aagcattcta tttcagggga tactactctc atgtctctaa | 74940 |
| caaacatact cagtggcata acaatttcac tcttaggaat tattttaaa agtaaacatg | 75000 |
| gaaacaaaaa atcgaaatga ttttagata aataaatgca atcattaaaa tcaagctttt | 75060 |
| gaagaatatt taataacact gggaaatgtt cataatctaa cattaaataa aaggcaagac | 75120 |
| aaaaaaattc ttgcagaatc tcagtttga aattgtacat atgtgcaagg aaaaataact | 75180 |
| gaagaaaata taacaaaaga gtagcttggt aaactttggg tggtagtata tggggtgaat | 75240 |
| tttatttcct tctttataat tattttata ttttgaaatt cttaataata agaatgtgtt | 75300 |
| acttttctaa tcaagaaaaa aatttcttct tttcatttgt ttgttttcta gagacagggt | 75360 |
| cttgctctgt tgaccaagct ggagtacttt tctaatcagg aaaagaaatt cttcattta | 75420 |
| tttatttatt ttctagagac agggtcttgc tctgttgacc aagctggagt agactaggct | 75480 |
| ggagtgcaat ggcaggatca aggctcactg cagcctgaaa ctccctggcg atcttcctac | 75540 |

```
ctctgcctcc ggagtagctg ggactacagg caagtgccac catgcctggc taattaaaaa   75600
aaaaaaattg tagagacgga atctggctat attgcccacg gtggttttga actcctggcc   75660
acaagcaatc ctcccatctt gtcctcccaa agtgttgaga ttataggtca gctgcggtgt   75720
ccagctgaaa ctcctctttt taaatatggg tacagcctaa aagactaact ttagggaaat   75780
cgttttctaa attatgacaa cttctttcat tgcatattat gcaatctaaa aatagcactt   75840
agaagactgc ataacttga ggaattgctt aggacacaga aaatgtacag tatgttttca    75900
aaccaaatta ggttgtgtat aactaggttg aggggaaggg gaacaaaaag taactattaa   75960
cagtggttaa aaattataaa acatacacgt tgaaacaatt ttttaatttt aaaaggggct   76020
gtttataaaa aagttttaaa agtagctctg tgttttaaga cccgtgttct acttgctgcg   76080
atcgggatag tttttttttc cactttgagg ctctttttttt ttttttttaa ggggcaggaa   76140
catcattttg catcaggccc tgtaaaaaaa aaagggggg ggggtgggt aggaaccagg     76200 atgttgggga aaattatttc aatgtgttga gtctgaagct ttttggaaag caatgtagat   76260
gtgatctcgt ttgctctgaa tcgaattcca cagaaaccgc tgtgccgaat actgcaaatc   76320
cttaactttc ataaacgccg gcaccgaact caacgcaaaa ctacccaagt gccaaagacc   76380
atttctggga agctcattcc atgagacctt cgcattttc caaatcaaag gcttcccttc    76440
ggatctaatt atttctcctc tacagggctg cgggagggg aggggatgtg agactagggc    76500
aacagattaa gattgaaagt cctttctcgc agcttcattt tcgcccccac actgtcccaa   76560
atgcttagaa ccctcctcgt cagaatggga acggtgcccc cgcttgtcct aaaagacaca   76620
gaccaggtcc gtgaacttga cccaggcgcc cacgcctctt ttccccgaag gtcagacaaa   76680
ggcagaaggg ttggctggat tctttcccgg gccgcgaagg cctgggatc gcaagttgag    76740 gaggagaaga ccgcaaaccc ctttggttca agcaagctct gcggcaggta aaaggcaaat   76800
tggtggggac gggtaggaca gggagagcat tatctggcta actcccgcag gcctcttccg   76860
atttgtcggc ggggacctga ctccctgcgg tgtctctggc cccaaatacg gaggccagga   76920
gcttttcgtt gtctcgcccg atttggtatc ttattagccg gtgtcgctga gccgcggggg   76980
actcccggct ggaaaggaag ccctgcgctc gaagcgcccc acgccagacg gagtggcccc   77040
tgcgcctccc cgcgcgccgg cgcgccctgt tcaccttcga ctggatgtta ccgagccagg   77100
gagagacccg gagatcgagt gtttgatctt cccttgctcc aggatcctga attctttaaa   77160
cacactcgca cgcgctcgca cacaaacaca cacacacaca cacacacaca cacacacgca   77220
cacgcagcac tactaccgtc tgagcaggcc gctcctcgca gcctccgcag tcggcgggtc   77280
gcctggaaag acgcgccggt ttcccgggtc ggatggctct ccaggccgct atttcctccg   77340
ccaccgagta gggagacgcc ccatttgcga agtttaagtt tccaggtcct gggaaggcag   77400
ctgggaaacc cgcggggctc ggcagccgcc ctggtagcag ccagggatcg gatagcgcgg   77460
cgggcgacag ccccccggat aaccccgccg agggaggggc gcttgtaaaa ccgagcggcg   77520
acggcctcgt tacgaccgac tcgaacattc tctaataaat catcggcctt agctagtatt   77580
cgtttgtgta cgcatctgtt tatcctgatt attaaaataa attaaggatt agactgccta   77640
gaataaggta aacgaacatg aaatgccaag gaggaaaaca gaaaaagtta caccatgtcg   77700
atcccgacca aaacattggc ctgacttgcc ggatggcctc aagaatccgg cttttagctg   77760
caggcccggc gggtgttccc cggaaggcaa ggattggaag ctctttgata agccgcgcg    77820 aggcccggtt tctcgcgttt cggtcgctc cacagccccc tccgcccttc ccctccaccc    77880
ctccgcgtct cggcctggct ccggagggt gaaggaatgt ttatagcctg actcaagttc    77940
```

```
aatgacaaaa acctgcctgg aatgggaggt gcggcgagct tcagccatca acatgacaaa   78000
ggctggacgc aggtctcggg cgggggcgac gggctgggcc cacctagaga tgggagctg    78060 agggcccaca ggatgggtac ggaccccgca gaccaagagc tgcctctctg ccctcagcct   78120
ggggtctgcg gagtttggcg agtagtgcgg gtgtgtgccc gcctggatga gggtaaggcg   78180
atcagcctct gagtgggcaa ggggacgtct gattactgcc caggcttcgc ctgggggtcc   78240
aggaccctgt gagatgcccc tgctctctgc ctggccagct ctagctcacc cggagtaagg   78300
atccgcaccg tccttctatc caccgcgacc tgcattttct ggcctcctcc gagttttgtt   78360
cacatcttcc ctcccggatt tgatattcca agcatcttct ccagggaaga ctcccagaag   78420
ccttgcttgt ctgtgtgtgt gtgtatcttt ctctttccct gttccccgtc ctgttcccca   78480
tttgttctga ttgtagtcat ttggtcatgg aataaaatcc tctggcctca ggtcacatat   78540
ggggaagctg cagacccaag atttaccagc ataggagtca ggcctggtgg aagggagag    78600 catatttcca actctttcct cctgtcttcc accccctagtg gaagattttg catactcaat   78660
taatgagtag ttggttgaca aaaatgtcca cacgtgttta atccctgtt  tgcatatatg    78720 cagatctgtc cagtgcctga ggaggggctg ggtctagggt gtttgggtgc acctgtgtga   78780
tctcagctgg gtgactccgg atggaagcag gtgcttgtta gtgtctgaag ggccttgcag   78840
ggagaggtat gttgacaata gaggagtccc tgggctttct attttttcag ttggtggtag   78900
aggttaagcg ctcctgtttt gggacccaga tcaagtaact taccctctta gtttcaattt   78960
ctttaggtta taaagtgctc actcaattgt gggttttgtc attatgggag ggggaactgg   79020
cagggaagga gccagctgtg gggagaagag agttaggtga gtcctgagtg tttttgtgga   79080
ttactgtgcc caccccaaga ccaatgactt ggcaatatca gtggttggct gaagatgtga   79140
gcatgtggtc cccagcctgc ttctgtactg gacccagagc ccctgtgcgc acacatgcct   79200
gctgtggcat tgatcccaca cttggcaagg cagagcttct gagagggtgc aggaaaggga   79260
ataaggaagc caggggccca gagaaaaagg tgcaattatt attattatta ttatttgtca   79320
cagagtctca ctctgtcaca taggctggag tgcaatggca taatctcagc tcactgcaac   79380
ctccacctcc caggttcgag caattcttgt gcttcagcct cttgagtagc tggaattaca   79440
ggtgtgagcc accatgccca gctaattgtt gtatttttag tagagacagt tttcactatg   79500
ttggccaggc tgatctcaaa ctcttggcct caagttatct gcccacttca gcctcccaaa   79560
gtgctgggat tacagccatg agccactatg cctggcccgt ttttattttt ttaaggccca   79620
gagcttttgc cttaaggatg agttagttta aaaagaaaa attgttataa tcacagttaa    79680
ctttcaccca gtttccttt  ttaaaaaat tttattgtat aaatagagac agcgtcttgc    79740
tacattgccc aggctggtct ggaactcctg tgctcaagga atcttcctgc ctcggcctcc   79800
cgaaattcca gaattacagg ctgagccatc actcctggtc tcgcccagta gatgtttcaa   79860
agtagatgtt ttctaaaata ttttacaata tttacaaatt ttaaataata ataacgttat   79920
caatattaat tttgcttatg ccaggactcc atcccattgg agacaaacat taagtcttat   79980
ggcagacctt acagcgggtg ctagttccca ctcccaagcc tctcccccgc ctaggtcctg   80040
caggtcccgc gtgctgcgaa acattttctt tgtccctttc tgcccagggc ggctgccggt   80100
ctctccagga accgcgagta ggtgctcccg ccaggtggta tcggtgaaag cctgctgctc   80160
acccttccct tgtttcccaa aacttctgaa ggctcccaaa ttcctgggag accctctccc   80220
agggcctcct gatgcagcta ccatactgag cgatccgtcg ataacgccct tggcccaccg   80280
```

```
atcagtttac cttattagag agaaaagcac tcttggaggt agtaagatgg gccggtcctt    80340
gatctgagaa atgggcgcac aacatcgctg ttctctctgc aaaggtgggg accagaatcc    80400
agcttgcctg accttgcaag caagcatcgg cctaaaggtt tcagcctccc agtggcgctc    80460
tgtttgcacg ccttaggcta ggagaggaag gacgggagca cagcactggg tgccctctc    80520 cctgtagagt ctggggcggg gctcagtaag aaggcctgcg gttggtggct ccccacctca    80580
tagctgcaag taggggcgaa agctggagtg tctcctccca gcagcctcct cgcctccccg    80640
caaacctccg aatctccctg gacctcctgg ttgctgtggc ccttcctccc ctgattggct    80700
tcctccctct ttcccaaggc cagagaagtc ctctcttccc ctcaccttcc tccctcttcc    80760
cataaaactt ttaggaaaat gggggcgggg gcggtggaga ccaccagcct ggaacttcaa    80820
gttcaatggc aaagtccctg accctccccc caggctgggc gccagcatta ttctaggggc    80880
gattaaactc ttttgctgcc ccctgtgcac ctcccagttc gggggcagtt taggggagga    80940
gagaaggtaa tggtggaatt ctttcccctca ctctcccccg accacttcgt ccctccccc    81000 tcatcccctc tacacagaac taactggtag ggagagagga agaaaggctg gcatcggttc    81060
ctcattggat gttttaaatc tgtctcaggc ccaggccagt gcctgggggg aggggcgggg    81120
tgtcctgctt ttgggctaga ggcccggggc cgctcccgag ctttctcccc tcttccctgg    81180
agagcgactg ttcgggaggg tgagaatggt ataaatttca aaaacaacga aaccttctt    81240 tgcccccctcc gcagcagtcg cctccgggct ttattgcaag tttacggtaa cgagttcatc    81300
tatttaattc gcggttgcag ctcggggatt tctattagac aggacgggtt ggggccgggg    81360
ggcacagggt ctcccctgaa ggaaacccaa ttagagtgca gcacttagca ccttcaatat    81420
aactttaatg aagggggga ggggagctgc agggaagaga agtttgctct aggttgggga    81480
aggaaagctg gagctgctcc cgagaactgg ggggcctgga tgaggctttt tcctgcttcg    81540
agggctttcc agcttccggc ccgggaacta ctatttggag tagggatcgc ctgcagggaa    81600
ggcggggcgg attctcggct ggcggcggcc tcgcagggtt cccggaagcg ctagccagcc    81660
ggagtaaaac ccgaaagatg gagcctcagg ttcgcgctct gcgttgcggg tgctggaacc    81720
gagattcaaa aagagcttcc ggaggtagtt tctacgcatt gcgccactac tcccttattc    81780
ggcttctgga ggcctaataa aatccacttg ctttggagtt agaaattatt tcgggcctgg    81840
agcccgcgta gacgcgaccc tgtgatccca tttcgtagct tgctgagaga ttcgctgcgg    81900
gagtttggct ctgagggagg ggaacggtct ggagggcagc tcagggtaca attgcgcctt    81960
gttagtgaaa aggcgccctg cttatttttcc ggagtatatg tgtgtgcctc tgcgtttatt    82020
cgtctgtgag ctcattgtct ggattcacct attgtgacat tgtgttcaca cgtttgtccg    82080
aatggtaagc aaaacatttc ctcctgtagc ttaacatagc ccttatgtaa aaataaatat    82140
ctgcaggcga atataggttt gtagattttg ttgtgattta aacacaaata agtgagagat    82200
ttcaatgtgg tcgtccaggg ataggtggga gactaaaatt gggaagggat tcccaatgaa    82260
agcgtttaat acaaaacgaa attaaatatt ttttgcacag gttccataca agtaaatccg    82320
aaaaaaagtg tgtgtggggg ggtccacacc actaattatt atggcgagga agataaagaa    82380
gacatggaca gaaggcggat ggctctgcgg cctggctccc gcagaccgac cgccttcttc    82440
ttccattcga gatggctcgt accgaacctc cttgccttct tcctgggtct ctcggggct    82500 ggaccaatac atctgccgat gccctggccg aatggcaggc gacatcgggt cctggacccc    82560
cacacgcagc tcagtaccca cgaggcccca ggccgctgga agcctgtagc tccgcggacg    82620
atgaaagcct gcccgcaggt tctcctggag tggtgagcct ctgtcggaag ggggcgccca    82680
```

```
cgtctttta  atggtcctaa  cacaccagtg  gaataaatct  ctaagattcc  acatcttttg   82740
tttgctctga  atttattgcg  agtgaaaaac  agagaaaatc  ctcaagttta  agtttctgat   82800
agcagagtgt  gggagttaga  gcatggggag  tccagaggtt  ccagacccc   aaaggtctct   82860 accagggcca  tctccgttag  tggcggtggc  agccctctt   gtggcctttt  tcctctctcc   82920
aaggggtcac  cccgcaccat  gccgctcccc  ctcatctatc  ttgccccctc  cccacaggcc   82980
catctgcgct  gaactctcgc  cagttccgaa  gtcggcgagg  gaggggtttt  acttgcccga   83040
tcgttggtgg  gtttgagctt  atagaggcag  aggagtaaga  acctgcgata  ttgaaagcta   83100
cccacatggg  gcttccttga  aggaggacgt  ggaaggcaga  aagtgacctg  ctctgagcgg   83160
cgcatgtaac  cgaggacctt  aagctggacc  acggggcttg  gacgattttt  taaatcagga   83220
aatcgacctc  atcttcctcc  tcctcgtcct  cttccctga   accccagtc   cgcatgcact   83280 cacactcttt  ggccttttcc  ctcagtcccg  ggctcctctt  tggtaaatag  atttgtaggt   83340
gtctaagtca  cgtcccaccc  tcactccttc  ccaggagagg  agacagggct  aggatcccac   83400
ccgaccgcgg  gccataaaca  cttggctgcg  gcggccgccg  cggggtttct  aggagagctg   83460
gctccgggag  ggaaatgtcc  tcgaggtagt  ggcggccgcg  gcccaccacc  aactgctcgc   83520
caccgacccc  actactcgcc  accgacccgc  tgctcggagc  ttcggttctg  cgggttgtcc   83580
agacttcagg  cctgtgcgct  caatcgtgga  gaatgcgccg  gcaggccccc  cacccccagc   83640
ctaaggtgca  ggaaggacca  gcacgaaccc  gctggctttg  ctgcgcggcc  aggagatgag   83700
tcccaccggg  cactgagccc  aggtacagga  catcagagaa  tgaacacaga  ggcagaggcc   83760
ctcatgtccc  tctcagagtc  ccggctctgc  aaagagcccg  tctgtctcca  gcttccagaa   83820
ttccgcactg  tgaatctgtc  tacgtggact  gggaaaacag  ggttggcacc  actctgccac   83880
tccgtttgtg  cctgggaagg  gctaagtatg  caaggctaca  aacatctact  tcactgggat   83940
cccaaatgct  caacaaacca  tgacctgctt  tggtcagaac  caccagaaat  attaaggaa   84000 gactcagaga  gtttggggga  ggaaattaat  ggtgaattac  ccaggcactt  tctcaaatct   84060 cttttctct   ggaaggaagg  actgactagg  ggcagcctgc  tggcttcatt  ttcacacgac   84120
agaaaaatca  tcgtattaag  gatgggtgct  tccaagacca  gtgggtacac  cctatggggt   84180
ggacaaggag  ggaggaagag  acagcctcta  caattgtcca  cctacccagc  tgtcagctga   84240
gaaaaatgct  aaacggacat  cacagccaca  caacgaatct  gcccgttccc  ctctcctcag   84300
tcttcctgct  gttaccaggg  tgagaggtgt  aatggaaggg  ggtctgagag  aaagcttccc   84360
tgcaaaggga  tcgccttcca  aatttattca  taattagctc  aattcatgaa  agcggtttct   84420
aaagtgctct  acagagctct  agatagaaaa  tatgaggcta  acgatcatgg  cagctagtac   84480
tggttatcgt  gattattgcc  actgtcagga  tgaatgatta  tgactgggcc  aggttctttg   84540
ggaaccctgg  tggagtgggc  tgtcacatgg  ggttccgtct  ccctgcacat  actgggtacc   84600
caggccgctc  ctgaggaaca  gtccagcagc  cagtggcctg  ggaagggtgt  tgtctctagg   84660
ggcctctcag  cagagtcctt  ggccccagcc  tgggcttggc  aggttcctgg  tctccccagg   84720
acacccccac  tttcgctcct  cccacccagg  caaggagatc  tcttaagggg  tagcgctgtt   84780
cttcaccttg  gcgagaacct  tcttctcttt  gacccggcgg  ttctgaaacc  agatggtaat   84840
ctggcgctcc  gagaggctgg  tggctgccga  gatcttgcgc  ctcttgtcct  tggtgatgaa   84900
cttgttagcc  gcatactccc  gctccagctc  ccgcaactgc  cccttgctgt  acggaatgcg   84960
tttcttgcgg  ccgcgacgaa  aggcgcaggc  gtcaggaggg  tgctgcccgc  tggagtctgc   85020
```

```
gcggcgtgaa agggagggag gaaaaggcat ggtcagatac ccacccatgc agacccaggc    85080
cttgcaagcc ccaagctaag tcatctcaca ggtgcacaca ggtcaccta  caggcgcacg    85140 tgcaatcctg ttcctccaaa gcataccagg acagcaccct ggcttccggc ttgttctctc    85200
accaccgctc agccttggct cctgaaggcc accctcaccc atcactgctc tcacacccgc    85260
gaatctgcaa acatacccac acaccacaca cagtcaggcc tttgcccacc atcacatacg    85320
tccagtcttc atgcatttcc agactcttgg ccactctttt agattctaca ggcaaattct    85380
ggaaacacgt ttctgccccc actcccaata catgcgcata cacacacaca cacacatt     85440 aacccatccc agtgcacaca catatgtcac ggctgcagga aacctaaatt tttctttgga    85500
aattggaaaa ctcatctaat agaaagtgag aggttgtatt ctctacagta catccaatac    85560 cttttaccc  atctcccaca cccactcccc acgcaccgaa ttgagagtta tttagctttt     85620
gtgtagaatt agtttggaat tgtgctgggt agggacaccc tgatccccac tcaacagcaa    85680
agagatctaa acctctcaga catgttgaaa ggctggtccc agggcctcct ggagaagtga    85740
ggtggccttc aggcttcaga tagcaccccag ctcaggcccc tcacactgac ctccatccag    85800
gccctccagc tactcagacc tccttcagag tcctaataac caaggaggga gcaccaagct    85860
catcctcacc agctccaagt ctccctcctc ctcctcccag ggaaatgcca ttgggaccca    85920 caacccccagg ctcagagaca aggggaccca gggtaataga ggtacctgca aatgctgcct   85980
tccaaagggg acctggtggg ttctgttctc cctggcaaca catctggctg ttccagccac    86040
cagcgagagc ccaagactgg taactgtcca caggcaacag ggagtcatgt cgcggttctc    86100
caggagcacc cagagtctgc accacagaca cgtccaggta actggccata ggctggtagg    86160
ttcccggata tcccggatag aaggcaaact cagtgggggcg gctggggtac tcttccccgg   86220
ccgtgggagt ctccgcgggg tacgcggcca gggtggctgc ctgggcacag ggtttcagcg    86280
agctccggga cactcggcag gagtagtacc cgcctccaaa gtaaccataa ggcacgggag    86340
ctggggacgt cccctgggggc acccagggc atggtgggca ttgctttggc ggctccgccg    86400
agcctggcag atccaagggg gcatagttga cagcaggcat cagcgtaggc gccgctgggt    86460
ggctggtcag aggggagtgg gcgaccagat tccgccccccc tcccgctccc agcaagcctt   86520
cgatatcctt ggctccatcc aaggtggcat aattgccggg ctccatggag ccgagggtcg    86580
gctcatgagg tgcgggggcg gggaatctag ggggcaccca gctcgctctc cccacccagg    86640 ccggggggaat ccaaagcgtt ttaaatcgct cccagctcgc aagtcgcctg cattcgctca   86700
gcacggccgt cttgacgcaa gagacgcagg ggcccgggca cgcgcgctga ttggctgcgg    86760
cctgggggag agaagctaat aaaatcctaa aggcagaaac tgcgaaaata ctttacccca    86820
gcttattctc tctctctctc tctctctttc tctctctctc tctctctctc tctctctctg    86880
tctctgtctc tctctctcgc tctctcgctc tttctctcct ctctctcttc tccctctctc    86940
tcttcttttc cctctccact cctctctctc tcattccact taaaaacaac aagagagaaa    87000
aggaaggagg tgtccttttcg ctgctttcca gtttgcagag tctcatttac acgtccgggg   87060 ggaggggggagg cgtggtgggc ggaggaagag gggacgagga gccgggcccc acctccttct  87120
cctcctctcc ctcccctagct ttctgtctcc tgcgctttga caggtttaac gagagaataa   87180
aaagctctct ctataaagtg tccatctcct ggggggggaag gggagtcggg ggtggggctg   87240
ggaggccgct cccggcctca gaggagaacc cgggaatgcg cctgtgtaag aggaggctgg    87300
gaaatggggg ttaataggta tttctggcag cccctggctt tgggtcctgg gtactagcac    87360
cccagttcat tcccggtacc cttcctgtcc cagatgtcct ggaatgagct gctccgggcc    87420
```

```
ccagggaggt gccctggacg ccccttaccc agggactcgc tactgcccag aatgctctgg    87480
aggccctgat tcgggtgagg ctgagggaag aggcgggaga cacgaacgta gacgtagaag    87540
acatgcgatc tggatggaac ccaggacact ccacttccgg acctgaaggg gaaatggagc    87600
ctctagagtg gcctgtggaa gggtctggat ttccctttaa gtaaagacat acggaggac    87660
ggagacccac aggacttgag ggagggacgg ggagagggag agatgagact cagggacagc    87720
aacacaaaga gggaaagaga gaagctgaca gagcggatgg gacaaaatct tgtaaaatcc    87780
tgaagtgtca gtcagaaaag agaaagaaga gaggcacttt ccccctttt tgggatctaa     87840
agaagtctga ggaagccaag cctggctgac tgccagaaac cagctgcggg agttctggac    87900
cccaagaata cagacgcctg tgtggagatg ccagtctccc tgccctgcag tcctctccct    87960
atggtctgca aggggcccag gaaactgtcc ctgatactgg catactccca cacaagctga    88020
gtacccagaa agcccaagac ccctatctgc ctcctgcaag ctttaaactt ccttacaagg    88080
aaaagggaat ggaaggggaa accccagcca ctggcagaat tgcttgaggc ccctctgttg    88140
gggcctaatg tgcagtgcaa ttcagaagaa tcaaacggtt tgtttcacaa atctgtcttt    88200
agaggttttc cgcttccttt actacccctc ccaaatcaaa tccttctgtc tgctttttct    88260
agaactccca gttttctgg agaagacagg aatgtttcca ttctacacga gggtcttgac     88320
aattatatgg aatggcttac cctaaactct gggcagactc aatcatagcc tctcaccaac    88380
ctgaccttga acttgagcca cttttgtggga aagggcccac aggcagtagt gtacatcact   88440
cctaatgagc attgctataa ttgaagacac caagcacgaa atcttcacta gatcgcattt    88500
gaaaacaata tggaagaaaa gggaggagat gtctcttcag tgctttccag tttctcacca    88560
gagtttcttg cttgtctaat tatgaactgc agaaatatcc agactttac ctaaagacta     88620
agaattttc accaattttt acttggtaga tgatagatat gtagggcatg tccacagttt     88680
tagtttccac taggcaaaca cccacacatg cacatttatt catccttgta cagtagaggc    88740
attaatagat ccctaaattt aaaaaataat aatagtcata gtcatgccct atgacccagc    88800
aattccattc ctgggcataa acccaacaga atgaaccttt tatatccatc aaaagtcatg    88860
tactagtagg tccacagcag ctttatctgt agttgctcaa agccaccat ggcagcgcac     88920
gcctgtaatc ctagctacta atcctagtgg aggtgggaag atcgcttgag ccccggtgtt    88980
caagactagc ctggggccag gcacagtggc tcaggtctgt aatcccagca ctttgggagg    89040
ccaaggcagg tggatcactt gaggtcagga gttcgagacc agactggcta acatggtgaa    89100
actctctcta tactaaaaact acaaaaaaaa aaaaaaaaa agccaattgt ggtggtggac     89160
acctataacc ccagctactc aggaggctga ggcaggagaa tcgcttgaat ttggaaggca    89220
gagtttgcag tgagccgaga tcgtgccact gcactccagc ctgggtgaca gagcaagact    89280
ccatctcaaa aaaaaaaaaa aaaaaaaaaa aaaaaaaaa aaccagcctg gcaacaggg      89340
gtaatagga taatagggat accccatctc ataatgaaat caaatatag tagctcaaaa      89400
ctagaaacaa cccaaaagtc tatcagcagt agcatgaata agaaagcac agtataatta     89460
tacaatgaag tactacacag ccatttgaaa aagaataaac cactactaca cacaacattg    89520
atgaatcaca gatatgtgga tgaaagaagc cagacacaaa agagtaactt ttgtatgatt    89580
cagtttctac atttctatgc agttcaatga caagcaaaat tatggtatag tgatagaggt    89640
cagaatagag attggcatgg ggagaggtct cctgactgga aaaggacata aagaagcctt    89700
ctggggtgct ggaaatagtc tccatctcaa tctgtctgct agttacaaga ctttgttcac    89760
```

```
tgtgaaaatt catcaagcta tacacttggt atttctgcac tttattgcat atcagctata    89820
tctcaaatgt taaggaaaat aattaaaaac aaaaattttt ttaattcatt gcaacacttc    89880
ctgaaactgt gcttttggat gtatagcatt cttatccatg ttcattgaaa taagtagcca    89940
agtgcatgta actgcagtgt tgtggaatgc agagatggtt aacttaaact tggcgggagt    90000
gaaggtcacc agctgtgctg gagaccctcc tgtaaatgga tacatttcaa tacaaataaa    90060
ttctatagtg cttgttttat ttgctttaca atttatttag catctgctag atcccaggga    90120
acagttctgg atctcatttt tctttcattt catttcattt attttgagac agagtctcac    90180
tctgtcaccc aggctggagt gcaattgtac aatctcagct cactgcaacc tccgcctccc    90240
aggttcaagt gattctcatg cctcagcctc ctgagtagct gggattacag gtgtgtgcca    90300
ctatggccca gctaattttc tatatttta gtagagacag ggttttgctg tgttggtcag    90360
actggtttcg aactcctggc ctcaagtgat ccccctgtct tggcctccca atgcgctggg    90420
attacaggca tgagccacca cacccagctt tggatctcat atttattaac acttgggtat    90480
gtgcccctat ttcctgtaca taggtatgtg tgtgcatctg cccatgacct atcatagatc    90540
tcaaccggca tcaggtaaag taagattaag tctccttatc tgtaaaatat ggataataat    90600
tctttcctca catactgtga tgatataatg agattttgca cataaaagca tttcacaatc    90660
tgaataaata tgagctctat ttgtattcct ccatgtgttt ctgtttctaa tgaattacaa    90720
gcaacctgct tttacctgaa aaggacagtt gccctaaaga gtgtcagtca cttctcactt    90780 gcccccctcag ccctgcgtaa gctacatagt tctcgcatcg ggaaactgag gctcagagcc    90840
tccaagtcct ccctgggggct ctacatgggt tcagcgggga agtccctgca aacccaggc    90900 gtcctgatct tccagactga ctgggctgag cctggccttc ccctaacccc acagatgcct    90960
ttgtgtcctg ctgggagcct cctggcagac cctcgggag cccggagcct ccccagctt    91020 tctttactga cccagccaaa agcgctgaaa gcctcagcgt gctcctttac atacccgcca    91080
gacacctcca ggaaggtaaa ggccaagttg aaagttaaga gtctgtttac ctccaggagc    91140
ccattcagct cggcccaca gacagcctgt gacctttaca gcccggcctt tgagcgcggc    91200
cgccgcgccc ccgggggttc cggcaacggg gacttggcac ctcggtgtca gctcccgccc    91260
ccacccaggc tagggacccg ccaacgaggg gtggggcgg gaggcgccca cccgtcgcac    91320
tagtgggcat ttgctaaact acgttttatt ttttgtaaa gtgagcgccc gctgccttcg    91380
ttctcccaac tggagcaaac tctgtggcgg cgacgatggc ggccgtcagg tcggtggtga    91440
tgaatagaga ggatttctct gcagcgcgac gctcccctct cccgaaaggt tggctccacg    91500
gtcccgccgg ccgcgcaggt ctggctgaac tgcttggggt cgcccggctc ctctcgattt    91560
tatgaaaatg gcctaattga ggtgtgctct tttctttcct tcctcttttc atctttcct    91620 tccgtctgca ttttctctcc tctgtcttag gcttggtatc ttcttttctt tttatatttg    91680 tgttttctc accgcctttg cttccttcca tttcagttat cttgctttt gtgtgttctt    91740 tcttgatttc tttctttcct tttcttgtta ttgctcactc tctggctccg ccacccaccc    91800
cttgctctat cttcattttc cctttagtac ttttctccct atctttcatc tcacttacac    91860
tatttttctc tttgttgct ttttcttcct catttttcct tcttcagttt tctcattttt    91920
ccttcctcct tcctttttt tcctctctct tctctatttc tttttctttt ctctcatctc    91980
cgttttactt ccccttcctcc gccgccaca cacgtttttc ctttgcagcg ctctcgccca    92040 gttttttccat tgttcttctc tgaagtctgg aaagggcctg cggggctata gctctcagcg    92100
gccggagcct gcgcttggca ggggacggcc tggaggacgg cctagtgtgg ctggtgggtt    92160
```

```
cgcggagccc tgccctggag ctctgcctga ggctagaaca gcacccgctg gagatgaagg   92220
gtgactccgg cctttcgccc tgaaacgaag tcaagcgggg cctctcctgg ccttagagga   92280
aaatcttttg acaacttga cagagggatc ccagagctaa gagctcagag gatggaggca   92340
tggctggtca ggaggaggcc cctctcacct cctccttcct tctccaaccc agtcagccct   92400
gcgacatcct caggaattag aaccctctcg ggataagcct aagtgcctct gaggccaggg   92460
ctgagggagc cagctatcaa aaccatggga caaatggatc tgaggaggaa tcgaaggatg   92520
gacagctgaa gggagaggct tgctccaaca acagggcggc cacggcagct gctgcgcgcc   92580
ctgacgccgc ctagaaaccg gaggagggcc tagccaagcc cagagaactg tgagtggggt   92640
ccaaagagga gggagggagg agaaagggag gaaggggggtc aaatatgagg gtcactgaac   92700
acagaccaag agtctccctt cctctggtcc ggcagctcta ggggaacaag ccagctgttc   92760
ttgcctatca cgcatcacac gtgctgagta gggagactgg ctggcccag agtccccagc   92820 ccccttctcc aaacctgggc tttaatgggg agttacccaa ttcggagaaa cagcccagat   92880
cagaccccaa ccattaggaa gtctggtcct aggtggctgc actgcagagc aatgcagagt   92940
ctcatgtaag gttctgttct agctcagtgt gctggaccaa gtcagttgcc ctctctgtgc   93000
ctcagttttc ctatctgcac tgtgtaagga gggaaggact ggaccagcgg acctttgaat   93060
ccctgccagt gttcaccttg cacagaagag tgacgacggg cagcaggagg aagggagct   93120 ttaccggaag gagagggaag aaaactgtag aaggaacaag aaagagtcca ggaagctgcc   93180
acggattttt catgcgtgtc tagtgcaggc acggttatta gtgctttgag ggagcccagc   93240
ctctgtggag gcaactgtca tgttctgact cagttggagc agccagcccc acagtgtaaa   93300
ttctgcagtg gctcattaaa ggggaccaaa ctgtgtggga gttcacctcc tccctacttt   93360
ccctataaat ccctccagcc acccagcaca gagacacttg aaagtaaagg aataggaatg   93420
ggatcctcaa atggggaccc acaattagag tctttagggg tttcaacgac ttccagggtc   93480
atgggagact gggctttctt tgttccaacc cctgggatac tggataggac tcaggaatta   93540
ggaatgtatc aaaaaaccta tctgcaaatt gaagaaagca atttgagtca cttcaagctc   93600
tcccaccatc tccactttgt ttttccttc agggaatgtg ggtgttgatg atataactat   93660
taggaaaatg ctggctactc tcaggactgc tagtgtagac cctgccagag ataaagatcg   93720
agtcttcatt tcttaaatca agaggaatgt cagcaccaag gccctggccc ctcaagtcct   93780
aaacccacct atttggcctg aagtggagct gtagcattaa cgcctagggg aaagtacagt   93840
ttgaaagatt tgatttctta ctttgattcc cccatttacc ttaatgaaag tcctgggatc   93900
cttccaaaaa cccagaacgt gaccatcttg tggcctacct ccctcctcac tgtcccctca   93960
accccaatcc ctacagcaaa agcctttccc ctgtcttccc actaagatct ctgttccaag   94020
aaacaaagtt gggagaggaa gaaggcaggc atttcgcaca cacacagaca cacaaggtgg   94080
aggaaaaaaa tggtccataa ttcatcccta ccaagtccta tccaattcat ggtgctcatg   94140
ggttcccact cctgagtgcc acaaaagact accctcttgg ggctcaatga aggcttgaaa   94200
ataacactgc tccaagagta tctgcctttc tgaatctcag ccccagcttg agatgagcat   94260
tgggcagttc caagttactg ccctgaggac tctaacctgg ggaaagtcca tgttagccag   94320
gccctcaagg ttctgggcca gccatttacc ccaaatcctg acaccttctg agactggaga   94380
agtctggctg atggtctgca gcctgtctgc attgaccctg ctagtccaga agtgatatcg   94440
ggccatacac ataggactcc tcatcaaagt gggatttggg attggaacag agctctgggc   94500
```

```
ttttagtctg ccttggctct gaatcacttg aacttaaact gatcattctt tccctttact   94560
ccttcagagg ttttctaaga gttctgagag ggaaagtaaa atgctcttca ctttaaattg   94620
taaaatcatg cacttaggaa ggccgaggtg ggaggatcac ttgaactcag gatttcgaga   94680
ccagcctggg caacatggcg aaaccccatc tctacaaaaa atagcccagt gtggtggcac   94740
acgcctgtag tcccagctac ttgggaggct gaggcgagag gatcacttga acctgggagg   94800
ttgaagctac agtgagccga gactgtgcca ctgctctcca gccttggtga cagagtgaga   94860
ccctgtctca aaaaaaaaa gaaaagaaa aagaaagaa aaagaaaga aaagaaaaa        94920
aaaaagaaa agggaaaatt actcggaggt ttttttttt tctatttggt ccctgtaacg     94980
tctatggttt tgttcataat tggaagggac tctagccact gctgaagaga caatgaagat   95040
ctttgctctc ccctcatgtt gctcataggt agggcttgga tttgagagga gattccaatt   95100
ctggaggcta ctgtgttgaa actgacacca ggggaagctt agaagcttag aaaagcttcc   95160
tcctggccgg gcgcagtggc tcaagcatgt aatcccagca ctttgggagg ccgaggcggg   95220
tggatcacct gaggtcagga gttcaagacc agtctggcca acttggtgaa actccatctc   95280
tactaaaaaa tacaaagaat tagctaggcg tggtggtggg tgcctgtaat ctcagcaact   95340
tgggaggctg aggcacgaga atcgcttgaa tccaggaggt ggaggttgca gtgatccaag   95400
atggtgccac tgcactccag cctgggcaac tgagagggac tccttcgaaa gagagaaaga   95460
gagaaagaaa gaaagaaaga aagaggaagg aaggaaaga aagagagaca gaaagagaga    95520
gaggaagaga gagaaaggga gagagaaaga gagagaaaga aagaaaaaga aagaaaagaa   95580
aagaaggaag gaaggaaaga aggaaggaag gagaatcctt ctatgaaatc cttaattagg   95640
gctctctgct taggggatat gtagagctcc ccacctttcc cttctcttaa agagcagaga   95700
gctccaaatt ccctggctcc ccaaactagt cagttggtgt ttgggggttag gagaatcctt  95760
ggagatcatg cagtgctagc aagctttgta cttgggtagc tgggtggcag atgccttggc   95820
aagtttgctg tcttgcccaa ttcagagaga aatgacctca ggcaacccat ggccagttct   95880
gtggtaccag gcagctctga gctactgaag tgggagcagg agaagaaata aagaatacaa   95940
aaggcagaca gctatggcag ctggatgcag ttttagagtt tctggtgatg ccctgactgt    96000
tctccatgcc tgccccagga gaatccaaaa agtcaggcag tccgggactt gtgtatgtgg   96060
aagctcacac attcaggatg ttgttctggt tccagctcaa tgtccactaa gtcctaagga   96120
ctcaaagctt ggtcacaagg gtagcccctc ccaggctgaa aaactgctgg tctagctctg   96180
tgaggcaagg ccagggctcc ccgtttctta atttcgaggt gaacctggaa actttcccta   96240
gaaatggtgc ttagccccag agacaggttg gggagctggg gaagaaccat gggaagcaaa   96300
ccctggtctc tccatgccct ccaccctctc aataacctgt ccggcccaga cccagcccag   96360
atctccagct gccttgggtg ggggatgcag atagagattg tgggggcagg ggtgctctct   96420
gccctggaat tggaatcccc cacaccagtc taccggtaga ttctgcttcc tttgccctt    96480
tatcctccac ccccatctgc atggtttttc tagcctcggg aatcacctgc cctgggagtg   96540
caggccaagc tttggacgag ggaaagcaca gactgacgcc gaccagccca tcctccccgg   96600
ccttgcactg cccgagatcc gtgcaggtca agcgggcaag gtgggacgct tcaggtgggg   96660
agaattcata ggaattaagg ggaacccact aactcttcat caagactaga ggccagccta   96720
aagaattttc cccctttttg tcccagagac attcttcct tccttctgcg tgtgtaaaca    96780
cacctggtcg ggcagatttt tcagtaatcc caatactgag tcacctcacc ggccggggtt   96840
tactccccag ctcctggatg gtaaagcgcc ctgcggcccg cgggtcaggt ctttaacggt   96900
```

```
ccagccagcg cagcaagaga gctggggagt cttcttgcag tcccttcctc ctactcacgc   96960
aaagatctcc tctatgctgg taggtgcacc tgccctccac cgatcctcac cctgagcgca   97020
ggtcgtacct caaggcgaaa acccgcttag tgcgttggcg ggtggagagc tgccgccttc   97080
ttgatccggg actgagaagc tgcactccct gacgccactg tggccagcac ctcgggccga   97140
gcagacccct acatctctaa tcccatagcc ctccaggggt ccttgggca gtccctttgg    97200 aaagtcttcg aagtgcaggg tactttaagt accctgtaga cgccttttat ttaatccgca   97260
caacaaaaga acgggcagg agtgggggga aattgttact tccgttttgt agataagaga    97320
actgagccgg gacggtggct cacgcctgca gtcccagcac tttgggaggc caaggccggc   97380
ggatcgcttg agcccaggag ttccagatca gcctggcttg aaccctgaat ttctgttgaa   97440
tccgaagttg gatggtgcag tgagccgtga ttgcgctgct gcactccagc cagggagaca   97500
gagggagaac cagtctcaaa aaagtaaaag aaaacaagaa agctgaggtt taggagataa   97560
tttgtccaac ttctagaggc aaatcgaggc tttatggcac caaatcctga ttctgatatt   97620
ttcacttctc ttccctctcc aaacacaaat cgttgacaca ttttattttt atttatttt    97680 atttattttt atttattttt atttattttt gacacagggt ctcattccct cacctagcct   97740
ggagtgcatt ggcgcgatct cgactcactg cagcctcgac ctcccgagct caagcaatcc   97800
tcccacttca gtcccctcag tagctgggac cacaggcact taccaccacg cccagctaat   97860
tttaaaattt tttatagaga cgaggtctcg ccatgttacc caggctggtc tcaaactgct   97920
gagctcaagc gacccttcca cctcagcctc ccaaagtgct gggacgacag gcatgagcca   97980
ctgcaaccga ccatgacaaa ttttaaaatg gaaataaatt tcattatatc tcattagtat   98040
ctcaaactaa tactaaaaac agacttaaga tatttgggaa attattaaag ggaaaaggga   98100
aaaattaagg aatttggaaa aatcaaaaca tgaactctaa aataaagaaa cccggctggg   98160
agtggtggct caagcctata atctcagcat tttgggaggc cgaggcaggt ggatccttga   98220
ggtcaggagt tcaagtccag cctggccaac atggtgaaac cccatctcta caaaaataaa   98280
taaataaata aataaattag ccgggcgtgg tggcatatgc ctgttgtccc agccactcgg   98340
gaggctaagg caggagaatt gcttgaaccc gggtggcaga ggttgcagtg agccaagatc   98400
gtgccactgc actccagctt gggtgacaga gtgagactcc gtctcaaaaa atgaaataaa   98460
atgaagaaaa ccctttaata cactgtcatc ttttttatca gtgcccccca tgacttctaa   98520
aactacaaaa gtgggaacca atttctgtcc tcttcctccc accccattcc tcccaccctg   98580
ttttactttg gaggctgagt ccacatgagt aacaaaggag ctatacctgg caaatgttca   98640
cctagagttg aattgtggga ggctcaaact cctctaatgg ctctgttacc cacactgaca   98700
gcagaaaact gtcatgtttg ggtcaacaag catggttggg tcaacctggt gccaaaacac   98760
cttccaagcc tgtcccttct atgggggaaa aaatgggta tttggtgggc actgaggatt    98820
ctgaatttga tttatgggt ggctctcaaa gcctcaccct ttaaaattga gggtgaacat    98880
tggtgtacat gtgtggtttt ttaggacatg agcctactgc tttattcttt tcttttcttt   98940
gagacggagt ctcgctctgt tgcccaggct ggagtgtggt ggcgtgatct cggctcactg   99000
caaccttcgc ctcccgagtt caagcgattc tcctgcctca gcctcctgag tagttgggat   99060
tataggcaca catcaccatg cctggctaat tcttgtattt ttagtagaga cagggtttca   99120
ccatgttggt caggctggtc ttgaacccct gacctcgtga tccacccgcc acagcctccc   99180
aaagtgctgg gattacaggt gtgagccacc gtgcccagcc tattgatttg ttttctaatg   99240
```

```
gcaaatttta cagatacaga aaagtaaaca aaaaagtgta attcaacccc tcatacctat  99300
cactcagctt caacaataat caactcatag cccatcttat tgcatttctt tctggaggtt  99360
ttttgtttcg ttttgttttg ttttgttttg ttttttttgag acagagtctc actctgcctc  99420
ccaagtagct gggactacag gcgcccacca ccacacctgg ctaattttt gtattttag    99480 tagagacagg gtttcacctt gttagccagg atggtctcca tctcctgacc tcgtgatcca   99540
cccaccttgg cctcccaaag ttatgatgag caccgggctc agccttcttt ctggagtatt   99600
ttaaagcaaa tcccagactt cttttctttt tttttctttt ttttgttcc aaaattcttc    99660 agtttgaatc tttaacaggt ttaaaaaaat ttttttttgt ttttagagat ggatcttgct   99720
ctgtcaccca ggcaggagtg cagtgtcact gaagccttga actcctgggc tcaagggatc   99780
ccacgcctag gactacagga ctacaggcat gtgctaccat gcctgggtac attttttttt  99840
ttttggtcga gacgggggtt cccagatggg tctcaaactc ccttgttcaa gtgatctgcc   99900
tctttggctt cccaaagtgg tgggattata ggcatgagcc actgcgccca gcctagtttt   99960 atttattt tgtagagac aaggtctcgc ttgttgccca ggctggtctc taaactcctg     100020
gcctcaaggg atcctccaac cttggccttt tgaagtgttg ggattatggg cgtaagccac   100080 tcttctttg ctttttttat atataacctt tatgtgattg tcacacagga caaaattgag   100140
aataattcct taatactatc catgtttgaa tttcctaagt tttctcaaaa atgtctttt    100200 acagttagtt taagtcagga tctaaacaaa gttcatacat tacatttgct tgatgtctct   100260
caactgtctt ataacctata acaattgctc ccaatccatt tttcatgcca ttactttatt   100320
taaaaacctg ggccaaccca gttctcaaaa ggtattggac atcctcagaa aagatgactg   100380
ctctatgttg aaccaaacaa ctgattctta caggtttctt cctcacttgt cctctggctg   100440
tggcagccag atatgacag gagagctaca tccttccctc cactccctgc caaagaaagg   100500
agagctggga taagcagtgc cctcccctgc ccacccacta tgtcactttc tgactccctt   100560
tggtcccctc attgctcttg gagtgagaga cctcattcct tctctcactg gaggcagcca   100620
agaatgggat cctctggtgg gtctttggat tatgtaagtt tcaaacactg gatacacagc   100680
tccagatcta aaggcaagat tgctgctcta gaggcaggac tgttcatttc ctgccttggg   100740
gatgcaccca gaggcctgaa tgcttcccaa ggaaaccaaa gaaagaacat ggtctgtttc   100800
agaggtggag tggccagtct agctctgcca tctctcactc cttcctgcct ttagggtacc   100860
actgaggtgg aaagcctgaa ctgctgtctc tgctctggct tgtgctcaag ctgtgtgtcc   100920
ttggactggc catctcctct ctgcagccct cggtcttctc atttgtaaaa tggaagtgat   100980
cctctctgcc catacttcct tacagggctg cttggagaca atcaatcaag atgagggaaa   101040
ttgagattct acaaagagtg tgatgcctac ataacaaagt attgttttc tcacagttgg    101100 tggtatttga ggagaaggtg aagattttgg ttggaagagg gaccagcaga caaacttgtt    101160
ctcttgtgta taaaaagcca taacacgccc cacatccctc aagctaggaa gaaacctggg    101220
ctggatggtg acccactgga gaagctgtga catcctagca tggggaagag taccaggatg    101280
cccactcctc ttccccagga accaccaagg agcctggagc ctggctttat ctcagccctg    101340
agtcccccct ccccggtgcg cacacccta acttttttt tttagatgga atcttgctct    101400
gtcgcccagg ctggagtgca acggcagctc actgtaacct ccacctccca ggttcaagcg   101460
attctcctgc ctcagcctcc cgagtagctg ggattacagg cgcgtgactc catgcctggc   101520
taatttttgt attttagta gaggtagggt ttcaccatgt tgaccaggt ggtctggaac    101580 tcctgatctc aggtgatctg cctgcctcca cctcccaaag tgctggaatt acaggtgtga   101640
```

```
gctaccgcgc ccggccaatc tgggctcct  agctttggtg caccaactac tcaaatcccc 101700
aacttctctc caagaggaat ttcaagaaac actgaccaat ctggttacag aagctgaagg 101760 ggcccccaacc aggctgcaat aaacctgctt taccctcta  agctgaagtc tctcttgccc 101820
aaaactttgt tctctgggac ctggtgagag ggtgactccg tgagtgcaga atgcagtgca 101880
gacgttattg aagaggcctc acattttca  tttccagact acacctagct cgtaagaagc 101940
cagggaatat aataaattct cccctgcagg acctggtttt aattaattat tgggttattc 102000
aaggtgactc atgtgtgaaa tgcaatgtgc actcgtaaac tgaatctcac ataatccatt 102060
ctaagtaact ggctgcgagc tatcctctcc agagacttac acaaaactta tatttatcct 102120
ttgagggtct tggggcaaaa tgtaagggtg acttcagttt aaagagagct cacttggctg 102180
gctaggggta ctaagaaact gggtcttgtt ttctcaactg ctgatttgat gaggtttatt 102240
tcttagaaca tctggtgttt ttatatgtat agtatatata taagatatat gtacgtgt   102300 atacacacat atacatttat atattttagt catttgtttt gcagtatctg caaaggatat 102360
gtgaagccag ctcattgcag aatagaaatt gatgctgagt ttttctacag ctaacctggc 102420
agctgaagct cctcctactg ccaggacctc tgaaatttgg tctttatcac ccacgatcca 102480
tgttcatctc acatctcaag gtctctcctg tacagcgtgg aattgctctt gtctgggatt 102540
tatattccct tctgtgtaac ttaaaaactc caggccccat atcttcaaaa caggcttctg 102600
ttcagaatgg gtgtgagtct cccgcaaaga gccattaaca ctgcagagcc tcttggtctg 102660
cagcattagg gagtctacat ttttgaaacc attttgggat ggtagggttg ggggctgagt 102720
ctgttcatgt aaacaggatc tggaaatggt gagggagtgc atctggctac tctacatagc 102780
tccacctgtt tgccaggtgc cttctccaga cccaggcaat gcagaggagg gggttgggtg 102840
ggggagggga agggatccaa gggagactgt gagcccccta cccagagttc agccagagaa 102900
ggaaagggag actctggcat tgcacctggg ttcctgcccc agaaaagagg gtaagatctg 102960 atttttttg  gcgaaggaag gaaggagaaa ctgaaggaag aacgggatgg tttatttct  103020 ctcagttttt gtctgacccc tgggttggaa gtggaaggct ctgctagggg ccctgcacta 103080
agccagttct gagcggagga agcctccagc tttttttctt cctggttttc ttttccctt  103140 tgcctccttt aattcccttt cttgacctgg aagccagaca ttttttttc  taggtaaaag 103200 agaggctaga ttcaaatac  cccctcagct ccctgcagac cctggaactc tgtcctgact 103260
ggtccctgaa gttcctctgg gccttccaaa cagtggataa agtctgtgtc tcagctagag 103320
tctcagcctg gaattctttt ttcatgcatg ggcaggccta gggactctaa acttttgaaa 103380
aaaaataaaa ttttcttcct ttctctgacc tacttgaact ttcagttcca ggaggaagga 103440
aataaatgtg atgtagtttc aaagtatgtg ggaatttaat aaatgcaggc cgtggagggt 103500
cactttcccc atgaagacaa ctttatctgc cccactaggc atctgaaaca gtgccatccg 103560
aaacagtgcc atgcgaaaca gtgcccacaa gcacccacct gcaaaaagac acagtgacgg 103620
agcaacagca gctgcgtcct tacacgcaga tgagctgatc caggctttga aggagccagt 103680
taaccagaga tgggttaatt cctttgccag accagaggta ttgaatccag agaaccctca 103740 ctccagaaa  atggaagaag tctgtgacag acaggcagag ggacagaggg acagatggga 103800
gctcacatag ggaaaagaaa aaggatgaaa attgtagtta aagaaatcag ggactttcag 103860
ggcacgcaga gcagagctga tgggaagtcc cagagagctg gataggaggg tagtggaggc 103920
tgggattatc cagaacttgt tttaacacag gtatacctgg ctcggctcag cacctgctag 103980
```

```
gttggctttc taggatgaca aaataaccag ccagccctgc caattctggg agaaatcagc 104040
cagagccatt gtttggcttg tcttcgacca aacaatagtt gattggctgg aattttcact 104100
ttccctgagt tgttagctcc tgtaaggagc tggtcaagtc cccttgccct tagctaagag 104160
tagaccccag cccttctct cccggccaag agctgatcga cctgtcagtg caggaaaatc 104220
tctcaattac tcacctctac cgattgaata ttgagaggga agtgttttgg tttgttgctt 104280
gtaaacaaaa caatctagag tgatccagaa gttttatcag ctctaatctc atctctttca 104340
tcaagttata ggcccagaat caggactaga gacccaccca cattttaaa gccccagaca 104400 gcctacacgt ttgtgtgtgt gtgtgtgtgt gtgtgtgtgt gtgtgtggtg tgcgtgtgtt 104460
tggtagcctg tataggggaag ttttttatttt tattttcatt ttcatcatta gtcttattct 104520
tggttatctc tacttgtttg atgtgacaga gccacagcta tattcacaac aaagaaggct 104580
gaagcatttg ggcaaatact cagattctaa tctccgcccc aaccccccac ccctccattt 104640
agccacatca gtcagagggc cccccgccag gggaaagaga gtggaatggg ggattgagaa 104700
acaagattcc aagggccgtg cttggctgac agtggtcttt ccttctttta gtagtttctt 104760
tggagggact gatgagggac agcagaatcc ccaggaaggg agtggaggag gtgaaatgct 104820
gccatcagtg aaatgagaa agaaggaaag cggagggttt gctggttccg gggggagta 104880 aatcagtcgc tttataattc cacgatgttt gcatcatttt ggcttctgag aggctgcgtt 104940
ttgaggagac accagaagcc tgggaagttc gcttactggt tctcaagtca gagtcccct 105000 tcccggggct ccttctgggg actccggggg agagggatct ctctgtccat cctgcaactc 105060
ctctcctggc atagatgccc cgcaccccca ccttgggcca tccttatctg cctgttcccc 105120
atcacgattg atcctccagg gtcgccaagg ctcctgctga ctacaaaaac atccccaaga 105180
ttcccttctt gacccggttc aggcatatct ctttatactt ccatgtctcc gtttctctat 105240
atttttactg tggaggactc agaagagagc tgaggctatt gtccggggag gaaaggaatt 105300
cgggcaaatt tgtgggtagg ggcccagacc caagacccgt gttctcctg cgtgggttgg 105360 agtctgtctc aggtcgctcc agggacatca agagcccgcg ccgccgagag cccgcgccgc 105420
cgtccagcgg gaagcagcgg acccacaggg gcctccagcc gcctcccgc tcccgccccg 105480 tgtttctcct gggcctccag ctccgtggag agagctgaga gttctcggcc cgcgggcttc 105540
ctcaccaaat ccccaaaaac cgacgcaggc acagagggct gactgtgttt tgagtaatgc 105600
acgcgaggca gtccaatccg gcgagatggc ccgaagcggg gcccagcggt cggggtgtg 105660 ggtctggaga gagagggtct ccccacttcc ttcctccggc tgctcggtca cccatcgact 105720
acccgggcgg aagcggggcg cagaggggcg cagagggagg cattgccctc caggagtatc 105780
tattcccatc ggggtatggt gaatgccatc taggcccatg ctccattccc agggcccct 105840 cggttcctcc aaaggcgtcc acccagaagc agccccagtg tcgcgcattg actcccgccg 105900
gccaagtcgc cgccgaaaca ggatctccta aagcgggctc caccgggtcc cagggcgaaa 105960
aggtccgaag atctacgctg tcggaaagac ctggagaact cgggaagccc agcaacaaca 106020
aacaggtttc aacttggaaa caaaccatta aagtttggct tagttttttgg tgtgaatggt 106080 gcaaataatt tctcctcttc actcttcagt cgatctcagc tgtatagagc tgctctgcaa 106140
gctaaaaaga aattagtatc tattccccc gccaacaatt tttttttaac ccgggctacc 106200
agcttaagca actggtatca ttcttgttga attaagctct gaaagctcgc ctcagaaaaa 106260
aagtttttat tttaaaaaac gaattattaa gtcggcagtc tgattttat tggttttaat 106320 tatctgagaa aactctgcct tttagttgtg ataacgagta tgtagaacag accttaataa 106380
```

```
gcagaaatgt aattaattta aaatccatag tagttttatt acctacatat ttaaaaacaa 106440
acactactaa aataatttcc cgattttaat ctatctttaa aaaatagggg ccggtgtagt 106500
ggcttacaac tgtaatccca gcactttggg aggctgagac gggagcatct cttgagccca 106560
ggagttagag acctgcctgg gcattagagt gagaacccca gtttctattt tttttaataa 106620
aataaagaaa aagaaaaaat aggtaatgta tgctaaagga aagagtcaaa agttacattg 106680
gggacataca ttaaaagta aaataggtct tcctctcacc tcttatccca gcttcccttc 106740
caaaaagcaa ctacgattcc catagtatcc ttagagaaat gtatataaat aaaaattttt 106800
aagacaaatg acaacattcc acataccgag ctttatattt cgcctttat tttaaaaact 106860 tagtgcaact taatgacgat tttatatctt tactactgcc tcttccttta taatggttcc 106920
atttcgtttt ctgaatatat cttaatttat gtaattagat gacaattgag aaatatttag 106980
attgtttcca attttatttt cttctttttt ctggtggtgc acacaatata cactattctg 107040
tgtatatgca agtatatctg tatgatatat tgttagaaat ggatgatctc aaaggacttg 107100
tgcactttaa aattttgaag tggttgaaca tatttgcaga attacaagca atttgtatgt 107160
tcttttccag aaaactttgt tcatgttttc ccatttctg ttgtttttca ttgttctcgt 107220
aatttgtttt tatcgtattt tgtgtttcgt tgttctcata atttgttttc atggtatttt 107280
gctaaaatgt aagattgtgt ttcggtttgg ttttgtcaat aaaagttatg ctcgtgacta 107340
atgtaaagtc tctccgtcta tacttattgg aattttccag acaattttc ctagagatgg 107400 aggacaaaat ggagggatg ccgaatgtcg actattgtca gcttagattt ttttctctta 107460
cggaattccg accttattga aaaaaatgag gagaggtttg ttttgtttct taatcatttc 107520
ttcgccatct ctgactctct ttaaggttag aagacacgga aaagttccac attgggccgg 107580
gatggcaaag gctggatcac tgcagaacaa agacctcagt cctcgcatcc ccaccccgac 107640
ccccggcagc ctctttcgct ctaagcctca gcctagggca aactcccctc cgcaggtcat 107700
cagcctccca tgcctgagcc tcacggaaaa ccactagaag gaaagtaagc tagggtctaa 107760
gctgtagccc ctccaggcac ctggcttgtt gacattaccc cttcctccca agcagagggg 107820
tgtcggtcag gcagagggt gtcgattgcc ttggcctcca gttcccagtg aactaagaga 107880
aagcagctgg tccccattcc cagctcctgg gacctagtga tcgccatgag cttatgtatg 107940
ttccttggag gacaggcggc tgcttaggag tgggacagta aggactaggc tgggtctgga 108000
gggctggcgg gcaggagtt gggggccagg taggaaagcc aggggtcgaa gggatcgatt 108060
ctaggggccg cagaggctac tctcgtgctc tggagaagca ccgcatcttt ctccggaccc 108120
ccgcgctcag ccaatcgccc caaagtctcc aggtgggggc tccgcattac cagtcttggt 108180
cgcaaaagca gcccttcaa tcgcaccgaa t                                 108211
```

<210> SEQ ID NO 2
<211> LENGTH: 284
<212> TYPE: PRT
<213> ORGANISM: Homo sapiens

<400> SEQUENCE: 2

Met Glu Pro Gly Asn Tyr Ala Thr Leu Asp Gly Ala Lys Asp Ile Glu
1               5                   10                  15

Gly Leu Leu Gly Ala Gly Gly Gly Arg Asn Leu Val Ala His Ser Pro
            20                  25                  30

Leu Thr Ser His Pro Ala Ala Pro Thr Leu Met Pro Ala Val Asn Tyr
        35                  40                  45

```
Ala Pro Leu Asp Leu Pro Gly Ser Ala Glu Pro Pro Lys Gln Cys His
    50                  55                  60
Pro Cys Pro Gly Val Pro Gln Gly Thr Ser Pro Ala Pro Val Pro Tyr
65                  70                  75                  80
Gly Tyr Phe Gly Gly Tyr Tyr Ser Cys Arg Val Ser Arg Ser Ser
                85                  90                  95
Leu Lys Pro Cys Ala Gln Ala Ala Thr Leu Ala Ala Tyr Pro Ala Glu
            100                 105                 110
Thr Pro Thr Ala Gly Glu Glu Tyr Pro Ser Arg Pro Thr Glu Phe Ala
        115                 120                 125
Phe Tyr Pro Gly Tyr Pro Gly Thr Tyr Gln Pro Met Ala Ser Tyr Leu
    130                 135                 140
Asp Val Ser Val Val Gln Thr Leu Gly Ala Pro Gly Glu Pro Arg His
145                 150                 155                 160
Asp Ser Leu Leu Pro Val Asp Ser Tyr Gln Ser Trp Ala Leu Ala Gly
                165                 170                 175
Gly Trp Asn Ser Gln Met Cys Cys Gln Gly Glu Gln Asn Pro Pro Gly
            180                 185                 190
Pro Phe Trp Lys Ala Ala Phe Ala Asp Ser Ser Gly Gln His Pro Pro
        195                 200                 205
Asp Ala Cys Ala Phe Arg Arg Gly Arg Lys Lys Arg Ile Pro Tyr Ser
    210                 215                 220
Lys Gly Gln Leu Arg Glu Leu Glu Arg Glu Tyr Ala Ala Asn Lys Phe
225                 230                 235                 240
Ile Thr Lys Asp Lys Arg Arg Lys Ile Ser Ala Ala Thr Ser Leu Ser
                245                 250                 255
Glu Arg Gln Ile Thr Ile Trp Phe Gln Asn Arg Arg Val Lys Glu Lys
            260                 265                 270
Lys Val Leu Ala Lys Val Lys Asn Ser Ala Thr Pro
        275                 280

<210> SEQ ID NO 3
<211> LENGTH: 3047
<212> TYPE: DNA
<213> ORGANISM: Homo sapiens

<400> SEQUENCE: 3
tcttgcgtca agacggccgt gctgagcgaa tgcaggcgac ttgcgagctg ggagcgattt      60
aaaacgcttt ggattccccc ggcctgggtg gggagagcga gctgggtgcc cctagattc     120
cccgccccg cacctcatga gccgaccctc ggctccatgg agcccggcaa ttatgccacc     180
ttggatggag ccaaggatat cgaaggcttg ctgggagcgg gaggggggcg gaatctggtc     240
gcccactccc ctctgaccag ccacccagcg gcgcctacgc tgatgcctgc tgtcaactat     300
gcccccttgg atctgccagg ctcggcggag ccgccaaagc aatgccaccc atgccctggg     360
gtgcccaggg gacgtcccc agctcccgtg ccttatggtt actttggagg cgggtactac     420
tcctgccgag tgtcccggag ctcgctgaaa ccctgtgccc aggcagccac cctggccgcg     480
taccccgcgg agactcccac ggccggggaa gagtacccca gccgccccac tgagtttgcc     540
ttctatccgg gatatccggg aacctaccag cctatggcca gttacctgga cgtgtctgtg     600
gtgcagactc tgggtgctcc tggagaaccg cgacatgact ccctgttgcc tgtggacagt     660
taccagtctt gggctctcgc tggtggctgg aacagccaga tgtgttgcca gggagaacag     720
aacccaccag gtccctttg gaaggcagca tttgcagact ccagcgggca gcaccctcct     780
```

```
gacgcctgcg cctttcgtcg cggccgcaag aaacgcattc cgtacagcaa ggggcagttg      840
cgggagctgg agcgggagta tgcggctaac aagttcatca ccaaggacaa gaggcgcaag      900
atctcggcag ccaccagcct ctcggagcgc cagattacca tctggtttca gaaccgccgg      960
gtcaaagaga agaaggttct cgccaaggtg aagaacagcg ctaccccta agagatctcc     1020
ttgcctgggt gggaggagcg aaagtggggg tgtcctgggg agaccaggaa cctgccaagc     1080
ccaggctggg gccaaggact ctgctgagag gcccctagag acaacaccct tcccaggcca     1140
ctggctgctg gactgttcct caggagcggc ctgggtaccc agtatgtgca gggagacgga     1200
accccatgtg acagcccact ccaccagggt tcccaaagaa cctggcccag tcataatcat     1260
tcatcctgac agtggcaata atcacgataa ccagtactag ctgccatgat cgttagcctc     1320
atattttcta tctagagctc tgtagagcac tttagaaacc gctttcatga attgagctaa     1380
ttatgaataa atttggaagg cgatcccttt gcagggaagc tttctctcag accccttcc     1440
attcacctc tcaccctggt aacagcagga agactgagga gaggggaacg ggcagattcg     1500
ttgtgtggct gtgatgtccg tttagcattt ttctcagctg acagctgggt aggtggacaa     1560
ttgtagaggc tgtctcttcc tccctccttg tccaccccat agggtgtacc cactggtctt     1620
ggaagcaccc atccttaata cgatgatttt tctgtcgtgt gaaaatgaag ccagcaggct     1680
gcccctagtc agtccttcct tccagagaaa aagagatttg agaaagtgcc tgggtaattc     1740
accattaatt tcctccccca aactctctga gtcttcccttt aatatttctg gtggttctga     1800
ccaaagcagg tcatggtttg ttgagcattt gggatcccag tgaagtagat gtttgtagcc     1860
ttgcatactt agcccttccc aggcacaaac ggagtggcag agtggtgcca accctgtttt     1920
cccagtccac gtagacagat tcacagtgcg gaattctgga agctggagac agacgggctc     1980
tttgcagagc cgggactctg agagggacat gagggcctct gcctctgtgt tcattctctg     2040
atgtcctgta cctgggctca gtgcccggtg ggactcatct cctggccgcg cagcaaagcc     2100
agcgggttcg tgctggtcct tcctgcacct taggctgggg gtgggggggcc tgccggcgca     2160
ttctccacga ttgagcgcac aggcctgaag tctggacaac ccgcagaacc gaagctccga     2220
gcagcgggtc ggtggcgagt agtggggtcg gtggcgagca gttggtggtg ggccgcggcc     2280
gccactacct cgaggacatt tccctcccgg agccagctct cctagaaacc ccgcggcggc     2340
cgccgcagcc aagtgtttat ggcccgcggt cgggtgggat cctagccctg tctcctctcc     2400
tgggaaggag tgagggtggg acgtgactta gacacctaca aatctattta ccaaagagga     2460
gcccgggact gagggaaaag gccaaagagt gtgagtgcat gcggactggg ggttcagggg     2520
aagaggacga ggaggaggaa gatgaggtcg atttcctgat ttaaaaaatc gtccaagccc     2580
cgtggtccag cttaaggtcc tcggttacat gcgccgctca gagcaggtca ctttctgcct     2640
tccacgtcct ccttcaagga agcccatgt gggtagcttt caatatcgca ggttcttact     2700
cctctgcctc tataagctca aacccaccaa cgatcgggca agtaaacccc ctccctcgcc     2760
gacttcggaa ctggcgagag ttcagcgcag atgggcctgt ggggagggg caagatagat     2820
gaggggggagc ggcatggtgc ggggtgaccc cttggagaga ggaaaaaggc cacaagaggg     2880
gctgccaccg ccactaacgg agatggccct ggtagagacc tttgggggtc tggaacctct     2940
ggactcccca tgctctaact cccacactct gctatcagaa acttaaactt gaggattttc     3000
tctgtttttc actcgcaata aattcagagc aaacaaaaaa aaaaaaa                   3047
```

<210> SEQ ID NO 4

```
<211> LENGTH: 18
<212> TYPE: DNA
<213> ORGANISM: Homo sapiens

<400> SEQUENCE: 4
ggttactttg gaggcggg                                                    18

<210> SEQ ID NO 5
<211> LENGTH: 6
<212> TYPE: PRT
<213> ORGANISM: Homo sapiens

<400> SEQUENCE: 5

Gly Tyr Phe Gly Gly Gly
1               5
```

COMPOSITIONS AND METHODS FOR THE TREATMENT OF PROSTATE CARCINOMA

CROSS-REFERENCE TO RELATED APPLICATIONS

This application is the U.S. national stage pursuant to 35 U.S.C. §371, of United States international application Ser. No. PCT/US2012/064179, filed Nov. 8, 2012, designating the United States and published in English on May 16, 2013, a publication WO 2013/070933 A2, which claims the benefit of the following U.S. Provisional Application Ser. Nos. 61/556,850, filed Nov. 8, 2011, and 61/583,882, filed Jan. 6, 2012, the entire contents of which are incorporated herein by reference.

STATEMENT OF RIGHTS TO INVENTIONS MADE UNDER FEDERALLY SPONSORED RESEARCH

This work was supported by the following grant from the National Institutes of Health, Grant Nos.: CA89600 and CA86323. The government has certain rights in the invention.

BACKGROUND OF THE INVENTION

Prostate cancer is a leading healthcare concern in North America and Europe. There were an estimated 232,090 new cases of prostate cancer diagnosed in 2005 in the United States, and over 30,350 deaths from advanced metastatic disease. Prostate cancer is now the most commonly diagnosed lethal malignancy, and the second leading cause of cancer death of men in the United States. Although curative treatment (e.g., radical prostatectomy or radiotherapy) is feasible for many patients with the earliest stage disease, early diagnosis remains a challenge. If prostate cancer becomes metastatic, the median survival for such patients is approximately one year. There remains an urgent need for determining those at risk for or susceptible to prostate cancer, early-stage prostate cancer prognosis, and early intervention.

Prostate specific antigen (PSA) screening has led to earlier detection of PCA and significantly reduced PCA-associated fatalities. However, a major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed. This has resulted in a surge of equivocal prostate needle biopsies. Thus, development of additional serum and tissue biomarkers or additional methods to detect a patient at risk for prostate cancer are urgently required.

SUMMARY OF THE INVENTION

As described below, the present invention features compositions and methods for the diagnosis, treatment and prevention of prostate cancer, as well as for treatment selection.

In one aspect, the invention provides a method for identifying a subject as having an increased propensity to develop prostate cancer, the method involving detecting an alteration in a HoxB13 nucleic acid sequence or amino acid sequence in a biological sample derived from the subject (e.g., where detecting an alteration by direct nucleic acid or amino acid sequencing, PCR, hybridization, TaqMan® probe, molecular beacon, FRET hybridization probe, 5' nuclease probe, primer extension, Restriction Fragment Length Polymorphism (RFLP), mass spectrometry, or using a protein or nucleic acid microarray).

In another aspect, the invention provides a method of determining the prognosis of a subject identified as having prostate cancer, the method involving identifying an alteration in a HoxB13 nucleic acid sequence or amino acid sequence in a biological sample derived from the subject, where the subject is identified as having a positive family history for prostate cancer and is younger than age 55, thereby identifying the subject as having a poor prognosis relative to a reference subject.

In still another aspect, the invention provides a method for selecting a therapy for a subject identified as having prostate cancer, the method involving detecting an alteration in a HoxB13 nucleic acid sequence or amino acid sequence in a biological sample derived from the subject, where detection of such alteration is indicative that aggressive treatment (e.g., radical prostatectomy, radiation therapy, chemotherapy, hormone therapy, and/or androgen ablation) is required.

In another aspect, the invention provides an isolated HoxB13 nucleic acid molecule having one or more of the following mutations: a change of adenosine for guanine in the second position of codon 84 (GGA→GAA) resulting in a nonconservative substitution of glutamic acid for glycine (G84E); a missense mutation 685C→G resulting in the substitution of glycine for arginine at position 229 (R229G); a substitution of proline for leucine at codon 144 (431T→C); and a substitution of aspartic acid for tyrosine (Y88D) at codon 88 (262T→G).

In a related aspect, the invention provides an expression vector including a nucleic acid molecule according to any of the aspects described herein (e.g., having a promoter operably linked to a HoxB13 nucleic acid molecule). In another related aspect, the invention provides cell containing a vector according to any of the aspects described herein.

In another aspect, the invention provides an isolated nucleic acid molecule for detecting one or more of the following alterations in HOXB13: a change of adenosine for guanine in the second position of codon 84 (GGA→GAA) resulting in a nonconservative substitution of glutamic acid for glycine (G84E); a missense mutation 685C→G resulting in the substitution of glycine for arginine at position 229 (R229G); a substitution mutation 431T→C resulting in a substitution of leucine for proline (L144P); and a substitution of aspartic acid for tyrosine (Y88D) at codon 88 (262T→G).

In another aspect, the invention provides an isolated antibody that specifically binds a HoxB13 protein variant having Y88D, L144P, R229G, or G84E, but that does not specifically bind a wild-type HoxB13 protein.

In various embodiments of any of the aspects delineated herein, the alteration in HOXB13 is one or more of: a change of adenosine for guanine in the second position of codon 84 (GGA→GAA) resulting in a nonconservative substitution of glutamic acid for glycine (G84E); a missense mutation 685C→G resulting in the substitution of glycine for arginine at position 229 (R229G); a substitution of proline for leucine at codon 144 (431T→C); and a substitution of aspartic acid for tyrosine (Y88D) at codon 88 (262T→G).

In various embodiments of any of the aspects delineated herein, the subject is identified as having a positive family history for prostate cancer and is younger than age 55. In various embodiments of any of the aspects delineated herein, the G84E mutation is identified in a subject of Nordic descent. In various embodiments of any of the aspects delineated herein, the R229G mutation is identified in a subject of African-American descent. In various embodiments of any of the aspects delineated herein, the sample is a tissue sample, tissue biopsy sample, or biological liquid.

In various embodiments of any of the aspects delineated herein, the method identifies the subject as in need of increased surveillance for prostate disease (e.g., annual measurement of PSA levels in the subject. In various embodiments of any of the aspects delineated herein, the detection of increased PSA identifies the subject as having prostate cancer or in need of further testing.

In various embodiments of any of the aspects delineated herein, the nucleic acid molecule is suitable for amplification of the alteration. In various embodiments of any of the aspects delineated herein, the nucleic acid molecules hybridize or fail to hybridize to the mutant sequence. In various embodiments of any of the aspects delineated herein, the nucleic acid molecule includes a detectable moiety.

The invention provides compositions and methods for diagnosing, treating or preventing prostate cancer. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "Homeobox B13 polypeptide" or "HOXB13 polypeptide" is meant a polypeptide or fragment thereof having at least 85% amino acid identity to NCBI Accession No. NP_006352 and having DNA binding activity.

By "HOXB13 nucleic acid molecule" is meant or a polynucleotide encoding a HOXB13 polypeptide. An exemplary HOXB13 nucleic acid molecule is provided at NCBI Accession No. NM_006361.

By "alteration" is meant any change in the nucleic acid or amino acid sequence of a molecule relative to a reference sequence. Such alteration may be a missense, frameshift or substitution mutation. The reference sequence is typically a wild-type HoxB13 nucleic acid or amino acid sequence.

As used herein, the term "antibody" means not only intact antibody molecules, but also fragments of antibody molecules that retain immunogen-binding ability.

By "biologic sample" is meant any tissue, cell, fluid, or other material derived from an organism.

By "clinical aggressiveness" is meant the severity of the neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

By "detect" refers to identifying the presence, absence, level, or concentration of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "genotype" is meant the genetic composition of a cell, organism, or individual. With reference to the invention, the genotype of an individual is determined as heterozygous or homozygous for one or more variant alleles of interest.

By "genotyping" is meant the characterization of the two alleles in one or more genes of interest (i.e., to determine a genotype).

By "heterozygous" is meant that a chromosomal locus has two different alleles. In one embodiment of the invention, heterozygous refers to a genotype in which one allele has a wild-type HOXB13 sequence and the other allele has a sequence encoding a HOXB13 variant that has an alteration at glycine 84 (e.g. G84E or rs138213197).

By "homozygous" is meant that a chromosomal locus has two identical alleles. In the invention, homozygous wild-type is meant to refer to a genotype in which both alleles have a wild-type HOXB13 sequence. In some embodiments, homozygous can refer to a genotype in which both alleles have a sequence encoding a HOXB13 variant that does not has an alteration at at glycine 84 (e.g. G84E or rs138213197).

By "increases" is meant a positive alteration of at least 10%, 25%, 50%, 75%, 100%, 200%, 300%, 400%, 500%, 1000%, or more.

By "propensity" is meant that a subject has an increased risk of developing disease relative to a reference subject. Such an increased risk is associated with the presence of an alteration in a HoxB13 nucleic acid or amino acid sequence that predisposes the subject to develop prostate cancer relative to the risk of prostate cancer in a reference subject carrying a wild-type HoxB13 sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "reference" is meant a standard of comparison. For example, the nucleotide sequence in a patient sample may be compared to the nucleotide sequence present in a corresponding healthy cell or tissue.

By "positive family history" is meant the presence of prostate cancer is a first degree relative (e.g., son, father, uncle, brother).

By "periodic" is meant at regular intervals. Periodic patient monitoring includes, for example, a schedule of tests that are administered daily, bi-weekly, bi-monthly, monthly, bi-annually, or annually.

By "severity of neoplasia" is meant the degree of pathology. The severity of a neoplasia increases, for example, as the stage or grade of the neoplasia increases.

By "marker" is meant any protein or polynucleotide having an alteration in activity, expression level, or sequence that is associated with a disease, disorder, or condition.

By "Marker profile" is meant a characterization of the expression or expression level of two or more polypeptides or polynucleotides.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

By "reduces" is meant a negative alteration of at least 10%, 25%, 50%, 75%, or 100%.

By "reference" is meant a standard or control condition. In various embodiments of the invention, the reference is the wild-type sequence of a gene or gene isoform.

By "specifically binds" is meant a compound or antibody that recognizes and binds a polypeptide of the invention, but which does not substantially recognize and bind other molecules in a sample.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

By "single nucleotide polymorphism" or "SNP" is meant a DNA sequence variation occurring when a single nucleotide in the genome differs between members of a biological species or paired chromosomes in an individual. SNPs are used as genetic markers for variant alleles.

By "target nucleic acid molecule" is meant a nucleic acid or biomarker of the sample that is to be detected.

By "variant" as is meant a polynucleotide or polypeptide sequence that differs from a wild-type or reference sequence by one or more nucleotides or one or more amino acids. An exemplary HOXB13 variant includes HOXB13 (G84E or rs138213197).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. C. in 750 mM NaCl, 75 mM trisodium citrate, and 1% SDS. In a more preferred embodiment, hybridization will occur at 37° C. C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The New England Journal of Medicine

FIG. 4 depicts immunohistochemical staining for HOXB13 (Panels A, C, and E) and Alpha-methylacyl-CoA racemase (AMACR; Panels B and D) in benign (Panel A) and malignant prostate tissue (Panels B-E). Prominent staining of HOXB13 was observed in nuclei of both normal luminal epithelial cells and cancer cells. Tumor-specific staining of AMACR was present in the cytoplasm of cancer cells. Sections of Formalin-Fixed, Paraffin-Embedded (FFPE) tissue from a HOXB13 G84E carrier were stained with antibodies against HOXB13 (F-9, Santa Cruz Biotechnology) or AMACR (13H4, Dako North America Inc).

Figure 3:
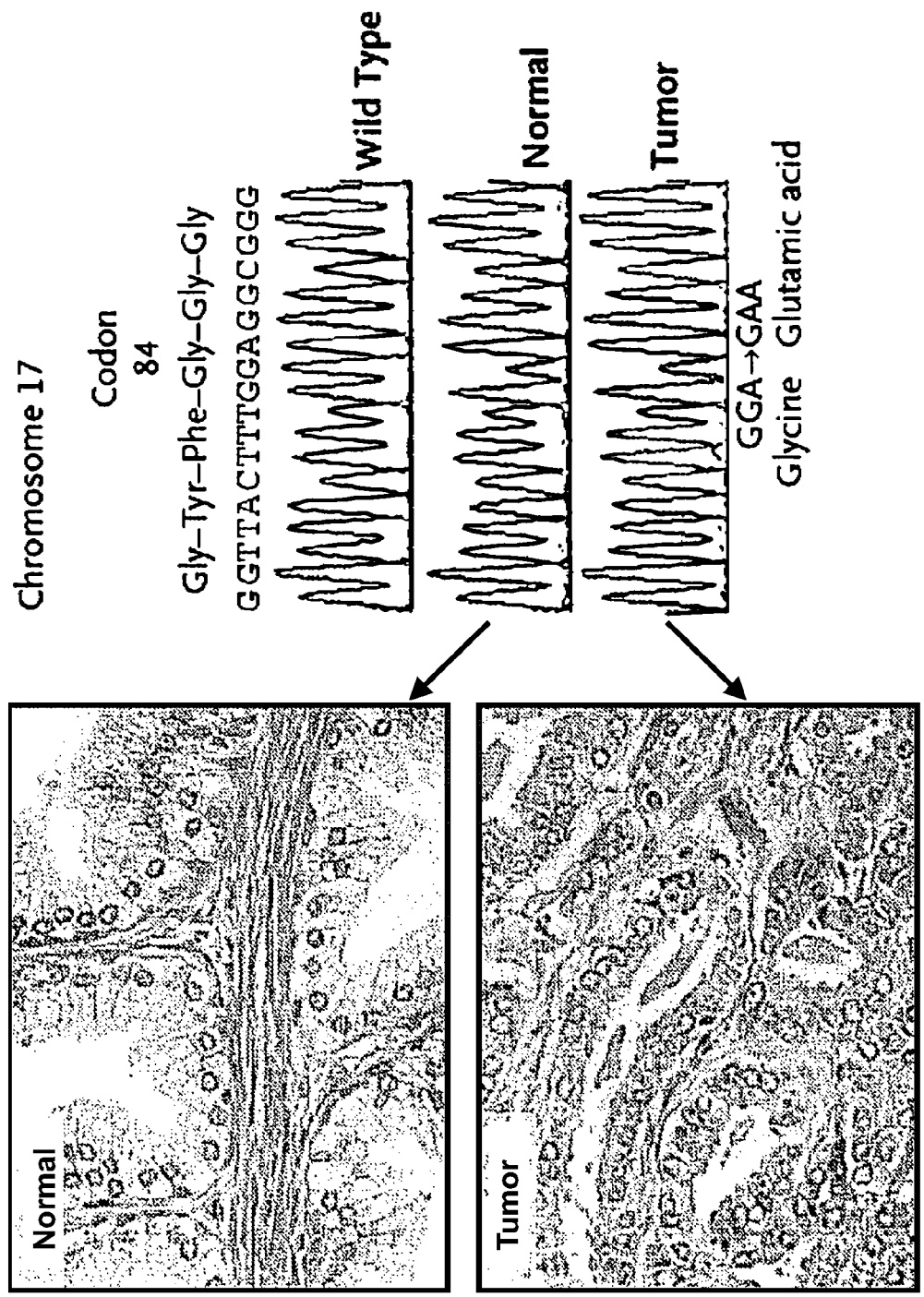
FIG. 3 depicts DNA sequence chromatograms and associated histologic findings obtained from normal prostate and prostate-cancer tissue from a heterozygous carrier of the HOXB13 G84E variant. Wild-type and mutant DNA are present in both normal prostate tissue and prostate-cancer tissue from HOXB13 G84E carriers. DNA was extracted from sections of paraffin-embedded blocks of tissue obtained during a radical prostatectomy performed in a patient who was heterozygous for the HOXB13 G84E variant. The blocks were selected and trimmed to contain either normal or tumor tissue, as shown on hematoxylin and eosin staining (at left), and were subjected to Sanger sequencing. The chromatograms (at right) show the presence of both wild-type (GGA) and mutant (GAA) alleles at codon 84 in normal prostate tissue (middle) and ale maintenance of both alleles in the matched sample of prostate tumor tissue (bottom). The top chromatogram is a homozygous wild-type sequence (5'-GGTTACTTTGGAGGCGGG-3' (SEQ ID NO: 4); translation: N-GYFGGG-C (SEQ ID NO: 5)) from a subject without the G84E mutation. The genome position shown (44,160,704) is based on the National Center for Biotechnology Information database, build 36 (hg18).
Figure 4C:
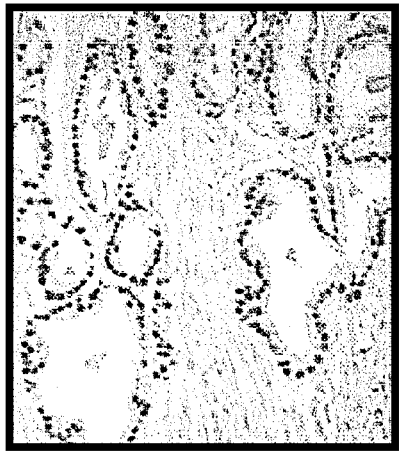
Figure 4E:
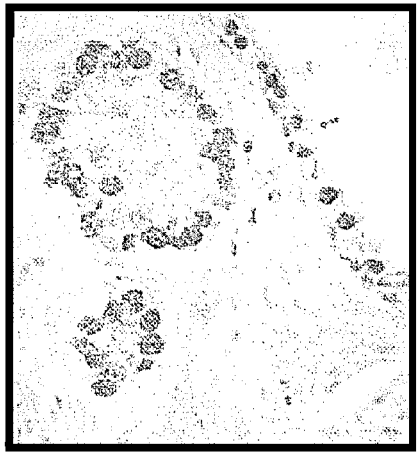
Figure 4B:
Figure 4D:
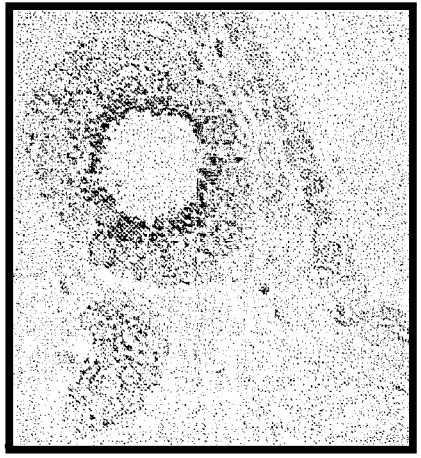
Figure 4A:
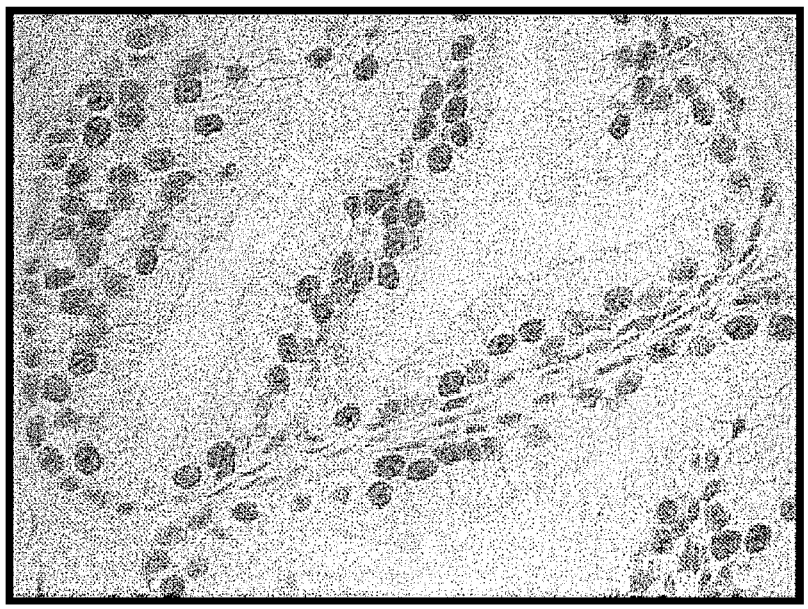

FIG. 5 provides genomic sequences of chromosome 17q21-22 (SEQ ID NO: 1). The HOXB13 G84E mutation is at chr 17 base pos. 46,805,705 GRCh37/hg19 (pos. 44,160, 704 GRCh36/hg18). The DNA sequence surrounding this mutation is shown in FIG. 3. The GRCh37/hg19 coordinate for the Y88D mutation is at chr 17 base pos. 46,805,694; the L144P mutation is at 46,805,525; the G216C mutation is at 46,804,361; the R229G mutation is at 46,804,322.

DETAILED DESCRIPTION OF THE INVENTION

The invention features compositions and methods that are useful for the diagnosis, treatment and prevention of prostate cancer, as well as for treatment selection. The present invention is based, at least in part, on the discovery that having germline mutations in HOXB13 (e.g., G84E or rs138213197) increased the risk of developing prostate cancer. As reported in more detail below, the sequences of families having prostate cancer were analyzed at the 17q21-22 chromosomal locus to identify SNPs that were indicative of increased risk of prostate cancer. Despite a large degree of variability in the number of individuals sampled per pedigree, approximately 5% of prostate cancer families had at least one member with the G84E mutation (e.g., a germline mutation). Without being bound to a particular theory, the results are consistent with the hypothesis that HOXB13 G84E is a prostate cancer susceptibility allele that significantly increases the risk of prostate cancer. The identification and characterization of genetic variants reproducibly associated with substantial increases in prostate cancer risk would provide enhanced ability to identify men most likely to benefit from early disease screening.

Prostate Cancer

The development of human prostate cancer proceeds through a series of defined stages, beginning with prostatic intraepithelial neoplasia, progressing to invasive hormone-dependent cancer, and finally progressing to hormone-independent cancer. Most human prostate cancers are adenocarcinomas that express markers associated with luminal epithelial cells. Because of unbalanced cell proliferation, cell differentiation, and cell death, prostate cancer exhibits substantial histological heterogeneity. To date, DNA and tissue microarrays of tumors have failed to account for cellular heterogeneity and differences in the proliferative potential of different populations within tumors. At present, all of the phenotypically diverse cancer cells are treated as though they have unlimited proliferative potential and can acquire the ability to metastasize. In patients with metastic disease, conventional therapies are ineffective. Metastatic prostate tumor cells are able to survive extreme conditions within the circulation. Metastic cancer cells lodge in the capillary beds of distant organs where they undergo extensive proliferation, often in bone, lymph node, lung and brain [(Karhadkar et al., 2004; Swanson et al., 2006). Metastatic tumor cells share many characteristics (e.g., self-renewal, proliferation, and multi-potency) with pluripotent stem cells. Little is known about how human metastatic tumor cells maintain or acquire their multipotency. Recent studies suggest the existence of prostate cancer stem cells that are chemo-resistant and radiation-resistant. Therapies specifically directed against such cancer stem cells are likely to be more effective in curing prostate cancer and metastatic disease.

Accordingly, the present invention provides methods of treating prostate cancer and/or disorders or symptoms thereof which comprise administering a therapeutically effective amount of a pharmaceutical composition comprising an agent of the formulae herein to a subject (e.g., a mammal, such as a human). Thus, one embodiment is a method of treating a subject suffering from or susceptible to prostate cancer, metastatic prostate cancer, or prostate cancer having the propensity to metastasize or symptoms thereof. The method includes the step of administering to the mammal a therapeutic amount of an agent herein sufficient to treat the prostate cancer or symptom thereof, under conditions such that the prostate cancer is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the agents herein, such as an agent of the formulae herein to a subject (e.g., animal, human) in need thereof, including a mammal, particularly a human. Such treatment will be suitably administered to subjects, particularly humans, suffering from, having, susceptible to, or at risk for prostate cancer, including metastatic disease or prostate cancer having a propensity to metastasize, or a symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which prostate cancer or hyperplasia may be implicated.

In one embodiment, the invention provides a method of monitoring treatment progress. The method includes the step of determining the presence of a SNP (e.g., or any target delineated herein modulated by a compound herein, a protein or indicator thereof, etc.) or diagnostic measurement (e.g., screen, assay) in a subject suffering from or susceptible to prostate cancer, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Homeobox Protein B13 (Hox B13)

The HOX genes are a subfamily of the homeobox superfamily of transcription factors characterized by a highly conserved DNA-binding domain, or homeodomain. In humans, there are four HOX clusters, with each spanning approximately 200 kb on chromosomes 7 (HOXA), 17 (HOXB), 12 (HOXC), and 2 (HOXD). The combination of coordinated HOX expression provides a so-called HOX code that is essential for the pattern formation of the animal body. The genes within each HOX cluster are expressed temporally during development; 3' genes are expressed early in anterior and proximal regions, whereas 5' genes are expressed late in posterior and distal regions. HOX genes in paralogue group 13 are members of the abdominal B subfamily of such genes, which have posterior domains of expression, including in the developing urogenital system in vertebrates. Whereas multiple HOX13 paralogues are expressed during embryonic development of the prostate, HOXB13 maintains a high expression level into adulthood in normal prostate and, to a lesser level, in distal colon. In a study by Economides et al. (2003) mice that had been generated from embryonic stem cells with targeted disruption in HOXB13 had overgrowth of structures arising from the tail bud, including the spinal cord and tail vertebrae, with decreased apoptosis proposed as a possible mechanism. Further characterization of these animals showed subtle but definitive, lobe-specific abnormalities of the prostate gland but without evidence of preneoplastic lesions.

By sequencing coding regions of more than 200 genes in a previously identified region of linkage at 17q21-22, a rare but recurrent mutation (G84E) in HOXB13 was identified in four of 94 probands from hereditary prostate cancer families. The mutation co-segregated with prostate cancer in these four families and was found to be significantly more common among 5,083 unrelated prostate cancer patients (1.4%) than control subjects (0.1%) of Eu opean descent (p=8.5× $10^{-7}$) leading to odds ratio (OR) estimates of 10-fold or more. In the studies described herein, the frequency of the mutation was higher in prostate cancer patients with early-onset disease (age at diagnosis=55 years old, 2.2%) or with a positive family history (2.2%), and most common in patients with both of these features (3.1%). Without being bound to a particular theory, these findings provide support for the concept that rare, moderately penetrant mutations as well as common, low-penetrance prostate cancer risk-associated variants identified from genome-wide association studies (GWAS) both contribute to prostate cancer risk.

The amino acid sequence of human HOXB13 is provided at NCBI Accession No. NP_006352, which is reproduced below:

```
                                              (SEQ ID NO: 2)
  1  mepgnyatld gakdiegllg agggrnlvah spltshpaap
     tlmpavnyap ldlpgsaepp
 61  kqchpcpgvp qgtspapvpy gyfgggyysc rvsrsslkpc
     aqaatlaayp aetptageey
121  psrptefafy pgypgtyqpm asyldvsvvq tlgapgeprh
     dsllpvdsyq swalaggwns
181  qmccqgeqnp pgpfwkaafa dssgqhppda cafrrgrkkr
     ipyskgqlre lereyaankf
241  itkdkrrkis aatslserqi tiwfqnrrvk ekkvlakvkn
     satp
```

The nucleotide sequence of an mRNA transcript encoding HOXB13 corresponds to NCBI Accession No. NM_130468 (human HOXB13 encoded at nucleotides 157-1011), which is reproduced below:

```
                                              (SEQ ID NO: 3)
   1  tcttgcgtca agacggccgt gctgagcgaa tgcaggcgac
      ttgcgagctg ggagcgattt
  61  aaaacgcttt ggattccccc ggcctgggtg gggagagcga
      gctgggtgcc ccctagattc
 121  cccgccccg cacctcatga gccgaccctc ggctccatgg
      agcccggcaa ttatgccacc
 181  ttggatggag ccaaggatat cgaaggcttg ctgggagcgg
      agggggggcg gaatctggtc
 241  gcccactccc ctctgaccag ccacccagcg gcgcctacgc
      tgatgcctgc tgtcaactat
 301  gcccccttgg atctgccagg ctcggcggag ccgccaaagc
      aatgccaccc atgccctggg
 361  gtgccccagg ggacgtcccc agctcccgtg ccttatggtt
      actttggagg cgggtactac
 421  tcctgccgag tgtcccggag ctcgctgaaa ccctgtgccc
      aggcagccac cctggccgcg
 481  taccccgcgg agactcccac ggccggggaa gagtacccca
      gccgccccac tgagtttgcc
 541  ttctatccgg gatatccggg aacctaccag cctatggcca
      gttacctgga cgtgtctgtg
 601  gtgcagactc tgggtgctcc tggagaaccg cgacatgact
      ccctgttgcc tgtggacagt
 661  taccagtctt gggctctcgc tggtggctgg aacagccaga
      tgtgttgcca gggagaacag
 721  aacccaccag gtcccttttg gaaggcagca tttgcagact
      ccagcgggca gcaccctcct
 781  gacgcctgcg ccttcgtcg cggccgcaag aaacgcattc
      cgtacagcaa ggggcagttg
 841  cgggagctgg agcgggagta tgcggctaac aagttcatca
      ccaaggacaa gaggcgcaag
 901  atctcggcag ccaccagcct ctcggagcgc cagattacca
      tctggttca gaaccgccgg
 961  gtcaaagaga agaaggttct cgccaaggtg aagaacagcg
      ctacccctta agagatctcc
1021  ttgcctgggt gggaggagcg aaagtggggg tgtcctgggg
      agaccaggaa cctgccaagc
1081  ccaggctggg gccaaggact ctgctgagag gcccctagag
      acaacaccct tcccaggcca
1141  ctggctgctg gactgttcct caggagcggc ctgggtaccc
      agtatgtgca gggagacgga
1201  accccatgtg acagcccact ccaccagggt tcccaaagaa
      cctggcccag tcataatcat
1261  tcatcctgac agtggcaata atcacgataa ccagtactag
      ctgccatgat cgttagcctc
1321  atattttcta tctagagctc tgtagagcac tttagaaacc
      gctttcatga attgagctaa
1381  ttatgaataa atttggaagg cgatcccttt gcagggaagc
      tttctctcag acccccttcc
1441  attacacctc tcaccctggt aacagcagga agactgagga
      gaggggaacg ggcagattcg
1501  ttgtgtggct gtgatgtccg tttagcattt ttctcagctg
      acagctgggt aggtggacaa
1561  ttgtagaggc tgtctcttcc tccctccttg tccacccat
      agggtgtacc cactggtctt
1621  ggaagcaccc atccttaata cgatgatttt tctgtcgtgt
      gaaaatgaag ccagcaggct
1681  gcccctagtc agtccttcct tccagagaaa aagagatttg
      agaaagtgcc tgggtaattc
1741  accattaatt tcctccccca aactctctga gtcttccctt
      aatatttctg gtggttctga
1801  ccaaagcagg tcatggtttg ttgagcattt gggatcccag
      tgaagtagat gtttgtagcc
1861  ttgcatactt agcccttccc aggcacaaac ggagtggcag
      agtggtgcca accctgtttt
1921  cccagtccac gtagacagat tcacagtgcg gaattctgga
      agctggagac agacgggctc
```

-continued

```
1981  tttgcagagc cgggactctg agagggacat gagggcctct gcctctgtgt tcattctctg 2041  atgtcctgta cctgggctca gtgcccggtg ggactcatct cctggccgcg cagcaaagcc 2101  agcgggttcg tgctggtcct tcctgcacct taggctgggg gtgggggcc tgccggcgca 2161  ttctccacga ttgagcgcac aggcctgaag tctggacaac ccgcagaacc gaagctccga 2221  gcagcgggtc ggtggcgagt agtggggtcg gtggcgagca gttggtggtg ggccgcggcc 2281  gccactacct cgaggacatt tccctcccgg agccagctct cctagaaacc ccgcggcggc 2341  cgccgcagcc aagtgtttat ggcccgcggt cgggtgggat cctagccctg tctcctctcc 2401  tgggaaggag tgagggtggg acgtgactta gacacctaca aatctattta ccaaagagga 2461  gcccgggact gagggaaaag gccaaagagt gtgagtgcat gcggactggg ggttcagggg 2521  aagaggacga ggaggaggaa gatgaggtcg atttcctgat ttaaaaaatc gtccaagccc 2581  cgtggtccag cttaaggtcc tcggttacat gcgccgctca gagcaggtca ctttctgcct 2641  tccacgtcct ccttcaagga agccccatgt gggtagcttt caatatcgca ggttcttact 2701  cctctgcctc tataagctca aacccaccaa cgatcgggca agtaaacccc ctccctcgcc 2761  gacttcggaa ctggcgagag ttcagcgcag atgggcctgt ggggaggggg caagatagat 2821  gaggggagc ggcatggtgc ggggtgaccc cttggagaga ggaaaaaggc cacaagaggg 2881  gctgccaccg ccactaacgg agatggccct ggtagagacc tttgggggtc tggaacctct 2941  ggactcccca tgctctaact cccacactct gctatcagaa acttaaactt gaggattttc 3001  tctgttttc actcgcaata aattcagagc aaacaaaaaa aaaaaaa
```

Several studies have examined the role of HOXB13 in normal and cancerous prostate biology, although substantially different conclusions have been reached, with HOXB13 being implicated as both a tumor suppressor and an oncogene in prostate and other cancers. For example, the growth of the prostate-cancer cell line LNCaP has been shown to be suppressed by both experimental overexpression of HOXB13 by transfection and by reduction of endogenous HOXB13 expression by RNA interference. HOXB13 physically interacts with the androgen receptor, one of the most important growth and differentiation regulators in normal and cancerous prostate biology. Without being bound to a particular theory, the HOXB13 G84E mutation is located in a conserved domain of the HOXB13 protein that has been shown to mediate binding to members of the MEIS protein family, which are implicated in leukemia. The studies described herein indicate that tumors in G84E carriers continue to express HOXB13 and maintain the mutant allele (FIGS. 3 and 4).

Diagnostic Assays

The present invention provides a number of diagnostic assays that are useful for the identification or characterization of prostate cancer in a subject. Such methods may be used alone or in combination with standard methods for monitoring a subject for prostate cancer. In one embodiment, a subject is identified as being at risk of developing prostate cancer by the presence of the SNP rs138213197 (corresponding to the genetic variant HOXB13 G84E), alone or in combination with other standard methods. To determine the stage or grade of a neoplasia, grading is used to describe how abnormal or aggressive the neoplastic cells appear, while staging is used to describe the extent of the neoplasia. If desired, the grade and stage of the neoplasia in combination with the presence of the SNP rs138213197 (corresponding to the genetic variant HOXB13 G84E) is used to determine a subject's long-term prognosis (i.e., probable response to treatment and survival). Thus, the methods of the invention are useful for predicting a patient's prognosis, and for selecting a course of treatment.

The Gleason scale is the most common scale used for grading prostate cancer. A pathologist will look at the two most poorly differentiated parts of the tumor and grade them. The Gleason score is the sum of the two grades, and so can range from two to 10. The higher the score is, the poorer the prognosis. Scores usually range between 4 and 7. The scores can be broken down into three general categories: (i) low-grade neoplasias (score<4) are typically slow-growing and contain cells that are most similar to normal prostate cells; intermediate grade neoplasias (4<score<7) are the most common and typically contain some cells that are similar to normal prostate cells as well as some more abnormal cells; high-grade neoplasias (8<score<10) contain cells that are most dissimilar to normal prostate cells. High-grade neoplasias are the most deadly because they are most aggressive and fast growing. High-grade neoplasias typically move rapidly into surrounding tissues, such as lymph nodes and bones.

Stage refers to the extent of a cancer. In prostate cancer, for example, one staging method divides the cancer into four categories, A, B, C, and D. Stage A describes a cancer that is only found by elevated PSA and biopsy, or at surgery for obstruction. It is not palpable on digital rectal exam (DRE). This stage is localized to the prostate. This type of cancer is usually curable, especially if it has a relatively low Gleason grade. Stage B refers to a cancer that can be felt on rectal examination and is limited to the prostate. Bone scans or CT/MRI scans are often used to determine this stage, particularly if prostate specific antigen (PSA) levels are significantly elevated or if the Gleason grade is 7 or greater. Many Stage B prostate cancers are curable. Stage C cancers have spread beyond the capsule of the prostate into local organs or tissues, but have not yet metastasized to other sites. This stage is determined by DRE, or CT/MRI scans, and/or sonography. In Stage C a bone scan or a PROSTASCINT scan is negative. Some Stage C cancers are curable.

Stage D cancer has metastasized to distant lymph nodes, bones or other sites. This is usually determined by bone scan, PROSTASCINT scan, or other studies. Stage D cancer is usually incurable.

Types of Biological Samples

The presence of SNP rs138213197 (corresponding to the genetic variant HOXB13 G84E) can be detected in different types of biologic samples. In one embodiment, the biologic sample is a tissue sample that includes cells of a tissue or organ (e.g., prostatic tissue cells). Prostatic tissue is obtained, for example, from a biopsy of the prostate. In another embodiment, the biologic sample is a biologic fluid sample. Biological fluid samples include blood, blood serum, plasma, urine, seminal fluids, and ejaculate, or any other biological fluid useful in the methods of the invention.

Genotyping of HOXB13 Polymorphisms

A HOXB13 isoform is amplified by PCR to determine the genotype of the isoform, e.g., HOXB13 G84E. The amplified nucleic acid corresponding to HOXB13 may be analyzed using a variety of methods for detecting variant alleles to determine the genotype. The presence or absence of a polymorphism (e.g., G84E) in the HOXB13 gene may be evaluated using various techniques. For example, the HOXB13 gene is amplified by PCR and sequenced to determine the presence or absence of a single nucleotide polymorphism (SNP). In certain embodiments, real-time PCR may be used to detect a single nucleotide polymorphism of the amplified products. In other embodiments, a polymorphism in the amplified products may be detected using a technique including hybridization with a probe specific for a single nucleotide polymorphism, restriction endonuclease digestion, primer extension, microarray or gene chip analysis, mass spectrometry, or a DNAse protection assay.

Polymerase Chain Reaction (PCR)

Polymerase chain reaction (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

In the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

The methods of the present invention involve amplifying regions of a polynucleotide with high fidelity using a thermostable DNA polymerase having 3'→5' exonuclease activity. As defined herein, "3'→5' exonuclease activity" refers to the activity of a template-specific nucleic acid polymerase having a 3'→5' exonuclease activity associated with some DNA polymerases, in which one or more nucleotides are removed from the 3' end of an oligonucleotide in a sequential manner. Polymerase enzymes having high fidelity 3'→5' exonuclease activity are useful, for example, when primer extension must be performed over long distances (i.e., when the desired PCR amplification product is greater than about 5 kb). Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs). Exemplary methods for performing PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. In various embodiments, PCR involves one DNA polymerase. In some embodiments, PCR may involve more than one DNA polymerase. When using a combination of polymerases in PCR, it is preferable to include one polymerase having 3'→5' exonuclease activity, which assures high fidelity generation of the PCR product from the DNA template. Typically, a non-proofreading polymerase, which is the main polymerase is also used in conjunction with the proofreading polymerase in PCR reactions. PCR can also be performed using commercially available kits, such as LA PCR kit available from Takara Bio Inc.

Sequencing

DNA sequencing may be used to evaluate a polymorphism of the present invention. One DNA sequencing method is the Sanger method, which is also referred to as dideoxy sequencing or chain termination. The Sanger method is based on the use of dideoxynucleotides (ddNTP's) in addition to the normal nucleotides (NTP's) found in DNA. Dideoxynucleotides are essentially the same as nucleotides except they contain a hydrogen group on the 3' carbon instead of a hydroxyl group (OH). These modified nucleotides, when integrated into a sequence, prevent the addition of further nucleotides. This occurs because a phosphodiester bond cannot form between the dideoxynucleotide and the next incoming nucleotide, and thus the DNA chain is terminated. Using this method, optionally coupled with amplification of the nucleic acid target, one can now rapidly sequence large numbers of target molecules, usually employing automated sequencing apparati. Such techniques are well known to those of skill in the art.

Pyrosequencing is another method of DNA sequencing that may be used to evaluate a polymorphism of the present invention, for example as described in U.S. Pat. Publ. No. 2006008824; herein incorporated by reference). Pyrosequencing, which is also referred to as sequencing by synthesis, involves taking a single strand of the DNA to be sequenced, synthesizing its complementary strand enzymatically one base pair at a time, and detecting by chemiluminescence the base that is added. In one embodiment, the template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. The templates for pyrosequencing can be made both by solid phase template preparation (streptavidin-coated magnetic beads) and enzymatic template preparation (apyrase+exonuclease).

In a specific embodiment, ssDNA template is hybridized to a sequencing primer and incubated with the enzymes DNA polymerase, ATP sulfurylase, luciferase and apyrase, and with the substrates adenosine 5' phosphosulfate (APS) and luciferin. The addition of one of the four deoxynucleotide triphosphates (dNTPs) (in place of dATP, dATPαS is added, which is not a substrate for a luciferase) initiates the second step. DNA polymerase incorporates the correct, complementary dNTPs onto the template, and the incorporation of the nucleotide releases pyrophosphate (PPi) stoichiometrically. ATP sulfurylase quantitatively converts PPi to ATP in the presence of adenosine 5' phosphosulfate. The ATP generated acts to catalyze the luciferase-mediated conversion of luciferin to oxyluciferin and generates visible light in amounts that are proportional to the amount of ATP. The light produced in the luciferase-catalyzed reaction is detected by a camera and analyzed in a program. Unincorporated nucleotides and ATP are degraded by the apyrase, and the reaction can restart with another nucleotide.

Pyrosequencing, optionally coupled with amplification of the nucleic acid target, can sequence large numbers of target molecules, usually employing automated sequencing apparati, including long sequences (e.g., 400 million bp/10 hr in a single run).

Various PCR testing platforms that may be used with the present invention include: 5' nuclease (TaqMan® probes), molecular beacons, and FRET hybridization probes. These detection methods rely on the transfer of light energy between two adjacent dye molecules, a process referred to as fluorescence resonance energy transfer (see, e.g., Espy et al (2006) Clin Microbiol Rev. 2006 January; 19(1): 165-256 for a review of various rtPCR approaches that may be used with the present invention).

5' Nuclease Probes

In certain embodiments, a 5' nuclease probe may be used to detect a polymorphism of the present invention. 5' nuclease probes are often referred to by the proprietary name, TaqMan® probes. A TaqMan® probe is a short oligonucleotide (DNA) that contains a 5' fluorescent dye and 3' quenching dye. To generate a light signal (i.e., remove the effects of the quenching dye on the fluorescent dye), two events must occur. First, the probe must bind to a complementary strand of DNA, e.g., at about 60° C. Second, at this temperature, Taq polymerase, which is commonly used for PCR, must cleave the 5' end of the TaqMan® probe (5' nuclease activity), separating the fluorescent dye from the quenching dye.

In order to differentiate a single nucleotide polymorphism from a wild-type sequence in the DNA from a subject, a second probe with complementary nucleotide(s) to the polymorphism and a fluorescent dye with a different emission spectrum are typically utilized. Thus, these probes can be used to detect a specific, predefined polymorphism under the probe in the PCR amplification product. Two reaction vessels are typically used, one with a complementary probe to detect wild-type target DNA and another for detection of a specific nucleic acid sequence of a mutant strain. Because TaqMan® probes typically require temperatures of about 60° C. for efficient 5' nuclease activity, the PCR may be cycled between about 90-95° C. and about 60° C. for amplification. In addition, the cleaved (free) fluorescent dye can accumulate after each PCR temperature cycle; thus, the dye can be measured at any time during the PCR cycling, including the hybridization step. In contrast, molecular beacons and FRET hybridization probes typically involve the measurement of fluorescence during the hybridization step.

Genotyping for the G84E polymorphism in the HOXB13 gene may be evaluated using the following (5' endonuclease probe) real-time PCR technique. Genotyping assays can be performed in duplicate and analyzed on a Bio-Rad iCycler Iq® Multicolor Real-time detection system (Bio-Rad Laboratories, Hercules, Calif.). Real-time polymerase chain reaction (PCR) allelic discrimination assays to detect the presence or absence of specific single nucleotide polymorphisms in a HOXB13 gene, Gly143Glu (genomic: nt 9486; Cdna: nt 428) and Asp260fs (genomic: nt 12754; Cdna: nt 780), may utilize fluorogenic TaqMan® Probes.

Real-time PCR amplifications may be carried out in a 10 μl reaction mix containing 5 ng genomic DNA, 900 Nm of each primer, 200 Nm of each probe and 5 μl of 2× TaqMan® Universal PCR Master Mix (contains PCR buffer, passive reference dye ROX, deoxynucleotides, uridine, uracil-N-glycosylase and AmpliTaq Gold DNA polymerase; Perkin-Elmer, Applied Biosystems, Foster City, Calif.). Cycle parameters may be: 95° C. for 10 min, followed by 50 cycles of 92° C. for 15 sec and 60 C.° for 1 min. Real-time fluorescence detection can be performed during the 60° C. annealing/extension step of each cycle. The IQ software may be used to plot and automatically call genotypes based on a two parameter plot using fluorescence intensities of FAM and VIC at 49 cycles.

Molecular Beacons

Molecular beacons are another real-time PCR approach which may be used to identify the presence or absence of a polymorphism of the present invention. Molecular beacons are oligonucleotide probes that are labeled with a fluorescent dye (typically on the 5' end) and a quencher dye (typically on the 3' end). A region at each end of the molecular beacon probe is designed to be complementary to itself, so at low temperatures the ends anneal, creating a hairpin structure. This hairpin structure positions the two dyes in close proximity, quenching the fluorescence from the reporter dye. The central region of the probe is designed to be complementary to a region of a PCR amplification product. At higher temperatures, both the PCR amplification product and probe are single stranded. As the temperature of the PCR is lowered, the central region of the molecular beacon probe may bind to the PCR product and force the separation of the fluorescent reporter dye from the quenching dye. Without the quencher dye in close proximity, a light signal from the reporter dye can be detected. If no PCR amplification product is available for binding, the probe can re-anneal to itself, bringing the reporter dye and quencher dye into close proximity, thus preventing fluorescent signal.

Two or more molecular beacon probes with different reporter dyes may be used for detecting single nucleotide polymorphisms. For example, a first molecular beacon designed with a first reporter dye may be used to indicate the presence of a SNP and a second molecular beacon designed with a second reporter dye may be used to indicate the presence of the corresponding wild-type sequence; in this way, different signals from the first and/or second reporter dyes may be used to determine if a subject is heterozygous for a SNP, homozygous for a SNP, or homozygous wild-type at the corresponding DNA region. By selection of appropriate PCR temperatures and/or extension of the probe length, a molecular beacons may bind to a target PCR product when a nucleotide polymorphism is present but at a slight cost of reduced specificity. Molecular beacons advantageously do not require thermocycling, so temperature optimization of the PCR is simplified.

FRET Hybridization Probes

FRET hybridization probes, also referred to as LightCycler® probes, may also be used to detect a polymorphism of the present invention. FRET hybridization probes typically comprise two DNA probes designed to anneal next to each other in a head-to-tail configuration on the PCR product. Typically, the upstream probe has a fluorescent dye on the 3' end and the downstream probe has an acceptor dye on the 5' end. If both probes anneal to the target PCR product, fluorescence from the 3' dye can be absorbed by the adjacent acceptor dye on the 5' end of the second probe. As a result, the second dye is excited and can emit light at a third wavelength, which may be detected. If the two dyes do not come into close proximity in the absence of sufficient complimentary DNA, then FRET does not occur between the two dyes. The 3' end of the second (downstream) probe may be phosphorylated to prevent it from being used as a primer by Taq during PCR amplification. The two probes may encompass a region of 40 to 50 DNA base pairs.

FRET hybridization probe technology permits melting curve analysis of the amplification product. If the temperature is slowly raised, probes annealing to the target PCR product will be reduced and the FRET signal will be lost. The temperature at which half the FRET signal is lost is referred to as the melting temperature of the probe system. A single nucleotide polymorphism in the target DNA under a hybridization FRET probe will still generate a signal, but the melting curve will display a lower Tm. The lowered Tm can indicate the presence of a specific polymorphism. The target PCR product is detected and the altered Tm informs the user there is a difference in the sequence being detected. Like molecular beacons, there is not a specific thermocycling temperature requirement for FRET hybridization probes. Like molecular beacons, FRET hybridization probes have the advantage of being recycled or conserved during PCR temperature cycling, and a fluorescent signal does not accumulate as PCR product accumulates after each PCR cycle.

Primer Extension

Primer extension is another technique which may be used according to the present invention. A primer and no more than three NTPs may be combined with a polymerase and the target sequence, which serves as a template for amplification. By using less than all four NTPs, it is possible to omit one or more of the polymorphic nucleotides needed for incorporation at the polymorphic site. It is important for the practice of the present invention that the amplification be designed such that the omitted nucleotide(s) is(are) not required between the 3' end of the primer and the target polymorphism. The primer is then extended by a nucleic acid polymerase, in a preferred embodiment by Taq polymerase. If the omitted NTP is required at the polymorphic site, the primer is extended up to the polymorphic site, at which point the polymerization ceases. However, if the omitted NTP is not required at the polymorphic site, the primer will be extended beyond the polymorphic site, creating a longer product. Detection of the extension products is based on, for example, separation by size/length which will thereby reveal which polymorphism is present. For example, U.S. Ser. No. 10/407,846, which is which is hereby incorporated by reference, describes a form of primer extension.

RFLP

Restriction Fragment Length Polymorphism (RFLP) is a technique in which different DNA sequences may be differentiated by analysis of patterns derived from cleavage of that DNA. If two sequences differ in the distance between sites of cleavage of a particular restriction endonuclease, the length of the fragments produced will differ when the DNA is digested with a restriction enzyme. The similarity of the patterns generated can be used to differentiate species (and even strains) from one another.

Restriction endonucleases in turn are the enzymes that cleave DNA molecules at specific nucleotide sequences depending on the particular enzyme used. Enzyme recognition sites are usually 4 to 6 base pairs in length. Generally, the shorter the recognition sequence, the greater the number of fragments generated. If molecules differ in nucleotide sequence, fragments of different sizes may be generated. The fragments can be separated by gel electrophoresis. Restriction enzymes are isolated from a wide variety of bacterial genera and are thought to be part of the cell's defenses against invading bacterial viruses. Use of RFLP and restriction endonucleases in SNP analysis requires that the SNP affect cleavage of at least one restriction enzyme site.

Mass Spectrometry

Mass spectrometry may also be used to detect a polymorphism of the present invention. By exploiting the intrinsic properties of mass and charge, mass spectrometry (MS) can resolved and confidently identified a wide variety of complex compounds. Traditional quantitative MS has used electrospray ionization (ESI) followed by tandem MS (MS/MS) (Chen et al., 2001; Thong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). Methods of mass spectroscopy that may be used with the present invention include: ESI, ESI tandem mass spectroscopy (ESI/MS/MS), Secondary ion mass spectroscopy (SIMS), Laser desorption mass spectroscopy (LD-MS), Laser Desorption Laser Photoionization Mass Spectroscopy (LDLPMS), and MALDI-TOF-MS.

Hybridization

There are a variety of ways by which one can assess genetic profiles, and may of these rely on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Microarrays

The invention provides diagnostic microarrays for detecting the SNP rs138213197 (corresponding to the genetic variant HOXB13 G84E) in a biological sample. HOXB13 nucleic acid molecules or polypeptides are useful as hybridizable array elements in the microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g. a tissue sample obtained by biopsy). For some applications, cultured cells (e.g., lymphocytes) or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 .mu.g/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Protein Microarrays

Proteins, such as those described herein, may also be analyzed using protein microarrays. Such arrays are useful in high-throughput low-cost screens to identify peptide or candidate compounds that bind a polypeptide of the invention, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins (e.g., polypeptides encoded by a nucleic acid molecule listed at table 2 or Table 4 or antibodies against such polypeptides) are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

The protein microarray is hybridized with a detectable probe. Such probes can be polypeptide, nucleic acid, or small molecules. For some applications, polypeptide and nucleic acid probes are derived from a biological sample taken from a patient, such as a bodily fluid (such as blood, urine, saliva, or phlegm); a homogenized tissue sample (e.g. a tissue sample obtained by biopsy); or cultured cells (e.g., prostate cancer cells). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Antibodies

Antibodies that selectively bind a variant HOXB13 polypeptide (e.g., G84E) are useful in the methods of the invention. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

In one embodiment, the antibody is a polyclonal antibody. The preparation and use of polyclonal antibodies are known to the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing a HOXB13 polypeptide (e.g., G84E), or fragments thereof. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide involved in chondroitin sulfate biosynthesis or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a HOXB13 polypeptide (e.g., G84E), or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface. Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In other embodiments, the invention provides "unconventional antibodies." Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

Patient Monitoring

After a subject is identified as at risk of developing prostate cancer (e.g., by the detection of SNP rs138213197 (corresponding to the genetic variant HOXB13 G84E), the subject may be monitored for the development of prostate cancer. Typically, those at risk of developing prostate cancer have a familial history of prostate cancer. In men of European or Nordic descent, the detection of SNP rs138213197 (corresponding to the genetic variant HOXB13 G84E) is particularly informative, and this test is initially performed at an early age (e.g. at about 20, 25, 30, 35, 40, 45 yrs of age or younger). Subjects testing positive for the SNP rs138213197 under the age of 55, should be actively monitored for the development of prostate cancer once a year or more (e.g. annually). Tests for monitoring an individual identified at risk of developing prostate cancer includes measurement of levels of a marker (e.g., PSA) in the subject or a biological sample obtained from the subject. Such monitoring may be useful, for example, in assessing the onset of cancer in a patient. In prostate cancer, curative treatment (e.g., radical prostatectomy or radiotherapy) by early stage detection correlates with positive outcomes.

Selection of a Treatment Method

After a subject is diagnosed as having prostate cancer, a method of treatment is selected. In prostate cancer, for example, a number of standard treatment regimens are available. The detection of SNP rs138213197 (corresponding to the genetic variant HOXB13 G84E) in a biological sample may be used in selecting a treatment method. In one embodiment, less aggressive neoplasias may not have the SNP rs138213197 (corresponding to the genetic variant HOXB13 G84E) compared to more aggressive neoplasias. In one embodiment, a neoplastic cell that has a SNP rs138213197 (corresponding to the genetic variant HOXB13 G84E) correlates with a poor clinical outcome, such as metastasis or death. In other embodiments, the presence of SNP rs138213197 (corresponding to the genetic variant HOXB13 G84E) is indicative of a poor prognosis, i.e., identifying the prostate cancer as an aggressive prostate cancer. The absence of SNP rs138213197 (corresponding to the genetic variant HOXB13 G84E) correlates with a good clinical outcome. Such prostate cancers are identified as less aggressive.

While methods of neoplasia treatment vary depending on the type of neoplasia, the stage of neoplasia, and the patient's age, health, and physical condition, more aggressive treatment regimens will be used in patients having a poor prognosis (e.g., patients having a metastatic prostate carcinoma or a prostate carcinoma with metastatic potential). As described above, the methods of the invention are useful in determining the prognosis of a patient having neoplasia, such as a neoplasia with increased metastatic potential. In such patients aggressive therapies may be used. These include therapies having increased toxicity and those having an increased risk of adverse side-effects. Aggressive therapies are employed earlier and at higher doses in patients having a poor prognosis.

Less aggressive prostate cancers are likely to be susceptible to conservative treatment methods. Conservative treatment methods include, for example, cancer surveillance, which involves periodic patient monitoring using diagnostic assays of the invention, alone or in combination, with PSA blood tests and DREs, or hormonal therapy. Cancer surveillance is selected when diagnostic assays indicate that the adverse effects of treatment (e.g., impotence, urinary, and bowel disorders) are likely to outweigh therapeutic benefits.

More aggressive neoplasias are less susceptible to conservative treatment methods. When methods of the invention indicate that a neoplasia is very aggressive, an aggressive method of treatment should be selected. Aggressive therapeutic regimens typically include one or more of the following therapies: radical prostatectomy, radiation therapy (e.g., external beam and brachytherapy), hormone therapy, and chemotherapy.

Methods of the invention may be used alone or in combination with conservative or aggressive therapeutic regimens to treat a prostate cancer. While methods of neoplasia treatment vary depending on the type of neoplasia, the stage of neoplasia, and the patient's age, health, and physical condition, more aggressive treatment regimens will be used in patients having a poor prognosis (e.g., patients having a metastatic prostate carcinoma or a prostate carcinoma with metastatic potential). As described above, the methods of the invention are useful in determining the prognosis of a patient having neoplasia, such as a neoplasia with increased metastatic potential. In such patients aggressive therapies may be used. These include therapies having increased toxicity and those having an increased risk of adverse side-effects. Aggressive therapies are employed earlier and at higher doses in patients having a poor prognosis.

Standard neoplasia therapies, which methods are known to the skilled artisan (e.g., Wadler et al., Cancer Res. 50:3473-86, 1990), include, but are not limited to, chemotherapy, hormone therapy, androgen ablation, immunotherapy (include, but are not limited to, immunotherapy that will specifically target cancer stem cell transcription factors), radiotherapy, cryotherapy, surgery (e.g., radical prostatectomy), and any other therapeutic method used for the treatment of neoplasia. Prostate cancer depends in part on androgenic signaling for growth and survival. Androgens exert their cellular and physiologic effects through binding to the androgen receptor (AR), a member of the steroid hormone receptor family of transcription factors. Androgen binding to the AR ligand binding domain allows entry of the ligand-bound receptor into the nucleus and subsequent transcriptional regulation of androgen-responsive genes. Androgen ablation suppresses or blocks the production or action of male sex hormones for the treatment of cancers that rely upon male hormones for growth (e.g., removal of the testicles removed, taking female sex hormones, or taking antiandrogens). Hormonal therapy has been used since 1941 for the treatment of metastatic prostate cancer. Hormone deprivation therapies employing surgical and/or medical castration as well as their combination with anti-androgens have since become the mainstay of systemic treatment for advanced prostate cancer. Hormonal therapies for advanced prostate cancer target AR-mediated functions by suppressing the production of androgens and/or androgen binding to the AR ligand binding domain.

Treatment may include administration of one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine. Other examples of chemotherapeutic agents can be found in Cancer Principles and Practice of Oncology by V. T. Devita and S. Hellman (editors), 6th edition (Feb. 15, 2001), Lippincott Williams & Wilkins Publishers.

Compounds of the present invention may be administered by any appropriate route for the treatment or prevention of neoplasia. These may be administered to humans, domestic pets, livestock, or other animals with a pharmaceutically acceptable diluent, carrier, or excipient, in unit dosage form. Administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols. Methods well known in the art for making formulations are found, for example, in Remington: The Science and Practice of Pharmacy (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Kits

The invention also provides kits for genotyping a HOXB13 gene, particularly for the treatment or prevention of prostate cancer having a HOXB13 germline mutation (e.g., SNP rs138213197 corresponding to the genetic variant HOXB13 G84E). Such kits are useful for the diagnosis of a sequence alteration in HOXB13 relative to wild-type HOXB13 in a biological sample obtained from a subject. Alternatively, the invention provides for selecting a drug treatment regimen or adjusting a dosage. In various embodiments, the kit includes at least one primer pair that identifies a HOXB13 nucleic acid sequence, together with instructions for using the primers to genotype in a biological sample. In additional embodiments, the kit also includes instructions for selecting an appropriate therapy for a subject, monitoring drug therapy in a subject, identifying a subject as responsive to drug therapy, or identifying a subject as sensitive to a drug. Advantageously, such testing is carried out prior to drug administration or after an adverse event associated with drug administration. Preferably, the primers are provided in combination with a thermostable DNA polymerase capable of long-range PCR amplification (e.g., a high density array). In yet another embodiment, the kit further comprises a pair of primers capable of binding to and amplifying a reference sequence. In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Targeted Sequencing of 202 Candidate Genes Identified an SNP in HOXB13, a Change of Adenosine for Guanine (Transition, c.251G→A), Associated with Risk of Developing Prostate Cancer Sequence data was reviewed for the presence of nonsense or missense mutations in 202 genes in the genetic region of interest (chromosome 17q21-22) (Lange et al., 2007). Exons (2009 exons) were sequenced from genes in the chromosome 17 candidate interval. The average depth of coverage across all loci was 49.5X. There were a total of 20 loci that yielded an average depth of coverage <1X (<1%), while 2040 loci had an average depth of coverage >10X (97%). On average 705 variants per sample were detected across the target region. Approximately 694 variants on average were present in dbSNP134 (98%), with an average of ~12 novel variants per individual. The sequencing results are shown at Table 1.

Probands from four families were observed to have the same nonsynonymous mutation in HOXB13, a change of adenosine for guanine (transition, c.251G→A) in the second position of codon 84 (GGA→GAA), resulting in a nonconservative substitution of glutamic acid for glycine (G84E).

At the time of this analysis, this mutation, now identified as rs138213197, was not reported in dbSNP, the database of known DNA sequence variants of the National Center for Biotechnology Information (NCBI), nor in the May 2011 release of the NCBI 1000 Genomes sequencing project, which included 1094 subjects, including 381 of European descent.

Figure 1:
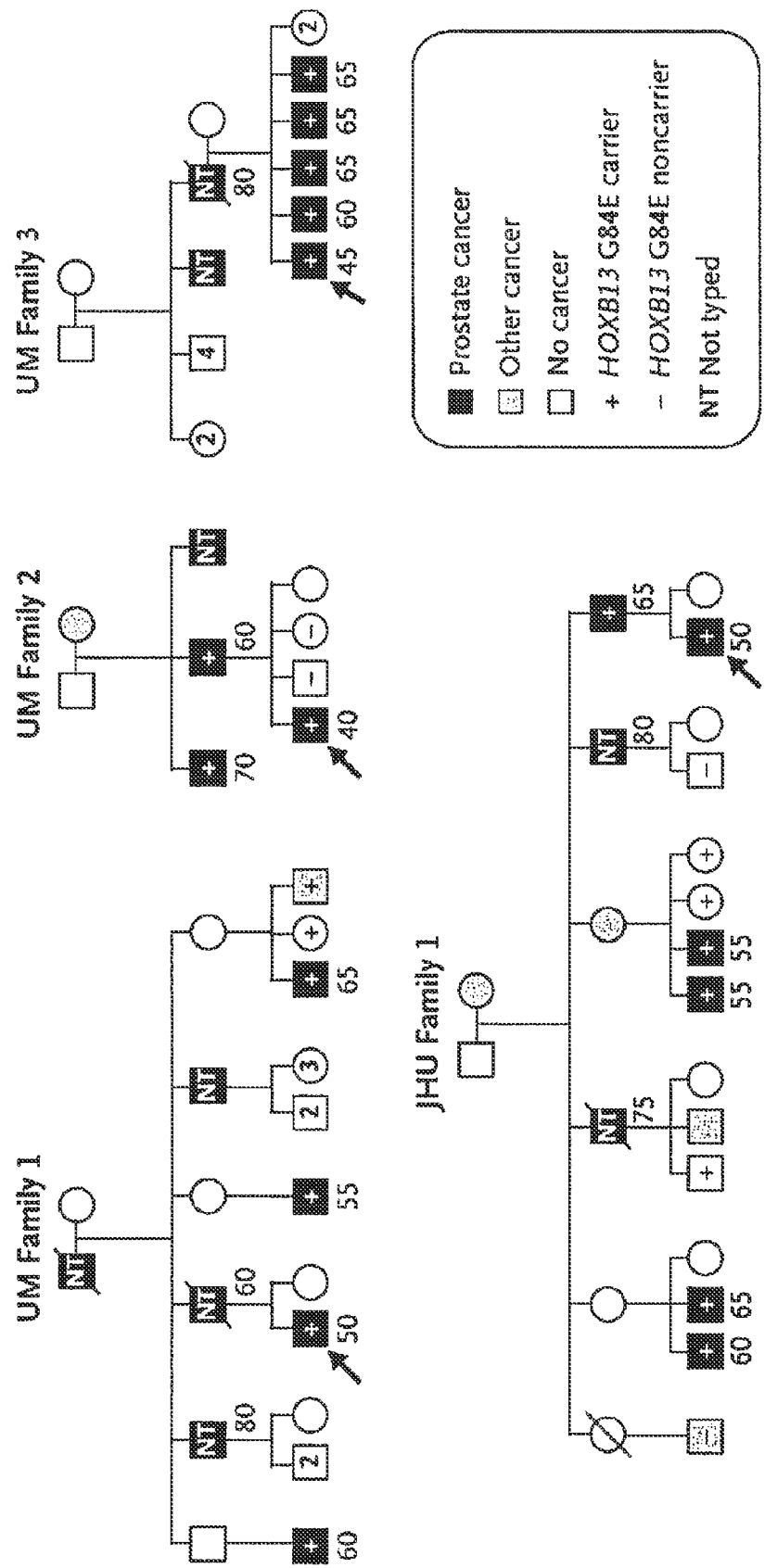
FIG. 1 is a genetic pedigree chart showing the pedigrees of four subjects with the HOXB13 G84E Mutation on Initial Targeted Sequencing. The proband who was selected for sequencing is indicated by the arrow in each pedigree. The remaining symbols are described in the key. Squares indicate male sex, and circles female sex. Ages of subjects, rounded to the nearest 5-year interval, are shown under the symbols. A slash through the symbol indicates that the subject is deceased. Two subjects in two families, Family 1 from the University of Michigan Prostate Cancer Genetics Project (UM) and Family 1 from Johns Hopkins University (JHU), who were inferred to be obligate carriers of the HOXB13 G84E mutation, died from prostate cancer. The unaffected G84E carrier in JHU Family 1 was 70 years of age at last contact.

Given the importance and specificity of HOXB13 in prostate biology, further characterization of this mutation was performed. DNA samples from family members from each of these four pedigrees were sequenced to identify carriers of the HOXB13 G84E mutation. Cosegregation of the mutation with disease was observed in all 18 affected men with available DNA in the four families (FIG. 1).

Example 2

A HOXB13 G84E Mutation is Associated with Risk of Developing Prostate Cancer

To further assess HOXB13 G84E as a prostate cancer susceptibility allele, several additional populations of European descent were studied with a total of 5083 unrelated case subjects and 1401 unrelated control subjects. Clinical characteristics of genotyped samples are shown at Table 2.

The case subjects included a cohort of 1130 patients with early-onset or familial prostate cancer from the Prostate Cancer Genetics Project, 161 patients with hereditary prostate cancer from Johns Hopkins University, a series of 3499 men with localized prostate cancer who were treated with radical prostatectomy at Johns Hopkins Hospital, and 293 men who were treated for advanced prostate cancer at Johns Hopkins Hospital; the control population of 1401 men were found to have no prostate cancer during screening. Among men in the latter screening group, the G84E

TABLE 2

Clinical features of genotyped samples.
All men studied described themselves as European descent and the sample sizes are variable due to missing data.

|  | Mean | St. Dev. | Median | Range |
|---|---|---|---|---|
| University of Michigan | | | | |
| Age at Dx (yrs) (n = 1130) | 52.2 | 6.3 | 52 | 27-77 |
| RP Gleason Grade (n = 938) | 6.60 | 0.85 | 7 | 3-10 |
| Johns Hopkins University | | | | |
| Age at Dx (yrs) (n = 3797) | 58.5 | 6.7 | 59 | 35-85 |
| RP Gleason Grade (n = 3752) | 6.47 | 0.79 | 6 | 4-10 |

Abbreviations: RP = radical prostatectomy, Dx = diagnosis, St. Dev. = standard deviation mutation was found in only 1 man, resulting in a carrier-frequency estimate of 0.1%. Homozygous carriers were not identified among either case or control subjects.

Overall, men with prostate cancer were significantly more likely to carry the HOXB13 G84E allele (carrier frequency, 1.4%) than were those without prostate cancer (carrier frequency, 0.1%) (P=$8.5 \times 10^{-7}$; odds ratio, 20.1; 95% confidence interval [CI], 3.5 to 803.3). HOXB13 G84E mutation in sets of prostate cancer cases are shown at Table 3.

The carrier frequency varied as a function of age at diagnosis and family history, with the highest rates among men with both a positive family history and early diagnosis (≤55 years of age). The carrier frequency in this group (3.1%) was significantly higher than in men with early-onset prostate cancer who did not have a family history of the disease (1.0%, P=0.002) or in men with a family history in whom prostate cancer was diagnosed after the age of 55 years (1.2%, P=0.004). Frequencies of HOXB13 G84E

TABLE 1

Complete HOXB13 Sequencing Results from 94 Men with Prostate Cancer

| Chrm 17 Location* | Ref Allele/Variant Allele | dbSNP ID | Variant Type | Substitution | # Individuals [N(%)] |
|---|---|---|---|---|---|
| HOXB13 variants identified in 85 Caucasian samples | | | | | |
| 44157313 | G/T | rs116931900** | 3' UTR | NA | 7 (8.2) |
| 44157328 | T/C | rs79812861** | 3' UTR | NA | 5 (5.9) |
| 44157843 | G/C | novel | 3' UTR | NA | 1 (1.2) |
| 44158537 | C/T | rs11653611 | 3' UTR | NA | 51 (60.0) |
| 44160442 | A/G | rs9900627 | Synonymous | S171S | 13 (15.3) |
| 44160589 | G/A | rs8556 | Synonymous | S122S | 20 (23.5) |
| 44160704 | C/T | rs138213197** | Nonsynonymous | G84E | 4 (4.7) |
| 44161086 | T/C | novel | 5' UTR | NA | 2 (2.4) |
| HOXB13 variants identified in 7 African American samples | | | | | |
| 44157328 | T/C | rs79812861** | 3' UTR | NA | 1 (14.3) |
| 44158537 | C/T | rs11653611 | 3' UTR | NA | 2 (28.6) |
| 44159094 | C/T | rs141179592** | 3' UTR | NA | 1 (14.3) |
| 44159321 | G/C | novel | Nonsynonymous | R229G | 1 (14.3) |
| 44160442 | A/G | rs9900627 | Synonymous | S171S | 2 (28.6) |
| 44160589 | G/A | rs8556 | Synonymous | S122S | 5 (71.4) |
| HOXB13 variants identified in 2 Asian American samples | | | | | |
| 44157328 | T/C | rs79812861** | 3' UTR | NA | 2 (100) |
| 44158537 | C/T | rs11653611 | 3' UTR | NA | 2 (100) |
| 44160589 | G/A | rs8556 | Synonymous | S122S | 2 (100) |

*Location based on hg18 reference sequence
**These dbSNP ID numbers were not available at the completion of sequencing.

carriers in prostate cancer cases of European descent stratified by family history and age at diagnosis are shown at Table 4.

The lowest carrier frequency was observed in men in whom prostate cancer was diagnosed after the age of 55 years and who did not have a family history, although this frequency was still higher than in control subjects (0.6%; odds ratio, 8.7; 95% CI, 1.2 to 381.3; P=0.02). A summary of results comparing age at diagnosis and family history strata to controls are shown at Table 5.

TABLE 3

Summary of HOXB13 G84E mutation in sets of prostate cancer cases and controls of European descent

|  | G84E Carriers | Non-Carriers | Carrier Frequency | p-value[#] | Odds Ratio[#] | p-value[##] | Odds Ratio[##] |
|---|---|---|---|---|---|---|---|
| 85 UM-PCGP and JHU Sequenced HPC Families | 4 | 81 | 4.9 | $4.8 \times 10^{-5}$ | 68.4 | $5.4 \times 10^{-5}$ | 32.6 |
| All UM-PCGP and JHU Cases* | 72 | 5011 | 1.4 | $8.5 \times 10^{-7}$ | 20.1 | $2.4 \times 10^{-9}$ | 9.5 |
| UM PCGP Data |  |  |  |  |  |  |  |
| UM-PCGP Early-onset and HPC* Cases | 26 | 1104 | 2.3 | $1.0 \times 10^{-8}$ | 33.0 | $1.3 \times 10^{-10}$ | 15.6 |
| Johns Hopkins Data |  |  |  |  |  |  |  |
| JHU HPC*, Prostatectomy and Oncology Cases | 46 | 3907 | 1.2 | $1.6 \times 10^{-5}$ | 16.5 | $6.0 \times 10^{-7}$ | 7.8 |
| Controls |  |  |  |  |  |  |  |
| JHU Controls | 1 | 1400 | 0.071 | n.a. | n.a. | n.a. | n.a. |
| Exome Sequencing Project + CEU HapMap | 3 | 1258 | 0.24 | n.a. | n.a. | n.a. | n.a. |

*Unrelated cases (the case with earliest age at diagnosis selected from HPC families) excluding 85 European-descent families used for discovery.
[#]Comparison to 1401 JHU controls.
[##]Comparison to 1401 JHU controls + 1235 Exome Sequencing Project subjects + 28 CEU unrelated genotyped subjects.

TABLE 4

Frequencies of HOXB13 G84E carriers in prostate cancer cases of European descent stratified by family history and age at diagnosis

|  | G84E Carriers | Non-Carriers | Carrier Frequencies | p-value | Odds Ratio 95% CI | Comparison Group |
|---|---|---|---|---|---|---|
| FH+ | 45 | 2019 | 2.2 | $1.2 \times 10^{-4}$ | 2.8 (1.6, 5.1) | FH− |
| FH− | 19 | 2391 | 0.79 | — | — | — |
| Age Dx < 55 | 46 | 2084 | 2.2 | $1.1 \times 10^{-4}$ | 2.7 (1.6, 4.7) | Age Dx > 55 |
| Age Dx > 55 | 22 | 2681 | 0.81 | — | — | — |
| FH+ and Age Dx < 55 | 33 | 1040 | 3.1 | $2.0 \times 10^{-6}$ | 5.1 (2.4, 12.2) | FH−, Age Dx > 55 |
| FH+ and Age Dx > 55 | 12 | 993 | 1.2 | 0.18 | 1.9 (0.75, 5.2) | FH−, Age Dx > 55 |
| FH− and Age Dx < 55 | 10 | 943 | 1.0 | 0.25 | 1.7 (0.62, 4.8) | FH−, Age Dx > 55 |
| FH− and Age Dx > 55 | 9 | 1447 | 0.62 | — | — | — |

Additional Comparisons: FH+ and Age Dx < 56 vs. FH+ and Age Dx > 55: p = 0.0038, OR = 2.6 (1.3, 5.6) FH+ and Age Dx < 56 vs. FH− and Age Dx < 56: p = 0.0017, OR = 3.0 (1.4, 6.8)

TABLE 5

Summary of Results Comparing Age at Diagnosis and Family History Strata to Controls

|  | G84E Carriers n (%) | Non-Carriers n (%) | Carrier Frequency | 1401 JHU Controls | | 2662 Controls (JHU, ESP, HapMap) | |
|---|---|---|---|---|---|---|---|
|  |  |  |  | p-value | Odds Ratio (95% CI) | p-value | Odds Ratio (95% CI) |
| FH+ (n = 2064) | 45 (2.2) | 2019 (97.8) | 2.2 | $1.8 \times 10^{-9}$ | 31.2 (5.3, 1253.3) | $1.7 \times 10^{-12}$ | 14.8 (5.4, 56.8) |
| FH− (n = 2410) | 19 (0.8) | 2391 (99.2) | 0.79 | 0.0018 | 11.1 (1.8, 461.7) | 0.0011 | 5.3 (1.8, 21.4) |
| Age Dx < 55 (n = 2130) | 46 (2.2) | 2084 (97.8) | 2.2 | $2.4 \times 10^{-9}$ | 30.9 (5.3, 1240.7) | $1.3 \times 10^{-12}$ | 14.7 (5.3, 56.2) |
| Age Dx > 55 (n = 2703) | 22 (0.8) | 2681 (99.2) | 0.81 | 0.0014 | 11.5 (1.9, 473.5) | 0.00052 | 5.5 (1.8, 21.8) |
| FH+ and Age Dx < 55 (n = 1073) | 33 (3.1) | 1040 (96.9) | 3.1 | $1.6 \times 10^{-11}$ | 44.3 (7.4, 1792.6) | $1.7 \times 10^{-14}$ | 21.1 (7.5, 82.0) |
| FH+ and Age Dx > 55 (n = 1005) | 12 (1.2) | 993 (98.8) | 1.2 | 0.00022 | 16.9 (2.5, 721.3) | $9.8 \times 10^{-5}$ | 8.0 (2.4, 34.2) |
| FH− and Age Dx < 55 (n = 953) | 10 (1.0) | 943 (99.0) | 1.0 | 0.00080 | 14.8 (2.1, 642.8) | 0.00053 | 7.0 (2.0, 30.8) |

TABLE 5-continued

Summary of Results Comparing Age at Diagnosis and Family History Strata to Controls

| | G84E Carriers n (%) | Non-Carriers n (%) | Carrier Frequency | 1401 JHU Controls | | 2662 Controls (JHU, ESP, HapMap) | |
|---|---|---|---|---|---|---|---|
| | | | | p-value | Odds Ratio (95% CI) | p-value | Odds Ratio (95% CI) |
| FH− and Age Dx > 55 (n = 1456) | 9 (0.6) | 1447 (99.4) | 0.62 | 0.022 | 8.7 (1.2, 381.3) | 0.017 | 4.1 (1.2, 18.4) |

Abbreviations: Dx = diagnosis, FH = family history

Carrier frequencies in men with early-onset prostate cancer or those who had a family history were similar in findings from both the Prostate Cancer Genetics Project and Johns Hopkins University. Results were slightly more significant but odds ratios were attenuated for comparisons with data from an expanded control population, including subjects from the Exome Sequencing Project and HapMap (Tables 3 and 5).

G84E carriers were significantly younger than noncarriers (52.9 vs. 57.1 years, $P=7.4 \times 10^{-7}$). Case-only analyses of clinical characteristics by G84E carrier status are shown at Table 6.

TABLE 6

Case-Only Analyses of Clinical Characteristics in Combined UMPCGG and JHU Cases by G84E Carrier Status

| | G84E Carriers | | Non-Carriers | | |
|---|---|---|---|---|---|
| | Mean | Standard error | Mean | Standard error | p-value |
| Age at Dx (yrs) | 52.9 | 0.9 | 57.1 | 0.1 | $7.4 \times 10^{-7}$ |
| RP Gleason Grade | 6.42 | 0.10 | 6.49 | 0.01 | 0.49 |
| RP Gleason Grade adjusted for Age at Dx* | 6.44 | 0.10 | 6.49 | 0.01 | 0.65 |

Abbreviations: RP = radical prostatectomy, Dx = diagnosis

On the basis of clinical data collected for patients who had undergone radical prostatectomy at the Prostate Cancer Genetics Project and Johns Hopkins University, no evidence was found supporting significant differences in Gleason grade between G84E carriers and noncarriers before or after accounting for the age at diagnosis (Table 6). The G84E mutation was found in 6 of 293 men (2.0%) who were being treated for metastatic disease. Finally, no additional G84E carriers were identified among 84 unrelated subjects of African descent with prostate cancer (i.e., unrelated to the 7 subjects of African descent who were included in the initial sequencing data set).

Example 3

Additional Novel Nonsynonymous HOXB13 Mutations

In the initial targeted sequencing study of 94 families with hereditary prostate cancer, 1 proband from an African-American family was observed to have a novel HOXB13 missense mutation (transversion c.685C→G), resulting in the substitution of glycine for arginine at position 229 (R229G). The same mutation was detected in the patient's 2 brothers with prostate cancer. To search for additional HOXB13 variants that were not observed in the original sequence analysis, both exons of HOXB13 were sequenced in additional men of European and African descent from the Prostate Cancer Genetics Project and Johns Hopkins University. A novel substitution of cysteine for glycine at codon 216 (transversion c.646G→T, p.G216C) was found in an African-Caribbean family. This mutation was present in both subjects with prostate cancer (2 half-brothers) for whom DNA was available. Neither the R229G nor the G216C mutation was observed in approximately 1100 African-American subjects in the Exome Sequencing Project.

HOXB13 was also sequenced in eight available prostate-cancer cell lines (LNCaP, PC3, DU145, CRW22Rv1, E006AA, VCaP, MDAPCa2b, and LAPC4) (Liu et al., 2008). LNCaP and LAPC4, both androgensensitive human prostate adenocarcinoma cell lines, were found to have nonsynonymous mutations: substitution of proline for leucine at codon 144 (transition c.431T→C, L144P) in LNCaP and aspartic acid for tyrosine at codon 88 (transversion c.262T→G, p.Y88D) in LAPC4. Neither missense mutation was observed in sequencing of the 94 probands or the database of the Exome Sequencing Project, although a lack of available germline DNA for these cell lines precluded the determination of a definitive origin for these changes as somatic or germline.

Figure 2:
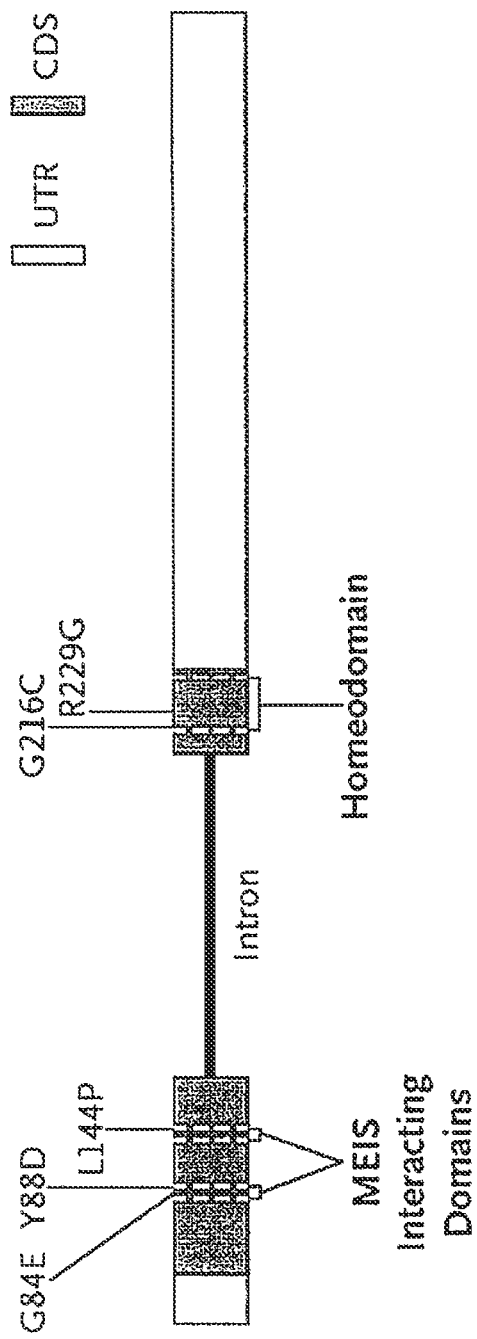
FIG. 2 depicts the structure of HOXB13. The HOXB13 gene is the most 5' member of the HOXB gene cluster on chromosome 17q21-22. The locations of the five missense mutations are indicated in the two exons of HOXB13. The homeodomain region and MEIS interacting domains are indicated. CDS denotes coding sequences, and UTR untranslated regions.

The locations of the HOXB13 G84E mutation and the four additional rare HOXB13 mutations are shown in FIG. 2. All the changes are in highly conserved functional domains of HOXB13 and are predicted to be damaging to protein function on the Sorting Intolerant from Tolerant (SIFT) (Ng et al., 2006) or PolyPhen (Ramensky et al., 2002) algorithms. The G84E and the Y88D mutations are located in the same nonhomeobox domain that was previously shown to mediate the binding of HOX13 paralogues (including HOXB13) to the MEIS family of HOX cofactor proteins (Williams et al., 2005). The L144P change is in the second of two MEIS-binding domains. Both mutations that were found in subjects of African descent, R229G and G216C, reside in the N-terminal portion of the homeobox domain, and both changes affect highly conserved amino acid residues.

Example 4

Mutational Carriers of the SNP (Transition, c.251G→A), in HOXB13 were Found in Prostate Cancer Families of African Descent There are three chromosome 17q loci that have been implicated in prostate cancer susceptibility: 17q12 (rs4430796, HNF1B), 17q21 (discussed below) and 17q24 (rs1859962) (Gudmundsson et al., 2007). The 17q12 and 17q24 loci are over 10 and 20 Mb, respectively, from HOXB13 and, therefore, likely independent. However, the 17q21 SNP identified by Haiman et al. (2011) is within 1 Mb from HOXB13 and additional experiments were conducted to uncover a possible relationship between these two genetic loci. Because the 17q21 risk allele is uniquely identified in African American men, studies in this population were performed.

Recently, Haiman et al. (2011) observed an association between a SNP at 17q21 and prostate cancer risk in men of African descent. This risk locus (rs7210100) lies ~630 kb telomeric of HOXB13. To explore a potential relationship between rs7210100 and HOXB13 variants, both exons of HOXB13 were sequenced in 24 African American male carriers of the rs7210100 risk associated allele (4 homozygous carriers and 20 heterozygotes). All 24 men, including 12 prostate cancer cases (2 homozygotes and 10 heterozygotes) and 12 prostate cancer free controls, were included in the original report by Haiman et al. No rare HOXB13 mutations were identified in either the cases or controls that were either homozygous or heterozygous for the rare cancer associated allele at rs7210100. The data suggests that rs7210100 and HOXB13 variants play an independent role in prostate cancer susceptibility in African Americans.

It is unclear how HOXB13 variants, especially G84E, relate to prostate cancer risk in African Americans. G84E carriers were not observed among 91 unrelated prostate cancer cases of African descent. As reported by the ESP Exome Variant Server, 4 only 2/933 (frequency=0.0021) African American subjects were reported to carry the G84E variant "T" allele. Age and gender are not reported in the Exome Variant Server and thus it is not clear if the two carriers were adult males. Two missense variants were observed at highly-conserved amino acid residues (neither of which had been reported by ESP or observed among the subjects of European descent in the study) among these 91 prostate cancer cases of African descent, suggesting there may be HOXB13 risk variants that are important to this population. Larger sample sizes of African American men with prostate cancer may confirm the association between HOXB13 variants and prostate cancer in this population.

Example 5

Mutational Carriers of the SNP (Transition, c.251G→A), in HOXB13 were Found in Prostate Cancer Families of European Descent Prostate cancer demonstrates wide differences in incidence and mortality across populations within the United States and throughout the world. The frequency of HOXB13 G84E mutations was examined in prostate cancer families across different ancestries and geographic regions. The G84E mutation and other known variants in HOXB13 were genotyped in 2,443 hereditary prostate cancer families recruited by members of the International Consortium for Prostate Cancer Genetics (ICPCG), a large NCI-funded collaborative resource for studies of genetic susceptibility for hereditary prostate cancer.

Among five previously observed mutations in HOXB13, two were further studied—R217C (rs13945791) and G84E (rs138213197). The rare R217C variant was found one time each in two families of European descent and did not co-segregate with prostate cancer. The G84E mutation was found in 283 subjects from 112 families of European descent, including 194 men with prostate cancer (Table 7). This represented 4.6% of all 2,443 prostate cancer families and 4.8% of 2,298 prostate cancer families of European descent. The proportion of families with at least one G84E mutation carrier differed significantly across the 15 ICPCG groups ($P=9.4\times10^{-8}$). The proportion was highest

TABLE 7

G84E mutation of HOXB13 in prostate cancer families of International Corsortium for Prostate Cancer Genetics (ICPCG)

| | # of families | | # (%) of families with G84E carriers | | Subjects in families with at least one G84E carrier | | | | | |
|---|---|---|---|---|---|---|---|---|---|---|
| | | | | | Affected | | Unknown(Men) | | Unknown(Women) | |
| | | | | | # (%) of | | # (%) of | | # (%) of | |
| | All | European descent | All | European descent | # | G84E carriers | # | G84E carriers | # | G84E carriers |
| Europe | | | | | | | | | | |
| Finland, University of Tampere | 76 | 76 | 17(22.4%) | 17(22.4%) | 54 | 37(69%) | 69 | 22(31%) | 97 | 29(30%) |
| Sweden, UmeA University | 110 | 110 | 9(8.2%) | 9(8.2%) | 17 | 13(76%) | 15 | 5(33%) | 13 | 4(31%) |
| Germany, University of Ulm | 378 | 378 | 13(3.4%) | 13(3.4%) | 21 | 19(90%) | 1 | 0(0%) | 2 | 0(0%) |
| UK, ACTANE | 145 | 142 | 5(3.4%) | 5(3.4%) | 12 | 7(58%) | 1 | 0(0%) | 1 | 0(0%) |
| France, CeRePP | 159 | 156 | 2(1.3%) | 2(1.3%) | 5 | 3(60%) | 1 | 0(0%) | 0 | 0 |
| North America | | | | | | | | | | |
| BC/CA/HI | 98 | 83 | 6(6.1%) | 6(7.2%) | 20 | 12(60%) | 7 | 1(14%) | 7 | 1(14%) |
| Fred Hutchinson Cancer Research Center | 255 | 241 | 14(5.5%) | 14(5.8%) | 45 | 25(56%) | 14 | 5(36%) | 16 | 2(13%) |
| Johns Hopkins Hospital* | 234 | 176 | 5(2.1%) | 5(2.8%) | 20 | 14(70%) | 7 | 2(29%) | 10 | 4(40%) |
| MAYO Clinic | 185 | 185 | 6(3.2%) | 6(3.2%) | 15 | 10(67%) | 2 | 0(0%) | 0 | 0 |
| University of Michigan* | 317 | 282 | 11(3.5%) | 11(3.9%) | 36 | 26(72%) | 13 | 4(31%) | 5 | 2(40%) |
| McGill University | 18 | 7 | 1(5.6%) | 1(14.3%) | 2 | 2(100%) | 0 | 0 | 0 | 0 |
| North Western University | 33 | 32 | 0(0%) | 0(0%) | 0 | 0 | 0 | 0 | 0 | 0 |
| University of Utah | 348 | 348 | 21(6%) | 21(6%) | 132 | 23(17%) | 6 | 2(33%) | 11 | 3(27%) |
| Louisiana State University | 10 | 10 | 0(0%) | 0(0%) | 0 | 0 | 0 | 0 | 0 | 0 |
| Australia | | | | | | | | | | |
| Australia | 77 | 73 | 2(2.6%) | 2(2.7%) | 3 | 3(100%) | 1 | 1(100%) | 3 | 2(67%) |
| Total | 2443 | 2299 | 112(4.6%) | 112(4.9%) | 382 | 194(51%) | 137 | 42(31%) | 165 | 47(28%) |
| Total* | 1892 | 1841 | 96(5.0%) | 96(5.2%) | 326 | 154(47%) | 117 | 36(31%) | 150 | 41(27%) |

*A subset of families from these centers were included in the original discovery report (Ewing et al). These total values reflect the results obtained after omitting all families from these two centers.

TABLE 8

Family-based association test for SNPs at HOXB13 region in ICPCG families

| Chr | Position | rs# | Gene | Mutation | Rare allele | Allele frequency | # of informative families | S-E(S) | Var(S) | Z | P |
|---|---|---|---|---|---|---|---|---|---|---|---|
| 17 | 46,719,399 | rs890435 | intergenic | | G | 0.41 | 509 | −7.38 | 243.77 | −0.47 | 0.64 |
| 17 | 46,720,565 | rs2326017 | intergenic | | T | 0.33 | 496 | 3.10 | 248.24 | 0.20 | 0.84 |
| 17 | 46,727,289 | rs7212669 | intergenic | | G | 0.10 | 244 | −4.89 | 107.42 | −0.47 | 0.64 |
| 17 | 46,780,829 | rs8064938 | intergenic | | A | 0.16 | 353 | −6.12 | 136.42 | −0.52 | 0.60 |
| 17 | 46,784,039 | rs3809773 | intergenic | | A | 0.33 | 485 | 1.42 | 245.54 | 0.10 | 0.93 |
| 17 | 46,799,812 | rs1054072 | PRAC | | C | 0.47 | 518 | −13.41 | 268.62 | −0.82 | 0.41 |
| 17 | 46,804,250 | | HOXB13 | T253P | | 0 | 0 | N/A | N/A | N/A | N/A |
| 17 | 46,804,322 | | HOXB13 | R229G | G | 0.0001 | 1 | −−0.40 | 0.16 | −−1.00 | 0.32 |
| 17 | 46,804,358 | rs139475791 | HOXB13 | R217C | A | 0.0001 | 2 | −−1.60 | 1.36 | −1.37 | 0.17 |
| 17 | 46,805,590 | rs8556 | HOXB13 | | T | 0.15 | 342 | −10.77 | 145.60 | −0.89 | 0.37 |
| 17 | 46,805,642 | rs140492479 | HOXB13 | T105I | A | 0.0001 | 2 | 1.64 | 1.41 | 1.38 | 0.17 |
| 17 | 46,805,705 | rs138213197 | HOXB13 | G84E | A | 0.02 | 38 | 17.50 | 15.07 | 4.51 | 6.53E−06 |
| 17 | 46,807,919 | rs3809771 | 5' | | G | 0.06 | 171 | −8.92 | 64.24 | −1.11 | 0.27 |
| 17 | 46,813,531 | rs4793980 | 5' | | T | 0.16 | 306 | 2.22 | 116.03 | 0.21 | 0.84 |
| 17 | 46,827,590 | rs3110601 | 5' | | C | 0.12 | 274 | −7.46 | 114.18 | −0.70 | 0.49 |

Based on family-based association test (FBAT) analysis of 2,437 pedigrees (10,217 nuclear families; 40,246 subjects)

TABLE 9

FBAT Result Excluding Families from Univ Michigan and Johns Hopkins

| Chr | Position | rs# | Gene | Mutation | Rare allele | Allele frequency | # of informative families | S-E(S) | Var(S) | Z | P |
|---|---|---|---|---|---|---|---|---|---|---|---|
| 17 | 46,719,399 | rs890435 | intergenic | | G | 0.409 | 314 | −10.669 | 154.21 | −0.859 | 0.390275 |
| 17 | 46,720,565 | rs2326017 | intergenic | | T | 0.335 | 304 | 0.481 | 141.878 | 0.04 | 0.967797 |
| 17 | 46,727,289 | rs7212669 | intergenic | | G | 0.091 | 145 | −4.004 | 73.134 | −0.468 | 0.639675 |
| 17 | 46,780,829 | rs8064938 | intergenic | | A | 0.155 | 219 | −15.429 | 80.317 | −1.722 | 0.085144 |
| 17 | 46,784,039 | rs3809773 | intergenic | | A | 0.337 | 303 | 7.869 | 143.099 | 0.658 | 0.510669 |
| 17 | 46,799,812 | rs1054072 | PRAC | | C | 0.472 | 327 | 0.788 | 157.103 | 0.063 | 0.949858 |
| 17 | 46,804,250 | | HOXB13 | T253P | | 0 | 0 | N/A | N/A | N/A | N/A |
| 17 | 46,804,322 | | HOXB13 | R229G | G | 0 | 0 | N/A | N/A | N/A | N/A |
| 17 | 46,804,358 | rs139475791 | HOXB13 | R217C | A | 0 | 2 | −1.6 | 1.36 | −1.372 | 0.170067 |
| 17 | 46,805,590 | rs8556 | HOXB13 | | T | 0.152 | 210 | −0.597 | 88.136 | −0.064 | 0.949286 |
| 17 | 46,805,642 | rs140492479 | HOXB13 | T105I | A | 0.001 | 1 | 0.636 | 0.405 | 1 | 0.317311 |
| 17 | 46,805,705 | rs138213197 | HOXB13 | G84E | A | 0.018 | 29 | 13.083 | 11.509 | 3.857 | 1.15E−04 |
| 17 | 46,807,919 | rs3809771 | 5' | | G | 0.055 | 109 | −3.231 | 40.36 | −0.509 | 0.611016 |
| 17 | 46,813,531 | rs4793980 | 5' | | T | 0.16 | 191 | −0.279 | 63.319 | −0.035 | 0.927066 |
| 17 | 46,827,590 | rs3110601 | 5' | | C | 0.119 | 180 | −0.116 | 68.299 | −0.014 | 0.988831 |

TABLE 10

FBAT Result Including only families from Univ Michigan and Johns Hopkins

| Chr | Position | rs# | Gene | Mutation | Rare allele | Allele frequency | # of informative families | S-E(S) | Var(S) | Z | P |
|---|---|---|---|---|---|---|---|---|---|---|---|
| 17 | 46,719,399 | rs890435 | intergenic | | G | 0.405 | 195 | 3.29 | 89.56 | 0.35 | 0.73 |
| 17 | 46,720,565 | rs2326017 | intergenic | | T | 0.326 | 192 | 2.62 | 106.36 | 0.25 | 0.80 |
| 17 | 46,727,289 | rs7212669 | intergenic | | G | 0.105 | 99 | −0.89 | 34.28 | −0.15 | 0.88 |
| 17 | 46,780,829 | rs8064938 | intergenic | | A | 0.159 | 134 | 9.31 | 56.10 | 1.24 | 0.21 |
| 17 | 46,784,039 | rs3809773 | intergenic | | A | 0.302 | 182 | −6.45 | 102.44 | −0.64 | 0.52 |
| 17 | 46,799,812 | rs1054072 | PRAC | | C | 0.465 | 191 | −14.19 | 111.52 | −1.34 | 0.18 |
| 17 | 46,804,250 | | HOXB13 | T253P | | 0 | 0 | N/A | N/A | N/A | N/A |
| 17 | 46,804,322 | | HOXB13 | R229G | G | 0.001 | 1 | −0.40 | 0.16 | −1.00 | 0.32 |
| 17 | 46,804,358 | rs139475791 | HOXB13 | R217C | A | 0 | 0 | N/A | N/A | N/A | N/A |
| 17 | 46,805,590 | rs8556 | HOXB13 | | T | 0.14 | 132 | −10.175 | 057.46 | −1.34 | 0.18 |
| 17 | 46,805,642 | rs140492479 | HOXB13 | T105I | A | 0 | 1 | 1.00 | 1.00 | 1.00 | 0.32 |
| 17 | 46,805,705 | rs138213197 | HOXB13 | G84E | A | 0.01 | 9 | 04.42 | 3.56 | 2.34 | 1.92E−02 |
| 17 | 46,807,919 | rs3809771 | 5' | | G | 0.074 | 62 | −5.69 | 23.88 | −1.16 | 0.24 |
| 17 | 46,813,531 | rs4793980 | 5' | | T | 0.148 | 115 | 2.49 | 52.71 | 0.34 | 0.73 |
| 17 | 46,827,590 | rs3110601 | 5' | | C | 0.122 | 94 | −7.35 | 45.88 | −1.08 | 0.28 | in families from the Nordic countries of Finland (22.4%) and Sweden (8.2%) and lower in North America (0-6.1%) and Australia (2.6%). The G84E mutation was not found in families of any other race or ethnicity, including those of African (N=58), Ashkenazi Jewish (N=46), or other descent (N=28).

relatives, the carrier rate was significantly higher in affected men (75%) than those with an unknown phenotype (48%), P=0.002, OR=4.26 (95% CI: 1.69-10.75). Among the second-degree relatives or higher, the carrier rate was also significantly higher in affected men (58%) than unknown men (23%), P=0.004, OR=4.81 (95% CI: 1.64-14.12).

TABLE 11

G84E HOXB13 mutation carriers among randomly selected affected probands and their relatives

| Proband G84E Carrier | G84E Carriers in First-degree relatives | | | | G84E Carriers in Second-degree relatives or higher | | | |
|---|---|---|---|---|---|---|---|---|
| | Affected | Unknown | OR (95% CI) | P-value | Affected | Unknown | OR (95% CI) | P-value |
| Yes (51) | 56/75(74.7%) | 16/34(47.6%) | 4.26(1.69-10.75) | 0.002 | 11/19(57.9%) | 9/39(23.1%) | 4.81(1.64-14.12) | 0.004 |
| No (1755) | 21/2502(0.8%) | 3/759(0.4%) | 2.31(0.82-6.51) | 0.11 | 15/973(1.5%) | 6/651(0.9%) | 2.21(0.39-12.71) | 0.37 |

In the 112 families with at least one G84E mutation carrier, the mutation was found in both affected and unaffected men. However, the carrier rate was significantly more common in affected men (194 of 382, 51%) than other men in these families (i.e. men of unknown status [(42 of 137, 31%), p=9.9×10$^{-8}$]) (Table 7). Using a statistical test that considered the relatedness of subjects within carrier families, the odds ratio (OR) for prostate cancer was 4.42 [95% confidence interval (CI)=2.56-7.64] for the G84E mutation carriers. The analyses were repeated excluding families from the University of Michigan and Johns Hopkins Hospital, some of which were included in the initial report describing HOXB13 as a prostate cancer susceptibility gene. In particular, the former study included HOXB13 G84E genotype data from only the youngest prostate cancer case in a subset of University of Michigan and Johns Hopkins Hospital families. The carrier rate in ICPCG families remained significantly more common in affected men (154 of 326, 47%) than unknown men [(36 of 117, 31%), P=3.3×10$^{-6}$] and the OR for prostate cancer was 4.3 [95% confidence interval (CI)=2.32-7.96] for the G84E mutation carriers after excluding all families from these two institutions (Table 7).

A mixed pattern of co-segregation of the G84E mutation with prostate cancer was found in these 112 families. While complete co-segregation was found in 34 families, incomplete co-segregation was more commonly observed, revealing genetic heterogeneity (affected but not carriers) and incomplete penetrance of the mutation (carriers but unaffected men).

Transmission of G84E mutation and alleles of other genotyped SNPs at the region was also examined in all 2,443 families using a family-based association test (Table 8). The risk allele (A) corresponding to the G84E mutation was observed to be transmitted significantly more often than expected from parents to affected sons (P=6.5×10$^{-6}$). A significant result was also observed when all families from the University of Michigan and Johns Hopkins Hospital were removed from this analysis (P=1.2×10$^{-4}$) (Tables 9 and 10), strongly indicating the G84E mutation is associated with prostate cancer risk.

To assess association in the family set while adjusting for variable pedigree structures, one affected man (proband) was randomly selected in the second generation from each of 2,443 pedigrees and then counted the number of G84E carriers among probands, first-relatives, and second-degree relatives or higher (Table 11). The G84E mutation carrier rate among probands was 2.8%. Among the first-degree The 194 prostate cancer patients who carried the mutation had a wide spectrum of clinical disease, including cancers with high risk of disease progression (Table 12), as indicated by moderate to poor tumor differentiation (tumor grade of Gleason score 7 or higher) in over one third of the cases, and over one quarter having non-organ confined disease at diagnosis (tumor stage T3 or higher). The mean age at diagnosis of carriers was 62.8 years. In comparison, the mean age at diagnosis for the 6,172 prostate cancer patients without the mutation was 64.4 years (P=0.04; relatedness of subjects within families was considered).

TABLE 12

Clinicopathologic variables of prostate cancers in HOXB13 G84E carriers

| | # of patients | % of patients |
|---|---|---|
| Tumor Grade (Gleason Score) | | |
| <=6 | 67 | 63.2% |
| 7 | 32 | 30.2% |
| 8 | 4 | 3.8% |
| >=9 | 3 | 2.8% |
| Tumor Stage | | |
| T1c or lower | 47 | 39.2% |
| T2 | 41 | 34.2% |
| T3 or higher | 32 | 26.7% |
| Metastasis at diagnosis | | |
| Yes | 4 | 3.1% |
| Seum PSA level at diagnosis | | |
| <=10 | 49 | 48.0% |
| 11-20 | 25 | 24.5% |
| >=20 | 28 | 27.5% |
| Age at diagnosis | | |
| <=55 | 24 | 18.6% |
| 56-80 | 105 | 81.4% |
| >=80 | 0 | 0.0% |
| Death from prostate cancer | | |
| Yes | 9 | 7.0% |

To assess a potential founder effect for the G84E mutation, haplotypes were estimated based on the 15 genotyped SNPs in this region. The mutation (allele A) of G84E was predicted to be on 8 different haplotypes. However, 95% (269 out of 284) of the occurrences were predicted to be on a single rare haplotype (frequency of 2%). Among the 269 G84E mutation carriers predicted to carry the common haplotype, 83 were from Finland while the remaining were from 12 other ICPCG groups. One individual from Finland was homozygous all 15 markers, allowing unambiguous assignment of the haplotype. The genotype data for all 269 G84E mutation carriers were consistent with a single shared haplotype spanning the 15 genotyped SNPs (i.e. there were no SNPs that had homozygous genotypes for opposite alleles among the 269 carriers) and it is possible that with additional genotype data the most likely haplotype configuration for G84E carriers would be a single founder haplotype.

The search for hereditary prostate cancer genes has been challenging due to a number of factors including the late-onset nature of the disease and the high background rate of sporadic disease in the general population. Although rare variants of other genes such as RNASEL, MSR1, and ELAC2, have been previously identified in prostate cancer families and proposed as prostate cancer susceptibility alleles, although follow-up studies have not supported their candidacy. On the other hand, mutations in BRCA2 have been reproducibly associated with prostate cancer risk, but their frequency is low in prostate cancer families.

More recently, GWAS studies have led to the identification of over 40 prostate cancer risk-associated SNPs that have been replicated in multiple study populations. These variants are common in the general population (5% or higher), confer low risk with ORs, typically in the range of 1.1-1.4, and have been estimated to account for ~25% of the risk associated with a positive family history. Although more common prostate cancer risk-associated variants are likely to be identified in the future, rare variants with larger effects have been proposed as an alternative mechanism to account for 'missing inheritance'. In this respect, the establishment of a rare and moderate to high-penetrance mutation in HOXB13 as a prostate cancer susceptibility allele provides empirical evidence for this alternative hypothesis.

The estimated frequency of the HOXB13 G84E mutation in prostate cancer families is influenced by the number of individuals in any given family as well as family structure. For example, some extended families, particularly in the Utah collection, have more than 100 subjects and have multiple affected generations. Similarly, estimated ORs for G84E in relation to prostate cancer risk are impacted by the mixed degrees of relatedness among relatives, as the covariance matrices used in the GEE models do not explicitly account for family structure. The analysis presented in Table 3 was designed to provide better odds ratio estimates for first- and second-degree relatives of G84E carriers. Of interest, the carrier rate was lower among second-degree affected relatives (58%) compared to first-degree affected relatives (75%), suggesting the presence of genetic heterogeneity across families. The OR estimates from the analyses should be interpreted only in the context of the current study. The odds ratios are calculated based on many "controls" that have limited phenotype information; most have not been screened for disease or screening results are missing. Further, familial controls not currently affected by prostate cancer are more likely to develop disease in the future compared to randomly selected men from the general population given the strong history of disease in these families. Finally, familial cases are more likely to carry moderate to high penetrance risk alleles compared to typical unselected prostate cancer cases. Large population-based studies that include screened men will be necessary to obtain more accurate measures of G84E mutation frequency and penetrance. As observed, the frequency of G84E mutations are likely population specific.

The results implicate a geographical frequency gradient of the G84E mutation across the European continent, with the mutation being more common in Nordic countries, notably Finland. This finding highlights the strength of the current study as family-based association methods provide the strongest protection against type I error due to population stratification. It remains to be seen how various analytic methods (e.g. those based on principal components that capture the major sources of genetic variation between subjects across common genetic variants) will protect against population stratification when analyzing uncommon genetic variants that disproportionately occur in specific European-derived populations in case-control settings.

Results reported herein were obtained using the following methods and materials unless indicated otherwise.

Study Subjects

For data from the Prostate Cancer Genetics Project, subjects were restricted to men with prostate cancer who had at least one living first- or second degree relative who also had prostate cancer or those in whom prostate cancer had been diagnosed at an age of 55 years or less, regardless of family history. Diagnosis of prostate cancer was confirmed by reviewing medical records, whenever possible. Ancestry was self-reported. All subjects provided written informed consent to participate in the study. The protocol and consent documents were approved by the institutional review board at the University of Michigan Medical School.

For data from Johns Hopkins University, families with hereditary prostate cancer each had at least three first-degree relatives with prostate cancer. Diagnosis of prostate cancer was verified by reviewing medical records. Included in the study were men who had undergone radical prostatectomy for the treatment of clinically localized prostate cancer at Johns Hopkins Hospital. Advanced prostate cancer was defined as biochemical recurrence of prostate cancer or metastatic or castration-resistant disease that was identified at the Sidney Kimmel Comprehensive Cancer Center at Johns Hopkins Hospital. The average age at diagnosis in this latter group was 60.9 years.

Control subjects for this study included men who had undergone screening for prostate cancer. Such screening included measurement of serum prostate-specific antigen levels and digital rectal examination at Johns Hopkins Hospital, Johns Hopkins Bayview Medical Center, Johns Hopkins University Applied Physics Laboratory, and several other locations in the mid-Atlantic area. Inclusion criteria for control subjects included a knowledge of ancestry and no diagnosis of prostate cancer. For all studies at Johns Hopkins University, research proposals were reviewed and approved by the institutional review board.

The International Consortium for Prostate Cancer Genetics (ICPCG) study cohort has been described in detail previously. Fifteen groups participated in the present study, including those from Europe (Finland (Tampere University), Sweden (Karolinska Institute), UK (Institute of Cancer Research and Royal Marsden NHS Foundation Trust, University of Cambridge, ACTANE), Germany (University of Ulm), and France (CeRePP)), North America (Fred Hutchinson Cancer Research Center, Johns Hopkins Hospital, Louisiana State University, Mayo Clinic, McGill University, Northwestern University, Stanford University, University of Michigan, and University of Utah), and Australia (University of Melbourne) (Table 13).

TABLE 13

Prostate cancer families of International Corsortium for Prostate Cancer Genetics (ICPCG) included in the current study

| | | Number of families by race/ethnicity | | | | Number of genotyped subjects | | |
|---|---|---|---|---|---|---|---|---|
| | # of families | European descent | African descent | Ashkenazi Jewish | Others | Affected (Men) | Unknown (Men) | Women |
| Europe | | | | | | | | |
| Finland, University of Tampere | 76 | 76 | 0 | 0 | 0 | 233 | 307 | 395 |
| Sweden, Ume5 University | 110 | 110 | 0 | 0 | 0 | 205 | 137 | 125 |
| Germany, University of Ulm | 378 | 378 | 0 | 0 | 0 | 645 | 130 | 81 |
| UK, ACTANE | 145 | 142 | 0 | 2 | 1 | 318 | 18 | 13 |
| France, CeRePP | 159 | 156 | 0 | 0 | 3 | 369 | 73 | 86 |
| North America | | | | | | | | |
| BC/CA/HI | 98 | 83 | 7 | 0 | | 252 | 75 | 58 |
| Fred Hutchinson Cancer Research Center | 255 | 241 | 8 | 0 | | 743 | 320 | 277 |
| Johns Hopkins Hospital | 234 | 176 | 21 | 31 | 6 | 707 | 273 | 278 |
| MAYO Clinic | 185 | 185 | 0 | 0 | 0 | 465 | 63 | 0 |
| University of Michigan | 317 | 282 | 21 | 13 | 1 | 856 | 222 | 199 |
| McGill University | 18 | 7 | 1 | 0 | 0 | 37 | 0 | 0 |
| North Western University | 33 | 32 | 0 | 0 | 1 | 67 | 17 | 4 |
| University of Utah | 348 | 348 | 0 | 0 | 0 | 1352 | 189 | 212 |
| Louisiana State University | 10 | 10 | 0 | 0 | 0 | 28 | 30 | 29 |
| Australia | | | | | | | | |
| Australia | 77 | 73 | 0 | 0 | 4 | 145 | 48 | 46 |
| Total | 2443 | 2299 | 58 | 46 | 30 | 6422 | 1902 | 1803 |

Each ICPCG group recruited its study population via different methods of pedigree ascertainment and utilized different methods to confirm prostate cancer diagnosis. In this study, men were considered "affected" if their prostate cancer diagnosis was confirmed by either medical records or death certificates. All other men were assigned as "unknown phenotype." A total of 2,443 families were included in the study, including 6,422 affected men and 1,902 men without a prostate cancer diagnosis (unknown), and 1803 women whose DNA samples were available (Table 13). Research protocols and study documentation were approved by each group's Institutional Review Board.

Targeted Sequencing of Genes in Candidate Region

The youngest patient with prostate cancer who had available DNA was selected from 94 families (54 families from the Prostate Cancer Genetics Project and 40 from Johns Hopkins University) on the basis of evidence of 17q21-22 linkage. Seven of the families were of African descent, 2 were of Asian descent, and the remaining 85 were of European descent. Two hundred two (202) genes in the genetic region of interest (approximately 15.5 Mb) were identified.

A primer library was designed for amplification of ~2800 amplicons representing 2009 exons from the target region. The RainDance RDT 1000 system (RainDance Technologies, Inc., Lexington Mass.) was used to amplify 3 ug of sheared genomic DNA from each sample using our primer library. Purified amplicons were used as template for sequencing using the Life Technologies SOLiD™ system, version 4.0 fragment library methodology (Life Technologies Corporation, Carlsbad, Calif.). Sequence data processing was performed using Life Technologies Bioscope to align the sequences to the genomic reference (Build 36, hg18). Variant detection was performed using SamTools 1.31 and SolSNP 1.1. All variant sequences were confirmed and tested in family members using standard Sanger sequencing, capillary electrophoresis technology and Big-Dye® Terminator chemistry (Applied Biosystems, Carlsbad Calif.).

Genotyping of HOXB13 Variants

Variants of HOXB13, a gene encoding transcription factor homeobox B13, which is within the candidate interval, were genotyped using the MassARRAY system (Sequenom) and TaqMan assays (Applied Biosystems/Life Technologies). All variants found on either of these platforms were confirmed using Sanger sequencing.

In the ICPCG dataset, five mutations in the HOXB13 gene (Ewing et al. and the ESP database (Exome Variant Server, NHLBI Exome Sequencing Project, Seattle, Wash. (evs.gs.washington.edu/EVS/) [January 2012]) were genotyped, including G84E (c.251G>A, rs138213197), T105I (c.314C>T, rs140492479), R217C (c.649C>T, rs13945791), R229G (c.685C>G), and T253P (c.757A>C). In addition, 10 polymorphic SNPs (rs890435, rs2326017, rs7212669, rs8064938, rs3809773, rs1054072, rs8556, rs3809771, rs4793980, rs3110601) flanking the HOXB13 gene and spanning 108,191 base pairs (bp) from 46,719,399 to 46,827,590 (Build 37) were genotyped to estimate allele frequencies and haplotypes. The G84E mutation, due to a change in the second position of codon 84 (GGA→GAA), results in a nonconservative substitution in a conserved putative protein-protein binding motif of HOXB13. Genotyping was performed using the MassARRAY iPLEX (Sequenom, Inc., San Diego, Calif.). Duplicates and negative controls were included in each 96-well plate to ensure quality control (QC). Genotyping was performed by technicians blinded to the sample status. The average concordance rate was 99.7% for 6,300 genotypes among QC duplicates.

Statistical Analysis

Association analyses for the HOXB13 G84E variant were performed using Fisher's exact tests and linear regression models implemented in the statistical program R (cran.r-project.org). Genotype data were included for 5083 unrelated men in whom prostate cancer had been diagnosed and for 1401 unrelated men who were presumed to be free of prostate cancer. These subjects were not part of the discovery sequencing study and were of self-reported European descent. Additional case-control association analyses for G84E included the use of publicly available data for 1233 subjects of European descent from the Exome Sequencing Project, funded by the National Heart, Lung, and Blood Institute, and 28 unrelated genotyped samples from the Centre d'Etude du Polymorphisme Humain from Utah (CEU) HapMap. The association between HOXB13 G84E and two quantitative clinical variables: the age at diagnosis and Gleason grade was tested.

In the ICPCG dataset, frequency of the G84E mutation was determined at either family level or individual level. At a family level, the proportion of families with at least one G84E mutation carrier was determined for the entire set as well as for each ICPCG group. The difference in the proportion among different ICPCG groups was tested using chi-square with a degree of freedom (df) of 14. At an individual level, the proportion of G84E mutation carriers was compared among men with a diagnosis of prostate cancer (affecteds) and the remaining men within the families (unknowns). The difference of G84E mutation carrier rate between affected and unknown men was tested based on a marginal model that accounts for relatedness of subjects within families using generalized estimating equations (GEE). An exchangeable working correlation matrix was assumed. A family-based association test was performed to test association of the G84E mutation and other SNPs with prostate cancer by assessing over-transmission of alleles from parents to affected offspring using the computer program FBAT.23 Empirical variance test statistics were used to account for the correlation of transmitted alleles among multiple affected individuals in the same family. Haplotypes of each individual based on these 15 SNPs were estimated using Genehunter-plus24 and PLINK. 25 The haplotypes with the highest likelihood were selected. For subjects whose inferred haplotypes were different based on these two methods, manual inspection was performed to resolve the difference, with priority given to haplotypes based on linkage disequilibrium among markers in this study population.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

The following documents are cited herein.
1. Siegel R, Ward E, Brawley O, Jemal A. Cancer statistics, 2011: the impact of eliminating socioeconomic and racial disparities on premature cancer deaths. CA Cancer J Clin 2011; 61:212-236
2. Langeberg W J, Isaacs W B, Stanford J L. Genetic etiology of hereditary prostate cancer. Front Biosci 2007; 12:4101-4110
3. Kim S T, Cheng Y, Hsu F C, et al. Prostate cancer risk-associated variants reported from genome-wide association studies: meta-analysis and their contribution to genetic variation. Prostate 2010; 70:1729-1738
4. Kote-Jarai Z, Olama A A, Giles G G, et al. Seven prostate cancer susceptibility loci identified by a multi-stage genome-wide association study. Nat Genet 2011; 43:785-791
5. Lange E M, Gillanders E M, Davis C C, et al. Genome-wide scan for prostate cancer susceptibility genes using families from the University of Michigan Prostate Cancer Genetics Project finds evidence for linkage on chromosome 17 near BRCA1. Prostate 2003; 57:326-334
6. Gillanders E M, Xu J, Chang B L, et al. Combined genome-wide scan for prostate cancer susceptibility genes. J Natl Cancer Inst 2004; 96:1240-1247
7. Xu J, Dimitrov L, Chang B L, et al. A combined genomewide linkage scan of 1,233 families for prostate cancer-susceptibility genes conducted by the International Consortium for Prostate Cancer Genetics. Am J Hum Genet 2005; 77:219-229
8. Lange E M, Robbins C M, Gillanders E M, et al. Fine-mapping the putative chromosome 17q21-22 prostate cancer susceptibility gene to a 10 cM region based on linkage analysis. Hum Genet 2007; 121:49-55
9. Exome variant server. Seattle: NHLBI Exome Sequencing Project (snp.gs.washington.edu/EVS).
10. The International HapMap Consortium. A haplotype map of the human genome. Nature 2005; 437:1299-1320
11. 1000 Genomes: a deep catalog of human variation (www.1000genomes.org/home).
12. Lange E M, Salinas Calif., Zuhlke K A, et al. Early onset prostate cancer has a significant genetic component. Prostate 2011 May 2 (Epub ahead of print).
13. Lange E M, Beebe-Dimmer J L, Ray A M, et al. Genome-wide linkage scan for prostate cancer susceptibility from the University of Michigan Prostate Cancer Genetics Project: suggestive evidence for linkage at 16q23. Prostate 2009; 69:385-391
14. Xu J, Zheng S L, Komiya A, et al. Germline mutations and sequence variants of the macrophage scavenger receptor 1 gene are associated with prostate cancer risk. Nat Genet 2002; 32:321-325
15. Zheng S L, Sun J, Cheng Y, et al. Association between two unlinked loci at 8q24 and prostate cancer risk among European Americans. J Natl Cancer Inst 2007; 99:1525-1533
16. Liu W, Xie C C, Zhu Y, et al. Homozygous deletions and recurrent amplifications implicate new genes involved in prostate cancer. Neoplasia 2008; 10:897-907
17. Ng P C, Henikoff S. Predicting the effects of amino acid substitutions on protein function. Annu Rev Genomics Hum Genet 2006; 7:61-80
18. Ramensky V, Bork P, Sunyaev S. Human non-synonymous SNPs: server and survey. Nucleic Acids Res 2002; 30:3894-3900
19. Williams T M, Williams M E, Innis J W. Range of HOX/TALE superclass associations and protein domain requirements for HOXA13:MEIS interaction. Dev Biol 2005; 277:457-471
20. Haiman C A, Chen G K, Blot W J, et al. Genome-wide association study of prostate cancer in men of African ancestry identifies a susceptibility locus at 17q21. Nat Genet 2011; 43:570-573

21. Gudmundsson J, Sulem P, Steinthorsdottir V, et al. Two variants on chromosome 17 confer prostate cancer risk, and the one in TCF2 protects against type 2 diabetes. Nat Genet 2007; 39:977-983
22. Graham A. Developmental patterning: the Hox code out on a limb. Curr Biol 1994; 4:1135-1137
23. Goodman F R, Scambler P J. Human HOX gene mutations. Clin Genet 2001; 59:1-11
24. Economides K D, Zeltser L, Capecchi M R. Hoxb13 mutations cause overgrowth of caudal spinal cord and tail vertebrae. Dev Biol 2003; 256:317-330
25. Economides K D, Capecchi M R. Hoxb13 is required for normal differentiation and secretory function of the ventral prostate. Development 2003; 130:2061-2069
26. Thorsteinsdottir U, Kroon E, Jerome L, Blasi F, Sauvageau G. Defining roles for HOX and MEIS1 genes in induction of acute myeloid leukemia. Mol Cell Biol 2001; 21:224-234
27. Jung C, Kim R S, Zhang H J, Lee S J, Jeng M H. HOXB13 induces growth suppression of prostate cancer cells as a repressor of hormone-activated androgen receptor signaling. Cancer Res 2004; 64:9185-9192
28. Norris J D, Chang C Y, Wittmann B M, et al. The homeodomain protein HOXB13 regulates the cellular response to androgens. Mol Cell 2009; 36:405-416
29. Kim J H, Dhanasekaran S M, Mehra R, et al. Integrative analysis of genomic aberrations associated with prostate cancer progression. Cancer Res 2007; 67:8229-8239
30. Fukasawa S, Kino M, Kobayashi M, et al. Genetic changes in pT2 and pT3 prostate cancer detected by comparative genomic hybridization. Prostate Cancer Prostatic Dis 2008; 11:303-310
31. Edwards S, Campbell C, Bohr P, et al. Expression analysis onto microarrays of randomly selected cDNA clones highlights HOXB13 as a marker of human prostate cancer. Br J Cancer 2005; 92:376-381.
32. Thompson D, Easton D F. Cancer incidence in BRCA1 mutation carriers. J Natl Cancer Inst 2002; 94:1358-1365.
33. Ostrander E A, Udler M S. The role of the BRCA2 gene in susceptibility to prostate cancer revisited. Cancer Epidemiol Biomarkers Prev 2008; 17:1843-1848.
34. Schehl-Sinclair C, Berry R, Schaid D, Thibodeau S N, Couch F J. BRCA1 and BRCA2 have a limited role in familial prostate cancer. Cancer Res 2000; 60:1371-1375.
35. Zuhlke K A, Madeoy J J, Beebe-Dimmer J, et al. Truncating BRCA1 mutations are uncommon in a cohort of hereditary prostate cancer families with evidence of linkage to 17q markers. Clin Cancer Res 2004; 10:5975-5980.
36. Li H, Handsaker B, Wysoker A, et al. The Sequence Alignment/Map format and SAMtools. Bioinformatics 2009; 25:2078-9.
37. Cropp C D, Simpson C L, Wahlfors T, Ha N, George A, Jones M S, Harper U, Ponciano-Jackson D, Green T A, Tammela T L, Bailey-Wilson J, Schleutker J. Genome-wide linkage scan for prostate cancer susceptibility in Finland: evidence for a novel locus on 2q37.3 and confirmation of signal on 17q21-q22. Int J Cancer 2011; 129:2400-7.
38. Gudmundsson J, Sulem P, Manolescu A, et al. Genome-wide association study identifies a second prostate cancer susceptibility variant at 8q24. NatGenet 2007; 39:631-7.
39. Yeager M, Orr N, Hayes R B, et al. Genome-wide association study of prostate cancer identifies a second risk locus at 8q24. NatGenet 2007; 39:645-9.
40. Thomas G, Jacobs K B, Yeager M, et al. Multiple loci identified in a genome-wide association study of prostate cancer. NatGenet 2008; 40:310-5.
41. Gudmundsson J, Sulem P, Rafnar T, et al. Common sequence variants on 2p15 and Xp11.22 confer susceptibility to prostate cancer. NatGenet 2008; 40:281-3.
42. Eeles R A, Kote-Jarai Z, Giles G G, et al. Multiple newly identified loci associated with prostate cancer susceptibility. NatGenet 2008; 40:316-21.
43. Sun J, Zheng S L, Wiklund F, et al. Evidence for two independent prostate cancer risk-associated loci in the HNF1B gene at 17q12. NatGenet 2008; 40:1153-5.
44. Yeager M, Chatterjee N, Ciampa J, et al. Identification of a new prostate cancer susceptibility locus on chromosome 8q24. NatGenet 2009; 41:1055-7.
45. Gudmundsson J, Sulem P, Gudbjartsson D F, et al. Genome-wide association and replication studies identify four variants associated with prostate cancer susceptibility. NatGenet 2009; 41:1122-6.
46. Eeles R A, Kote-Jarai Z, Al Olama A A, et al. Identification of seven new prostate cancer susceptibility loci through a genome-wide association study. NatGenet 2009; 41:1116-21.
47. Xu J, Zheng S L, Isaacs S D, et al. Inherited genetic variant predisposes to aggressive but not indolent prostate cancer. ProcNatlAcadSciUSA 2010; 107:2136-40.
48. Takata R, Akamatsu S, Kubo M, et al. Genome-wide association study identifies five new susceptibility loci for prostate cancer in the Japanese population. Nat Genet 2010; 42:751-4.
49. Akamatsu S, Takata R, Haiman C A, et al. Common variants at 11q12, 10q26 and 3p11.2 are associated with prostate cancer susceptibility in Japanese. Nat Genet 2012; 44:426-9, 51.
50. Schaid D J, Chang B L. Description of the international consortium for prostate cancer genetics, and failure to replicate linkage of hereditary prostate cancer to 20q13. The Prostate 2005; 63:276-90.
51. Kruglyak L, Daly M J, Reeve-Daly M P, Lander E S. Parametric and nonparametric linkage analysis: a unified multipoint approach. American Journal of Human Genetics 1996; 58:1347-63.
52. Purcell S, Neale B, Todd-Brown K, et al. PLINK: a tool set for whole-genome association and population-based linkage analyses. AmJHumGenet 2007; 81:559-75.
53. Carpten J, Nupponen N, Isaacs S, et al. Germline mutations in the ribonuclease L gene in families showing linkage with HPC1. Nature Genetics 2002; 30:181-4.
54. Tavtigian S V, Simard J, Teng D H, et al. A candidate prostate cancer susceptibility gene at chromosome 17p. Nature Genetics 2001; 27:172-80.
55. Edwards S M, Kote-Jarai Z, Meitz J, et al. Two percent of men with early-onset prostate cancer harbor germline mutations in the BRCA2 gene. AmJHumGenet 2003; 72:1-12.
56. Agalliu I, Karlins E, Kwon E M, et al. Rare germline mutations in the BRCA2 gene are associated with early-onset prostate cancer. BrJ Cancer 2007; 97:826-31.
57. Iyengar S K, Elston R C. The genetic basis of complex traits: rare variants or "common gene, common disease". Methods Mol Biol. 2007; 376:71-84.
58. Bodmer W, Bonilla C. Common and rare variants in multifactorial susceptibility to common diseases. Nat Genet. 2008 June; 40(6):695-701.

What is claimed is:

1. A method of and treating prostate cancer in a subject, the method comprising:
    (a) detecting an alteration in a HoxB13 nucleic acid sequence or amino acid sequence in a biological sample obtained from the subject, wherein the alteration in HOXB13 is selected from the group consisting of:
    a change of adenosine for guanine in the second position of codon 84 (GGA-GAA) resulting in a nonconservative substitution of glutamic acid for glycine (G84E);
    a missense mutation 685C-G resulting in the substitution of glycine for arginine at position 229 (R229G);
    a substitution mutation 431T-C resulting in a substitution of leucine for proline (L144P); and
    a substitution of aspartic acid for tyrosine (Y88D) at codon 88 (262T-G), and
    (b) administering a therapeutic regimen selected from the group consisting of radical prostatectomy, radiation therapy, hormone therapy and chemotherapy, for treating the subject.

2. The method of claim 1, wherein the subject is further identified as having a positive family history for prostate cancer and is younger than age 55.

3. The method of claim 1, wherein the G84E mutation alteration is identified in a subject of Nordic descent.

4. The method of claim 1, wherein the R229G mutation is identified in a subject of African-American descent.

5. The method of claim 1, wherein the sample is a tissue sample, tissue biopsy sample, or biological liquid.

6. The method of claim 1, wherein said method identifies the subject as in need of increased surveillance for prostate disease.

7. The method of claim 5, wherein said surveillance comprises annual measurement of PSA levels in said subject.

8. The method of claim 1, further comprising administering a PSA test to the subject and detecting elevated PSA levels in the subject.

9. The method of claim 1, wherein said detecting comprises annealing an amplification product to a fluorescent hybridization probe selected from the group consisting of a 5' nuclease probe oligonucleotide containing a 5' fluorescent dye and 3' quenching dye, a molecular beacon and a FRET hybridization probe.

10. The method of claim 9, wherein the 5' nuclease probe oligonucleotide containing a 5' fluorescent dye and 3 quenching dye comprises the GGA to GAA variant of SEQ ID NO: 4.

* * * * *

UNITED STATES PATENT AND TRADEMARK OFFICE
CERTIFICATE OF CORRECTION

PATENT NO. : 9,593,380 B2
APPLICATION NO. : 14/357034
DATED : March 14, 2017
INVENTOR(S) : William B. Isaacs and Kathleen A. Cooney Page 1 of 1

It is certified that error appears in the above-identified patent and that said Letters Patent is hereby corrected as shown below:

In the Specification

Column 1, please replace the second paragraph as follows:
STATEMENT OF GOVERNMENTAL INTEREST
This invention was made with government support under grant numbers CA086323, 089600, CA079596, CA069568, awarded by the National Institutes of Health. The government has certain rights in the invention.

Signed and Sealed this
Twentieth Day of November, 2018

Andrei Iancu
*Director of the United States Patent and Trademark Office*